(12) United States Patent
Sutton et al.

(10) Patent No.: US 8,512,970 B2
(45) Date of Patent: Aug. 20, 2013

(54) RAPID BIOLUMINESCENCE DETECTION ASSAY

(75) Inventors: Mark J. Sutton, Salisbury (GB); Toryn Poolman, Salisbury (GB); Richard J. Hesp, Salisbury (GB)

(73) Assignee: The Secretary of State for Health, London (GB)

( * ) Notice: Subject to any disclaimer, the term of this patent is extended or adjusted under 35 U.S.C. 154(b) by 112 days.

(21) Appl. No.: 13/143,722

(22) PCT Filed: Jan. 7, 2010

(86) PCT No.: PCT/GB2010/050018
§ 371 (c)(1),
(2), (4) Date: Aug. 15, 2011

(87) PCT Pub. No.: WO2010/079357
PCT Pub. Date: Jul. 15, 2010

(65) Prior Publication Data
US 2011/0318729 A1    Dec. 29, 2011

(30) Foreign Application Priority Data
Jan. 7, 2009   (GB) ................................ 0900151.2

(51) Int. Cl.
*C12Q 1/48*    (2006.01)
(52) U.S. Cl.
USPC ........................................................ 435/15
(58) Field of Classification Search
USPC ........................................................ 435/15
See application file for complete search history.

(56) References Cited

U.S. PATENT DOCUMENTS

| 5,246,834 A | 9/1993 | Tsuji et al. |
| 6,811,990 B1 | 11/2004 | Corey et al. |

FOREIGN PATENT DOCUMENTS

| CN | 1946857 A | 4/2007 |
| GB | 2370113 A | 6/2002 |
| WO | WO 96/02666 | 2/1996 |
| WO | WO 00/46357 | 8/2000 |
| WO | WO 00/70082 | 11/2000 |
| WO | WO 2004/090089 A1 | 10/2004 |
| WO | 2005/093085 A1 | 10/2005 |
| WO | WO 2005/093085 A1 | 10/2005 |
| WO | WO 2009/194013 A1 | 8/2009 |

OTHER PUBLICATIONS

Squirrell et al., Rapid and specific detection of bacteria using bioluminescence, Analytica Chimica Acta, 457:109-114 (2002).
Office Action for Chinese Patent Application No. 201080008250.X, mailed Feb. 27, 2013, Chinese.
English Translation of NPL2 (Office Action for Chinese Patent Application No. 201080008250.X).
Blasco et al., Specific Assays for Bacteria Using Phage Mediated Release of . . . Journal of Applied Microbiology, 84:661-666 (1998), Wiley-Blackwell, Hoboken, NJ.
Hesp et al., Thermostable Adenylate Kinase Technology . . . , Journal of Hospital infection, 74(2):137-143 (Feb. 2010), Elsevier, The Netherlands.
Ito et al., Highly Sensitive Simultaneous Bioluminescent Measurement . . . , Analytical Sciences, 19(1):105-109 (2003), The Japan Society for Analytical Chemistry, Japan.
International Preliminary Report on Patentability, Application No. PCT/GB2004/001517, International Bureau of WIPO, Switzerland, mailed Oct. 15, 2005.
Written Opinion of the International Searching Authority, Application No. PCT/GB2004/001517, European Patent Office, Germany, mailed Apr. 8, 2004.
Maeda et al., New Label Enzymes for Bioluminescent Enzyme Immunoassay, Journal of Pharmaceutical and Biomedical Analysis, 30:1125-1734 (2003), Elsevier, The Netherlands.
Maeda at al., Development of New Label Enzyme for Bioluminescent Enzyme Immunoassay, Analytical Letters, 28(3):383-394 (1995), M. Dekker, New York.
Murakami et al., Bioluminescent Enzyme Immunoassay Using Thermostable Mutant Luciferase and . . . , Analytica Chemica Acta, 361:19-26 (1998), Elsevier, The Netherlands.
Squirrell et al., Rapid and Specific Detecton of Bacteria Using Bioluminescence, Analytica Chemica Acta, 457(1):109-114 (2002), Elsevier, The Netherlands.

*Primary Examiner* — Maryam Monshipouri
(74) *Attorney, Agent, or Firm* — Nevrivy Patent Law Group P.L.L.C.

(57) ABSTRACT

An assay is provided for detecting the activity of a reporter kinase comprising (i) adding said reporter kinase to an assay mixture wherein said reporter kinase is contacted with bioluminescent reagent no more than minutes after being contacted with ADP, and wherein, prior to contacting the reporter kinase with ADP, the assay mixture is substantially free from kinase other than reporter kinase; and (ii) detecting light output from the assay mixture. Methods for detecting the presence of an analyte in a sample and methods for validating a treatment process using the above assay are also provided. Further provided are devices for conducting these assays and methods.

20 Claims, 12 Drawing Sheets

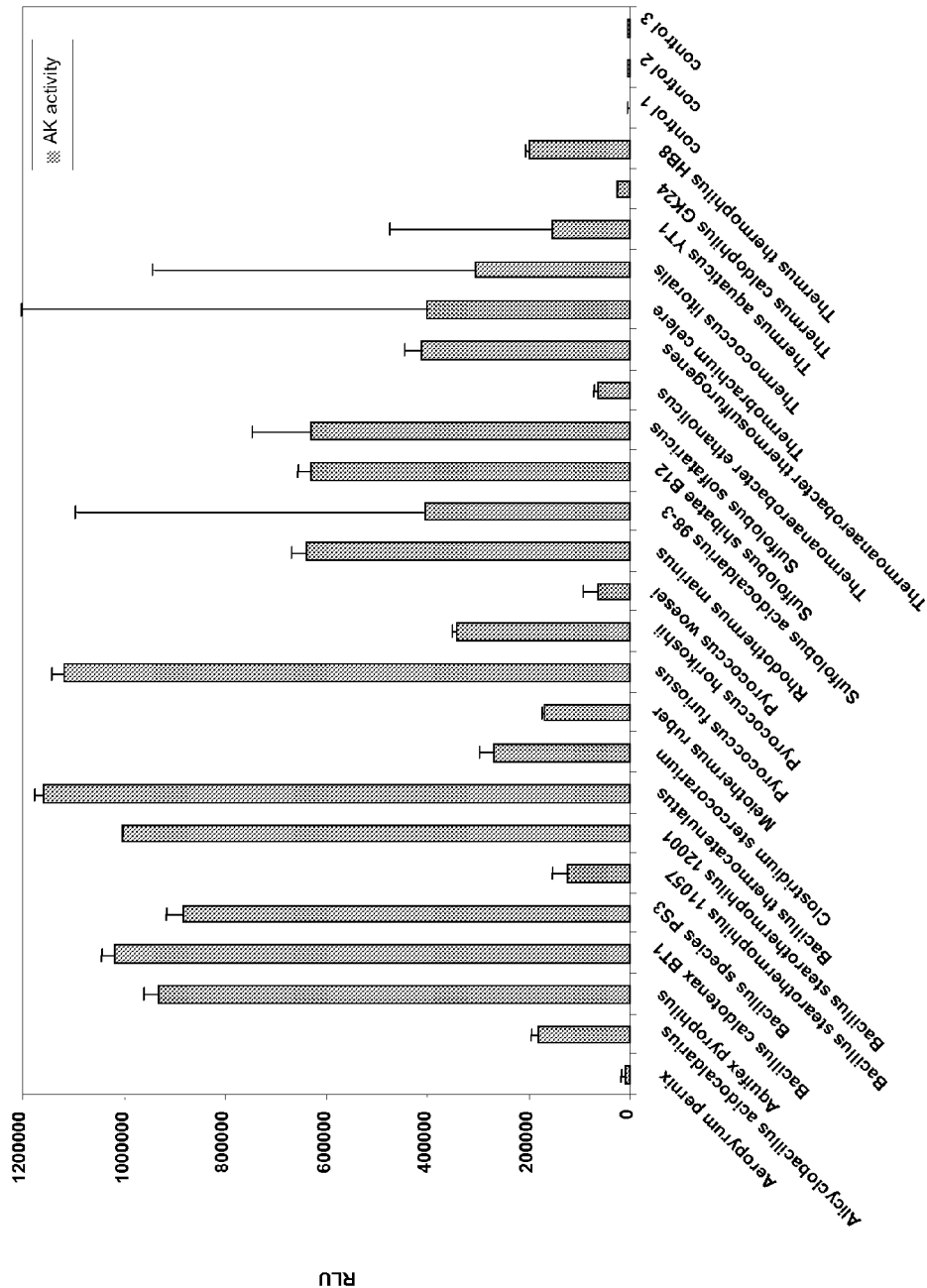

Figure 7A - Comparison of inhibition of adenylate kinases by Ap6A
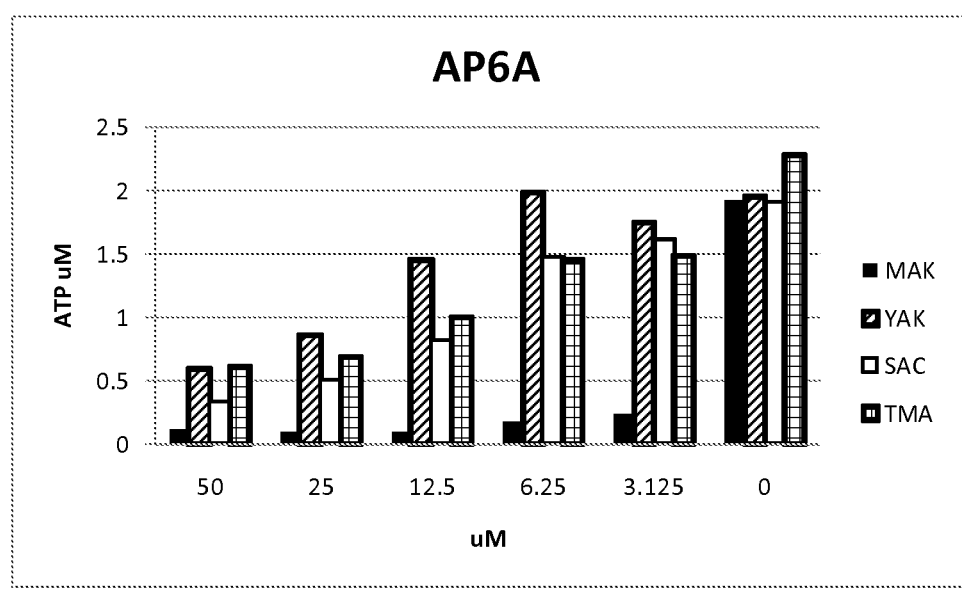
MAK = rabbit muscle AK (myokinase); YAK= yeast AK; SAC= S.acidocladarius AK; TMA = T.maritima AK

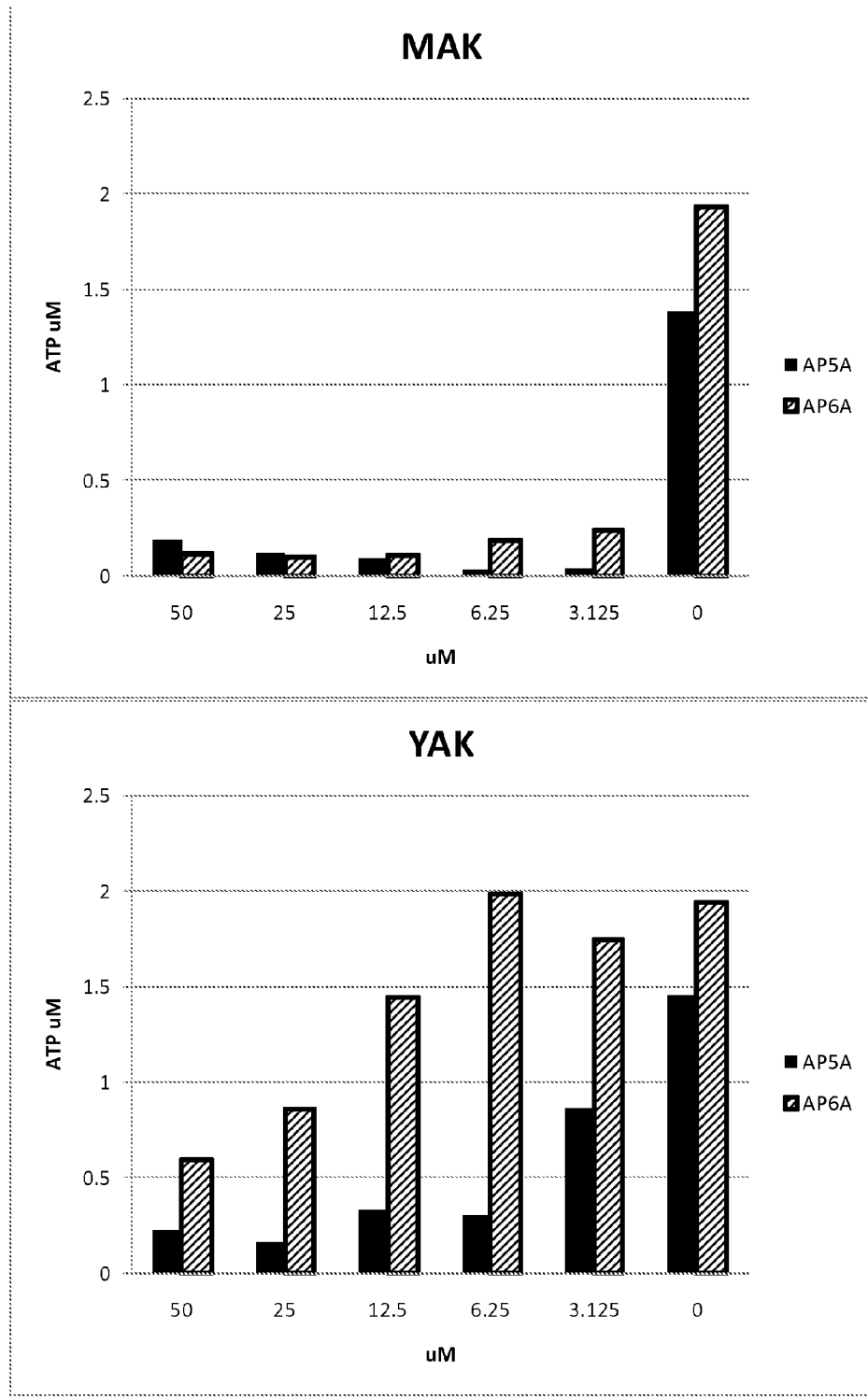
Figure 7B - Comparison of Ap5A and Ap6A for inhibition of contaminating background adenylate kinase from either mammalian cells (MAK) or yeast (YAK)

RAPID BIOLUMINESCENCE DETECTION ASSAY

This application is a 371 of PCT/GB10/50018 filed Jan. 7, 2010, which claims foreign priority to British Application No. 0900151.2, filed Jan. 7, 2009.

REFERENCE TO A SEQUENCE LISTING SUBMITTED ELECTRONICALLY VIA EFS-WEB

The content of the sequence listing (Name: Sequence_Listing.txt, Size: 180,647 bytes; and Date of Creation: Jul. 6, 2011) electronically submitted via EFS-Web is incorporated by reference in its entirety.

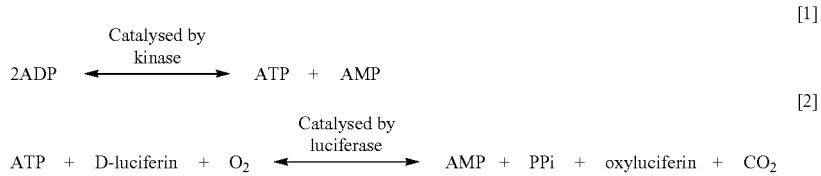

The invention relates to the field of rapid bioluminescence detection systems, in particular to rapid and very sensitive bioluminescence detection systems for detecting the activity of reporter kinases. Bioluminescent assays, devices, and kits for detecting the activity of reporter kinases are also provided.

The use of kinases as reporter enzymes has been described in the art. By way of example, the present inventors have described the use of reporter kinases in diagnostic systems for detecting the presence of an analyte in a sample (see WO00/46357), and also in systems for validating the effectiveness of decontamination processes (see WO2005/093085). The activity of these reporter kinases is typically detected using an ATP bioluminescence system (e.g. luciferin-luciferase), which generates a light output signal. The light output generated is measured using a luminometer, and these measurements are then correlated with the amount of kinase activity.

A potential problem associated with reporter kinase systems is the length of time required to obtain the output signal. To date, the typical time required to obtain an output signal ranges from 30 minutes to several hours. There is thus a need in the art for a quicker and/or simplified reporter system.

One or more of the above-mentioned problems is solved by the present invention, which, in a first aspect, provides an assay for detecting the activity of a reporter kinase, comprising:

(i) adding said reporter kinase to an assay mixture, wherein said reporter kinase contacted with ADP, and, no more than 5 minutes after being contacted with ADP, said reporter kinase is contacted with a bioluminescent reagent, wherein, prior to contacting the reporter kinase with ADP, the assay mixture is substantially free from non-reporter kinase (ie. kinase other than reporter kinase); and (ii) detecting light output from the assay mixture.

In one embodiment of the invention, the method further comprises the step of recording the light output data obtained in step (ii) on a suitable data carrier.

In another embodiment of the invention, the reporter kinase is contacted with the bioluminescent reagent no more than 2 minutes, no more than 1 minute, no more than 30 seconds, or no more than 10 seconds, after being contacted with the ADP. In another embodiment, the reporter kinase is contacted simultaneously with the ADP and the bioluminescent reagent.

Thus, there is no significant incubation period (or only a very short incubation period) between contacting the reporter kinase with the ADP and contact with the bioluminescent reagent. The invention can therefore be said to employ a "one-step" bioluminescent detection process.

In contrast to the above rapid detection system, conventional reporter systems typically employ a "two-step" detection process:

In the first step, the reporter kinases are exposed to a source of ADP substrate, and incubated for a sufficient time to sallow the generation of ATP [1]. Then, in a second, separate, step, the luciferin/luciferase reagent is added to convert the ATP generated by the reporter kinase into light [2]. This "two-step" bioluminescent assay has been shown to provide accurate kinase detection. However, its "two-step" nature (i.e. the addition of ADP, incubation, and then separate addition of bioluminescent reagent) has proved cumbersome and slow when detection is carried out "in the field", and not in a laboratory setting.

To date, the two reaction steps (illustrated above) have been considered incompatible as AMP generated during step [2] drives the equilibrium of step [1] over to the left-hand side, thereby favoring the re-conversion of ATP generated in step [1] into ADP. Since the light signal output of the system is dependent on the presence of ATP, this makes the detection of kinase activity more difficult. Thus, to date, steps [1] and [2] have been separated either temporally (i.e. by including an incubation step as described above), or spatially (i.e. where the reactions are carried out in separate compartments).

Contrary to this dogma, the present inventors have found that reaction steps [1] and [2] can in fact be performed simultaneously, without any significant adverse effect on the sensitivity of the detection of the reporter kinases. The resulting "one-step" bioluminescent assay provides significant advantages in terms of speed and convenience, and is particularly advantageous in point-of-care diagnostic tests, and rapid process release indicators, i.e. for the detection of kinase activity in the field rather than in the laboratory.

In addition, in order to ensure a high sensitivity and accuracy of detection, the present inventors have found it advantageous to ensure that, prior to the addition of any ADP, the sample containing the reporter kinase is substantially free from any non-reporter (ie. contaminating) kinase activity, and/or any endogenous ATP. As will be clear from the reaction schemes above, the presence of either of these contaminants can significantly adversely affect the sensitivity/accuracy of the detection of kinase activity. By way of example, non-reporter kinases may convert ADP to ATP and thus generate a false for increased) light output signal. Thus, it has been found advantageous to treat the sample containing the reporter kinase to remove or inactivate any non-reporter kinase and/or any endogenous ATP.

In one embodiment of the invention, non-reporter kinase is removed and/or inactivated using one or more of the treatment steps described below. In this regard, preferred non-reporter kinases that are inactivated or removed in accordance with the present invention are mammalian, fungal and/or plant kinases (eg. a mammalian, fungal or plant adenylate kinase). These treatments may be used in any number (preferably one or more, or at least two, or at least three) and/or in any combination. In all cases, however, the treatment leaves the reporter kinase substantially intact (eg. active in terms of kinase activity). Any one or more of the following treatment steps can be applied to any aspect of the invention.

In one embodiment, non-reporter kinase is inactivated by exposure to a temperature of between 50 to 120 C for a period of between 1 and 30 minutes, for example 90 C for 10 minutes, 90 C for 3 minutes, 90 C for 1 minute, 120 C for 3 minutes, or 120 C for 1 minute. The temperature and duration of the inactivation process denature non-reporter kinase whilst leaving the activity of the reporter kinase substantially intact.

In a further embodiment, non-reporter kinase is removed/inactivated using a chemical denaturation treatment. Example of suitable treatments include exposure to a chaotrope such as urea (e.g. concentrations greater than 2M urea) or guanidine (e.g. concentrations greater than 1M guanidine), exposure to a detergent (e.g. greater than 0.5% SOS, sarcosyl or triton X-100) exposure to a free-radical generator (e.g. >1000 ppm active chlorine derived from sodium hypochlorite or equivalent reagents) or exposure to an oxidative treatment.

In another embodiment, non-reporter kinase is removed/inactivated using an enzymatic denaturation treatment. Examples of suitable enzymes include highly processive proteases, such as e.g. Prionzyme®, Properase®, proteinase-K, and thermolysin.

In a further embodiment, non-reporter kinase is removed/inactivated by exposure to a selected pH (e.g. below pH 4, or greater than pH 11 using buffers such as 50 mM CAPS pH 11), a selected salt concentration (e.g. >2M ammonium sulphate), EDTA, or combinations thereof.

In a further embodiment, non-reporter kinase is removed/inactivated by the addition of an inhibitor, which selectively or specifically inhibits the non-reporter kinase (i.e. the inhibitor inactivates the non-reporter kinase, whilst leaving the activity of the reporter kinase substantially intact). Examples of suitable inhibitors include: staurosporine; vanadate (eg. orthovanadate or decavanadate); glycerophosphate; Diadenosine phosphates such as Ap6A (Diadenosine hexaphosphate), Ap5A (Diadenosine pentaphosphate), Ap4A (Diadenosine tetraphosphate), and/or Ap3A (Diadenosine triphosphate); vitamin C; AMP-PCP; AMP-PNP; AMP-S; ATP-γS; and Ara-ATP. Competitive inhibitors of non-reporter kinases (eg. of non-reporter adenylate kinase) are preferred (eg. Diadenosine phosphate inhibitors such as Ap4A and/or Ap5A), in one embodiment, the inhibitor selectively or specifically inhibits mammalian and fungal (eg. yeast) and plant non-reporter kinases. In another embodiment, the inhibitor (eg. Ap5A) selectively or specifically inhibits mammalian and fungal (eg. yeast) non-reporter kinases. In a further embodiment, the inhibitor (eg. Ap4A and/or Ap6A) selectively or specifically inhibits mammalian non-reporter kinases.

Inhibitors may be determined empirically, for example for different samples or matrices. For example a range of different inhibitors have been shown experimentally to provide discrimination between a reporter kinase (e.g. a kinase from *S. acidocaldarius*, *T. maritima*, or *Chlamydia pneumonae*) and a non-reporter kinase such as a mammalian tissue-derived kinase as represented by rabbit muscle adenylate kinase (FIG. 4 and FIG. 7). Thus, in one embodiment, the use of one or more inhibitor such as Ap4A, Ap5A and/or Ap6A substantially reduces the activity of non-reporter kinase (eg. endogenous tissue-derived kinase such as adenylate kinase)—the employed inhibitor concentrations are typically in the low micromolar range and have no significant effect on a reporter kinase. By way of further example, Ap5A discriminates reporter kinase from non-reporter kinase (eg. fungal adenylate kinase) represented here by the enzyme from *Saccharomyces cerevisiae*. On this basis inhibitor selection may be based on both the nature of the reporter kinase and the background (ie. non-reporter kinase) of the sample.

Examples of suitable reporter kinase applications of the present invention are illustrated in Table 1 (below)—also shown are examples of contaminating non-reporter kinases typically encountered in said applications. Table 1 also lists, purely by way of example, a selection of inhibitors that may be employed (eg. by addition to sample preparation buffers) in the context of the present invention.

TABLE 1

| Example of reporter kinase | Example of non-reporter kinase | Example of inhibitor | Utility |
| --- | --- | --- | --- |
| Bacterial kinase (eg. AK); e.g from *Chlamydia pneumonia* | Mammalian-derived tissue, cell or sample | Mammalian kinase inhibitor (eg. Ap4A, Ap5A and/or Ap6A) | Detection of bacterial infection in a patient |
| Bacterial kinase (eg. AK): e.g. from *Burkoldheria pseudomallei* | Mammalian-derived tissue, cell or sample | Mammalian kinase inhibitor (eg. Ap4A, Ap5A and/or Ap6A) | Detection of viable bacterial pathogens in a cell culture model |
| Archaeal kinase (eg. AK); e.g from *S. acidocaldarius* | Mammalian-derived tissue, cell or sample | Mammalian kinase inhibitor (eg. Ap4A, Ap5A and/or Ap6A) | Detection of an analyte in a patient sample |
| Bacterial kinase (eq. AK); e.g from *Thermotoga maritima* | Fungal-derived cell or culture | Fungal kinase inhibitor (eg. Ap5A) | Detection of bacterial contaminant in a brewing vessel |
| Fungal kinase (eg. AK); e.g. from *S. cerevisiae* | Mammalian-derived tissue, cell or sample | Mammalian kinase inhibitor (eg. Ap4A and/or Ap6A) | Detection of a fungal contaminant in a tissue culture |

TABLE 1-continued

| Example of reporter kinase | Example of non-reporter kinase | Example of inhibitor | Utility |
|---|---|---|---|
| Bacterial kinase (eg. AK): e.g. from *Pseudomonas aeruginosa* | Plant-derived tissue, cell or sample | Plant kinase inhibitor (eg. Ap4A and/or Ap5A) | Detection of a bacterial contaminant in a plant cell culture |
| Fungal kinase (eg. AK); e.g. from *Phytophthora ramorum* | Plant-derived tissue, cell or sample | Plant kinase inhibitor (eg. Ap4A and/or Ap6A) | Detection of a fungal pathogen in a plant |
| Protozoan kinase (eg. AK); e.g. from *Plasmodium falciparum* | Mammalian-derived tissue cell or sample | Mammalian kinase inhibitor (eg. Ap3A and/or Ap4A) | Detection of a malarial infection in a patient blood sample |

In another embodiment, non-reporter kinase may be separated from reporter kinase on the basis of size. By way of example, the sample containing the reporter kinase can be run on a filtration device, which separates the non-reporter kinase and the reporter kinase on the basis of size, with the reporter kinase being retained on a suitable filter whilst the non-reporter kinase passes through (see e.g. Example 14, and FIG. 6). This may be achieved by coupling the reporter kinase to a particle or within a vesicle which is preferentially retained by the filter. In either case the adherence of the reporter kinase to the filter does not result in the significant loss of the reporter kinase activity. Suitable filter matrices include: nitrocellulose, cellulose acetate or paper filters. Fitter matrices typically employ a range of pore sizes, such as from 0.2 μm to 20 μm or larger depending on the nature of the particulate carrier employed.

Physical size may also be used as a basis for separation of non-reporter kinase from reporter kinase using gel filtration or size exclusion chromatography. In one embodiment, the reporter kinase has a lower molecular weight than the non-reporter kinase. In another embodiment, the reporter kinase has a higher molecular weight than the non-reporter kinase. By way of example, the reporter kinase may have a molecular weight of at least 40 to 80 kDa, whereas the non-reporter kinase may have a molecular weight of no more than 30 kDa. When run through a size exclusion resin or membrane, this provides very efficient separation with the larger protein (eg. the reporter kinase) running at or near the void volume of the matrix (hence running quickly) whilst the non-reporter kinase (eg. endogenous kinase such as mammalian tissue kinase) interacts with the pores of the matrix and elutes more slowly. Suitable "higher molecular weight" reporter kinases may be obtained from Archael sources (e.g. trimeric adenylate kinases enzymes from Aracheal sources), which are in the region of 60 kDa in size compared to the 21-22 kDa of contaminating non-reporter kinase (eg. endogenous kinase such as mammalian tissue kinase). In addition, the size differential between the reporter and non-reporter kinase may be enhanced by the addition of a protein or antibody fragment (e.g. a single chain antibody variable region (scFv), by either chemical conjugation or genetic fusion and recombinant expression) to the reporter kinase. For example, a trimeric adenylate kinase fused to a single chain antibody variable region (scFv) has a size in the order of 120 kDa (based on an scFv size of approximately 20 kDa, attached to each of the three subunits).

In a further embodiment, separation of non-reporter kinase from reporter kinase can be achieved by the use of surface charge. In one embodiment, the isoelectric point of the reporter kinase may be lower than that of the non-reporter kinase. In another embodiment, the isoelectric point of the reporter kinase may be higher than that of the non-reporter kinase. As such, the reporter kinase can be separated from the non-reporter kinases with selective binding of either the reporter kinase or the non-reporter kinase to a cation exchange matrix or anion exchange matrix at a suitable pH. The isoelectric point of reporter kinase is frequently in the high basic range; e.g. the tAK from *S. acidocaldarius* has a predicted pI of 9.03 (although the inventors have demonstrated that the actual pI is in excess of pH10—see Table 2). By contrast, the majority of non-reporter kinases that could interfere with the assay typically have a lower isoelectric point, e.g. a pI in the region of pH7. As such, the reporter kinase can be separated from the non-reporter kinases with selective binding of the reporter kinase, by the use of either a cation exchange resin, membrane or other solid matrix at a pH of at least 8, or using an anion exchange resin, membrane or other solid matrix above pH10. Many of the reporter kinases of the invention retain enzymatic activity in this pH range. Alternatively, non-reporter kinases can be selectively removed by binding them to suitable matrices, e.g. an anion exchange matrix up to pH9.

In another embodiment of the invention, non-reporter kinase can be separated from reporter kinase using a "hydrophobic capture" technique. Reporter kinases (eg. those from the Sulfolubus family, and related Sulfolobaceae families such as *acidianus, metallosphaera, stygiolobus*, and *sulfurisphaera*) show exceptionally tight binding to a variety of surfaces, even when such surfaces are pre-treated or pre-coated (termed "blocked") with other proteins or detergent-based blocking agents. In contrast, the "blocking" of surfaces substantially prevents the binding of non-reporter kinases (eg. mammalian, fungal and/or plant non-reporter kinases). This difference in physical binding properties allows for an effective separation of reporter kinase from contaminating non-reporter kinases by adherence onto a surface, with the measurement of the reporter kinase being made on that surface after capture. For example, use of a polypropylene of polycarbonate surface) coated with either of the commonly used blocking agents bovine serum albumen (eg. BSA; 3% w/v in neutral buffer) or skimmed milk (eg. 5% w/v in neutral buffer) will completely prevent the binding of non-reporter kinases (eg. endogenous kinases such as mammalian tissue kinases) but not reporter kinase. In this regard, the trimeric reporter kinases such as those derived from *S. acidocaldarius, S. solfataricus* and related genera are particularly adherent in these circumstances.

One or more of the above treatments for removing/inactivating non-reporter kinase can be combined to achieve or enhance the desired effect. This may mean that the relative concentrations of one or more of the chemical components may be reduced in the presence of second component. For example, the level of urea required to inactivate non-reporter kinase may be around 2M on its own but can be reduced to 1M in the presence of 0.5% SDS, as they both exert an effect on the target molecule.

Some of the above treatments may also have other beneficial effects in clarifying samples being processed and providing greater access to molecules to be detected. In this regard, a preferred application of the present invention is the detection of a microbial infection in a biological sample. Accordingly, the present application provides a sensitive and rapid point-of-care microbial assay. The invention is particularly suited to the rapid detection of bacterial, viral and/or fungal infections in biological samples, such as the microbial sources under 'reporter kinase' in Table 1. Additional microbial infections include those described in the Examples, such as hepatitis species, measles species, norovirus species, *legionella* species, *chlamydia* species, *listeria* species, *salmonella* species, and *burkholderia* species. The present invention facilitates the detection of microorganisms in stool samples (for example, by the addition of urea and SDS), both in terms of more uniform samples and in the release of the microbial antigens from dumps or aggregates. Similarly, the addition of sodium hypochlorite to a stool sample may simultaneously sterilise the sample (minimising the chance of infections) and reduce the activity of the non-reporter kinase.

The precise order/timing of the steps for removing non-reporter kinase is not critical, provided that these steps are carried out before the reporter kinase comes into contact with ADP. Thus, they can be carried out in the sample preparation phase, or during the assay before the reporter kinase comes into contact with ADP. In one embodiment, the treatment is instead of, or in addition to, a washing step.

TABLE 2

Summary of properties of reporter kinases (eg. AKs).

| Adenylate kinase (AK) origin | Structure | Mw | pI Predicted/ Actual (if known) |
| --- | --- | --- | --- |
| S. acidocaldarius | Trimer | 63330 (3 × 21110) | 9.03/>10 |
| S. solfatarious | Trimer | 63975 (3 × 21325) | 8.31 |
| P. furiosus | Trimer | 70602 (3 × 23534) | 9.10 |
| A. pernix | Trimer | 70149 (3 × 23383) | 9.31 |
| T. maritima | Monomer | 26458 | 6.44/~6.7 |
| P. abyssi | Monomer | 26793 | 8.70 |
| A. fulgidus | Monomer | 24703 | 5.74 |
| C. trachomatis | Monomer | 27784 | 4.63 |
| C. pneumoniae | Monomer | 23952 | 7.19 |
| C. difficile | Monomer | 23700 | 5.29 |
| B. pseudomallei | Monomer | 24169 | 8.03 |
| B. anthracis | Monomer | 23743 | 4.80 |
| S. aureus | Monomer | 23974 | 4.69 |
| M. tuberculosis | Monomer | 20124 | 4.91 |
| A. baumanii | Monomer | 24022 | 4.98 |
| R. prowazekii | Monomer | 24501 | 9.25 |
| Francisella tularensis | Monomer | 24361 | 8.06 |
| E. coli | monomer | 23589 | 5.56 |

As mentioned above, the presence of endogenous ATP may adversely affect the accuracy sensitivity of the assay of the present invention. Thus, in one embodiment, any ATP present prior to addition of ADP is optionally removed using one or more of the treatment steps described below. These treatments may be used in any number (preferably one or more, or at least two, or at least three) and/or in any combination. In all cases, however, the treatment leaves the reporter kinase substantially intact. The treatment steps can be applied to any aspect of the invention.

In one embodiment, the removal of endogenous ATP is achieved using an ATPase (e.g. apyrase). The ATPase may then be removed and/or inactivated before the contact with ADP, to avoid the presence of the ATPase adversely influencing the signal obtained using the reporter kinase. By way of example, an ATPase can be used to remove ATP and then the ATPase is itself destroyed by use of elevated temperature. Alternatively, the ATPase can be immobilised on a device (such as a lateral flow device or filtration device described elsewhere in this specification), such that when ATP flows over the ATPase, the ATP is inactivated. As above, this inactivation step must occur before the reporter kinase comes into contact with the ADP.

In a further embodiment, endogenous ATP can be removed by physical means. By way of example, a filtration device can be used, which separates out the ATP on the basis of size in a similar way to that described above for separation of the reporter kinase from non-reporter kinases. Advantageously, the removal of both the ATP and non-reporter kinase can be achieved simultaneously as they are both much smaller than the reporter kinase, either when the latter is on its own or when attached to an antibody, structure or other diagnostic reagent.

In another embodiment, endogenous ATP can be removed on the basis of surface charge as described above. The negative charge of the ATP at pH 5.5 allow it to bind to an anion exchange resin, along with non-reporter kinases, but not the reporter kinase. This again effectively separates the contaminating ATP and non-reporter kinase from the signal-generating reporter kinase in a single step.

The precise order/timing of the steps for removing endogenous ATP is not critical, provided that these steps are carried out before the reporter kinase comes into contact with ADP. Thus, they can be carried out in the sample preparation phase, or during the assay before the reporter kinase comes into contact with ADP. In one embodiment, the treatment is instead of, or in addition to, a washing step.

Data of the type presented in FIG. 3 are helpful when deciding on the type and/or number of background-reduction steps (i.e. removal or inactivation of non-reporter kinase and/or ATP) to use in the assay of a particular sample (although this information does not preclude the use of these steps in any assay type, particularly where infections can influence the background levels of either ATP or reporter kinase).

Any suitable kinase enzyme may be used as the reporter kinase in the present invention. In one embodiment, the reporter kinase is an adenylate kinase, acetate kinase or pyruvate kinase, or a combination thereof.

The reporter kinase used in the invention may have a trimeric or monomeric structure—these tertiary structures are associated with an improved stability of the kinase to conditions such as e.g. temperature, pH, chemical denaturants, or proteases.

In one embodiment, the reporter kinase is a non-mammalian, a non-fungal, and/or a non-plant kinase.

In one embodiment, the reporter kinase is a microbial kinase—suitable kinases include *Pyrococcus* species kinases such as *Pyrococcus furiousus* kinase, *P. abyssi* kinase, *furiosus* kinase, *P. horikoshii* kinase, *P. woesii* kinase; *Sulfolobus* species kinases such as *Sulfolobus solfataricus* kinase. *S. acidocaldarius* kinase, *S. shibatae* kinase; *Rhodothermus* species kinases such as *Rhodothermus marinus* kinase; *Thermococcus* species kinases such as *Thermococcus litoralis* kinase; *Thermotoga* species kinases such as *Thermotoga maritima* kinase, *Thermotoga neapolitana* kinase; and *Methanococcus* species kinases such as *M. ruber* kinase. In another embodiment, the kinase is an *Archeoglobus* species kinase such as *A. fulgidus* kinase; an *Aeropyrum* species kinase such as *A. pernix* kinase; an *Aquifex* species kinase such as *A. pyrophilus* kinase, an *Alicyclobacillus* kinase such as *A. acidocaldarius* kinase; *Bacillus* species kinase such as *B. caldotenax* BT1 kinase, a *Bacillus* species PS3 kinase, *B. stearothermophilus* 11057 kinase, *B. stearothermophilus* 12001 kinase, *B. thermocatenulatus* kinase; a clostridial species kinase such as *C. stercocorarium* kinase; a *Thermoanaerobacter* species kinase such as *T. ethanolicus* kinase, *T. thermosulfurogenes* kinase, *T. celere* kinase. *T. aquaticus* YT1 kinase, *T. caldophilus* GK24 kinase, *T. thermophilus* HB8 kinase. In preferred embodiment, the kinase is a *T. litoralis* kinase, *T. maritima* kinase, or a *T. neapolitana* kinase.

In one embodiment, the reporter kinase is thermostable. As well as being resistant to high temperatures, thermostable kinases are also found to be resistant to other biochemical and physical processes that routinely damage or destroy proteins or render them inactive, such as exposure to certain chemicals e.g. chaotropes, free-radical damage, detergents, extremes of pH, exposure to proteases, protein cross-linking, encapsulation within non-permeable or semi-permeable membranes or polymers, or irreversible immobilisation onto surfaces, (See for example: Daniel R M, Cowan D A, Morgan H W, Curran M P, "A correlation between protein thermostability and resistance to proteolysis", Biochem J. 1982 207:641-4; Rees D C, Robertson A D, "Some thermodynamic implications for the thermostability of proteins", Protein Sci. 2001 10:1187-94; Burdette D S, Tchernajencko V V, Zeikus J G, "Effect of thermal and chemical denaturants on *Thermoanaerobacter ethanolicus* secondary-alcohol dehydrogenase stability and activity", Enzyme Microb Technol. 2000 27:11-18; Scandurra R, Consalvi V, Chiaraluce R, Politi L, Engel P C., "Protein thermostability in extremophiles", Biochimie. 1998 November; 80(11):933-41; and Liao H H., "Thermostable mutants of kanamycin nucleotidyltransferase are also more stable to proteinase K, urea, detergents, and water-miscible organic solvents", Enzyme Microb Technol. 1993 April; 15(4):286-92, all of which are hereby incorporated by reference in theft entirety).

In another embodiment, the reporter kinase may be an *E. coli* kinase, *Clostridium difficile* kinase, *Bacillus anthracis* kinase, *Acinetobacter baumanii* kinase, *Burkholderia pseudomallei* kinase, *Chlamydia trachomatis* kinase, *Chlamydia pneumonia* kinase, *Staphylococcus aureus* kinase, *Klebsiella pneumonia* kinase. *Rickettsia prowazekii* kinase, *Mycobacterium tuberculosis* kinase, *Saccharomyces cerevisiae* kinase, *Leishmania donovanii* kinase, *Trypanosome cruzii* kinase, *Shigella flexneri* kinase, *Listeria monocytogenes* kinase, *Plasmodium falciparum* kinase, *Mycobacterium marinum* kinase, *Cryptococcus neoformans* kinase. *Francisella tulraensis* kinase, *Salmonella* spp. kinase, *Coxiella burnetii* kinase, and/or *Brucella abortus* kinase, In several of the embodiments, the kinase derived from these organisms is non-thermostable, but can be distinguished from non-reporter kinase by the use of different sample treatment, extraction or separation techniques. Many of these reporter kinases, in combination with the method to distinguish their activity from non-reporter kinases, may be used in rapid assays to detect the presence/absence, viability or destruction of the organism from which they originate. Such methods are suitable for assessing the presence of an infection within patient sample, tissue or cell population and the effectiveness of different therapeutic regimes or drugs.

Examples of specific kinases that have been sequenced and that are suitable for use in the invention are SEQ ID NOs 1-25, 31-36, 38, 40, 42, 44, 46, 48, 50, 52, 54, 56, 58, and 61-84. In one embodiment, the kinases used in the invention have at least 70%, 80%, 85%, 90%, 95%, 99% or 100% identity to SEQ ID Nos: 1-25, 31-36, 38, 40, 42, 44, 46, 48, 50, 52, 54, 56, 58, and 61-84.

Other examples of suitable reporter kinases may be found in WO00/46357 and WO2005/093085, which are hereby incorporated by reference in their entirety.

The stability of the reporter kinases may be increased using a variety of methods well-known to those familiar with the art.

By way of example, stabilising agents (such as sorbitol up to a concentration of 4M, or other polyols such as ethylene glycol, glycerol, or mannitol at a concentration of up to 2M) may improve the stability of the kinase. Other additives such as xylan, trehalose, gelatin may also provide additional stabilisation effects either individually or in combination. Addition of a range of divalent metal ions, most notably $Ca^{2+}$, $Mg^{2+}$ or $Mn^{2+}$ may also improve stability of the kinase.

Chemical modification of the kinases can also be used to improve their stability. Reductive alkylation of surface exposed amino groups by glyoxylic acid (e.g Melik-Nubarov (1987) Biotech letts 9:725-730), addition of carbohydrates to the protein surface (e.g. Klibanov (1979) Anal. Biochem. 93:1-25) and amidation (e.g. Klibanov (1983) Adv. Appl. Microbiol. 29:1-28) may all increase the stability of the kinase. Further methods including the use of chemical cross-linking agents and the use of various polymeric supports for enzyme immobilisation are also relevant methods for increasing the stability of enzymes (reviewed in Gupta (1991) Biotech. Appl. Biochem. 14:1-11).

Formulation of the kinase, in a solution containing up to around 10 mg/ml of a suitable carrier protein such as casein or albumin, or the addition of free amino acids such as glycine, tyrosine, tryptophan or dipeptides to the formulation, may increase the stability of the kinase to protease treatments.

The genetic modification of enzymes has been shown to provide significant increases in thermal stability and by analogy such mutations are also likely to significantly enhance the stability of the enzymes to other conditions such as protease treatment or gaseous phase "sterilisation". The comparison of the thermostability of the kinase enzymes taken with the defined 3-D structure of the trimeric (archaeal) AKs (Vonrhein et al (1998) J. Mol. Biol. 282:167-179 and Criswell et al (2003) J. Mol. Biol. 330:1087-1099) has identified amino acids that influence the stability of the enzyme.

Genetically engineered variants of kinases showing improved stability can be generated in a number of ways. Essentially these involve the specific site-directed mutagenesis of amino acids believed to form part of the central core packing region of the trimeric molecule and random "directed evolution" methods where the whole molecule is subjected to subsequent rounds of mutagenesis and selection/screening of molecules with improved properties. Specific modified enzymes are set out in SEQ ID NOs: 17-19 (several variants are embraced by each reference). These modifications outlined are based on a hybrid approach using a consensus based approach to define regions likely to influence the thermostability of the enzymes based on observed differences between structurally related molecules. This is followed by either defined changes to incorporate the amino acids that correlate with the best thermostability or a random replacement to incorporate every available amino acid at the positions defined as being essential for thermostability.

In one embodiment of the invention, the reporter kinases may be bound onto a solid support.

Suitable solid supports include a plastic (e.g. polycarbonate, polystyrene or polypropylene) surface, a ceramic surface, a latex surface, a magnetic surface, a steel or other metallic surface, a flow matrix (as described elsewhere in this specification), a filter membrane, or other polymer surface. The solid support can take the form of e.g. strips, dipsticks, microtitre plates, beads.

Binding of the reporter kinase to the solid support may be achieved using any of a wide variety of methods known in the art.

In one embodiment, the reporter kinase is bound onto the solid support via standard protein adsorption methods, such as outlined below.

Binding of the reporter kinase onto the solid support may be achieved by methods routinely used to link protein to surfaces, e.g. incubation of protein in 0.1M sodium bicarbonate buffer at about pH 9.6 at room temperature for about 1 hour. Alternatively the protein is covalently coupled to the surface using any of a wide range of coupling chemistries known to those familiar with the art. For example an adenylate kinase fusion protein (e.g. to Sup35) derivatised with SPDP (Pierce chemicals; using manufacturer's instructions), reduced with DTT to provide free sulfhydryl groups for cross-linking, is covalently attached to a polystyrene support with a maleimide surface. Plastic surfaces with such sulfhydryl-binding surfaces are well described in the literature. The reporter kinases described in this application have the property that their activity is retained upon derivatisation and cross-linking to such supports.

Alternatively an amine reactive surface on a polystyrene or polycarbonate support is used, with a bifunctional cross-linking agent such as monomeric glutaraldehyde, to provide direct non-cleavable cross-linking of the kinase via free amine groups on the protein. UV treatment can also be used to directly link the indicator to a suitable support. Steel surfaces can be treated in a similar way to plastic surfaces to mediate covalent attachment of the kinase.

A wide variety of protein cross-linking reagents is available from companies such as Pierce chemical company (Perbio). Reagents reactive to sulfhydryl, amino, hydroxyl and carboxyl groups are designed for coupling proteins but they can equally be used for cross-linking proteins to either naturally reactive or coated solid supports such as plastics, other polymers, glass and metals. Reactive chemistries are also available for cross-linking the enzymes to carbohydrates. For example, the reagents BMPH ((N-[β-Maleimidopropionic acid]hydrazide.TFA), KMUH ((N-[k-Maleimidoundecanoic acid]hydrazide), and MPBH (4-(4-N-Maleimidophenyl)butyric acid hydrazide hydrochloride) can be used to cross link the indicator containing either a free sulfhydryl in the form of a cysteine residue or a chemically derivatised protein reduced to generate a sulfhydryl reactive group, to carbohydrates. This may be particularly important for a solid support which is either a complex carbohydrate (e.g. paper, cellulose-based membranes, gels or resins) or can be coated or treated with a carbohydrate solution to generate a suitably reactive surface.

For each type of support the reporter kinase may be formulated in a solution that enhances binding and/or stabilises the bound protein. Such formulations include solutions containing up to 10% (w/v) sucrose, sorbitol, mannitol, cellulose, or polyethylene glycol (PEG). In addition the kinase can be formulated as part of a gel that is applied to the surface or lumen of a suitable support. Examples include alginate, agar or polyacrylamide matrices.

In another embodiment, the reporter kinase may be attached to a solid support via a linker that comprises a binding agent specific for an analyte. Details of suitable methods for achieving this attachment are given elsewhere in this specification.

The assay described in the first aspect of the invention is particularly suitable for detecting kinase activity in kinase-based analyte detection assays such as those described in the applicant's earlier filing, WO00/46357, the entirety of which is hereby incorporated by reference.

Thus, in a second aspect of the invention, there is provided a method for determining the presence of an analyte in a sample, comprising:
(i) exposing the sample to a reporter kinase coupled to a binding agent specific for the analyte, so that a complex is formed between the reporter kinase and any analyte present in the sample:
(ii) separating complexed reporter kinase from uncomplexed reporter kinase; and
(iii) measuring the activity of the complexed reporter kinase using an assay according to the first aspect of the invention.

The binding agent used in this method (and in any other method described in this specification) is typically an antibody (or a fragment thereof) that binds specifically to the analyte under investigation. The antibody may be obtained using conventional techniques for identification and isolation of specific antibodies, and the assay is thus of application to substantially all analytes against which an antibody can be raised. Alternatively, the binding agent may be selected from the group consisting of lectins, growth factors, DNA/RNA aptamers, phage or other species that bind specifically to the analyte under investigation. Where a first and second binding agent are involved, these binding agents may be the same or different.

The reporter kinase may be coupled to the specific binding agent by conventional techniques. For example, there are numerous ways of labelling immunoreactive biomolecules with enzymes (conjugation). Antibodies, the majority of antigens, and enzymes are all proteins and, therefore, general methods of protein covalent cross-linking can be adapted to the production of immunoassay reagents. The preparation of antibody-enzyme conjugates requires mild conditions to ensure the retention of both the immunological properties of the antibody and the catalytic properties of the enzyme. Common methods include, glutaraldehyde coupling, the use of periodate oxidation of glycoproteins to generate dialdehydes capable of forming Schiff-base linkages with free amino groups on other protein molecules, and the use of heterobifunctional reagents, for example, succinimidyl-4-(N-maleimidomethyl)cyclohexane-1-carboxylate (SMCC).

In one embodiment of the invention, the above method is a performed as a "capture assay", such as a sandwich assay (sometimes referred to as a two antibody capture assay), an antigen capture assay, or an antibody capture assay. In an example of an antibody capture assay, an analyte is first bound to a solid support, by e.g. non-specific binding. The analyte is then exposed to a reporter kinase linked to a binding agent (e.g. an antibody) specific for the analyte. A complex is thus formed between the analyte and the reporter kinase. Any uncomplexed reporter kinase is removed by one or more routine washing steps. ADP and luciferin/luciferase are then added to the solid support where the ADP is converted to ATP by the reporter kinase complex. The luciferin/luciferase converts the ATP to a light output, which can then be measured and correlated to the amount of analyte present on the solid support.

In one embodiment, at any point prior to step (iii), the sample is treated to remove/inactivate non-reporter kinase and/or ATP. Suitable treatments that may be employed in this regard are described earner in this specification.

In one embodiment, the method described in this aspect of the invention is completed within less than 15 minutes, less than 10 minute, less than 5 minutes, or less than 2 minutes.

Example 10 describes the use of a method according this aspect of the invention to detect the presence of Hepatitis C in an or swab sample. An oral swab sample is taken from the mouth of a patient and dried in an oven at 90 C for 1 minute to remove any non-reporter kinase (eg. endogenous kinase such as mammalian tissue kinase). The swab is then exposed to a conjugate comprising a reporter kinase coupled to an antibody for Hepatitis C antigen. The reporter kinase conjugate forms a complex with any Hepatitis C antigen present on the swab sample. The swab is then rinsed to remove any uncomplexed reporter kinase conjugate, and is inserted into a reagent tube containing ADP and luciferin and luciferase. The reagent tube is transferred to a hand-held luminometer and the light output is measured. The light output can then be correlated with the amount of analyte present in the sample.

In a third aspect, the invention provides a method for determining the presence of an analyte in a sample, comprising:
(i) providing a solid support comprising a reporter kinase, wherein the reporter kinase is attached to the solid support via a linker that comprises a binding agent specific for the analyte;
(ii) applying the sample to the solid support, whereby any analyte present in the sample displaces reporter kinase from the solid support; and
(iii) measuring the activity of the displaced reporter kinase using an assay according to the first aspect of the invention.

In one embodiment, the method described in this aspect of the invention is completed within less than 15 minutes, less than 10 minutes, less than 5 minutes, or less than 2 minutes.

By way of example, a clinical sample is provided that is suspected to contain a bacterial toxin. A solid support is also provided, which comprises a reporter kinase linked to the solid support by a binding agent (e.g. an antibody) that is specific for the bacterial toxin. When the sample is applied to the solid support, any bacterial toxin present will competitively interfere with the binding of the antibody to the solid support and will thereby displace the reporter kinase from the solid support. The amount of displaced reporter kinase can then be measured using an assay according to the first aspect of the invention and correlated with the amount of bacterial toxin present in the sample.

Example 13 describes the use of this method to detect the presence of norovirus in a clinical sample. In this example, the solid support is coated with an antibody to norovirus (i.e. a binding agent specific for the analyte). A reporter kinase conjugate is formed comprising a reporter kinase conjugated to a VP1 norovirus protein (i.e. the analyte). By virtue of the interaction between the VP1 and the antibody, the reporter kinase attached to the solid support. The clinical sample is then applied to the solid support. Any norovirus (i.e. analyte) present in the sample displaces the reporter kinase conjugate from the solid support. The activity of this displaced reporter kinase is then measured and correlated with the amount of norovirus present in the sample.

In one embodiment, the solid support is a flow matrix. The term "flow matrix" is used throughout this specification to mean any liquid-transport solid material that allows for liquid flow therethrough, including materials such as nitrocellulose, nylon, rayon, cellulose, paper, glass fibre, silica, a gel matrix, or any other porous or fibrous materials. In one embodiment, the flow matrix is configured as a substantially planar elongate strip. The flow matrix material can be pre-treated or modified as required.

Suitable methods for attaching the reporter kinase to the solid support are described below. The binding agent is as defined above in relation to the second aspect of the invention.

An analyte is coupled directly to the surface of the solid support.
The reporter kinase is linked to a binding agent specific for the analyte (e.g. an antibody) and thereby associates with the analyte on the surface. The reporter kinase remains attached to the surface until displaced by the presence of either antibody or analyte in the sample.

An analyte is bound to the solid support via a first binding agent specific for the analyte.
The reporter kinase is conjugated to a second binding agent specific for the analyte and thereby associates with the analyte on the surface. The reporter kinase remains attached to the surface (in a sandwich-type arrangement) until displaced by the presence of either antibody or analyte in the sample.

A binding agent specific to the analyte is used to coat the solid support.
The reporter kinase is conjugated or genetically fused to the target analyte and thereby associates with the binding agent on the surface. The reporter kinase-analyte conjugate is released from the solid support by competing analyte or antibody in the test sample.

The reporter kinase is therefore indirectly attached to the solid support by a linker that comprises a binding agent specific for the analyte. The linker may also comprise the analyte for a fragment thereof).

In one embodiment, at any point prior to step (iii), the sample is treated to remove/inactivate non-reporter kinase and/or ATP. Suitable treatments are described elsewhere in this specification.

In a fourth aspect, the invention provides a method for determining the presence of an analyte in a sample, comprising:
(i) providing a solid support on which is attached a first binding agent specific for the analyte;
(ii) exposing the solid support to the sample so that any analyte present in the sample becomes attached to the solid support via said first binding agent;
(iii) exposing the solid support to a reporter kinase coupled to a second binding agent specific for the analyte, so that the reporter kinase becomes attached to the solid support via the interaction between the second binding agent and the already-bound analyte;
(iv) applying the mixture obtained in step (iii) to a filter membrane, wherein the solid support is retained on the filter membrane; and
(v) measuring the activity of the retained reporter kinase using an assay according to the first aspect of the invention.

In one embodiment, the method described above is completed within less than 15 minutes, less than 10 minutes, less than 5 minutes, or less than 2 minutes.

In one embodiment, the solid support is a latex support, or a magnetic support, e.g. a latex bead or a magnetic bead. When the solid support is magnetic, step (iv) may be replaced by exposing the mixture obtained in step (iii) to a magnet, so that the solid support is retained on the magnet.

Example 14 describes the use of this method for detecting the presence of *legionella* in a water sample. Antibodies specific for *legionella* are attached to a solid support (a latex bead). The latex beads are then exposed to (i) the sample to be tested (potentially containing *legionella*) and (ii) a reporter kinase coupled to a second antibody specific for *legionella*. Any *legionella* present in the sample binds to the antibody on the latex bead. Subsequently, the reporter kinase-antibody conjugate binds to the latex bead via the already-bound *legionella*. The mixture thus obtained is applied to a filter membrane, which retains the latex beads. The other components of the mixture (e.g. unbound reporter kinase conjugate, ATP, non-reporter kinase (eg. mammalian tissue kinase, plant and/or fungal kinase endogenous to the test sample etc.) pass through the filter membrane. The reporter kinase retained on the filter membrane is then exposed to ADP and a mixture luciferin/luciferase, and the light output measured using a luminometer. Optionally, the filter membrane can be treated using any of the treatment steps described above for removing any remaining ATP or non-reporter kinase.

Suitable filter membranes for use in this aspect of the invention include: nitrocellulose, cellulose acetate or paper filters. Filter matrices typically employ a range of pore sizes from 0.2 μm to 20 μm or larger depending on the nature of any particulate carrier used.

Example 17 describes the use of this method for detecting the presence of *Salmonella* in a food sample. The method is essentially as described for Example 14 above, except that a magnetic head is used as the solid support instead of a latex bead, and the mixture obtained in step (iii) is exposed to a magnet rather than a filter membrane.

In one embodiment, at any point prior to step (v), the sample is treated to remove or inactivate non-reporter kinase and/or ATP. Suitable treatments are described elsewhere in this specification.

The assay described in the first aspect of the invention is also suitable for detecting kinase activity in kinase-based biological indicator systems such as those described in the applicant's earlier filing, WO2005/093085, which is hereby incorporated by reference in its entirety.

A typical biological indicator is prepared by adsorbing a reporter kinase onto a solid support such as an indicator strip or dipstick. The indicator is then included with a sample (containing a contaminant) to be treated, and the indicator plus sample are subjected to a treatment process. The reduction in activity of the indicator kinase by the treatment is then correlated with the reduction in amount or activity of the contaminant. When a level of activity is determined that is known to correlate with an acceptable reduction in the contaminant, the treatment is then regarded as validated.

It has also been found that the performance of these kinase-based indicators can be improved by covalently cross-linking the kinase to a biological component, wherein the biological component is a mimetic/surrogate of the contaminant. This allows the indicator to more accurately reflect the reaction of the contaminant to the treatment process, which in turn leads to improved indicator accuracy/sensitivity, and thus fewer "false" process validations.

Thus, in a fifth aspect of the invention, there is provided a method of validating a treatment process for reducing the amount or activity of a contaminating biological agent in a sample, comprising the steps of:
(i) providing a sample that contains, or is suspected to contain, a contaminating biological agent;
(ii) subjecting the sample to a treatment process in the presence of a defined amount of a reporter kinase, wherein the reporter kinase and the contaminating biological agent are both exposed to the treatment process;
(iii) measuring the residual activity of the reporter kinase using an assay according to the first aspect of the invention; and
(iv) comparing said residual activity to a predetermined kinase activity, wherein the pre-determined kinase activity corresponds to a confirmed reduction in the amount or activity of the contaminating biological agent under the same conditions.

In one embodiment, steps (i) to (iv) are completed in less than 15 minutes, less than 10 minutes, less than 5 minutes, less than 2 minutes.

In one embodiment, at any point prior to step (iii), the sample is treated to remove/inactivate non-reporter kinase and/or ATP. Suitable treatments are described elsewhere in this specification.

The term "treatment" or "treatment process" encompasses any process that is designed to reduce the amount or activity of a contaminant in a sample. Suitable treatments include one or more of; a selected pH, temperature or pressure, exposing the sample to a protease or other lytic enzyme, exposing the sample to a detergent, a chemical sterilant, radiation, free radicals, or a gas-phase sterilant. In one embodiment, the treatment is designed to reduce the infectious activity (also known as the infectivity) of an infectious biological contaminant, such as TSE. The term "treatment" or "treatment process" also encompasses cleaning and inactivation processes such as high temperature autoclaving with wet or dry steam, ozone sterilisation. $H_2O_2$ sterilisation, rendering or other method designed to eliminate or inactivate the contaminant. In one embodiment of the invention, both the reporter kinase and the contaminant are directly exposed to the treatment process, i.e. there is no seal or barrier between the reporter kinase/contaminant and the treatment process. The reporter kinase and the contaminant are therefore both in direct contact with the treatment process, and are subject to the same treatment conditions.

In one embodiment, the contaminating biological agent is selected from the group consisting of bacteria, viruses, spores, toxins, prions, proteins and peptides. In a further embodiment, the reporter kinase is bound onto a solid support using any of the methods described in relation to the first aspect of the invention.

In another embodiment of the invention, the reporter kinase is covalently linked to a biological component.

The biological component is advantageously a mimetic or surrogate of the contaminant, and therefore reacts to the treatment process in substantially the same way as the contaminant. In one embodiment, the biological component may be the same as, but physically distinct from, the contaminant in the sample that is to be subjected to the treatment process, e.g. if the contaminant is a protein, then the biological component is also a protein; if the contaminant is a blood protein, the biological component is also blood protein; if the contaminant is a DNA molecule, then the biological component is also a DNA molecule; if the contaminant is an RNA molecule then the biological component is also an RNA molecule, etc. for each of the contaminants and biological components disclosed in this specification.

Examples of biological components that can be used in the invention include proteins, nucleic acids, carbohydrates and lipids.

In one embodiment, the biological component comprises a protein selected from the group consisting of a blood protein, a bacterial protein, a viral protein, a fungal protein, and a self-aggregating or amyloid forming protein.

In a further embodiment, the blood protein is selected from the group consisting of blood clotting proteins (e.g. fibrinogen, fibrin peptides, fibrin, transglutaminase substrates, thrombin), serum proteins (e.g. albumin and globulin), platelet proteins, blood cell glycoproteins, and haemoglobin.

In another embodiment, the bacterial protein is selected from the group consisting of a bacterial fimbrial protein (e.g CgsA from *E. coli* and AgfA from *Salmonella*), a bacterial toxin protein (e.g. toxins from *Bacillus anthracis, Corynebacteriurn diphtheriae, Clostridium botulinum*), a bacterial cell surface protein (e.g. peptidoglycan, lipoproteins), and a bacterial spore protein (e.g. from Gram positive bacteria and having a similar sequence or overall structure to the proteins forming ribbon appendages in *Clostridium taeniosporum*, chaplin proteins, rodlin proteins).

In yet another embodiment, the viral protein is selected from the group consisting of a viral envelope protein, a viral capsid protein, and a viral core protein. Preferably, the viral proteins are from a bacteriophage virus (e.g. the MS2 and PP7 proteins), norwalk virus (e.g. capsid protein), rotavirus (e.g. VP2, VP6 and VP7 proteins), coronavirus (e.g. SARS S, E and M proteins), bluetongue virus (e.g. VP2 protein), human papillomavirus (e.g. viral major structural protein, L1), hepatitis. B (e.g. small envelope protein HBsAg), Hepatitis C virus (e.g. core, E1 and E2 proteins), influenza virus (e.g. neuraminidase and hemagglutinin and matrix proteins), poliovirus (e.g. capsid VP0, 1 and 3 proteins), HIV (e.g. Pr55gag, envelope proteins) and dengue B virus (e.g. envelope (e) and pre-membrane/membrane (prM/M).

In a further embodiment, the fungal protein is selected from the group consisting of hydrophobin proteins (e.g. SC3 from *Schizophyllum commune*, RodA/B from *Aspergillus fumigates*, and equivalent proteins from yeast), fungal spore proteins, hyphal proteins, mycotoxins, and fungal prions (e.g. Sup35, Het S, URE 2, Rnq1, New 1).

In yet a further embodiment, the self-aggregating protein is selected from the group consisting of prions (e.g. PrP$^{Sc}$ and PrP$^{c}$, Sup35, Het S, Ure 2, Rnq1, New 1), prion mimetic proteins, amyloid fibrils, cell surface adhesins from floc forming and filamentous bacteria in activated sludge, beta amyloid protein, tau protein, polyadenine binding protein, herpes simplex virus glycoprotein B, lung surfactant protein C, CsgA protein from *E. coli*, AgfA protein from *Salmonella* species, bacterial fimbrial proteins, apolipoproteins (e.g. apolipoprotein A1), hydrophobias from fungal species (e.g. SC3 from *Schizophyllum commune*, RodA/B from *Aspergillus fumigates*), chaplins (e.g. Chps A-H from *streptomyces* spp), rodlins (e.g. Rd1A and Rd1B from *streptomyces* spp), gram positive spore coat proteins (e.g. P29a, P29b, GP85 and a SpoVM analogue), and barnacle cement-like proteins (e.g. the 19 kDa protein from *Balanus albicostatus*, and the 20 kDa protein from *Megabalanus rosa*, and the novel calcite-dependent cement-like protein from *Balanus albicostatus*).

In a further embodiment, the nucleic add is selected from a DNA molecule and an RNA molecule. Preferably, the nucleic acid is derived from neurological tissue.

In a further embodiment, the carbohydrate is selected from the group consisting of exopolysaccharide, lipopolysaccharide (EPS/LPS, sometimes known as endotoxin) (e.g. from *Legionella, E. coli, Staphylococcus* species, *Streptococcus* species, *Pseudomonas* species, *Acinetobactor* species, *Campylobactor* species, and *Bacillus* species), peptidoglycan, cell wall components of plants, fungi and yeast (e.g. chitin, lignin, glucan), mucin preparations, glycolipids (especially brain derived glycolipids), glycoproteins (e.g. cell surface glycoproteins, Eap1p), spore extracts (e.g. from *Bacillus* spp, *Clostridial* spp and other spore-formers), polysaccharides from yeast capsules, and invertebrate secretions (e.g. from molluscan gels).

In another embodiment, the lipid is selected from the group consisting of glycolipids (e.g. brain-derived glycolipids), gangliosides (e.g. neuronal cell gangliosides such as $GT_{1b}$, $GT_{1a}$ and gangliosides of more general cell origin such as $GM_1$), and plant oils and lipids.

Advantageously, the biological component is part of a biological matrix. The biological matrix may be a mimetic of the sample that is to be treated. In one embodiment, the biological matrix comprises one or more components selected from the group consisting of proteins, lipids, nucleic acids, and carbohydrates, or fragments or derivatives thereof. In another embodiment, the biological matrix may comprise a mixture of proteins. In a further embodiment, the biological matrix may comprise one or more components selected from the group consisting of blood, serum, albumin, mucus, egg, neurological tissue, food, culled animal material, and a commercially available test soil. In a further embodiment of the invention, the biological matrix comprises one or more components selected from the group consisting of fibrinogen, thrombin, factor VIII, $CaCl_2$, and, optionally, albumin and/or haemoglobin. Examples of reporter kinases, linked to biological components are described in SEQ ID NOs: 34-38, 40, 42, 48, 50, 52, 54, 61, 67, 72, and 73.

The biological indicator may be prepared by covalently linking a reporter kinase to an appropriate biological component. Any suitable method of covalent attachment known in the art may be used. In one embodiment, the kinase is genetically or chemically cross-linked to the biological component.

Chemical cross-linking may be achieved using a range of homo- and hetero-bifunctional reagents commonly used for cross-linking of proteins for the generation of enzyme conjugates or other related purposes. For example, in an indicator comprising fibrin as the biological component, the fibrin and the reporter kinase may be derivatised with the addition of SPDP (Perbio) to primary amine groups. The reporter kinase can then be reduced to generate a reactive thiol group and this is then mixed with the fibrin to produce covalent fibrin-kinase linkages.

The reporter kinases can also be chemically cross-linked to carbohydrates, lipids or other glycoconjugates using heterobifunctional agents following treatment of the target carbohydrate with meta-periodate.

Alternatively, the indicator may be prepared as a fusion protein. This is achieved by fusing a synthetic gene encoding an appropriate kinase (e.g. the gene encoding AK from *Sulfolobus acidocaldarius* or *Thermotoga neapolitana*) to a gene encoding an appropriate biological component.

Methods according to this aspect of the invention are illustrated in Examples 18-21.

In a sixth aspect of the invention, there is provided a device for detecting the activity of a reporter kinase in a sample, comprising:
an elongate flow matrix, wherein said flow matrix comprises:
(i) a sample-receiving zone; and
(ii) a detection zone, located downstream of the ample-receiving zone, comprising a mixture of ADP and a bioluminescent reagent;
wherein, in use, a sample is applied to the sample-receiving zone and is drawn along the flow matrix to the detection zone.

In use, the sample is applied to the sample-receiving zone of the device and is allowed to migrate to the detection zone where it comes into contact with the mixture of ADP and bioluminescent reagent. Here, any reporter kinase present in the sample acts on the ADP to generate ATP, which in turn reacts with the bioluminescent reagent to produce light. The light output from the detection zone can be readily measured using a luminometer, preferably a hand-held luminometer. In one embodiment, the detection zone of the device is snapped off and placed in a luminometer. The amount of light produced can then be correlated with the amount of reporter kinase activity.

In one embodiment, the device comprises a hacking strip on which the elongate flow matrix is positioned. The backing strip may be made from any suitable non-absorbing material, such as a plastic-adhesive backing card. In another embodiment, the flow matrix is at least partially sandwiched between a top and a bottom laminate. The top laminate may include a sample-application window, which provides access to the sample-receiving zone of the flow matrix, and may also include a detection window, which provides access to the detection zone of the flow matrix. The laminates may be made from any suitable non-absorbing material, e.g. a transparent or translucent adhesive plastic film.

In one embodiment, the device is a lateral flow device. Lateral flow devices and methods for their construction are well known in the art, being best known as the standard pregnancy test kit.

In a further embodiment, the device may comprise a background-reduction zone, situated between the sample-receiving zone and the detection zone. This zone functions to remove/inactivate any non-reporter kinase and/or ATP that may be present in the sample before the sample reaches the detection zone. Thus, these contaminants are prevented from interfering with the sensitivity or accuracy of the assay.

In one embodiment, the background-reduction removal zone comprises a substance that selectively (or specifically) inhibits non-reporter kinase, whilst leaving the reporter kinase substantially unaffected. Suitable inhibitors are described elsewhere in this specification. In another embodiment, the background-reduction zone comprises a protease that selectively destroys non-reporter kinase, whilst leaving the reporter kinase substantially unaffected. Suitable proteases are described elsewhere in this specification. In a further embodiment, the background-reduction zone may be arranged so as to physically capture out non-reporter kinases on the basis of their size, charge, or binding properties as described elsewhere in this specification. The captured non-reporter kinases are thus prevented from reaching the detection zone.

In another embodiment, the background-reduction zone comprises an immobilised ATPase, e.g. apyrase. In another embodiment, the background-reduction zone may be arranged so as to physically capture out ATP on the basis of its size or charge as described elsewhere in this specification. The captured ATP is thus prevented from reaching the detection zone.

In one embodiment, the ADP in the detection zone of the device is high purity ADP, and the bioluminescent reagent is a mixture of luciferin and luciferase. In another embodiment, the ADP and luciferin/luciferase are immobilised in the detection zone using conventional immobilisation methods.

In a further embodiment, the device is portable.

In a further embodiment, the detection zone may include a cationic membrane that retains and concentrates the reporter kinase conjugate for enhanced detection.

In another embodiment, the sample-receiving zone may include a suitable dye which also migrates to the detection zone, acting as a control for the proper flow of the sample through the device. This positive internal control may also exploit the use of a cation-binding membrane within the detection zone to help retain the dye to provide a clear visual signal.

In a seventh aspect of the invention, there is provided a lateral flow device for use in an assay for detecting the presence of an analyte in a sample, comprising:
a hacking strip on which is positioned an elongate flow matrix, wherein said flow matrix comprises:

(i) a sample-receiving zone comprising a reporter kinase attached to the flow matrix via a linker comprising a binding agent specific for the analyte; and
(ii) a detection zone, located downstream of the sample-receiving zone;
wherein, in use, a sample is applied to the sample-receiving zone and any analyte present in the sample displaces the reporter kinase from the flow matrix and thereby allows the reporter kinase to migrate to the detection zone.

In use, the sample is applied to the sample-receiving zone, and any analyte present in the sample displaces the reporter kinase attached to the sample-receiving zone. Any reporter kinase that is not displaced remains attached to the sample-receiving zone, and this is the case for a sample negative for the presence of the analyte. Thus, only the displaced reporter kinase proceeds to the detection zone where it can be detected and correlated with the amount of analyte present in the sample.

The backing strip of the device may be made from any suitable non-absorbing material, such as a plastic-adhesive backing card. In one embodiment, the flow matrix is at least partially sandwiched between a top and a bottom laminate. The top laminate may include a sample-application window, which provides access to the sample-receiving zone of the flow matrix, and may also include a detection window, which provides access to the detection zone of the flow matrix. The laminates may be made from any suitable non-absorbing material, e.g. a transparent or translucent adhesive plastic film. In a further embodiment, the detection zone comprises a mixture of ADP and a bioluminescent reagent.

The reporter kinase is attached to the flow matrix by a linker comprising a binding agent specific for the analyte. Binding agents and methods for attaching the reporter kinase to the flow matrix are as described in relation to the second aspect of the invention.

In one embodiment, the device may further comprise a background-reduction zone, situated between the sample-receiving zone and the detection zone. This zone functions to remove/inactivate any non-reporter kinase and/or ATP that may be present in the sample before the sample reaches the detection zone. Thus, these contaminants are prevented from interfering with the sensitivity or accuracy of the assay.

In one embodiment, the background-reduction removal zone comprises a substance that selectively (or specifically) inhibits non-reporter kinase, whilst leaving the reporter kinase substantially unaffected. Suitable inhibitors are described elsewhere in this specification. In another embodiment, the background-reduction removal zone comprises a protease that selectively destroys non-reporter kinase, whilst leaving the reporter kinase substantially unaffected. Suitable proteases are described elsewhere in this specification. In a further embodiment, the background-reduction zone may be arranged so as to physically capture out non-reporter kinases on the of theft size, charge, or binding properties as described elsewhere in this specification. The captured non-reporter kinases, are thus prevented from reaching the detection zone.

In another embodiment, the background-reduction zone comprises an immobilised ATPase, e.g. apyrase. In another embodiment, the background-reduction zone may be arranged so as to physically capture out ATP on the basis of its size or charge as described elsewhere in this specification. The captured ATP is thus prevented from reaching the detection zone.

In one embodiment, the ADP in the detection zone of the device is high purity ADP, and the bioluminescent reagent is a mixture of luciferin and luciferase. In another embodiment, the ADP and luciferin/luciferase are immobilised in the detection zone using conventional immobilisation methods.

In another embodiment, the device is portable.

In a further embodiment, the detection zone may include a cationic membrane that retains and concentrates the reporter kinase conjugate for enhanced detection.

In another embodiment, the sample-receiving zone may include a suitable dye which also migrates to the detection zone, acting as a control for the proper flow of the sample through the device. This positive internal control may also exploit the use of a cation-binding membrane within the detection zone to help retain the dye to provide a clear visual signal.

In an eighth aspect, the invention provides a method for detecting the activity of a reporter kinase in a sample, wherein the method is conducted using a device according to the sixth aspect of the invention, comprising the steps of:
(i) applying the sample to the sample-receiving zone of the device;
(ii) allowing the sample to flow through to the detection zone of the device; and
(iii) detecting the light output from the detection zone.

In one embodiment, after step (i), the method further comprises allowing the sample to flow through a background-reduction zone as described in relation to the sixth aspect of the invention.

In another embodiment, step (iii) is cared out by snapping off the detection zone of the device, and then placing the detection zone into a luminometer.

In a further embodiment, the method comprises the step of recording the light output data obtained on a suitable data carrier.

In a ninth aspect of the invention there is provided a method for detecting the presence of an analyte in a sample using the device described in relation to the seventh aspect of the invention comprising:
(i) applying the sample to the sample-receiving zone of the device;
(ii) allowing any reporter kinase displaced from the sample-receiving zone to migrate to the detection zone; and
(iii) detecting the light output from the detection zone.

In one embodiment, after step (i), the method further comprises allowing the sample to flow through a background-reduction zone described in relation to the seventh aspect of the invention.

In another embodiment, step (iii) is carried out by snapping off the detection zone of the device, exposing the detection zone to ADP and a bioluminescent reagent, wherein the detection zone is exposed to the bioluminescent reagent no more than 5 minutes (or no more than 2 minutes, 1 minute, 30 seconds, or 10 seconds) after having been exposed to the ADP, and then placing the detection zone into a luminometer. In one embodiment, the detection zone is exposed to the ADP and bioluminescent reagent simultaneously.

In a further embodiment, the method comprises the step of recording the light output data obtained on a suitable data carrier.

In a tenth aspect, the invention provides a kit comprising a device according to the sixth or seventh aspect of the invention, and a luminometer. In one embodiment, the luminometer is a hand-held (i.e. portable) luminometer.

DEFINITIONS SECTION

The term "light output" means the light that is emitted by the reaction of ATP with the bioluminescent reagent. This light output can be detected using entirely conventional technology, such as a standard luminometer (e.g. a Berthold Orion 96-well microplate luminometer, or a hand-held luminometer).

The term "flow matrix" refers to any liquid-transport solid material that allows for liquid flow therethrough, and includes materials such as nitrocellulose, nylon, rayon, cellulose, paper, glass fibre, silica, gel matrices, or any other porous or fibrous materials, in one embodiment, the flow matrix is configured as a substantially planar elongate strip. The flow matrix material can be pre-treated or modified as required.

The term "reporter kinase" refers to a kinase enzyme that is not a mammalian, plant and/or fungal kinase. Thus, in the context of a biological sample to be tested, a reporter kinase is a kinase that is not normally present (to any significant degree) in a sample taken from a healthy individual. Put another way, a reporter kinase of the present invention is a kinase that is not normally inherent or endogenous (to any significant degree) in a sample taken from a healthy individual. Reporter kinase may be added to the sample as a separate (ie. exogenous) reagent, e.g as an isolated kinase. Reporter kinases are preferably thermostable.

The term "non-reporter kinase" refers to kinase enzyme that is not a reporter kinase as defined above. Non-reporter kinases may also be referred to as endogenous kinases, contaminating kinases, or background kinases. Non-reporter kinases are typically present in a sample taken from a healthy individual. Non-reporter kinase activity can also be defined as activity that is not associated with the reporter kinase. Many non-reporter kinases are derived from mesophilic organisms, i.e. organisms that grow best at moderate temperatures (e.g. 25-40 C). Examples of non-reporter kinases include mammalian, plant and/or fungal kinases—in particular, any of the range of 7 human adenylate kinase isoforms found in varying amounts in clinical samples, equivalent proteins in animal species or food derived from them, or kinases (e.g. adenylate kinases) from common commensal organisms in humans or animals.

The term "thermostable kinase" refers to a kinase that retains activity after exposure to heat, i.e. that is relatively unaffected by high temperatures. Preferred thermostable kinases retain at least 70% activity for 30% activity, 90% activity, 95% activity, or 100% activity) after exposure to a temperature of between 50-120 C. Particularly preferred thermostable kinases retain at least 70% activity (or 80% activity, 90% activity, 95% activity, or 100% activity) after exposure to 50 C for 30 minutes, or after exposure to 60 C for 30 minutes, or after exposure to 70 C for 30 minutes, or after exposure to 80 C for 20 minutes, or after exposure to 90 C for 3 minutes, or after exposure to 120 C for 3 minutes. Thermostable kinases may also be more resistant than non-thermostable kinases to a range of other biochemical and physical processes that routinely damage or destroy proteins or render them inactive, such as exposure to certain chemicals e.g. chaotropes, free-radical damage, detergents, extremes of pH, exposure to proteases, protein cross-linking, encapsulation within non-permeable or semi-permeable membranes or polymers, or irreversible immobilisation onto surfaces. In a particular embodiment, thermostable kinases may retain at least 70% activity (or 80% activity, 90% activity, 95% activity, or 100% activity) after exposure to one or more of the biochemical and physical processes described above. In all cases, this "retained activity" can be readily confirmed using conventional tests. In brief, the kinase is incubated with ADP under the given treatment conditions for a given amount of time, and then analysed for residual activity by detecting the generation of ATP using luciferin/luciferase and a luminometer. From this, the % of kinase activity retained after the treatment can be determined.

The terms "kinase" and "kinase activity" are used interchangeably throughout this specification.

The term "sample" encompasses any item, instrument, surface, fluid or material. Examples include, but are not limited to clinical samples (such as whole blood, serum, oral samples such as saliva, pus, vaginal samples, stool samples, vomitus), environmental samples (such a water, soil, air samples), surgical and medical instruments, microtitre plates, dipsticks, lateral flow devices, hospital gowns, bedclothes, bulk liquids, culled animal material, pharmaceuticals, workbenches, walls and floors, biological matrices, and biological indicators.

The terms "substantially free from non-reporter kinase", "free from non-reporter kinase", "substantially free from kinase other than reporter kinase", and "free from kinase other than reporter kinase" are considered synonymous, and are used interchangeably throughout the specification to mean that the level of non-reporter kinase is sufficiently low or absent and does not interfere to any significant degree with the sensitivity or accuracy of the assay. In terms of assay read-out, the impact of the non-reporter kinase is usually defined in terms of the signal-to-noise ratio. As such, the term "substantially free" can also be defined as meaning that the non-reporter kinase does not account for more than 10% (preferably not more than 5% or 2%) of the total kinase signal at the limit of detection of the assay.

The terms "substantially free from ATP" and "free from ATP" are considered synonymous and are used interchangeably throughout the specification to mean that the level of endogenous ATP is sufficiently low or absent and does not interfere to any significant degree with the sensitivity or accuracy of the assay. Endogenous ATP may have an impact on the assay in terms of signal: noise—thus, the "substantially free" term means that any endogenous ATP accounts for not more than 10% (preferably not more than 5% or 2%) of the total signal at the limit of detection of the assay.

The term "simultaneously" means at the same time. In the context of the first aspect of the invention where, in one embodiment, the reporter kinase is contacted with ADP and bioluminescent reagent simultaneously, this means that there is no (or substantially no) separate incubation period between contacting the kinase with ADP and contacting the kinase with the bioluminescent reagent.

The term "bioluminescent reagent" refers to any substance or mixture of substances able to react with ATP to generate light. A preferred reagent is a mixture of luciferin and luciferase.

The term "RLU" means Relative Light Unit. Relative Light Units are a relative, not absolute, measurement. The figures given in the specification relate to measurements taken using a Berthold Orion 96-well microplate luminometer with injector system using a "flash" method of light measurement for 2 seconds immediately after the addition of the luciferase/luciferin reagents (technical specification photomultiplier measuring light emitted at a wavelength of 300-650 nm). To address this issue, manufacturers have generated data for RLU "factors", which allow the data generated by a given luminometer to be normalised to a calibrated standard. Thus, comparisons can be made between different instruments. The RLU factor for the Berthold Orion 96-well microplate luminometer is 1. Accordingly, the RLU values given in the specification can be regarded as standardised/normalised RLU values.

In terms of absolute values, an RLU value can be related to the concentration of ATP required to give said value with the reagents as described in the method. As an approximate conversion, and given the linear relationship between RLU values and ATP concentration, the following values can be used:

| RLU | Approximate concentration of ATP/μM |
|---|---|
| 12,000,000 | 1000 |
| 1,200,000 | 100 |
| 120,000 | 10 |
| 12,000 | 1 |
| 1,200 | 0.1 |
| 120 | 0.01 |

All references cited in this application are hereby incorporated by reference in their entirety.

SEQ ID NOs

SEQ ID 1 Protein sequence of Adenylate kinase from *Sulfolobus solfataricus*
SEQ ID 2 Protein sequence of Adenylate kinase from *Sulfolobus acidocaldarius*
SEQ ID 3 Protein sequence of Adenylate kinase from *Sulfolobus tokodaii*
SEQ ID 4 Protein sequence of Adenylate kinase from *Pyrococcus furiosus*
SEQ ID 5 Protein sequence of Adenylate kinase from *Pyrococcus horikoshii*
SEQ ID 6 Protein sequence of Adenylate kinase from *Pyrococcus abyssi*
SEQ ID 7 Protein sequence of Adenylate kinase from *Methanococcus thermolithotrophicus*
SEQ ID 8 Protein sequence of Adenylate kinase from *Methanococcus voltae*
SEQ ID 9 Protein sequence of Adenylate kinase from *Methanococcus jannaschii*
SEQ ID 10 Protein sequence of Adenylate kinase from *Methanopyrus kandleri*
SEQ ID 11 Protein sequence of Adenylate kinase from *Methanotorris igneus*
SEQ ID 12 Protein sequence of Adenylate kinase from *Pyrobaculum aerophilum*
SEQ ID 13 Protein sequence of Adenylate kinase from *Thermotoga maritima*
SEQ ID 14 Protein sequence of Adenylate kinase from *Aeropyrum pernix*
SEQ ID 15 Protein sequence of Adenylate kinase from *Archaeoglobus fulgidus*
SEQ ID 16 Protein sequence of Adenylate kinase from *Pyrococcus abyssi* (monomeric adenylate kinase (AdkE))
SEQ ID 17 Protein sequence of Adenylate kinase from *Pyrococcus furiosus* genetically engineered to provide improved stability
SEQ ID 18 Protein sequence of Adenylate kinase from *Pyrococcus horikoshii* genetically engineered to provide improved stability
SEQ ID 19 Protein sequence of Adenylate kinase from *Sulfolobus acidocaldarius* genetically engineered to provide improved stability
SEQ ID 20 Protein sequence of Acetate kinase from *Thermotoga maritima*
SEQ ID 21 Protein sequence of Pyruvate kinase from *Pyrococcus horikoshii*

SEQ ID 22 Protein sequence of Pyruvate kinase from *Sulfolobus solfataricus*
SEQ ID 23 Protein sequence of Pyruvate kinase from *Thermotoga maritima*
SEQ ID 24 Protein sequence of Pyruvate kinase from *Pyrococcus furiosus*
SEQ ID 25 Protein sequence of Acetate kinase from *Methanosarcina thermophila*
SEQ ID 26 DNA sequence encoding the Adenylate kinase from *Sulfolobus acidocaldarius*
SEQ ID 27 DNA sequence encoding the Adenylate kinase from *Sulfolobus acidocaldarius*, wherein codon usage has been optimised for expression of the gene in *E-coli*.
SEQ ID 28 DNA sequence encoding the Adenylate kinase from *Thermotoga maritima*
SEQ ID 29 DNA sequence encoding the Adenylate kinase from, *Thermotoga maritima*, wherein codon usage has been optimised for expression of the gene in *E-coli*.
SEQ ID 30 DNA sequence encoding the Adenylate kinase from *Archaeoglobus fulgidus*, wherein codon usage has been optimised for expression of the gene in *E-coli*.
SEQ ID 31 Protein sequence of Adenylate kinase from *Sulfolobus acidocaldarius*, wherein codon usage has been optimised for expression of the gene in *E-coli* (SEQ ID 27).
SEQ ID 32 Protein sequence of Adenylate kinase from *Thermotoga maritima*, wherein codon usage has been optimised for expression of the gene in *E-coli* (SEQ ID 29).
SEQ ID 33 Protein sequence of transglutaminase substrate
SEQ ID 34 Protein sequence of Adenylate Kinase from *Sulfolobus acidocaldarius* fused at the N-terminus with a transglutaminase (Factor XIII) substrate sequence
SEQ ID 35 Protein sequence of Adenylate Kinase from *Sulfolobus acidocaldarius* fused at the C-terminus with a transglutaminase (Factor XIII) substrate sequence
SEQ ID 36 Protein sequence of Adenylate Kinase from *Sulfolobus acidocaldarius* fused at the N-terminus and C-terminus with a transglutaminase (Factor XIII) substrate sequence
SEQ ID 37 DNA sequence of transglutaminase (Factor XIII) substrate sequence fused to the 5' end of Adenylate Kinase from *Thermotoga maritima*.
SEQ ID 38 Protein sequence of Adenylate Kinase from *Thermotoga maritima* fused at the N-terminal with a transglutaminase (Factor XIII) substrate sequence.
SEQ ID 39 DNA sequence of transglutaminase (Factor XIII) substrate sequence fused to the 3' end of Adenylate Kinase from *Thermotoga maritima*.
SEQ ID 40 Protein sequence of Adenylate Kinase from *Thermotoga maritima* fused at the C-terminal with a transglutaminase (Factor XIII) substrate sequence.
SEQ ID 41 DNA sequence of transglutaminase (Factor XIII) substrate sequence fused to both the 5' and 3' ends of Adenylate Kinase from *Thermotoga maritima*.
SEQ ID 42 Protein sequence of Adenylate Kinase from *Thermotoga maritima* fused at the N- and C-terminal with a transglutaminase (Factor XIII) substrate sequence.
SEQ ID 43 DNA sequence of complete Sup35 gene construct from *Saccharomyces cerevisiae*
SEQ ID 44 Protein sequence of complete Sup35 from *Saccharomyces cerevisiae*
SEQ ID 45 DNA sequence of sup35N (N-terminal domain) codon-biased for optimal expression in *E. coli*
SEQ ID 46 Protein sequence of sup35N (N-terminal domain)
SEQ ID 47 DNA sequence of *E-coli* codon biased Adenylate Kinase from *Sulfolobus acidocaldarius* fused at the N-terminus with Sup35 N-terminal domain from *Saccharomyces cerevisiae*
SEQ ID 48 Protein sequence of Adenylate Kinase from *Sulfolobus acidocaldarius* fused at the N-terminus with Sup35 N-terminal domain from *Saccharomyces cerevisiae*
SEQ ID 49 DNA sequence of *E. coli* codon biased Adenylate Kinase from *Sulfolobus acidocaldarius* fused at the C-terminus with Sup35 N-terminal domain from *Saccharomyces cerevisiae*
SEQ ID 50 Protein sequence of Adenylate Kinase from *Sulfolobus acidocaldarius* fused at the C-terminus with Sup35 N-terminal domain from *Saccharomyces cerevisiae*
SEQ ID 51 DNA sequence of Sup35N fused at the 5' end of Adenylate Kinase from *Thermotoga maritima*.
SEQ ID 52 Protein sequence of Adenylate Kinase from *Thermotoga maritima* fused at the N-terminal with Sup35N.
SEQ ID 53 DNA sequence of Sup35N fused at the 3' end of Adenylate Kinase from *Thermotoga maritima*.
SEQ ID 54 Protein sequence of Adenylate Kinase from *Thermotoga maritima* fused at the C-terminal with Sup35N
SEQ ID 55 DNA sequence encoding a short Sup35 peptide capable of aggregating to form amyloid fibrils; for use as a fusion peptide with tAK genes.
SEQ ID 56 Sup35 derived amyloid peptide
SEQ ID 57 DNA sequence encoding a Norovirus capsid protein (58 kDa)
SEQ SEQ ID 77 Protein sequence of a peptide derived from a barnacle cement protein
SEQ ID 78 Protein sequence of adenylate kinase from *E. coli*
SEQ ID 79 Protein sequence of pyruvate kinase from *E. coli*
SEQ ID 80 Protein sequence of acetate kinase from *E. coli*
SEQ ID 81 Protein sequence of adenylate kinase from *Methanococcus voltae* (MVO)
SEQ ID 82 Protein sequence of adenylate kinase from *Methanococcus thermolithotrophicus* (MTH).
SEQ ID 83 Protein sequence of adenylate kinase from *Bacillus globisporus*
SEQ ID 84 Protein sequence of adenylate kinase from *Bacillus subtilis*

SEQUENCE LISTING

SEQ ID NO: 1
Met Lys Ile Gly Ile Val Thr Gly Ile Pro Gly Val Gly Lys Thr Val Leu Ser Phe Ala Lys Lys Ile Leu Thr
Glu Lys Gly Ile Ser Lys Ile Val Asn Tyr Gly Asp Tyr Met Leu Asn Thr Ala Leu Lys Gly Tyr Val Lys Ser
Arg Asp Glu Ile Arg Gln Leu Arg Gln Lys Gln Arg Glu Gln Gln Leu Ala Leu Ala Arg Arg Ile Val Glu Asp
Leu Ser Leu Leu Gly Gly Ile Gly Ile Leu Asp Thr His Ala Ile Arg Thr Pro Ala Gly Tyr Ile Leu Pro Gly
Leu Pro Arg His Val Ile Glu Val Leu Ser Pro Lys Val Ile Phe Leu Val Glu Ala Asp Pro Lys Ile Leu Glu
Arg Gln Lys Arg Asp Ser Arg Ala Arg Thr Arg Asp Tyr Ser Asp Tyr Ser Asp Val Val Ile Gln Phe Ala
Arg Tyr Ser Ala Met Ala Val Leu Val Leu Gly Ala Ser Val Lys Val Val Asn Gln Asn Gly Asp Pro Ser
Ile Ala Ala Ser Glu Ile Ile Asn Ser Leu Met

SEQ ID NO: 2
Met Lys Ile Gly Ile Val Thr Gly Ile Pro Gly Val Gly Lys Ser Thr Val Leu Ala Lys Val Leu Ala Leu Asp Asn
Gln Gly Ile Glu Ala Asn Lys Ile Ile Asn Tyr Gly Asp Phe Met Leu Ala Thr Ala Leu Lys Gly Tyr Ala Lys Asp
Arg Asp Glu Met Arg Lys Gly Glu Val Glu Gln Lys Lys Asp Leu Gln Lys Ala Leu Ala Val Ala Lys Glu Glu
Ala Arg Ala Gly Ala Gly Lys Ile Phe Asp Thr His Ala Val Ile Arg Thr Pro Ala Gly Tyr Leu Pro Gly
Leu Pro Ser Tyr Val Ile Asp Glu Leu Asn Pro Ser Val Ile Leu Phe Glu Leu Ala Ala Pro Lys Ile Leu Ser
Arg Gln Lys Arg Asp Thr Thr Arg Asn Arg Ser Asp Tyr Ser Glu Val Leu Ile Thr Ile Asn Phe
Ala Arg Tyr Ala Ala Ala Ala Leu Ala Gly Leu Leu Ala Ser Val Lys Thr Ile Glu Val Asn Gly Asp Pro
Ser Ile Ala Ala Asn Glu Ile Ile Arg Ser Met Lys

SEQ ID NO: 3
Met Ser Lys Met Lys Ile Gly Ile Val Thr Gly Ile Pro Gly Val Gly Lys Thr Val Leu Ser Lys Val Lys Glu Ile
Leu Glu Glu Lys Gly Ile Ala Ile Asn Tyr Val Asn Tyr Gly Asp Tyr Met Leu Ala Met Ala Leu Lys Gly Tyr
Val Asn Ala Asn Arg Asp Asn Met Arg Lys Leu Pro Val Glu Gln Leu Lys Ile Met Gln Leu Glu Ala Arg Gly Ile
Ala Asp Leu Ala Lys Ala Gly Lys Val Ile Phe Asp Thr His Ala Val Ala Ile Arg Thr Ala Arg Gly Tyr Ile
Leu Pro Gly Leu Pro Lys Tyr Val Ile Glu Glu Leu Asn Pro Arg Val Ile Phe Leu Leu Glu Ala Asp Pro Lys Val
Ile Leu Glu Arg Leu Gln Lys Arg Asp Thr Ser Arg Ser Arg Ser Asp Tyr Ser Glu Ile Ile Ser Glu Thr Ile
Asn Phe Ala Arg Tyr Ala Ala Met Ala Ser Ala Val Leu Val Gly Ala Thr Val Lys Ile Val Asn Val Glu Val Gly
Asp Pro Ala Val Ala Asn Glu Ile Ile Asn Ser Met Leu

SEQ ID NO: 4
Met Pro Phe Val Val Ile Ile Thr Gly Ile Pro Gly Val Gly Lys Ser Thr Ile Thr Arg Leu Ala Leu Gln Arg Thr Lys
Ala Lys Phe Arg Leu Ile Asn Phe Gly Asp Leu Met Phe Glu Met Ala Val Lys Ala Gly Leu Val Lys Gly His Arg
Asp Glu Met Arg Lys Leu Pro Leu Glu Val Gln Leu Glu Leu Gln Met Leu Ala Ala Lys Lys Ile Ala Glu Met Ala
Lys Glu His Pro His Ile Val Ala Thr Phe Glu Ser Thr Leu Ala Thr Gly Lys Tyr Met Leu Pro Gly Leu Pro Tyr Glu
Val Val Lys Thr Leu Asn Pro Asn Phe Ile Leu Gln Ile Glu Leu Thr Ala Ser Asp Glu Ile Leu Arg Arg Leu Arg
Asp Ser Ile Arg Arg Gly Arg Asp Val Glu Val Glu His Ile Lys Glu Leu Gln Asp Ile Glu Lys Glu Ile Thr Ile
Ala Ile Ala Tyr Ala Met His Ser Arg Gln Ile Ile Ile Lys Asn Ile Ile Gly Asp Leu Asn His Glu Leu Ala Ala
Asn Glu Leu Val Lys Ile Leu Asp Val Ala Leu Asn Glu Lys Leu Val Asp Lys Leu Gly Leu Glu Glu Ala Val

SEQ ID NO: 5
Met Pro Phe Val Ile Ile Thr Gly Ile Pro Gly Val Gly Lys Ser Thr Ile Thr Lys Leu Ala Leu Gln Arg Thr Arg
Ala Lys Phe Lys Leu Ile Asn Phe Gly Asp Leu Met Phe Glu Met Ala Val Lys Glu Lys Leu Val Lys His Arg
Asp Glu Met Arg Arg Leu Pro Leu Glu Val Gln Glu Gln Leu Glu Gln Met Ala Leu Lys Asn Ala Leu Glu Met Ala
Ala Lys Asn Tyr Pro His Ile Val Ala Thr His Phe Glu Ser Thr Phe Lys Thr Gly Gln Tyr Ala Asp Ala Ala Ala
Glu Val Ile Pro Ile Lys Ala Ile Leu Glu Ile Glu Ile Gln Ala Ser Asp Glu Ile Leu Arg Arg Leu Arg Arg
Asp Ser Leu Lys Arg Ala Arg Asp Val Asp Val Glu Asn Ile Lys Lys Gly Leu Glu Glu Ala Val Leu Ala Val
Thr Tyr Ala Met His Ser Arg Asn Ala Leu Asn Glu Ile Ile Gln Arg Arg Asn Ala Tyr Pro His Ser Leu Pro Tyr Arg
Glu Leu Val Ile Leu Lys Val Leu Asp Ala Leu Lys Val Lys Glu Ala Lys Lys Gly Leu Glu Glu Ala Val Leu Arg Arg Asn

-continued

SEQUENCE LISTING

SEQ ID NO: 6
Met Ser Phe Val Val Ile Ile Thr Gly Ile Pro Gly Val Gly Lys Ser Thr Ile Thr Arg Leu Ala Leu Gln Arg Thr Lys
Ala Lys Phe Lys Leu Ile Asn Phe Gly Gly Met Phe Glu Gly Met Ala Val Ala Gly Lys Ile Val Ser Glu Met His Arg
Asp Glu Met Arg Leu Pro Leu Gly Ile Gln Arg Asp Leu Gln Met Lys Lys Leu Gly Tyr Leu Ser Glu Met
Ala Arg Gln Pro Ile Leu Asp Thr His Ala Thr Ile Lys Thr Pro Ser Gly Tyr Leu Pro Gly Leu Pro Arg Arg Leu
Glu Val Ile Lys Thr Leu Asn Pro Asn Phe Val Ile Glu Val Ala Thr Pro Ser Glu Ile Gly Leu Arg Arg Leu
Arg Asp Leu Lys Arg Asp Arg Asp Val Glu Thr Leu Gln Ile Gln Ile Glu Ser Asn Glu Ala His Arg Leu Ala Ala
Ala Ile Ala Tyr Ala Met His Ser Asn Ala Leu Ile Ile Lys Ile Glu Asn His Glu Asp Lys Leu Glu His Ala Val
Asn Glu Leu Val Glu Ile Leu Asp Leu Ala Val Lys Glu Tyr Ala

SEQ ID NO: 7
Met Lys Asn Lys Leu Val Val Leu Thr Gly Val Pro Gly Val Gly Thr Thr Ile Thr Gln Lys Ala Met Glu Lys
Leu Ser Glu Leu Gly Ile Gly Ile Asn Tyr Lys Met Val Asn Phe Gly Gly Phe Val Met Glu Val Ala Gln Glu Asn
Leu Val Glu Asp Arg Asp Gln Met Arg Lys Leu Asp Pro Asp Thr Gln Lys Arg Ile Gln Lys Leu Ala Gly Tyr Arg
Lys Ile Ala Glu Met Val Leu Gly Ser Pro Val Val Asp Pro His His Ser Thr Lys Thr Pro Lys Gly Tyr Leu
Pro Gly Leu Pro Val Trp Val Leu Asn Glu Leu Asn Pro Asp Ile Ile Ile Val Glu Thr Ser Gly Asp Glu Ile
Leu Ile Arg Arg Leu Arg Asp Glu Thr Arg Asn Arg Asp Leu Thr Ala Gly Thr Ile Glu Ile Glu Gln His Ile Met
Asn Arg Ala Ala Ala Met Thr Tyr Gly Val Leu Thr Gly Ala Thr Lys Ile Ile Gln Asn Lys Asn Asn Leu Leu
Asp Tyr Ala Val Glu Leu Ile Ser Val Leu Arg

SEQ ID NO: 8
Met Lys Val Val Val Leu Thr Gly Val Pro Gly Val Gly Ser Thr Thr Ser Ser Gln Leu Ala Met Asp
Asn Leu Arg Lys Gly Val Asn Tyr Lys Met Val Ser Phe Gly Ser Val Met Phe Glu Val Ala Lys Glu Glu
Gly Leu Val Ser Asp Arg Asp Gln Met Arg Lys Leu Asp Pro Asp Thr Gln Lys Arg Ile Gln Lys Leu Ala Gly Arg
Lys Ile Ala Glu Met Ala Lys Glu Ser Pro Val Ala Val Asp Thr His Ser Thr Val Lys Thr Pro Lys Gly Tyr
Leu Pro Gly Leu Pro Ser Trp Val Leu Asn Glu Leu Asn Pro Asp Leu Ile Ile Val Val Glu Thr Pro Leu Gly
Leu Ile Leu Met Arg Arg Arg Met Ser Glu Arg Asp Arg Val Arg Asp Leu Glu Thr Ile Glu Gln His Ile Gln Asn
Phe Met Asn Arg Cys Ala Ala Met Ser Tyr Gly Val Leu Thr Gly Ala Thr Lys Ile Val Gln Asn Arg Asn
Gly Leu Leu Asp Gln Ala Val Gln Leu Ile Glu Leu Thr Asn Val Leu Arg

SEQ ID NO: 9
Met Met Met Lys Asn Lys Val Val Val Ile Val Gly Val Pro Gly Val Gly Lys Ser Thr Val Thr Asn Lys Ala
Ile Glu Glu Leu Lys Lys Lys Gly Ile Gly Ile Tyr Lys Leu Val Asn Phe Gly Val Val Met Phe Glu Ile Ala Leu Glu
Glu Gly Leu Val Glu His Arg Asp Gln Met Arg Lys Leu Pro Pro Glu Glu Gln Lys Arg Ile Gln Lys Leu Ala
Gly Lys Ile Ala Glu Glu Ala Lys Lys His Pro Leu Leu Val Asp Thr His Ala Thr Ile Lys Thr Pro Lys Gly
Tyr Leu Pro Gly Leu Pro Ala Trp Val Leu Asn Glu Leu Asn Pro Asp Leu Leu Leu Leu Val Glu Thr Pro Lys Asp
Glu Ile Leu Met Arg Arg Leu Gly Asp Met Thr Arg Glu Arg Asp Ile Glu Thr Leu Glu Ser Ile Glu Glu His Ile
Phe Met Asn Arg Cys Ala Ala Met Thr Tyr Gly Val Leu Thr Gly Ala Thr Val Lys Ile Ile Gln Asn Arg Asn Ala Asn
Leu Leu Asp Gln Ala Val Gln Leu Ile Glu Leu Lys

SEQ ID NO: 10
Met Gly Tyr Val Ile Ala Thr Gly Val Pro Gly Val Gly Ala Thr Thr Thr Val Glu Ala Val Lys Glu Leu
Glu Gly Tyr Glu Leu Val Asn Tyr Gly Asp Val Met Leu Glu Ala Ala Leu Arg Gly Ile Glu Gly Leu Lys Pro Leu Pro Lys Arg Asp
Glu Ile Glu Arg Gly Ile Ile Glu Arg Gln Leu Lys Thr Ile His Cys Thr Lys Ile Gln Gln Ala Pro Glu Asp Ala Ala Glu
Gly Gly Gly Val Ile Glu Gly Leu Asn Asp Ile Leu Pro Asn Val Arg Ile Leu Tyr Pro Gly Leu Met Arg Met Ala Ala Arg
Leu Leu Leu Glu Gln Leu Arg Leu Glu Gln Ala Arg Leu Arg Glu Glu Gln Leu Glu Glu Met Arg Lys Asp Pro Asp Pro Glu Thr Ser Glu Asp Asp Tyr Asp Lys Met Lys Asp Lys Gln Asn Arg Asp Phe Leu Pro Pro Leu Arg Arg Asp Asp Asp Asp
Met Ala Tyr Ala Leu Thr Gly Ala Thr Val Lys Ile Ile Leu Glu Asn His Gln Leu Leu Asp Asn His Lys Ala Ala Val Arg
Glu Val Phe Glu Val Thr Arg Val Ser Leu

SEQUENCE LISTING

SEQ ID NO: 11
Met Lys Asn Lys Val Val Thr Gly Pro Val Gly Thr Leu Thr Gln Lys Thr Ile Glu Lys
Leu Lys Glu Gly Ile Tyr Glu Asp Tyr Lys Met Val Asn Phe Gly Thr Met Phe Glu Ala Lys Gly Gly
Leu Val Asp Arg Ala Glu Met Ala Lys Arg Leu Asp Pro Asn Val Asp Pro Ile Lys Leu Ala Arg
Lys Ile Ala Glu Met Lys Val Leu Trp Val Leu Glu Ser Asn Val Asp Pro Ile Glu Val Lys Tyr Gly Ile
Ala Gly Leu Pro Ile Trp Val Asp Gly Ile Met Glu Thr Pro Lys Gly Tyr Leu
Leu Met Arg Arg Leu Gly Asp Ala Thr Arg Asn Arg Asp Ile Glu Leu Thr Ser Glu Asp His Gln Phe
Met Asn Arg Cys Ala Ala Met Ala Tyr Gly Val Leu Thr Gly Ala Leu Lys Ile Ile Lys Asn Arg Asp Gly Leu
Leu Asp Lys Val Ala Gln Glu Leu Ile Leu Ser Val Leu Lys Lys Leu

SEQ ID NO: 12
Met Lys Ile Val Ile Leu Ala Leu Pro Gly Val Met Ile Ala Leu Asn Phe Val Gln Ile Lys Pro Asp
Val Val Lys Asn Tyr Gly Ala Val Met Ser His Phe Gly Ile Leu Arg Asp Ala Ser Met Gly Met
Arg Leu Ile Pro Asp Val Glu Leu Arg Arg Lys Val Gln Glu Ala Ala Glu Tyr Ile Ile Ala Ser Leu Thr Gly Asp Asp Lys
Lys Ile Ile Asp Thr His Ala Ser Ile Lys Gly Val Gly Gly Tyr Leu Pro Arg Ile Ile Ser Lys Ser Lys Leu
Lys Pro Asp Val Ile Lys Leu Glu Lys Tyr Asp Pro Lys Val Ile Leu Glu Gln Arg Arg Lys Ala Pro Arg Arg
Phe Arg Asp Leu Ser Gln Leu Gln Ile Glu Leu His Gln Ile Asn Ala Asp Asn Arg Tyr Pro Ala Phe Ala Ala Ala
Asn Ala Gly Leu Ser Thr Val His Val Leu Asn Phe Arg Ser Gly Leu Lys Ser Pro Phe Glu Leu His Ala Glu
Val Ala Ala Glu Tyr Ile Val Leu Leu Lys Arg Thr Lys Gln Leu Ser

SEQ ID NO: 13
Met Met Ala Tyr Leu Val Phe Leu Gly Pro Pro Gly Ala Gly Lys Gly Thr Tyr Ala Lys Arg Ile Gln Glu Lys Thr
Gly Ile Pro His Ile Ser Thr Gly Asp Ile Phe Arg Glu Ala Ile Lys Val Glu Val Asn Asp Leu Lys Val Leu Arg Gly Leu Lys Ser Ile
Lys Glu Ile Met Glu Gln Gly Glu Leu Val Pro Asp Glu Leu Val Asn Glu Val Leu Lys Arg Leu Phe Ser Glu
Lys Glu Ser Ala Asn Gly Tyr Leu Phe Asp Gly Phe Pro Arg Thr Val Pro Gln Ala Asp Ala Met Val Gln Ala Gly Val
Leu Glu Ser Arg Gly Ile Lys Leu Asp Ala Val Leu Asn Phe Glu Val Pro Glu Asn Met Ile Ser Arg Leu Leu Cys
Thr Ser Arg Arg Ile Cys Pro Lys Cys Gly Arg Ile Tyr Asn Met Ile Glu Thr Val Arg Gln His Val Tyr Lys Leu Tyr
Asp Lys Cys Lys Val Cys Gln Ser Leu Leu Val Arg Arg Asp Asp Asn Glu Glu Thr Val Arg Lys Arg Leu Glu Val Tyr
Leu Glu Lys Thr Gln Pro Leu Ile Asp Tyr Tyr Gln Lys Lys Gly Ile Leu Val Thr Ile Asp Gly Thr Gly Ile
Asp Ala Asn Val Ala Leu Val Leu Glu Ile Leu Lys Ser Leu Ile Gly Trp Pro Ser Lys Asp Pro Ser Lys

SEQ ID NO: 14
Met Val Arg His Pro Lys Phe Val Val Thr Gly Val Pro Gly Val Gly Lys Thr Thr Val Ile Lys Glu Ala
Leu Glu Gln Leu Gly Leu Asp Gly Val Lys His Ile Val Leu Pro Leu Ala Gly Ser Phe Met Lys Asp Thr Gln Leu Gln Arg
Val Lys Leu Gly Val Leu Asp Arg Asp Lys Leu Arg Thr Leu Pro Leu Leu Arg Gly Val Leu Pro Gln Gly Ile Ile Leu Asp Thr His Ala
Glu Ala Ala Lys Leu Ala Ala Glu Leu Ala Asp Leu Ala Val Leu Gly Val Arg Arg Val Leu Ile Pro Asp Met Ile Ala
Val Val Gly Ala Ser Pro Gly Asp Val Ala Arg Pro Gly Leu Pro Gly Tyr Ala Ile Ser Leu Leu Ile Pro Asp Ile Ala Ile Glu Ile Pro Leu
Val Val Leu Leu Thr Gly Val Leu Asp Ala Glu Ile Gln Glu Asp Ala Thr Arg Thr Arg Gly Asp Pro Asp Met Ala Ser Leu
Ala Ile Glu Ala Leu Ala Lys Arg Asn Ala Glu Ala Leu Arg Leu Ile Leu Lys Ala Asn Leu Leu Asn Leu

SEQ ID NO: 15
Met Asn Leu Ile Phe Leu Gly Pro Pro Gly Ala Gly Lys Gly Thr Gln Ala Gln Phe Ile Met Glu Lys Tyr Gly Ile
Pro Gln Ile Ser Thr Gly Asp Met Leu Arg Ala Ala Val Lys Ala Gly Ser Glu Leu Gly Lys Gln Ala Lys Ala Val Ile Asp Ala
Met Lys Leu Gly Glu Leu Val Pro Asp His Val Ile Ile Gly Leu Val Lys Glu Arg Ile Ala Gln Asp Asp Cys Gln Asn Gly Phe Leu
Leu Asp Gly Phe Pro Arg Thr Ile Pro Gln Ala Asp Ala Met Lys Glu Ala Gly Ile Asn Val Asp Tyr Val Leu Glu Phe Asp Val Pro Asp Glu Leu
Ile Val Asp Arg Ile Val Gly Arg Arg Val His Ala Pro Ser Gly Arg Val Tyr His Val Lys Phe Asn Pro Pro Lys Val Glu Gly Lys Asp Asp Val Thr Gly Glu Glu Leu Thr Thr Arg Lys Asp Asp Gln Glu Glu Thr Val Arg Lys Arg Leu Val Glu Tyr His Gln Met Thr Ala Pro Leu Ile Gly Tyr Tyr
Ser Lys Glu Ala Glu Ala Gly Asn Thr Lys Tyr Ala Lys Val Asp Gly Thr Lys Pro Val Ala Glu Val Arg Ala Asp Leu Glu Lys Ile Leu Gly

SEQUENCE LISTING

```
SEQ ID NO: 16
Met Asn Ile Leu Phe Gly Pro Pro Gly Ser Gly Lys Ser Thr Gln Ala Arg Arg Ile Thr Glu Arg Tyr Gly Leu
Thr Tyr Ile Ala Ser Gly Asp Ile Ile Arg Glu Ala Glu Ile Lys Ala Arg Pro Leu Gly Ile Glu Met Gly Arg Tyr Leu
Ser Arg Gly Asp Leu Ile Pro Asp Thr Val Asn Thr Leu Ile Ile Ser Leu Arg Arg Val Arg Glu Val Arg Asn Phe
Ile Met Asp Gly Tyr Pro Arg Thr Pro Glu Gln Val Ile Thr Leu Glu Asn Tyr Leu Tyr Asp His Gly Ile Lys Leu
Asp Val Ala Ile Tyr Ile Asp Val Lys Thr Glu Glu Ser Val Arg Arg Ile Ser Gly Arg Arg Ile Cys Ser Lys Cys Gly
Ala Val Tyr His Val Glu Phe Asn Pro Pro Lys Val Pro Gly Lys Cys Gly Gly Leu Cys Gly Ile Leu Ile Gln Arg
Pro Asp Asp Arg Pro Glu Thr Val Glu Leu Arg Tyr Asp Val Tyr Asp Ile Lys Thr Ser Asn Met Glu Pro Ile Lys Phe Tyr
Gln Lys Gln Gly Ile Leu Tyr Val Arg Ile Asp Gly His Gly Ser Ile Asp Val Trp Arg Ile Arg Pro Leu Leu
Asp Tyr Ile Tyr Ile Asn Gln Glu Asn Arg Arg

SEQ ID NO: 17
Met Pro Phe Val Ile Ile Thr Gly Ile Pro Gly Val Gly Lys Ser Thr Arg Leu Ala Leu Gln Arg Thr Lys
Ala Lys Phe Arg Arg Gly Leu Ile Asn Phe Gly Leu Met Phe Gly Glu Gln Ala Val Leu Val Leu Lys Xaa His Arg
Asp Glu Gly Met His Pro Leu Pro Leu Val Asp Thr His Ala Thr Ile Lys Ala Ala Lys Lys Ile Xaa Glu Leu Met
Glu Val Val Lys Thr Leu Asn Pro Asn Pro Asn Phe Ile Val Ile Glu Ile Pro Ser Glu Leu Gly Leu Gly Arg Arg Leu
Arg Asp Leu Lys Arg Asp Arg Ala Val Glu Val Glu Val Thr His Ile Leu Glu Gly Leu Arg Asn Arg Ala Ala Ala
Val Ile Ile Xaa Thr Ala Met Xaa Ser Asn Ala Leu Ile Glu Lys Ile Asn His Glu Asp His Asp Lys Gly Leu Glu Ala
Val Asn Glu Leu Lys Ile Leu Leu Asp Leu Asn Val Leu Asn Glu Tyr Ala

SEQ ID NO: 18
Met Pro Phe Val Ile Ile Thr Gly Ile Pro Gly Val Gly Lys Ser Thr Ile Thr Lys Leu Ala Leu Gln Arg Thr Arg
Ala Lys Phe Lys His Val Asn Phe Gly Asp Leu Met Arg Glu Gln Ala Leu Leu Glu Asn Ala Leu Ala Leu Lys Xaa His Arg
Asp Pro Val Arg Asp Met Arg Gly Leu Leu Glu Ala Thr Ile Ala Ala Ala Ala Lys Arg Arg Glu Lys Ala Leu Glu Met
Ala Lys Leu Asn Tyr Pro Leu Leu Asp Thr His Ala Thr Ile Lys Thr Ala Thr Gly Tyr Leu Pro Gly Leu Pro Tyr
Glu Val Ile Lys Ile Leu Asn Pro Asp Phe Val Ile Leu Leu Glu Thr Ser Ser Asp Glu Ile Leu Glu Arg Arg Leu Arg
Asp Glu Leu Lys Arg Asn Arg Arg Pro Gly Thr Leu Glu Glu Ile His Glu Gln Gln Glu Lys Arg Leu Ala Lys Ala Ala Ile
Xaa Tyr Ala Met His Ser Asn Ala Leu Val Ile Ile Val Asn Thr Leu Leu Ala Leu Arg Gly Leu Glu Ala Val Ala Asn
Glu Leu Val Lys Ile Leu Glu Asp Leu Ala Leu Lys Gly Glu Ile Tyr Ala

SEQ ID NO: 19
Met Lys Val Ile Gly Ile Val Thr Gly Ile Pro Gly Val Gly Lys Ser Thr Val Leu Ala Lys Val Ala Lys Glu Ile Leu
Asp Ala Asn Gly Ile Ile Asn Gly Gly Asp Leu Val Arg Gln Leu Ala Ser Gln Leu Gly Leu Ser Thr Thr Arg Glu Met Leu Ala Ala Lys Gly Ile Tyr Ile Leu Ala
Lys Asp Arg Asp Glu Met Glu Ala Gly Ile Met Lys Gly Tyr Gln Leu Phe Leu Ala Val Asp Lys Gly Leu Val Val
Ala Arg Leu Asp Ala Ala Gly Gly Leu Tyr Leu Glu His Lys Lys Tyr Arg Leu Gln Glu Asp Ala Thr Pro Ser Lys Ile Glu Leu Ile Ala
Pro Gly Leu Pro Ser Tyr Val Ile Phe Leu Glu Ile Pro Phe Leu Glu Val Ile Glu Arg Ile Glu Arg Arg Gly Ile Thr Ile Ile
Leu Ser Arg Gly Gln Lys Leu Arg Ala Tyr Asp Thr Arg Asn Arg Asp Asp Ser Val Thr Lys Val Ile Leu Thr Lys
Asn Pro Ala Arg Tyr Ala Tyr Pro Ala Thr Glu Leu Leu Thr Val Leu Ala Ser Ala Leu Ala Pro Phe Ala Phe Ala Asn Val Glu Leu Glu Ile
Glu Pro Ser Ile Ala Ala Asn Glu Ile Ile Arg Ser Met Lys

SEQ ID NO: 20
Met Arg Val Leu Ile Asn Ser Gly Ser Ser Ser Ile Lys Tyr Gln Leu Ile Glu Met Glu Gly Glu Lys Val Leu
Cys Lys Gly Leu Val Glu Ala Ile Gly Ile Gly Leu Leu Ser Arg Leu Gly Pro Val Leu Gly Gly Val Gly Asp Lys Leu Ala Lys Gly Ile Tyr Ala
Arg Gly Leu Pro Asp His Gly Leu Ala Leu Leu Lys Leu Leu Asn Thr Val Val Gly Arg Phe Glu Glu Val Lys Ser Glu Val Val Leu Glu
Lys Asp Leu Gly Val Gly Leu Ile Leu Asp Ala Val Leu Gly Pro Gly Pro Ile Val Asp Lys His Ile Ile Ser Glu Ile Leu Val Xaa Ile
Pro Gly Leu Pro Ser Tyr Val Phe Glu Leu Lys Val Ser Pro Asn Val Ala Pro Thr Ala Phe Ala Asn Pro Ser Gly Ile Ile
Lys Ser Arg Gln Lys Arg Ile Ala Thr Arg Asn Val Ala Ala Phe Arg Arg Tyr Leu Leu Lys Gln Gly Glu Val Gly Pro Glu
Asn Pro Ser Ile Ala Asn Glu Ile Ile Arg Ser Met Lys
Lys Ala Ala Met Leu Tyr Leu Ala Ile Leu Pro Gly Tyr Glu Tyr Glu Leu Lys Leu Tyr Lys Leu Tyr Lys Lys Lys Leu Glu Lys Val Leu Val Leu Val
His Arg Tyr Val Ser Arg Lys Arg Ala Glu Ala Leu Ile Leu Gly Leu Glu Lys Leu Glu Lys Ile Lys Lys Cys His Ile Ser Gly Ile Gly
```

-continued

SEQUENCE LISTING

Asn Gly Ala Ser Val Ala Ala Lys Tyr Gly Lys Cys Val Asp Thr Ser Met Gly Phe Thr Pro Leu Glu Gly
Leu Val Met Gly Thr Arg Ile Ala Ala Leu Asp Pro Ala Ile Tyr Gly Ala Ile Pro Phe Met Lys Gly Ile Ser Pro
Gln Ile Glu Tyr Asp Leu Asn Lys Gly Val Ser Gly Leu Trp Cys Lys Val Phe Ser Gly Phe Ser Asp Met Arg
Asp Ile Glu Ala Ala Leu Lys Gly Asp Glu Leu Cys Ile Tyr Lys Glu Ile Pro Tyr Arg Ile Ala Lys
Tyr Ile Gly Ala Tyr Ala Ala Met Ala Asn Gly Val Ala Ile Phe Val Phe Ala Gly Val Gly Glu Asn Ser Pro
Ile Thr Arg Glu Asp Val Cys Ser Tyr Leu Glu Phe Leu Gly Val Lys Leu Asp Lys Asn Glu Thr
Ile Arg Gly Lys Glu Ile Ser Thr Pro Asp Ser Arg Val Lys Val Leu Pro Thr Asn Glu Leu
Met Ile Ala Arg Asp Thr Lys Glu Ile Val Glu Lys Ile Gly Arg

SEQ ID NO: 21

Met Arg Arg Met Lys Leu Pro Ser His Lys Thr Lys Ile Val Ala Thr Ile Gly Pro Ala Thr Asn Ser Lys Lys Met
Ile Lys Leu Ile Glu Ala Gly Met Asn Val Ala Arg Phe Ser Phe Ser His Gly Glu His Ala His Ala Lys
Ile Ile Glu Met Arg Arg Ile Gly Gln Ser Arg Gly Lys Pro Val Ala Ile Leu Ala Asp Leu Pro Gly Pro Lys Leu Arg
Ile Arg Val Gly Ile Gly Gly Thr Ile Arg Leu Glu Arg Gly Lys Val Phe Thr Leu Thr Thr Lys Asp Ile Pro
Glu Gly Asp Glu Thr Ile Val Pro Val Ala Tyr Glu Gly Leu Val Glu Asp Val Lys Val Gly Ala Ile Leu Tyr Leu
Ser Asp Gly Tyr Ile Glu Leu Arg Val Glu Glu Ala Asp Leu Val Lys Val Glu Cys Lys Val Gly Glu Gly Gly Lys
Leu Phe Ser Arg Lys Gly Ile Asn Ile Pro Gly Val Ala Leu Asn Phe Pro Val Leu Thr Ala Lys Asp Ile Glu Ile Gly Ile Lys
Met Ile Ala Ile Glu Glu His Gly Val Asp Val Tyr Gly Asn Val Phe Pro Arg Asp Tyr Asn Val Leu Lys Ile Ala
Lys Ser Phe Leu Glu Arg Gly Ala Asn Gly Ile Met Ile Ala Arg Gly Ile Glu Gly Leu Glu Gly Pro Ala Pro Ile Glu Asn
Phe Ala Asn Glu Ile Leu Asn Ala Ala Leu Ile Lys Ala Asn Met Ala Gly Lys Pro Val Ile Thr Ala Thr Gln Met
Leu Pro Val Gln Leu Arg Thr Pro Arg Pro Val Val Asn Ala Val Ser Asp Val Ala Asn Ala Ile Leu Asp Gly
Met Val Ser Met Thr Met Glu Ile Gly Tyr Ala Lys Ser Phe Gly Val Glu Phe Pro Glu Val Leu Glu Leu Met Ala Arg Gly Ile
Thr Ala Lys Val Met Ala Leu Ile Glu Arg Glu Tyr Arg Thr Ser Ile Gly Pro Met Arg Asn Gly Leu Gly Phe Ala Val Lys Thr Arg Gly
Ala Lys Val Thr Gly Glu Gly Gln Val Ile Ile Glu Ile Ser Met Ile Ile Cys Thr Arg Thr Ile Leu Val Thr Pro Thr Lys
Thr Arg Arg Ala Arg Met Ile Ser Glu Arg Ile Arg Leu Val Pro Phe Glu Glu Phe Ala Phe Arg Arg Ala Val Glu
Cys Asn Asn Leu Met Ser Lys Val Gly Val Thr Ile Val Pro Met Cys Glu Ile Lys Gln Gly Leu Phe Asn Glu Asn Asp Pro Ile Val
Arg Leu Ile Gly Lys Ile Gly Val Leu Ile Val Ala Leu Asn Met Thr Glu Gly Lys Val Pro Ile Glu Lys Thr
Val Gly Thr Asn Ser Ile Leu Phe Gln Ala

SEQ ID NO: 22

Met Arg Lys Thr Lys Ile Val Ala Thr Leu Gly Pro Ser Glu Lys Val Glu Leu Ala Gly Lys Val Ala Asp
Val Phe Arg Ile Asn Phe Ala His Gly Asp Arg Ser His Arg Glu Arg Lys Tyr Phe Leu Lys Asp Val Phe Ala Pro
Glu Ser Ser Ile Ser Gln Lys Leu Pro Gly Pro Arg Leu Arg Val Gly Val Pro Arg Glu Thr Ala Ala Gly Gly Ile Gly Pro Lys
Gly Asp Ala Lys Val Phe Ser Gln Arg Lys Thr Gly Gly Ile Ile Lys Val Tyr Ile Ser Ala Asp Pro Leu Arg Tyr Thr Glu Val Lys
Asn Ser Asp Val Pro Ile Pro Leu Pro Val Arg Ile Asn Arg Val Arg Ile Asp Ser Ala Asp Leu Ile Lys
Gly Asp Ile Val Tyr Val Asp Asp Gly Arg Leu Thr Val Val Arg Val Ile Gly Gly Ala Val Ala Val Glu
Ile Val Val Gly Gly Ile Leu Lys Ser Lys Lys Gly Val Thr Ile Pro Arg Val Arg Leu Ser Leu Pro Ala Leu Ser Glu Lys Asp Lys Asn Asp Leu Asp Phe Ala Lys Gln Ile Gly Met Asp Phe Val Ala Ile Ser Phe Val Arg Lys Pro Thr Asp Val Gln Glu
Asn Asp Val Lys Leu Val Arg Glu Ala Leu Gly Pro Glu Ala Ala Ile Ile Ser Lys Ile Glu Arg Pro Glu Ala Val Ser Asn Ile Asp Glu Ile Leu Glu Val Ser Asp Gly Ile Met Val Ala Arg Gly Asp Met Gly Val Glu Ile Pro Ile Glu Lys Val Pro Leu Ala Gln Lys Lys Leu Ile Arg Val Cys Arg Gln Met Asn Lys Pro Val Ile Thr Ala Thr Gln Met Leu Asp
Ser Met Ile Lys Asn Pro Arg Pro Thr Arg Ala Glu Ala Ser Asp Val Ala Asn Ala Val Leu Asp Gly Thr Asp Ala Val Met Leu Ser Gly Glu Thr Ala Lys Gly Lys Tyr Pro Val Glu Ala Val Thr Thr Met Arg Thr Val Ala Leu Arg Ala Glu Arg Ala Leu Asn His Asn Ile Ile Leu Pro Gly Val Glu Gln Ala Pro Ala Ile Thr His Ala Ala Val Gly Thr Ala Val
Glu Thr Glu Ala Lys Ala Ile Val Val Leu Thr Arg Thr Gly Ser Ser Ala Leu Leu Val Ser Arg Ile Ser Ser Gly Leu Pro Ile Ile Ala Val Ser Ala Thr Pro Ser Val Ile Gln Lys Leu Asn Leu Ala Trp Gly Val Tyr Pro Ile Glu Val Ser Phe Ser Val Asp Asp Leu Ile Ala Trp Thr Leu Asp Arg Ala Leu Glu Gln
Asp Leu Asn Arg Arg Glu Met Val Tyr Pro Leu Ala Thr Arg Tyr Leu Asn His Asn Thr Ile Gln
Val Asp Lys Leu Glu Met Ala Arg Ile Ala Ile Glu Leu Ala Ser Glu Ala Gly Ile Gln Ala Ile Ile Ala
Ser Ala Thr Glu Ser Val Met Ser Glu Leu Ala Lys Ala Arg Pro Ser Leu Pro Ile Leu Ala Leu Ser Gly Gly Pro Val Thr Arg Arg Gln Arg Leu Asn Leu Arg Trp Gly Val Tyr
Ser Ala Thr Glu Asn Ala Leu Ser Leu Arg Lys Val Lys Asn Leu Ser Asn Ala Arg Met Val Ala Ile Ser
Val Arg Val Ile Ile Val Thr Val Ala Leu Thr Pro Val Thr Arg Leu Ala Lys Ala Ile Leu Lys
Arg Ser Thr Thr Leu Arg Ile Pro Lys Arg Leu Leu Asn Leu Arg Val Pro Val Leu Leu Arg Ala Ile Ala Ile Lys Ile Gly Ala Leu Val Ser Leu Ser Ala Leu
Val Ile Asp Asp Pro Leu Ile Ser Ile Leu Lys Met Ala Val Ile Glu Arg Val Tyr Ser Arg
Ile Lys Asp Lys Lys Ser Phe Lys Leu Ile Leu Ser Leu Ala Gly Ile Lys Ser Phe Leu Lys Met Glu Asn Gln Lys
Ile Val Lys Thr Leu Glu Gln Gln Leu Lys Lys Asp Val Gly Lys Leu Leu Lys Ala Arg Val Thr Asn Phe Val

SEQUENCE LISTING

SEQ ID NO: 23
Met Arg Ser Thr Lys Ile Val Cys Thr Val Gly Pro Arg Thr Asp Ser Tyr Glu Met Ile Glu Lys Met Ile Asp Leu
Gly Val Asn Val Phe Arg Ile Asn Thr Ser His Ile Gly Leu Ile Asp Trp Asn Glu Gln Gln Lys Ile Leu Lys Asp
Leu Arg Glu Lys Lys Leu Pro Val Ala Leu Asp Ile Leu Phe Thr Lys Lys Ala Gly Pro Lys Ile Arg Thr Gly Thr
Lys Glu Phe Val Gln Leu Gly Gly Gln Ile Pro Leu Thr Thr Thr Ile Lys Leu Gly Leu Ile Arg Thr Gly Ile Val
Ser Val Asn Leu Ser Glu Leu Pro Lys Val Leu Lys Asp Gly Asp Val Leu Leu Ser Lys Asp Gly His Ile Val
Leu Glu Val Ile Glu Thr Val Asp Leu Ser Thr Glu Val Gly Val Leu Gly Ile Thr His Leu Arg Arg Gly Ile Gly
Val Asn Val Pro Phe Thr Ala Pro Leu Ser Arg Phe Val Asp Val Ala Phe Ile Ile Gly Ile Ile
His Gly Ile Leu Pro Val Ile Ser Leu Pro Val Pro Glu Val Arg Ile Thr Ile Leu Lys Glu Leu Arg Asn Ile Lys Glu
Arg Lys Asp Asp Val Leu Arg Gly Leu Tyr Ala Leu Leu Lys Ile Pro Val Leu Pro Ile Glu Val Gln Ile Gln Glu
Ile Ser Asp Gly Ile Met Val Ala Arg Val Leu Gly Leu Val Ile Thr Asn Leu Pro Val Ile Pro Glu Val Asn Pro Phe
Pro Thr Arg Ala Glu Val Thr Tyr Ser Lys Ile Val Ala Asp Ser Ala Leu Thr Ala Phe Gly Thr Gly Thr Ala Glu Thr
Ala Val Gly Lys His Pro Leu Glu Ala Ile Ala Ile Gln Leu Glu Ile Leu Val Leu Leu Ala Ala Lys Cys Glu Leu Glu Phe
Phe Arg Gly Thr Ile Glu Tyr Asp Ser Leu Thr Ile Val Ala Arg Val Arg Val Leu Val Lys Tyr Ser Trp Gln Ser Ser
Asn Ala Lys Ile Leu Thr Ile Pro Gln Glu Tyr Tyr Arg Leu Val Ser Leu Lys Val Lys Val Lys Val Ser Asn Leu Val Ser Gln Pro Ile
Val Leu Thr Arg Asp Leu Glu Leu Thr Pro Gln Leu Phe Glu Ile Glu Leu Val Ile Gly Leu Met Gly Ala Leu Val Leu Ala Gly Lys
Cys Ser Gln Leu Leu Leu Glu Ile Pro Val Lys Ile Lys Glu Asp Val Lys Lys
Leu Val Leu Leu Thr Ser Gly Val Pro Gly Lys Gly Lys Leu Ala Leu Lys Val Asp

SEQ ID NO: 24
Met Arg Lys Val Leu Pro Ser His Lys Thr Ile Val Ala Thr Ile Gly Pro Ala Thr Asn Ser Arg Lys Met
Ile Lys Gln Leu Ile Lys Ala Gly Met Asn Val Ala Arg Ile Leu Asn Ala Leu Arg Val Gln Ala Phe Ser Glu His Gly Ala Arg
Val Ile Glu Leu Arg Gly Val Glu Gly Leu Ala Gln Ile Lys Leu Leu Asp Arg Tyr Ala Ala Val Glu Pro Gly Leu Leu Lys Leu
Arg Val Met Thr Gly Arg Thr Glu Gly Leu Val Arg Thr Lys Gly Thr Ser Tyr Ile Glu Tyr Ala Asp Gly Thr Ile Gln Met Leu
Gly Asp Glu Thr Lys Val Glu Leu Pro Val Asp Phe Lys Arg Leu Val Leu Asp Val Leu Lys Gly Thr Thr Ile Arg Tyr Asp
Asp Gly Tyr Ile Glu Leu Val Val Leu Glu Val Arg Gly Asp Ala Val Ala Val Leu Ile Ser Tyr Asp Ala Ser Ser Arg Phe Glu Gly His Ala Leu Lys Met
Phe Ser Arg Gly Ile Asn Ile Pro Ala Ala Tyr Leu Arg Pro Tyr Leu Lys Ser Val Glu Phe Ile Lys Glu Ile Leu Met
Lys Pro Ala Ile His Val Val Asp Ala Ile Asp Gly Cys Thr Ile Pro Tyr Ile Lys Asp Pro Thr Val Leu Arg Ala Asn Ala
Ser Leu Phe Glu Leu Asn Lys Ala Asn Ala Ala Asp Gly Val Met Phe Glu Leu Val Arg Asp Val Ala Val Ala Arg Asn
Glu Asp Ile Leu Gln Ile Arg Ala Ile Leu Leu Arg Tyr Ile Pro Val Ile Ala Lys Ile Glu Asn Val Glu Met Pro Ala Ile Glu
Leu Pro Ile Leu Ser Leu Arg Ala Asn Met Asp Gly Val Met Val Ala Arg Val Ala Glu Val Leu Thr Gln Met Leu
Val Ser Met Thr Val Pro Gly Phe Pro Ile Leu Ser Ala Ser Thr Ala Val Ala Glu Val Ala Ile Glu Leu Ala Ile Ala Lys
Ala Val Met Leu Ser Gly Glu Thr Ala Ile Gly Ala Arg Pro Glu Thr Gly Val Glu Met Glu Ala Val Ile Thr Ile Lys
Val Thr Glu Gly Tyr Arg Ser Phe Pro Leu Asp Ala Tyr Lys Lys Glu Phe Ile Leu Thr Pro Leu Arg Thr Lys Gly Arg
Thr Ala Ile Leu Thr Arg Gly Pro Pro Arg Ala Lys Ile Cys Thr Val Leu Cys Gln Thr Arg Pro Asn Thr Ala Arg Pro Asn Cys Asn
Asn Leu Met Pro Ser Tyr Arg Pro Val Leu Pro Cys Ser Leu Glu Glu Glu Pro Ala Leu Arg Val Arg Arg Ala Val Arg Leu Gly Ala
Ile Lys Gly Leu Val Leu Val Glu Leu Ser Pro Glu Asp Glu Gly Lys Leu Pro Gly Pro Ile Asp Leu Ala Leu Leu Ile Pro Lys Gly Val Ile Lys Lys
Thr Asn Ser Lys Ile Phe Gln Leu Thr Ala Leu Glu Met Thr Val Leu Met Val Ala Glu Lys Ala Glu Ala Lys Val Thr Lys Gly Val Gly

SEQ ID NO: 25
Met Lys Val Leu Val Ile Asn Ala Gly Ser Ser Ser Leu Lys Tyr Gln Leu Ile Asp Met Thr Asn Glu Ser Ala Leu
Ala Leu Gly Leu Leu Cys Glu Lys Gly Ile Glu Gly Ile Gly Phe Asn Asp Ser Ile Ile Thr Gln Lys Ile Phe Asp Gly Lys Leu Glu
Lys Leu Thr Asp His Ala His Ala Val Lys Ala Leu Ala Leu Leu Glu Val Val Lys Leu Ala Val Val Lys His Glu Lys Phe Gly
Val Ile Lys Asp Met Lys Glu Ile Asp Ala Val Gly His Arg Val Val His Gly Gly Glu Lys Phe Ala Thr Ser Ala
Leu Tyr Asp Glu Val Val Val Lys Ala Ile Lys Asp Cys Phe Glu Leu Ala Pro Leu His Asn Pro Ala Asn Leu Met
Met Gly Ile Ser Ala Met Pro Gly Leu Met Pro Asp Thr Pro Met Val Ile Val Phe Asp Thr Ala Phe His Gln Thr
Met Pro Glu Tyr Ala Tyr Met Tyr Ala Leu Pro Tyr Asp Leu Tyr Glu Lys Tyr Gly Val Arg Arg Tyr Gly Phe His Gly
His Ser His Arg Tyr Val Ala Glu Arg Ala Ala Glu Ile Leu Gly Lys Pro Leu Glu Glu Leu Arg Ile Ile Thr Cys His Leu Gly Asn Gly Ser Ser Ile Thr Ala Ile Arg Glu Gly Lys Ser Val Asp Thr Ser Met Gly Phe Thr Pro Leu Glu Gly Leu Val Met Gly Thr Arg Cys Gly Asp Ile Asp Pro Ala Ile Val Phe His Leu His Asp Thr Leu Gly Met Ser Val Asp Ala Ile Asn Lys Leu Leu Asn Lys Lys Ser Gly Val Leu Gly Leu Thr Glu Val Thr Ser Asp Cys Arg Tyr Val Glu Asp Asn Tyr Ala Thr Lys Glu Asp Ala Lys Arg Ala Met Asp Val Tyr Cys His Arg Leu Ala Lys Tyr Ile Gly Ala Tyr Thr Ala Leu Met Asp Gly Arg Leu Asp Ala Val Val Phe Thr Gly Gly Ile Gly Glu Asn Ala Ala Met Val Arg Glu Leu Ser Leu Gly Lys Leu Gly Val Leu Gly Phe Glu Val Asp His Glu Arg Asn Leu Ala Ala Arg Phe Gly Lys Ser Gly Phe Ile Asn Lys Glu Gly Thr Arg Pro Ala Val Val Ile Pro Thr Asn Glu Glu Leu Val Ile Ala Gln Asp Ala Ser Arg Leu Thr Ala

```
Pro Leu Glu Gly Leu Ala Met Gly Thr Arg Cys Gly Ser Ile Asp Pro Ala Ile Val Pro Phe Leu Met Glu Lys Glu
Gly Leu Thr Arg Glu Ile Asp Thr Leu Met Asn Lys Leu Asn Lys Ser Gly Val Leu Gly Ile Leu Phe Ala Tyr
Asp Phe Arg Asp Leu Asp Ala Ala Ser Arg Gly Ala Val Leu Asn Arg Lys Ala Glu Leu Ala Leu Glu Ile Gly
Lys Val Lys Phe Ile Gly Ile Glu Phe Ile Arg Ile Ser Ala Val Leu Asn Gly Ala Val Val Phe Thr Ala Gly Ile Tyr
Glu Asn Ser Ala Ser Ile Arg Gly Ile Arg Leu Thr Gly Leu Asn Gly Ile Ile Gly Ile Lys Ile Asp Asp Lys Ile Asn
Lys Ile Arg Gly Ile Gln Ile Asp Ile Ser Thr Pro Asp Ala Lys Val Val Phe Val Ile Pro Thr Asn Glu Val
Leu Ala Ile Glu Arg Ala Thr Lys Val Glu Thr Val Lys Leu Arg Ser Ile Pro Val

SEQ ID NO: 26
atgaagatty gtattgtaac tggaattcct ggtgtaggga aaagtactyt cttgctaaa gtaaagaga tattgdataa tcaaggtata
aataacaaga tcataaatta tgagatttt atgtagcaa attagctat gcaaaagata gagacgaaat gagaaaatta
tctgaagaa agcagaagaa attgcagatt gatgcggcta aagctataac tgaagaggca agagcaggtg gagaaggata tctgttcata
gatacgcatg ctgtgatacg tacaccgtg ggatatttac ctgttttacc gtcatatgta attacagaaa taaatccgtc tgttatcttt
ctactggaag ctgtatccta gataatatta tcaaggcaaa agagaatac aacaaggaaa agaaatgat atagtgacga atcagttata
ttagaaacca taaacttcgc tagatatgca gctactgctt ctgcagatat actgttcct acgtaag cgtgaagga
gatcctagta tagcagctaa tgagtatata aggtctatga agtaa SEQ ID NO: 27
atgaaaatcg gtatcgttac cggtgtggta aattccaccg gtgttggta attggctaaa tctgctgaca ctgatcagga ccaggttatc
aacacaaaa tctccaacta cgtcagcatc atcgctgcta acaaccacg aagttgaacc cgttctacgc gtctgaaggc gttgaagttg
cctctgtcat acgaataact ctgttgttga ctgctatcg tatcccgtac cggttactgc aactggtaac gtcttacagt tcaacctgc
caccgttcca tcctttatcc gccacctgg aatatttatc tctctcttc gaccgttc tgcactgga aactcatctg gccattctg
gcctcagge ctagcacgg ctcaacggtt cgtctctga actgtacgc tgcgttatct atgactaag cttgattcc acgcgttcac
ctgaaaaccta tctgcttaa gagatgtct gccactcttc gctgtctca acgcgttaag ttatctgacga ttatctgtta cgttcaaggt
gacccgtcta tgtctgctaa tgaactgtcg cgaactcatc aatggtgtcca SEQ ID NO: 28
atggggcgt acctttgtcct ttaggacct ccaggtgcag gaaaaggaac ctacgcaaag agattgcagg aaataccgg gattcctcat
atcctccacccg gttcatttt cagggacatt ctaaaaaag gaacgacga gctgggaaaa aagattaag agatcatgga tactactyga
aagggagaga ctcgttccgg acgaaggtt gaacgaagtt gtgaaaaga gactctcga aaactcaaaa caagagccec acggctgctg tactctttga
cggctatccg agaaccgttg ctcaggcgga attcctccgc cacggccaga aggatctgcc cgaatctgg aagaaattac aattgatttc cgctcctccc
agtcctgag gaagtggtcg gaactcaggct ttcagagcc atgattgcga agtgaagctc agtcagagag aagagaaca gtgagaaca
gataaagaga gcttatctcga aagcacagac cagtgattga ttccaaaact aaaaaggca ttcccaaacg agtgattggt
accataggg tagacaacgt gatcgctaga gtgttaaaga taatagggtg gagtgataaa tga SEQ ID NO: 29
atgatcgcgt atccggtttt tcttggtcca ccggggcag gcaaaggtac atatgcgaaa cgttacaagg aaatcaccgg catccgcgac
attagcacg gcgcaaattt tcgtgatatt gtcaaaaagg gctgtgctgc aacttaag aaccgattgc ttatttgga ggggggag
ttggtgccag acgaactgt gaactgaaagt gtcaaacgtc ggctctgaa cagaaaga gaacgtggct gctgcggg cggtacccg
cgatacgtag ttcagtcaga gttctcgac cgtatttac gagatctgaa taaggagtta acctgattac cctgttggg ggttacctgaa
cagtggtc ttcagtgct gaccccggtg cgtattgac agtgaacaga agagaaact gtgccatcc gctacaaagt atattcttga
gaactgtgtg atgatgcaa agtaaaacg gtgcaacgcg aagatgataa agagggaaact cgttcatggg accatccgga tcgataacgt gattgccaaa
aaaccaac cgttatcga ttaattatgat aaaaaaggca ttgaaacg gtagatcgg gaatattct tttgaaacg gtagatcgg gaataaccgat
gttctcaaaa tcatggggtg gagtgataaa tga SEQ ID NO: 30
atgaacctga tttcctgg tccgcctggg gcaccccaggc gaaacgtgtg tctgaaaagt acggtgtccc gcagattagt
accggcgata tgtcgcgta acggttgct aaggggacgg aacgcgaaa aaggcgaaaaa ccggatgta gaatatatgg acaaaggga
actgttccg gatgaagtag ttattggaat cgtgaagaa cgcctccagc gaaattga tgagaagggc tttattctgg acggtttcc
gcgtacgtta gccaaagccg aagtcctga cgaaatgtta aagagaaaat ataagaaaat tgacgccgta atcaacgcgg tcgtaccgga
```

-continued

SEQUENCE LISTING agaggaagt gtcaagcgta ttacctatcg tcgcacttgc cgcaattgcg gcgccgtgta ccatctcatt tatgcacctc caaaagagga
taataaatgt gataaatgcg gcgtgagct ttatcagcgt gatgacgata aagaagagac agtccggag cgtaccgtg tgtataaaca
gaacacagag ccattgatcg atattaccg taaaaggga atcctgtatg atcgaggag tactaaagac atcgaaggag tttgaaaga
aattgaggcg atcctgaaa aaattaaag c SEQ ID NO: 31
Met Lys Ile Gly Ile Val Thr Gly Ile Pro Gly Val Gly Lys Ser Thr Val Leu Ala Lys Val Gly Glu Ile Leu Asp Asn
Glu Gly Ile Asn Asn Lys Ile Glu Asn Tyr Gly Phe Met Leu Ala Thr Ala Leu Lys Leu Gly Tyr Ala Lys Ile Glu Asp
Arg Asp Glu Met Arg Gly Val Glu Lys Gln Lys Gln Ile Lys Asp Thr His Ala Val Ile Arg Thr Pro Ser Gly Tyr Leu Pro Gly
Ala Arg Ala Gly Ala Gly Tyr Ile Thr Glu Phe Leu Asn Pro Ser Val Ile Phe Leu Glu Ala Ala Asp Pro Lys Ile Ile Asn Phe
Leu Pro Ser Tyr Val Ile Thr Arg Asn Arg Asn Asp Tyr Ser Asp Tyr Ala Ser Val Ile Leu Glu Thr Ile Leu Asn Phe
Arg Gln Lys Asp Arg Thr Ala Ser Ala Val Leu Ala Gly Ser Thr Val Lys Val Ile Val Asn Val Glu Gly Asp Pro
Ala Arg Tyr Ala Ala Asn Glu Ile Ile Arg Ile Ile Ser Met Lys
Ser Ile Ala Ala Asn Glu Ile Ile Arg Ile Ile SEQ ID NO: 32
Met Met Ala Tyr Leu Val Phe Leu Gly Pro Pro Gly Ala Gly Lys Gly Thr Tyr Ala Lys Arg Leu Gln Glu Ile Thr
Gly Ile Pro His Ile Ser Thr Gly Asp Ile Phe Arg Asp Glu Val Lys Val Gly Glu Ile Val Lys Asp Ala Leu Gln Gly
Lys Glu Ile Met Glu Val Pro Arg Thr Val Ala Gln Ala Glu Glu Leu Ala Arg Leu Asp Gly
Lys Asp Cys Ile Leu Asp Gly Phe Pro Arg Thr Val Ala Gln Ala Glu Lys Leu Asp Gly
Phe Leu Thr Gln Phe Ile Leu Val Val Leu Glu Val Pro Glu Thr Val Arg Asn Arg Ile Ser Arg Arg Phe
Leu Thr Ala Arg Ile Cys Pro Lys Cys Gly Arg Ile Tyr Asn Leu Ile Ser Leu Pro Pro Lys Glu Asp Gly Leu
Cys Asp Cys Lys Val Leu Val Gln Arg Glu Asp Lys Glu Gly Ile Leu Lys Arg His Arg Tyr Lys Val
Tyr Leu Glu Lys Thr Gln Pro Val Ile Asp Tyr Tyr Gln Lys Lys Gly Ile Leu Arg Arg Val Asp Gly Thr Ile Gly
Ile Asp Asn Val Ile Ala Glu Val Leu Lys Ile Ile Gly Trp Ser Asp Lys SEQ ID NO: 33
Met Asn Gln Glu Gln Val Ser Pro Leu Gly Gly SEQ ID NO: 34
Met Asn Gln Glu Gln Val Ser Pro Leu Gly Gly Lys Ile Gly Ile Val Thr Gly Ile Pro Gly Val Gly Lys Ser Thr
Val Leu Ala Lys Val Gly Glu Ile Leu Asp Asn Gln Gly Ile Asn Asn Lys Ile Asn Tyr Gly Asp Phe Met Leu
Ala Thr Ala Leu Lys Leu Gly Tyr Ala Lys Ile Glu Asp Arg Asp Glu Met Arg Arg Gly Val Glu Lys Gln Lys Lys
Leu Gln Ile Lys Asp Thr His Ala Val Ile Arg Tyr Pro Ser Gly Tyr Leu Pro Gly Ala Arg Ala Ala Gly Gly Tyr
Ala Val Ile Glu Phe Leu Asn Pro Ser Val Ile Phe Leu Glu Ala Ala Asp Pro Lys Ile Phe Leu Asn Pro Ser Val Ile Phe
Leu Leu Glu Ala Ala Asp Pro Lys Ile Ile Ile Ser Tyr Arg Gln Asn Asp Thr Thr Arg Asn Asp Ser Tyr Ser
Asp Glu Ser Val Ile Leu Glu Thr Ile Leu Asn Phe Arg Gln Lys Asp Arg Thr Ala Ser Ala Val Leu Ala Gly Ser Thr
Val Lys Val Ile Asn Val Glu Gly Asp Pro Ser Lys Ile Ile Glu Ile Ala Arg Ser Met Lys SEQ ID NO: 35
Met Lys Ile Gly Ile Val Thr Gly Ile Pro Gly Val Gly Lys Ser Thr Val Leu Ala Lys Val Gly Glu Ile Leu Asp Asn
Gln Gly Ile Asn Asn Lys Ile Glu Asn Tyr Gly Phe Met Leu Ala Thr Ala Leu Lys Leu Gly Tyr Ala Lys Ile Glu Asp
Arg Asp Glu Met Arg Gly Val Glu Lys Gln Lys Gln Ile Lys Asp Thr His Ala Val Ile Arg Thr Pro Ser Gly Tyr Leu Pro Gly
Ala Arg Ala Gly Ala Gly Tyr Ile Thr Glu Phe Leu Asn Pro Ser Val Ile Phe Leu Glu Ala Ala Asp Pro Lys Ile Ile Asn Phe
Leu Pro Ser Tyr Val Ile Thr Arg Asn Arg Asn Asp Tyr Ser Asp Tyr Ala Ser Val Ile Leu Glu Thr Ile Leu Asn Phe
Arg Gln Lys Asp Arg Thr Ala Ser Ala Val Leu Ala Gly Ser Thr Val Lys Val Ile Val Asn Val Glu Gly Asp Pro
Ala Arg Tyr Ala Ala Thr Ala Ser Ala Leu Ala Leu Ala Gly Ser Met Lys Val Ile Val Asn Val Glu Gly Asp Pro
Ser Ile Ala Ala Asn Glu Ile Ile Arg Ser Met Lys Gly Gln Asn Gln Val Asn Val Ile Ser Pro Leu

SEQUENCE LISTING

SEQ ID NO: 36
Met Asn Gln Glu Gln Val Ser Pro Leu Gly Gly Lys Ile Gly Ile Pro Gly Val Gly Lys Ser Thr
Val Leu Ala Lys Val Lys Leu Glu Ile Leu Asp Asn Gln Ile Gly Ile Asn Lys Ile Gly Asp Phe Met Leu
Ala Thr Ala Leu Lys Leu Gly Tyr Ala Lys Asp Arg Asp Met Arg Lys Leu Ser Val Glu Lys Gln Lys Lys
Leu Gln Ile Asp Ala Ala Lys Gly Ile Gly Ile Ala Glu Gln Ala Arg Ala Gly Gly Tyr Leu Phe Ile Asp Thr His
Ala Val Ile Arg Pro Ser Gly Tyr Leu Pro Gly Leu Pro Ser Tyr Val Ile Thr Glu Ile Asn Pro Ser Val Ile Phe
Leu Leu Glu Ala Asp Pro Lys Ile Ile Leu Ser Arg Gln Lys Arg Asp Thr Arg Asn Arg Asn Asp Tyr Ser
Asp Ser Val Ile Leu Glu Thr Ile Asn Phe Ala Arg Tyr Ala Ala Thr Ala Ser Ala Val Leu Ala Gly Ser
Thr Val Lys Val Asn Val Glu Ile Gly Asp Pro Ser Ile Ala Asn Glu Ile Ile Arg Ser Met Lys Gly Gly
Asn Gln Gln Val Ser Pro Leu

SEQ ID NO: 37
atgaatcaag aacaagtcag ccgctgggc ggcatcatcg cctatctggt tttcctggt ccaccgggg caggcaaagg tacctatgcg
aacgttac aggaaatcac cggcatagca cggcgcggc cacattagca gagttgtgc cggaggaact ggtgtcaaa atgtcaaaa aggaaatga cgaattggt
aagaaatta gcttatttt ggacggttac ccgcgtacag agagttgtgc acggcttcc gacgttcaag gtgtccaaac gtcggttgtc tgaagactca gaataggag
tgcgaacgtg cgtccctgt cgaggtgcg gaagagtgg tcgttgagcg tctgaccgcg cggcgtgcac ctgtgcac ctgtgcaac gcccgagtg tggtcgtatt
ttacaactga cgtccctctc ccaaaagaa agtatactg ggaaaaaccc cgattattat gataaaaaag gcatttgaa acgcgttgat
actgtcgcc atcgctacaa cgtgattgcc gaagtctca aatcattgg gtgagtgat aataggccg acgc
gggaccatcg gcatcgataa SEQ ID NO: 38
Met Asn Gln Glu Gln Val Ser Pro Leu Gly Gly Ile Ile Ala Tyr Leu Val Phe Leu Gly Pro Pro Gly Ala Gly Lys
Gly Thr Tyr Ala Lys Arg Leu Gln Ile Thr Gly Ile Ile Pro Met Ser Thr Gly Asp Ile Phe Arg Glu Ile Val Lys
Lys Glu Asn Asp Leu Gly Leu Lys Ala Arg Ser Ala Cys Ser Glu Arg Gly Phe Ile Leu Asp Asp Val Leu Pro Arg Thr
Asn Glu Val Val Lys Ala Glu Phe Gly Leu Asp Ser Leu Lys Thr Gln Arg Ile Leu Lys Val Gly Arg Ile Leu Phe Glu
Val Ala Gln Ala Glu Val Val Gln Arg Leu Thr Lys Ala Arg Arg Ile Cys Pro Lys Cys Gly Arg Ile Tyr Asn Leu Ile
Ser Leu Pro Pro Lys Glu Val Asp Glu Cys Asp Lys Cys Gly Val Lys Leu Val Gln Arg Asp Asp Arg Asp Val Leu Lys Lys Gly Ile
Glu Thr Val Arg His Arg Tyr Val Tyr Leu Glu Val Leu Lys Ser Thr Gly Val Leu Thr Glu Ile Asp Tyr Arg Lys Gly Ile
Leu Lys Arg Val Asp Gly Thr Ile Gly Ile Glu Asp Val Ile Ala Glu Val Leu Lys Ile Ile Gly Trp Ser Asp Lys SEQ ID NO: 39
atgatggcct atccgttttt tcttggtcca ccgggggcag gcaaagtgac ctatgcgaaa cgtttacagg aaatcaccgg catcccgcac
attagcacgg gcgacattt tcgtgatatt gtcaaaaagg attatgacga attagtacga aaagattaag acgcggcgag
ttgtgccgg acgaactgt gtcaaacgtc gctctctga aaggactgc gaacgtgct tatttga cctgctcgcg ggtgcctga
caggtaga ttccgcgac gttctgaga gactcgagg cgaagtcta tgtattac aactgtgatt cactctccc aaaagaagt
gaggtgtg atgactgca agtacaacgc gtgcaacgg agatgataa agaggaaact gtgccatc gctacaaagt atatctgga
gaactgtg cgttactga tattatgat aaaaaaggca ttttgaaacg cgtgatggg accatcggca tgataacgt gattgccgaa
aaaacccac tcttccaaa tcaggataaa ctgggcggca gtcaccg ctgtaa
gttctcaaaa tcattgggtg gagtgataaa SEQ ID NO: 40
Met Met Ala Tyr Leu Val Phe Leu Gly Pro Pro Gly Ala Gly Lys Gly Thr Tyr Ala Lys Arg Leu Gln Glu Ile
Thr Gly Ile Pro His Ile Ser Thr Gly Asp Ile Phe Arg Asp Ile Val Lys Lys Glu Asn Asp Leu Gly Leu Lys Lys
Ile Leu Glu Met Gly Arg Gly Leu Val Pro Asp Glu Val Leu Val Asn Val Val Lys Arg Leu Ser Glu
Lys Asp Cys Glu Lys Gly Phe Ile Leu Asp Gly Tyr Pro Arg Thr Val Ala Gln Ala Glu Phe Leu Asp Gly Phe
Leu Lys Thr Gln Asn Lys Val Leu Phe Leu Thr Ala Ala Val Glu Val Pro Glu Val Val Val Glu Arg Leu Thr Ala Arg Arg Ile Cys Pro Lys Cys Gly Arg Ile Tyr Asn Leu Ile Ser Leu Pro Lys Glu Asp Glu Leu Cys
Asp Asp Cys Lys Thr Lys Val Gln Leu Val Ile Arg Glu Asp Lys Lys Glu Thr Val Arg His Arg Tyr Lys Val Tyr
Leu Glu Lys Thr Gln Pro Val Ile Asp Tyr Tyr Asp Lys Lys Gly Ile Lys Arg Val Asp Gly Thr Ile Gly Ile
Asp Asn Val Ile Ala Glu Val Leu Lys Ile Ile Gly Trp Ser Asp Lys Leu Gly Val Asn Gln Gln Val Ser Pro
Leu SEQ ID NO: 41
atgaatcaag aacaagtcag cccgctgggc ggcatcatcg cctatctggt tttcttggt ccaccggggg caggcaaagg tacctatggt
aaacgttac aggaaatcat cgcatccccg cacattagca cggcacca cggacgaact gttcgtgat atgtcaaga aggaaaatga cgaattaggt
aagaaattta aagaaattat ggagccgcgc gagttgtgc cggacgaact ggtgaatgaa gttgtcaaac gtcggtcgtc tgaaagaga
tgcgaacgtg gctttattt gacggtcac ccgcgtacag tagctcaagc gagttcctc gacgttctc tgaagacta gaataaggag
ttaacggctg cggtcctgt cggtcctgt cgaggtgcct cgagttcagc tcgacccgg tctgacccg gacgttacac cgcagatga tggtcgtt
tacaacctga tttcaacttco tccaaaagaa gatgaactgt gtgataccaa ctggtcaac aacgaagtga taaaggaa
actgtcgcc atcgctacaa agtatatctg gaaaaaaccc cgattattat cgattattat gataaaaaag gcatttgaa acgcgttgat
gggaccatcg gcatcgataa cgtgattgcc gaagttctca aatcattgg gtggagtgat aaactggggcg caatcaaga acaagtcagc
ccgctgtaa SEQ ID NO: 42
Met Asn Gln Glu Gln Val Ser Pro Leu Gly Gly Ile Ile Ala Tyr Leu Val Phe Leu Gly Pro Pro Gly Ala Gly Lys
Gly Thr Tyr Ala Lys Arg Leu Gln Glu Ile Ile Ala Ser Thr His His Gly Asp Ile Phe Arg Asp Ile Val Lys
Lys Glu Asn Asp Glu Leu Gly Lys Lys Leu Lys Glu Ile Met Glu Arg Gly Val Leu Val Pro Asp Glu Leu Val Val
Asn Glu Val Lys Glu Arg Leu Ser Glu Phe Ser Cys Glu Lys Ala Arg Gly Phe Ile Leu Asp Gly Tyr Pro Arg Thr
Val Ala Gln Ala Glu Phe Leu Asp Arg Leu Thr Ala Arg Leu Thr Gln Ala Arg Ile Asn Lys Thr Ala Leu Phe Glu
Val Pro Glu Val Val Val Gln Arg Leu Cys Asp Arg Arg Val Cys Pro Lys Cys Gly Arg Ile Tyr Asn Leu Ile
Ser Leu Pro Lys Glu Asp Glu Leu Cys Asp Asp Cys Lys Thr Lys Val Gln Leu Val Ile Arg Glu Asp Lys Leu Ile
Glu Thr Val Arg His Arg Tyr Lys Val Tyr Leu Glu Lys Thr Gln Pro Val Ile Asp Tyr Tyr Asp Lys Lys Gly Ile
Leu Lys Arg Val Asp Gly Thr Ile Gly Ile Asp Asn Val Ile Ala Glu Val Leu Lys Ile Ile Gly Trp Ser Asp Lys
Leu Gly Val Asn Gln Gln Val Ser Pro Leu SEQ ID NO: 43
gattcaaacc aaggcaacaa tcagcaaaac taccagcaat acagccagaa cgtaaccaa caacaggta acaacagata
ccaaggttat caagcttaca atgctcaagc acgccggtta ccaatcccc ccagcaacag gtggtact tataatccc aaggaggcta tcaacagtac aatcctcaag gcgttatca
gcaccaattc aatccaaacac acagctcaac aacttcaact acataacaa tttgcaagga ccgtcccaa cgtctcccca accaaagag acttgaagc
gttccaacc acagtctcaa ggtatgtctt tgaacagctt tcaaaagcaa gaagttgac atgtggcca agttgccaa cgaatcga taagaaagag gaagaagt
ttgctccag caaagaacca actaaagagc caaaaggt caaaagagc caaaagagc gtcaaacaaa accagcct tacaagtg accaccata gtcagact
gaagaaaaga cggaggaaaa atcgaaact caagaaacag aagaccttaa aatcctgaa tggtcgtaa gatgttttg gtgtaaga tgccatgtt
accagctg atgcctgat caaggaacag tgatcacga agttgtttac tctactacta tgaactggt ctgtgataa gagaactatt
ttaattttca tggctccgt tgatcgcaag caagcagtga ggcagactt gttgacttt gtcatgggtc ttatacaa ttccgccaga aaggtggc ctggatgtc acgaaccgg
aagaaatatg gtaagacta tcgaaaagag tcgaaagagc caaggcctac ttggaacctg tttgaaactg tttgtcat gatgttggt gccaagaccc aagtgttaa taagatggt gtcgtcgtaa ataagatgga
aatgtacgtt tcggatgatga tcggtctgatga ctcgtcagc ttcgcaact cgtcttagg atgtcgtaa aggtcgtaa aggtcgtaa atagatgga
tttgagaga ggtgtcaaa ctcgtcaaca cgtcagtca ttacgaccaa atgtcagcaa tttcttga
tgaccaacc gttaactgt ctaaggaacg ttacgaccaa atgtcagcaa tttcttga SEQ ID NO: 44
Asp Ser Asn Gln Gly Asn Asn Gln Gln Asn Tyr Gln Gln Tyr Ser Gln Asn Gly Asn Gln Gln Gln Gly Asn Asn
Arg Tyr Gln Gly Tyr Gln Ala Tyr Asn Ala Gln Ala Gln Pro Ala Gly Gly Tyr Tyr Gln Asn Tyr Gln Gly Tyr Ser
Gly Tyr Gln Gln Gly Gly Tyr Gln Gln Tyr Asn Pro Asp Ala Gly Tyr Gln Gln Gln Tyr Asn Pro Gln Gly Gly Tyr
Gln Gln Tyr Asn Pro Gln Gly Gly Tyr Gln Gln Gln Phe Asn Pro Gln Gly Gly Arg Gly Asn Tyr Lys Asn Phe

SEQUENCE LISTING

-continued

Asn Tyr Asn Asn Leu Gln Gly Tyr Gln Ala Gly Phe Gln Pro Gln Ser Gln Gly Met Ser Ser Leu Asn Asp Phe
Gln Lys Gln Lys Gln Ala Ala Pro Lys Pro Ala Gly Phe Leu Lys Thr Leu Lys Val Ser Glu Ala Ile Lys Leu Ala
Asn Ala Thr Lys Lys Val Asp Thr Lys Val Glu Glu Pro Ala Glu Ser Asp Lys Lys Glu Glu Lys Ser Ala Glu Thr
Glu Pro Thr Lys Glu Ser Glu Leu Pro Val Glu Gln Asp Leu Lys Leu Ile Ser Glu Glu Thr His Asn Thr Asn Ala Asn
Val Thr Ser Ala Asp Ala Leu Ile Lys Glu Lys Ile Glu Glu Val Asp Asp Val Val Asn Thr Met Gly
Gly Lys Asp His Val Ser Ile Phe Met Gly Val Asp Ala Gly Leu Ser Thr Met Gly Tyr Asn Leu Leu
Tyr Leu Thr Gly Val Asp Lys Arg Ile Glu Ala Thr Ile Glu Leu Gly Val Lys Glu Val Gly Lys Ala Tyr
Phe Glu Thr Trp Val Met Asp Thr Asn Ala Gly Arg Asn Asp Gly Val Glu Ala Gly Lys Ile Glu Met Tyr Ala Gly Trp
Ala Ser Gln Ala Arg Val Gly Arg Tyr Val Leu Ile Ser Ala Arg Lys Gly His Met Tyr Gly Phe Glu Arg Ile Gly Gly
Gln Thr Arg Glu His Ala Leu Leu Ala Lys Thr Gln Gly Val Asn Lys Val Met Val Val Val Ala Asn Val Gly Gly
Asp Pro Thr Val Glu Trp Ser Leu Lys Arg Tyr Asp Gln Cys Val Ser Asn Val Ser Arg Asn Phe Leu Val Met Lys Asp

SEQ ID NO: 45
atggactcta accaggqtaa caaccagcag aactaccagc agtactctca gaacgtgtaa cagcagcagg gtaacaccq
ttaccaggqt taccaggcct acaacggtca ggctcaqcag gctggtgqgtt actaccagaa ctaccaggt tactccggat atcaacaggq
tggtaccaa caatataatc cagacgctgg ctatcaacag aaaaacttca cgccaqcac ttaccagcag tacaaccgc aaggcggata
tcaacaccag ttcaatccgc aggtgqtcg aggtgqtcg tggtaactac oacctgcag gattacaqg ctggttaa SEQ ID NO: 46
Met Asp Ser Asn Gln Gly Asn Asn Gln Gln Asn Tyr Gln Gln Tyr Ser Gln Asn Gly Asn Gln Gln Gln Gly Asn
Asn Arg Tyr Gln Gly Tyr Gln Ala Gln Asn Ala Gln Ser Gln Gly Val Tyr Arg Gly Tyr Gln Gln Tyr Gln Gly Tyr
Ser Gly Tyr Gln Gln Gly Gly Tyr Gln Gln Tyr Asn Pro Asp Ala Gly Tyr Gln Gln Gln Tyr Asn Pro Gln Gly Gly
Tyr Gln Gln Tyr Asn Pro Gln Gly Gly Arg Gly Asn Tyr Lys Asn Phe Asn Tyr Asn Asn Asn Leu Gln Gly Tyr Gln
Phe Asn Asn Ser Ser Ser Asn Asn Asn Asn Asn Ser Ser Ser Asn Asn Asn Asn Val Gln SEQ ID NO: 47
atggactcta accaggqtaa caaccagcag aactaccagc agtactctca gaacggtaac cagcagcagg gtaacaacgg ataccagggt
taccaggcaa acgccagtca gqgctcagqgt ctatcaacag aaaaacttca ctccaqqgg ttaccagcag caactgcag gttgqacaac agqgacacaq
caagatcqqgc atttqqtaccg qcttqqqqaaq ccqtqqqcaaa qacacqqtc tqqqcaaaqqt qaaqqaqatc aaaaqqacqqqc qcaaactqqq
taacaaaatt attaattqa qttqtttat qctqqqctqqc qcqqctaactqt qcattqqqaac ttqqaqaqc aqqtqaqac aqqaactqaq
cqtqqaaaa caqaqaaqc tqcaqattqa tqqatccqca cccqaqcc tttatcqccq qqctqqcqt ttacqtqat taccqaaatc aaccqaqcq
ttatttttct qctqaaqca qaatcctqaa qtattctqaq aacccqaaqq cqcaataca cccqcaaccq caqqctctac cqttaaqtq aqcqacqaaa
qqctattcct qqaqcctqct aactttctqq cqqqttctqq caqqctctac caqqctctac cqttaaqtc atcqtqaacq
tqaqqqtqa tccaaqcatc qcqqaaqcq aaatcattcq caqcatqaaa taaqtcqacq c SEQ ID NO: 48
Met Asp Ser Asn Gln Gly Asn Asn Gln Gln Asn Tyr Gln Gln Tyr Ser Gln Asn Gly Asn Gln Gln Gln Gly Asn
Asn Arg Tyr Gln Gly Tyr Gln Ala Gln Asn Ala Gln Ser Gln Gly Val Tyr Arg Gly Tyr Gln Asn Pro Gln Gly Tyr
Ser Gly Tyr Gln Gln Gly Gly Tyr Gln Gln Tyr Asn Pro Gln Gly Gly Tyr Gln Gln Gln Phe Asn Pro Gln Gly Gly
Phe Asn Gln Tyr Asn Ser Asn Asn Leu Gln Gly Tyr Gln Asn Gln Ala Ala Leu Asn Gly Ile Met Lys Asn Asn Gln
Gly Lys Ser Thr Val Leu Ala Thr Leu Ala Lys Leu Gly Tyr Ala Leu Tyr Lys Leu Gly Ile Lys Asn Asn Val Glu
Asp Phe Met Leu Ala Leu Gln Lys Leu Asp Ala Lys Ile Leu Ile Glu Val Lys Arg Gly Met Ala Arg Lys Leu Phe
Lys Ile Asp Thr His Ala Val Ile Glu Leu Asn Ser Gly Tyr Val Leu Pro Ser Leu Pro Gly Leu Tyr Val Ile Asn Pro
Ser Val Ile Phe Leu Glu Ala Asp Pro Lys Ile Leu Ser Arg Gln Lys Leu Ser Arg Gly Tyr Asp Thr Thr Arg Asn Arg Asn

```
Asp Tyr Ser Asp Glu Ser Val Ile Leu Glu Thr Ile Asn Phe Ala Arg Tyr Ala Ala Thr Ala Ser Ala Val Leu Ala
Gly Ser Thr Val Lys Val Ile Val Asn Val Glu Gly Asp Pro Ser Ile Ala Ala Asn Glu Ile Arg Ser Met Lys

SEQ ID NO: 49
atgagagtcg gcattgtgac cgcattccg ggcgttggca aaagcaccgt tctgcacaa gtgaaggaga tctggcacat ccaggcgatt
aataacaaaa ttattaatta tgtgattt atgcggcga gtgcagatc gatgcggcga cagagaaaga tccgcgctgaa gctggctac gcaaagatc gtgacgaaat gcgcaaactg
agcgtggaaa aacagaagaa gtgcagatt gatgcggcga aggcattgc ggaagaggca cgcgcgggcg gtcttacgtg cgaaagctca
cctgttttatc gatacccatg cgtgatcg caccccagc ggttatctgc cggcctgcc accccgatac gtcctacgtg attacggaaa tcaacccgag
cgtattttt ggctgtgagg cagatccgaa gattatctg agcccgcaa agcgcgctga accccgcga cgcaaacgct atagcggcga
aagcgtatc ctgagacca tcaactttgc gcgctatgcg gcaaccgcga acagtgcag atgaacctgc ggcaggctct accgttaag tgatcgtgaa
cgtgaggt gatccagca cgcagcagca tcgcggcgaa cgaaatcatt cgcagcagca aacagtcgag tatggacttc aaccaggta
acaaccagca gaactaccag cagtacttc agaacgtaa ggtaacaacc gttaccaggt ttaccaggct
tacaaccgtc aggctaccg gggtggtgt tactaccaga actaccaag ttactccgg tatcaccagg gtggctacca acaatataat
ccagaggctg gctatcaaca gcaatataat cctgagggtg gtacccagca gtacaaccg caaggcggtt atcaacaaca gttcaatccg
caggagtggtc gtgtaacta caaaactgc aactacaaca gggttaccag gctggtttaag tcgacgc SEQ ID NO: 50
Met Lys Ile Gly Ile Val Thr Gly Ile Pro Gly Val Gly Lys Ser Thr Val Leu Ala Lys Val Leu Asp Ile Leu Asp Asn
Gln Gly Ile Asn Asn Lys Ile Ile Asn Tyr Gly Asp Phe Met Leu Ala Thr Ala Leu Lys Ala Lys Tyr Ala Lys Glu Glu
Arg Asp Arg Met Arg Lys Val Leu Ser Glu Val Gln Lys Gln Lys Leu Gln Leu Asp Ala Ala Thr Arg Pro Ser Gly Tyr Leu Pro Gly
Ala Arg Ala Ala Gly Ala Gly Gly Tyr Val Ile Phe Ile Asp Thr His Ala Val Ile Arg Thr Pro Ser Gly Tyr Leu Pro Gly
Leu Pro Ser Tyr Val Ile Thr Gly Glu Tyr Ser Val Ile Phe Leu Phe Leu Glu Ala Asp Pro Lys Ile Ile Asn Phe
Arg Gln Lys Arg Gln Lys Thr Arg Ala Ser Arg Asn Arg Val Ala Gly Val Ile Leu Val Asn Val Gln Gly Asp Pro
Ala Arg Tyr Ala Ala Thr Ala Ser Ala Val Leu Ala Gly Ser Thr Val Lys Val Ile Val Asn Val Glu Gly Asp Pro
Ser Ile Ala Ala Asn Glu Ile Arg Ser Met Lys Gln Ile Asn Ser Ser Met Arg Thr Arg Arg Ser Asn Gln Gln Asn
Tyr Gln Gln Tyr Ser Gln Asn Gly Tyr Tyr Gln Gln Tyr Gln Gln Tyr Ser Gln Ala Tyr Asn Ala
Gln Ala Gln Pro Gly Ala Gly Tyr Gly Gly Tyr Gln Gln Tyr Gln Gln Tyr Asn Pro Gln Gly Tyr Gln Gly Tyr
Asn Pro Asp Ala Gly Tyr Asn Gln Gln Tyr Asn Pro Gly Tyr Lys Asn Tyr Asn Asn Asn Leu Gln Gly Tyr
Gln His Gln Phe Asn Pro Gly Val Arg Gly Tyr Gln Gln Gln Phe Asn Tyr Lys Asn Asn Asn Leu Gln Gly Tyr
Gln Ala Gly SEQ ID NO: 51
atggactcta accaggta caaccagcag aactaccag agtactctca gaacgtaac cagcagcagg gtaacacccg
ttaccaggct taccaggt acaacgcct actaccaggt actaccagga ctaccggt taccccgg atcagcaag
tggctaccca caatataat cagaagctgg ctatcaacag ctatcaacag caattacttc tacccggtag ctgaattat
tcaacaaccg ttcaatccgc aggtgtgtca caaaagtac atgcaggc caacctcag gttaccaac atcaccggca tccgcacat
gatgcctat ctgttttc ttgggtacc ggggcaggc caaaaaagaa aatgcggca aattagagca gccgcagtt
tagcacggc gacatttc gtgatattgt caaacagtgt taggattgca aggagttcga acgtgcttt attttggacg tgttccccg
ggtgccggga gaactggta atgaagtgat tctccgagg cttcctgaag aggagttac gctgcggtc ctgttcgag tgcccgaaga
cagtagctc cagcagtcgt cegcggcga ttatctcccg gtattggtc gtattacaa cctgattca cttcctccaa aagaagatga
actgtgtgt gactgcaag taaaactgt gcaaaatgcg agaaactgt tgacccatgc gccaatgcg tacaaagtat tctgcgaaaa
aacccaccg gttatcgatt attatgataa aaaaggcatt aggaatgat ttgagggac catccgcatc gataacgtga ttgccgaagt
tctcaaaatc attggtttga gtgataata g SEQ ID NO: 52
Met Asp Ser Asn Gln Gln Asn Tyr Gln Gln Tyr Ser Gln Asn Gly Asn Gln Gln Gln Gly Asn
Asn Arg Gly Tyr Gln Gln Tyr Asn Ala Gln Ala Gln Pro Gly Ala Gly Tyr Gln Asn Tyr Gln Pro Gln Gly Tyr
Ser Gly Tyr Gln Gly Tyr Asn Pro Gln Asp Ala Gly Tyr Asn Gln Gln Tyr Asn Pro Gln Gly Tyr Asn Gly Tyr
Phe Asn Tyr Asn Asn Asn Leu Gln Gly Tyr Gln Ala Gly Ile Met Met Ala Tyr Leu Val Phe Leu Val Pro Pro
```

-continued

SEQUENCE LISTING

Gly Ala Gly Lys Gly Thr Tyr Ala Lys Arg Leu Gln Glu Ile Thr Gly His Ile Ser Thr Gly Asp Ile Phe Arg
Asp Ile Lys Val Glu Asn Asp Leu Gly Leu Arg Leu Gly Lys Ile Lys Met Glu Arg Gly Ile Glu Leu Val Pro Asp
Glu Leu Val Asn Gln Val Lys Ser Glu Leu Asp Lys Cys Thr Gln Asn Lys Asp Phe Ala Leu Asp Gly Tyr
Pro Arg Thr Val Ala Gln Ala Glu Ala Leu Asp Gly Phe Leu Lys Thr Ala Arg Arg Ile Glu Cys Pro Lys Cys Gly Arg Ile Tyr
Leu Phe Glu Val Pro Glu Val Val Lys Asp Arg Leu Val Val Leu Cys Asp Lys Cys Lys Lys Leu Val Gln Arg Glu Asp Val
Asn Leu Ile Ser Leu Pro Pro Lys Glu Asp Tyr Lys Val Tyr Leu Glu Lys Thr Gln Pro Val Ile Asp Tyr Tyr Asp Lys
Asp Lys Gly Glu Leu Thr Val Arg His Arg Gly Ile Ile Gly Asn Val Ile Ala Glu Val Ile Leu Lys Ile Gly Trp Ser
Asp Lys

SEQ ID NO: 53

Ala Thr Gly Ala Thr Gly Cys Cys Thr Ala Cys Thr Gly Gly Thr Ala Ala Gly Ala Thr Cys Thr Thr Gly Gly
Thr Gly Cys Cys Gly Cys Gly Gly Cys Gly Gly Cys Cys Ala Cys Ala Thr Gly Ala Gly Ala Cys Ala Gly Gly
Thr Gly Cys Gly Gly Cys Cys Ala Thr Cys Ala Cys Gly Cys Gly Cys Cys Ala Cys Ala Thr Ala Cys Cys Ala
Gly Ala Cys Ala Gly Cys Cys Gly Cys Gly Cys Gly Cys Gly Ala Cys Gly Ala Thr Ala Gly Cys Thr Gly Ala
Gly Ala Cys Gly Cys Cys Ala Ala Cys Thr Ala Cys Ala Gly Cys Cys Gly Ala Ala Thr Gly Ala Thr Ala Ala
Thr Gly Cys Ala Thr Gly Ala Ala Thr Gly Gly Cys Cys Ala Thr Ala Gly Cys Ala Thr Gly Ala Gly Ala Gly
Thr Gly Cys Ala Cys Gly Gly Ala Gly Cys Ala Gly Ala Cys Cys Cys Gly Ala Gly Cys Ala Gly Gly Ala Gly
Ala Cys Gly Cys Cys Thr Ala Gly Gly Ala Thr Gly Cys Cys Ala Thr Ala Cys Ala Gly Cys Thr Thr Gly Gly
Ala Gly Ala Cys Ala Gly Cys Thr Ala Cys Gly Cys Gly Thr Gly Thr Cys Ala Cys Cys Ala Gly Thr Gly Ala
Thr Gly Cys Gly Thr Cys Gly Cys Gly Thr Gly Thr Cys Thr Gly Cys Gly Thr Ala Gly Cys Cys Cys Thr Gly
Gly Gly Cys Cys Gly Cys Gly Thr Cys Ala Cys Gly Thr Ala Thr Cys Ala Gly Cys Ala Thr Ala Cys Gly Gly
Gly Cys Thr Cys Gly Thr Cys Thr Ala Ala Ala Ala Thr Cys Ala Cys Gly Cys Ala Gly Thr Gly Cys Cys Gly
Cys Cys Thr Cys Gly Thr Ala Cys Thr Cys Gly Ala Ala Ala Thr Ala Cys Ala Ala Gly Thr Cys Ala Cys Cys
Gly Cys Cys Gly Cys Cys Gly Cys Thr Ala Ala Ala Gly Gly Ala Gly Cys Gly Thr Cys Gly Gly Thr Cys Thr
Cys Cys Gly Cys Cys Cys Ala Ala Cys Ala Gly Cys Gly Cys Cys Ala Thr Gly Thr Cys Gly Gly Thr Ala Cys
Thr Ala Thr Cys Gly Thr Cys Cys Ala Cys Gly Cys Ala Ala Ala Cys Ala Thr Ala Cys Gly Gly Cys Ala Gly
Cys Cys Thr Cys Gly Thr Ala Cys Gly Gly Cys Thr Ala Cys Gly Gly Cys Ala Cys Cys Ala Thr Thr Thr Ala
Ala Gly Ala Cys Cys Gly Gly Gly Gly Ala Thr Ala Cys Ala Gly Cys Thr Ala Cys Ala Thr Thr Thr Ala Gly
Gly Thr Cys Cys Gly Gly Cys Ala Gly Gly Cys Cys Thr Cys Gly Gly Ala Cys Thr Ala Ala Cys Gly Gly Gly
Cys Ala Cys Gly Thr Cys Ala Ala Gly Ala Thr Cys Cys Gly Cys Cys Ala Thr Ala Cys Thr Ala Cys Ala Ala
Thr Cys Ala Ala Thr Cys Thr Ala Cys Ala Cys Thr Ala Gly Cys Ala Ala Ala Cys Cys Thr Ala Thr Ala Cys
Gly Gly Gly Gly Gly Cys Cys Gly Gly Cys Cys Cys Ala Gly Gly Cys Thr Gly Cys Ala Cys Cys Thr Gly Gly
Cys Cys Gly Cys Ala Cys Cys Ala Cys Gly Thr Cys Ala Cys Cys Cys Ala Ala Ala Cys Ala Cys Thr Ala Gly
Gly Thr Thr Ala Cys Ala Ala Gly Cys Cys Gly Cys Gly Cys Thr Cys Ala Ala Cys Ala Gly Thr Gly Cys Gly

Cys Ala Gly Gly Gly Thr Gly Gly Thr Gly Cys Gly Thr Ala Cys Ala Ala Ala Ala Ala
Cys Thr Cys Ala Ala Cys Thr Ala Ala Cys Ala Ala Cys Thr Ala Cys Thr Gly Cys Gly
Gly Gly Thr Gly Thr Ala Cys Cys Ala Gly Cys Gly Gly Thr Cys Thr Gly Cys Gly Gly
Cys

SEQ ID NO: 54
Met Met Ala Tyr Leu Val Phe Leu Gly Pro Pro Ala Gly Gly Tyr Ala Lys Arg Leu Gln
Gly Ile Pro His Ile Ser Thr Gly Asp Ile Phe Lys Val Lys Glu Asn Asp Gly Leu Lys
Lys Glu Met Glu Arg Ala Gly Leu Leu Asn Ala Val Val Lys Arg Arg Leu Ser Glu
Lys Asp Cys Glu Arg Gly Phe Ile Leu Asp Tyr Pro Arg Thr Val Ala Gln Ala Glu Phe
Leu Lys Thr Gln Asn Lys Ile Leu Thr Ala Ala Leu Pro Arg Val Leu Phe Leu Arg Leu
Thr Ala Arg Arg Ile Cys Pro Lys Cys Gly Arg Ile Tyr Asn Leu Ile Ser Leu Pro Pro Lys Asp Leu Cys
Asp Asp Cys Lys Leu Val Leu Gln Arg Glu Val Gly Glu Thr Val Arg His Arg Val Tyr
Leu Glu Lys Thr Gln Pro Val Ile Leu Lys Leu Lys Ile Gly Ile Leu Arg Val Asp Gly Thr Ile Gly Ile
Asp Asn Val Ile Ala Glu Leu Lys Ile Ile Gly Trp Ser Leu Lys Ser Ser Met Asp Ala Arg Val Gln Ala Gln Gly Asn
Ala Tyr Asn Ala Ile Ala Gln Pro Gly Gly Val Gly Gln Ala Gly Val Tyr Ser Arg Gln Gln Gly Gly
Tyr Gln Gln Tyr Asn Pro Asp Val Gly Leu Tyr Gln Gln Gly Gly Tyr Gly Gln Gly Gly Gly Gly Gly Gly
Gln Gly Gly Tyr His Gln Phe Asn Pro Gly Arg Gly Asn Tyr Lys Asn Phe Asn Asn
Leu Gln Leu Tyr Gln Ala Gly

SEQ ID NO: 55
ggtaacaacc agcagaacta c

SEQ ID NO: 56
Gly Asn Asn Gln Gln Asn Tyr

SEQ ID NO: 57
atgatgatgg cgtctaagga cgtactcatca agcgtgatg gcgtagtcag cgactgatg ttctgaccct
cttagactgt atcctgtacg aggttctctg acagcagtg ccaagcatc ccatcttaat ccattcttgc
gtcaagccc cccaagagtg attacatt aatggtggg ttgtaacat cgattctggg gtttggtcc ggagatatta
tccatctatc acaccctct ggttttgt cacatatct caagcaactc ccttccaca tgtactgcg gatgtaga
tagttccctg cattgagg ccttgaga atgttagaa tactatagca tgtttccaa acaaaccatg cgcctgtgt
ctctaggaac cattgaggg cccttgagaa tgttagaa catatataag ttcactacta acaaaccatg cgcctgtgt
gcatgctgta cacccccctc cgcactgtg gtggtactgg ttcacactcc caatctgcc atgagtct gactctgcc agtcctgat ttaattctt
gttttagtc ccctacgg tgagcagaa aaccaggcc agacactgt cagagctgc atgagtct tgagtcggtg actctgatg gccgctgt
tggcaccac ccagtttcat gcattccc tcaccatgt tgccaagata agaggacct tcaatcaac cttactgaat tggatggcc
accctttcac agtagtatg gcactgccc cattgggct ccagcctcg gtggttgta cccatcttgg tcaatcaag aatatgact agtttggcca
ttcagcagc accagtgtt gtgcaacac atctagcc cctctgttc tccggattc gctccaaagt tgacctttg atggtcttt tcaatgccag attggggtc
aagtattacc gagcaacac atctagccc cctgtctatt accacaagag tacatttcac atctgctac tgaacaagcc cctactgtg gtgaggccag
tccctgtgct tataattgt ccgtctatt ctgataccg tcggaatctt gggaattga aagcataccc ctactgttc tcccaatgg
cctgtccac tatgtgacc agtccgcgat caatgggtc tttgtcttg tttcatgggt gtccagattt tatcaattaa agcctgggg
ggcagctcg ggtccacac agtccgcgat caatgggtc tttgtcttg tttcatgggt gtccagattt tatcaattaa agcctgggg
aactgccagc tcggcaagag gtaggcttgg tctgcgccga taa SEQ ID NO: 58
Met Met Ala Ser Lys Asp Ala Thr Ser Ser Val Asp Gly Ala Ser Gly Ala Gly Gln Leu Val Pro Glu Val
Asn Ala Ser Asp Pro Leu Ala Met Asp Pro Val Ala Gly Ser Ser Thr Ala Val Ala Thr Ala Gly Val Asn
Pro Ile Asp Pro Trp Pro Val Phe Asn Ala Pro Gln Gly Phe Thr Ile Ser Pro Asn Asn Thr Pro

SEQUENCE LISTING

Gly Asp Val Leu Phe Asp Leu Ser Leu Gly Pro His Leu Asn Pro Phe Leu Leu His Leu Ser Gln Met Tyr
Asn Gly Trp Val Gly Asn Met Gly Arg Val Arg Ile Met Leu Ala Phe Leu Thr Ala Gly Lys Ile Ile Val Ser
Cys Ile Pro Pro Gly Phe Ser His Asn Leu Thr Ile Ala Gln Val Ala Arg Asn Val Leu Phe His Asn Asp Arg Gln
Arg Thr Leu Asp Pro Ile Glu Val Pro Leu Tyr Thr Pro Leu Glu Arg Thr Phe Gly Gly Tyr Gly Asp Ser Phe Val
Gln Met Arg Arg Leu Val Cys Met Leu Tyr Val Met Thr Gly Phe Gly Phe Asn Val Pro Leu Pro Gly Gln Lys
Ala Gly Arg Val Met Thr Cys Pro Ser Pro Asp Phe Asn Leu Phe Val Pro Arg Ala Pro Leu Pro Ile Ser Ser
Thr Arg Pro Phe Leu Pro Asn Leu Pro Leu Gln Asn Val Gln Phe Gln Ile Asn Gly Arg Cys Thr Leu Asp Arg Leu
Met Gly Ile Ser Pro Asp Ala Asn Val Ser Leu His Val Ala Lys Ile Ala Phe Ser Ala Asn Gly Thr Val Ile Asn Leu Thr
Val Gly Leu Asp Gly Thr Pro His Pro Phe Glu Gly Pro Ala Pro Ile Gly Phe Pro Asp Leu Gly Gly Cys Asp
Glu Leu Asp Gly Ile Asn Met Thr Gln Met Ser Gln Ile Tyr Gln Thr Val Asp Thr Val Leu Gly Trp Asp Thr Phe
Trp His Ile Leu Gly Ser Ile Ala Asn Gly Ile Leu Gly Ser Gly Ile Ser Ile Tyr Val Leu Gly Ile Ser Val Leu Thr Ser Pro
Val Pro His Leu Pro Ser Gly Gln Leu Trp Leu Pro Asn Tyr Val Ser Ile Pro Tyr Asn Tyr Ser Ser Ile Thr Glu Ala Thr His
Pro Ser Pro Val Tyr Pro Gly Pro Phe Gly Val Val Leu Leu Val Val Phe Phe Met Pro Ala Lys Met Ser Pro Gly Pro Gly
Leu Ala Pro Ser Leu Pro Cys Leu Pro Gln Glu Tyr Ile Leu Ser Leu His Ala Ser Glu Glu Gly Gln Ala Pro Thr Val Gly Glu
Ala Tyr Asn Leu Leu His Tyr Val Asp Pro Gly Thr Gly Arg Asn Leu Gly Leu Phe Lys Ala Tyr Pro Asp Gly Phe Leu Arg
Leu Thr Cys Tyr Pro Asn Gly Ala Ser Ser Gly Pro Gly Gly Pro Ile Asn Gly Val Leu Phe Val Leu Ala Arg
Trp Val Ser Arg Phe Tyr Gln Leu Lys Pro Val Gly Val Thr Ala Ser Ala Ala Arg Arg Leu Arg Arg

SEQ ID NO 59
atgatgatgg cttctaaaga cgtacctcct tctgttgacg ctgttctgcg aagttccgg ttctgacccg
ctggtcaggg accggttgc tggtttcttct accgctgttg ctaccgctgg ccgatcgac cgtgatcat caacaacttc
gttcaggctc cgcagggtga attccaccatc tctccgaaca acaccccggg tgacgttctg ttcgacctgt tctctggttc gcacctgaac
ccgttcctgc tgcacctgtc tcagatgtac aacggttggg ttggtaacat gctgcttcgt atcatgctgg ccgatcgct
ggtaaaatca tcgttctctg cagtccccg ggtttcggtt cgcgtgaag ctgctcgttc cacaacaaog agagaccatg cgttcccgca cgttatcgct
gacgtcgta ccctggaccg gatcgaagtt gcatgctgta cgtctgttc acgtgaacatg accccggacc tgctgtgcag
cgtctggttt gcatgctgta tcaactccct gtctcggtt ctgtaccgc ccgtcttctatg gtctgttctg cgaactgcg gtctcttct
tctccggact ctggcttct gtgccgatc tctctatgg ctatcctcc ggaacacgtt cagctctgtc agtccggag
aaccccggat gtcgctgc tgtaccacc cctctctcac tgtcctgct acctgttac cgtattcaac ctaacggtac cgtattcaac
cctgaccgaa ctggaccggg ccgttccac cctctccag agtccgctcc ctgacac cctgacac cctgacac ctgttccgg gtgatccgt
aacatgaccc agtccggtca tcggtcctg taactacgtt gtgtttcgt gtctgttcgt cctgtcct gtgacctgct
gctaacgta actacggtc tttataacc gaagctcgca accggttcc gtctgttac ccgtgtgag ttggcgtg tctcgtttc
aaaatccccgt aaatgccggg tccggttgct tacaacctgc tacaacctgc gccgaggaa tacatctccc aagctaccc tgaacaggct
ttcatgtcta gtgaagctgc ctgtgcac tacgtgacc cgtgtcgac agctccgagc caacggtgtt ttcgtttcg gtgacgttcc
ccgaccgtgc ttccgaacgg tgcttctct ggtccggag gtcgtccgtg gtcgctgtg tag
aaccggttgc tacgcttct tcgtcgtg ctgcgtcgg cgttccatg agaatccgtg cgcttctgg tcgtccggga agcggcccc actgcccgg SEQ ID NO 60
atgatgatgg cttctaaaga cgtacctcct tctgttgacg ctgttctgcg aagttccgg ttctgacccg
ctggtcaggg accggttgc tggtttcttct accgctgttg ctaccgctgg ccgatcgac cgtgatcat caacaacttc
gttcaggctc cgcagggtga attccaccatc tctccgaaca acaccccggg tgacgttctg ttcgacctgt tctctggttc gcacctgaac
ccgttcctgc tgcacctgtc tcagatgtac aacggttggg ttggtaacat gctgcttcgt atcatgctgg ccgatcgct
ggtaaaatca tcgttctctg catccccggg tgacgtgaag ctgctcgttc cacaacaaog cgtctcgttc gcagaccaag
gacgtcgta ccctggaccg gatcgaagtt gcatgctgta cgtctgttc acgtgaacatg accccggacc tgctgtgcag
gcagaccatg cgtctggtta accagggcta caccccgga gccggacacg cgtaaccatg tgactcttc gtgacctgct gtcgtttgat
gacctgccg tcccggact tcaactcct gtcctggtt ctaacttcct gtccgatcc tcccgaccg ttgaacagaa acccgttcc ttcacccgg cagtcctgtc ctaacctgcc agttccaga cgttatcaac
gctcttcct gtccggttct ctgctgtct cgttccgatc tcttctcttc tgtccggttc cggtccggtc ctaaaatc cggtacct ctaacggttc ctgtatcaac
acctgaccg gtgtctgtgt tgtaccaccg ccggttccacc ccggttccac cgttccaag gttccgacag cgttaccagg agtaaagtcc atgtgcacct
ctgaccgaac tggactggtg accggttctg gatcgctcgc gtcggctcc gtccgaatc cgatcgttca ccggacacgg gttctacaa ctgcgtcgt gttcgaccc cggctgc

SEQ ID NO: 61

Met Met Ala Ser Lys Asp Ala Thr Ser Ser Val Asp Gly Ala Gly Gln Leu Val Pro Glu Val
Asn Ala Ser Asp Pro Leu Ala Met Asp Pro Val Ala Gly Ser Ser Thr Ala Val Ala Gly Gln Leu Asn
Pro Ile Asp Pro Trp Ile Leu Phe Asp Asn Phe Val Gly Ser Gln Pro His Leu Asn Pro Phe Leu His Glu Thr Ile Leu Ser Gln Met Tyr
Gly Asp Val Leu Phe Asp Leu Ser Leu Gly Pro Val Pro Val Phe Val Asp Ile Cys Leu Asp Val Pro Phe Leu Leu Asn Ala Gln Phe Pro His Leu Phe Ile Ile Val
Asn Gly Trp Val Gly Asn Met Arg Arg Val Arg Phe Met Ile Met Asn Leu Ala Thr Leu Met Phe Pro His Val Ile Ala Asp Val
Cys Ile Pro Pro Gly Phe Ser His Asn Leu Thr Ile Ala Gln Val Ala Arg Val Ala Asn Val Arg Phe Gly Asp Ser Phe Val Ala Asp Gln
Arg Thr Leu Asp Pro Ile Leu Val Pro Leu Glu Asp Val Arg Thr Gly Gly Gly Thr Gly Gly Gly Thr Gly Gly Thr Gly Thr Leu Val Pro Glu Val Asn
Gln Thr Met Arg Leu Cys Met Leu Tyr Thr Pro Ser Pro Ala Phe Pro Leu Phe Asn Ala Arg Ala Pro Thr Val Pro Thr Val Glu Gln Lys
Thr Arg Pro Phe Leu Pro Asn Leu Pro Ser Pro Asn Leu Ser Pro Val Ala Val Val Ala Val Val Ala Pro Leu Pro Ile Ser Ser
Met Gly Ile Ser Pro Val Asp Asn Val Gln Phe Gln Asn Gly Arg Cys Thr Leu Asp Gly Tyr Val Ile Asn Leu Thr Pro Val
Gly Thr Thr Pro Val Ser Leu Ser His Pro Ala Lys Ile Leu Arg Gly Thr Ala Asn Gly Tyr Val Ala Gly Ile Gly Cys Ser Asp Trp Glu
Leu Pro Phe Thr Pro Phe His Pro Phe Ala Gly Leu Pro Phe Gly Tyr Arg Pro Pro Val Gly Ile Gly Phe Gly Pro Gly Asn Gly Thr Pro Leu Ile Gly Cys Ser Asp Trp Glu
His Ile Asn Met Thr Gly His Phe Ile Met Asn Gly Ile Tyr Gly Ile Phe Gly Asn Val Pro Pro Gly Val Gly Asp Gln Thr Gly Thr His Pro Phe Val
Pro His Leu Gly Ser Ile Gly Ala Asn Leu Ala Asp Ile Gly Ser Gly Phe Val Val Gly Val Leu Ser Pro Pro Pro Gly Val Ile Ile Thr Ala Thr His Leu
Ser His Pro Ser Gly Val Asp Asp Pro Gly Phe Met Asp Val Phe Met Ser Pro Gly Gly Pro Gly Ser Pro Pro Gly
Ala Tyr Asn Leu Pro Cys Leu Glu Pro Gly Phe Asp Tyr Ile Leu Ser Val Phe Leu Val Leu Asn Asp Val Val Leu Asn Asp Val Val Ala Gln Ala Pro Thr Val Pro Asp Val Gly Phe
Ala Ala Leu His Tyr Val Asp Pro Asp Ser Gly Pro Asp Gln Ile Asn Gly Ile Leu Pro Asn Ala Ser Ser Ala Arg Gly Val Leu Arg Gly Val Phe Val Ser
Leu Thr Cys Val Pro Asn Gly Ala Ser Arg Phe Tyr Gln Leu Pro Arg Gly Val Val Ala Thr Thr Tyr Ala Leu Gly Leu Arg Gly Ile Leu Thr
Trp Val Ser Arg Phe Tyr Leu Phe Leu Gly Ala Lys Ile Leu Gly Thr Ala Ala Gly Leu Pro Ala Gly Leu Pro Thr Phe Ser Ser Thr Val Ala Leu Gly Leu Pro Ile Pro Ser Gly Leu Ile
Met Met Ala Leu Tyr Leu Phe Leu Gly Pro Pro Gly Ile Phe Glu Asp Asp Leu Leu Pro Ala Ser Ala Ala Leu Asn Ala Asp Leu Asn Ala Lys Leu Gln Leu Gln Leu Gly Glu Val Gln Val Gln Val Gln
Gly Ile Glu Pro His Ile Met Glu Thr Gly Asp Leu Arg Gly Leu Glu Leu Phe Ala Arg Ile Leu Pro Arg Leu Gly Leu Val Ala Val Asp Lys Val Asn Ala Gly Gln Lys Leu Arg Glu Leu Arg Phe Gln Pro Pro Pro Gly Leu Arg Pro Gly Ile
Lys Glu Ile Met Glu Leu Gly Phe Pro Arg Ile Leu Pro Arg Val Leu Val Val Asn Val Ala Leu Glu Pro Thr Arg Val Pro Val Pro Gly Leu Pro Gly Leu Pro Gly Gly Gly Leu Lys Phe Lys Pro Arg
Lys Ala Cys Glu Arg Gly Phe Pro Lys Leu Val Ala Leu Pro Arg Thr Pro Ala Leu Pro Leu Ala Leu Pro Leu Pro Val Pro Phe Ala Gln Glu Pro Leu Pro Pro Arg Thr Gly Phe Gln Leu Gln Arg
Leu Leu Lys Arg Gly Thr Val Ala Ala Ala Ala Arg Gln Leu Ala Arg Leu Ala Leu Ala Leu Val Ala Leu Val Val Val Val Gly Leu Ile Phe Pro Thr
Thr Ala Arg Arg Ile Cys Pro Lys Leu Val Gln Phe Arg Pro Asp Asn Asn Leu Tyr Asn Leu Ile Leu Ile Glu Leu Glu Pro Pro Lys Ile Tyr Lys Val Tyr
Asp Asp Cys Lys Lys Thr Lys Leu Pro Thr Tyr Leu Ala Tyr Thr Tyr Ser Tyr Val Arg Val Asp Asp Val Arg Val Tyr Tyr Glu Leu Gly Leu Leu Cys
Leu Glu Lys Thr Gln Ile Leu Ala Pro Phe Leu Lys Ala Asn Asn Gln Ile Leu Pro Arg Asp Arg Val Gln Leu Gly Arg Gly Leu Leu Leu Val Asp Tyr Val Ala Thr Leu Val Leu Val Leu Pro Ser Leu Leu Ile Ile Tyr Arg Gly Ile Ile
Asp Ala Asn Val Ile Ala Glu Val Val Val Leu Val Lys Ile Leu Ile Gly Gly Leu Pro Ser Asp Lys Val Lys Leu Pro Arg Gly Asp Val Gly Val Ser Thr Asp Gly Ile
Lys Pro Ile Leu Leu Asp Pro Leu Asp Lys Pro Ile Phe Asp Ile Trp Gly Ser Asp Lys

SEQ ID NO: 62

Met Ala Ser Asn Phe Thr Gln Phe Val Leu Val Asp Asn Gly Gly Gly Thr Val Lys Ala Gly Phe Gly Asp Thr Val Pro Ser Asn
Phe Ala Asn Gly Val Ala Lys Trp Ile Ser Ser Arg Arg Ser Arg Ser Gln Ala Tyr Lys Val Thr Lys Arg Gln Leu Tyr Val Cys Ser Val Arg Gln
Ser Ser Ala Gln Asn Arg Lys Tyr Thr Ile Lys Pro Lys Ser Val Ala Thr Leu Gln Thr Val Gln Thr Val Gly Val Gly Val Glu

SEQUENCE LISTING

-continued

Leu Pro Val Ala Ala Trp Arg Ser Tyr Leu Asn Met Glu Leu Thr Ile Pro Phe Ala Thr Asn Ser Asp Cys Glu
Leu Ile Val Lys Ala Met Gln Gly Leu Leu Lys Asp Gly Asn Pro Ile Ala Ala Asn Ser Gly Ile
Tyr

SEQ ID NO: 63
Ser Lys Thr Ile Val Leu Ser Val Gly Glu Ala Thr Arg Thr Leu Thr Glu Ile Gln Ser Thr Ala Asp Arg Gln
Phe Glu Glu Lys Val Gly Val Pro Leu Arg Leu Arg Val Leu Thr Ala Ser Leu Arg Gln Ala Asn Gly Ala Lys
Ala Tyr Arg Val Asn Leu Leu Lys Leu Asp Gln Gln Ala Ala Val Leu Arg Asp Val Asp Ser Gly Leu Tyr Arg
Lys Val Arg Thr Trp Asp Val Thr Ser Ile His Asp Val Ala Ile Ala Ser Cys Ser Thr Glu Ala Leu Pro Thr
Tyr Asp Leu Thr Ser Leu Val Leu Gln Ala Thr Ser Leu Val Asn Leu Pro Val Gly Leu Arg

SEQ ID NO: 64
Met Ser Leu Thr Ile Val Leu Ser Val Gly Glu Ala Thr Arg Thr Leu Thr Glu Ile Gln Ser Thr Ala Asp Arg Gln
Ile Phe Glu Glu Lys Val Gly Val Pro Leu Arg Leu Arg Val Leu Thr Ala Ser Leu Arg Gln Ala Asn Gly Ala Lys
Thr Ala Tyr Arg Val Asn Leu Leu Lys Leu Asp Gln Gln Ala Ala Val Leu Arg Asp Val Asp Ser Gly Leu Tyr Arg
Gln Val Trp Ser His Asp Val Thr Ser Ile His Asn Ser Thr Glu Ala Leu Pro Lys Tyr Asp Leu Tyr Asp Leu Thr
Ser Leu Val Ala Thr Gly Glu Gln Thr Leu Asn Val Leu Asn Ala Ile Gly Leu Phe Glu Lys Ile
Val Leu Ser Val Gly Leu Val Arg Leu Arg Val Leu Thr Ala Asn Gly Ala Lys Tyr Arg Val
Asn Leu Leu Lys Leu Asp Gln Gln Ala Ala Val Leu Arg Asp Val Asp Ser Gly Leu Tyr Arg
His Asp Val Thr Ile Val Val Asn Ala Thr Glu Ala Leu Pro Lys Tyr Asp Leu Thr Ser Leu Val Ala
Thr Ser Gln Val Glu Leu Asn Val Leu Pro Leu Gly Arg

SEQ ID NO: 65
Met Leu Leu Lys Val Ala Ala Ile Ala Leu Phe Ser Gly Ser Ala Leu Ala Gly Val Val Pro Gln Tyr
Gly Gly Gly Asn His Gly Gly Gly Leu Asn Ser Gly Asn Ser Ile Tyr Gln Tyr Gly Tyr Gly Asn
Gly Asn Ser Ala Leu Ala Leu Gln Thr Ile Asp Asp Thr Ile Thr His Gly Gly Asn Ser Ala Leu Thr
Gly Ala Asp Val Gly Ser Gln Ser Asp Asn Ser Ile Asp Leu Thr Gln Arg Gly Phe Gly Asn Gly Ala Ala Val Asp
Leu Asp Gln Trp Asn Gly Leu Lys Ala Asn Ser Gly Leu Met Thr Val Lys Gln Phe Gly Asn Gly Ala Leu Ala His Asp
Gln Thr Ala Ser Ser Asn Ser Val Asn Val Thr Gln Val Gly Phe Gly Asn Ala Asn Thr Ala His Ala Tyr

SEQ ID NO: 66
Met Lys Leu Leu Lys Val Ala Ala Ile Ala Leu Ala Val Ala Leu Ala Gly Val Val Pro Gln Trp
Gly Gly Gly Asn His Gly Gly Gly Leu Asn Ser Gly Ser Ile Tyr Gln Tyr Gly Tyr Gly Ser
Ala Asn Ala Leu Ala Leu Gln Thr Ile Asp Asp Gln Ile Thr Ala Val Asn Gly Gly Tyr Asn Ala Ile
Ala Asp Val Gly Ser Gln Ser Asp Asn Ser Ile Asp Leu Thr Gln Arg Gly Phe Gly Asn Ser Ala Ala Val Asp
Leu Asp Gln Trp Asn Gly Leu Lys Ala Asn Ser Gly Leu Met Thr Val Lys Gln Tyr Gly Phe Gly Asn Ala Leu Asn Ala His Asp
Gln Thr Ala Ser Ser Asn Ser Val Asn Val Thr Gln Val Gly Phe Gly Asn Asn Ala Thr Ala His Ala Gln Gln Tyr

SEQ ID NO: 67
Met Met Ala Tyr Leu Val Phe Leu Gly Pro Gly Ala Gly Lys Gly Thr Gln Ala Lys Arg Ile Ala Gln Glu Lys Thr
Gly Ile Pro His Ile Ser Thr Gly Asp Ile Phe Arg Ala Ala Ile Lys Glu Gly Thr Pro Leu Gly Leu Lys Ala Lys Ser Tyr Ile
Lys Glu Ile Met Glu Lys Gly Gln Leu Val Pro Asp Glu Leu Val Asn Glu Val Val Lys Arg Arg Leu Ser Glu
Lys Asp Cys Glu Lys Gly Phe Ile Leu Asp Gly Phe Pro Arg Thr Val Ala Gln Ala Glu Ala Leu Asp Ser Phe
Leu Gln Ser Gln Asn Lys Ser Leu Thr Ala Val Leu Leu Phe Asp Val Pro Glu Asp Val Val Val Gln Arg Leu
Thr Ser Arg Arg Ile Cys Pro Lys Cys Gly Arg Ile Tyr Asn Met Ile Ser Leu Pro Pro Lys Val Glu Gly Leu Cys
Asp Asp Cys Lys Val Lys Leu Val Gln Arg Ala Asp Asp Lys Glu Glu Thr Val Arg Asp Arg Tyr Ile Val Tyr
Leu Glu Lys Thr Gln Pro Val Ile Asp Tyr Tyr Gly Ser Lys Gly Ile Leu Arg Lys Val Asp Gly Thr Gln Gly Gly
Asp Glu Val Val Ala Glu Ala Thr Leu Val Leu Asp Lys Leu Asn Ser Gly Pro Lys Glu Leu Thr Phe Gly Gly
Gly Gly Asn Val Glu His Gly Gly Asp Leu Gln Leu Thr Asn Arg Gln Ile Tyr Gln Tyr Gly Tyr Gly Gly
Asn Ser Ala Leu Ala Leu Gln Thr Ile Asp Asp Arg Ala Asn Ser Leu Thr Ile Gln His Gly Gly Asn Gly Gly

SEQUENCE LISTING

SEQ ID NO: 68
Ala Asp Val Gly Gln Gly Ser Asp Asp Ser Ile Asp Leu Thr Gln Arg Gly Phe Gly Asn Ser Ala Thr Leu
Asp Gln Trp Asn Gly Lys Asn Ser Glu Met Thr Val Lys Gln Phe Gly Gly Ala Val Ala His Gln
Thr Ala Ser Asn Ser Asn Val Thr Gln Val Gly Phe Gly Asn Ala Thr

SEQ ID NO: 69
Met Gln Phe Ser Thr Leu Leu Phe Ala Leu Val Ala Ala Ala Pro His Gly Ser Ser Gly
Gly Asn Asn Pro Val Cys Ser Ala Gln Asn Gln Val Cys Cys Asn Gly Leu Leu Ser Cys Ala Val Gln Val
Leu Gly Ser Asn Cys Asn Gly Asn Ala Tyr Cys Asn Thr Glu Ala Pro Thr Gly Thr Leu Ile Asn Val Ala
Leu Leu Asn Cys Val Lys Leu Leu

SEQ ID NO: 70
Met Phe Ser Leu Ala Val Ala Leu Gly Ala Val Ser Ala Leu Pro Ala Leu Pro Ala Asn Glu Lys Arg Gln
Ala Tyr Ile Pro Cys Ser Gly Leu Tyr Gly Thr Ser Gly Cys Val Leu Val Leu Ala Asp Leu
Asp Cys Gly Asn Pro Pro Ser Ser Pro Thr Asp Ala Asp Phe Ser Ala Val Cys Ala Glu Ile Gly Gln Arg
Ala Arg Cys Val Leu Pro Ile Leu Asp Gln Ile Leu Cys Asn Ser Thr Pro Gly Val Gln Asp

SEQ ID NO: 71
Val Pro Pro Pro Cys Leu Ser Ile Lys Ser Leu Lys Gln Val Leu Lys Ser Gly Ala Thr Ala Gly Asn Ala Ala Val Thr
Thr Thr Gly Thr Thr Ser Gly Val Ala Val Lys Cys Val Val Arg Thr Pro Ser Val Glu Gly Lys Lys Ala Ala
Val Glu Lys Thr Gly Leu Asn Thr Ala Val Ser Ala Ala Asn Gly Pro Phe Pro Lys Asn Leu Gly Lys Ala Thr
Thr Thr Ile Gln Ile Ala Asp Ala Ser Gly Ala Asn Gly Val Leu Thr Lys Leu Lys Ser Leu Leu Asp Thr Gly Gly
Lys Phe Val Lys Val Thr Glu Asn Glu Ala Glu Ile Gly Lys Leu Ser Ser Gly His Lys Ala Ser Gly Val Gly His
Ser Val Phe Lys Val Leu Asn Leu Thr Glu Leu Glu Lys Gly Leu

SEQ ID NO: 72
Met Lys Trp Phe Leu Phe Leu Leu Thr Thr Ala Val Leu Ala Ala Val Val Ser Ala His Glu Glu Asp Gly Val
Cys Asn Ser Arg Asn Ala Pro Cys Tyr His Cys Asp Ala Asn Gly Ala Asn Ser Cys Gln Leu Phe
Asp Cys Glu Ala Lys Pro Asp Gly Ser Tyr Ala His Pro Cys Arg Gly Ala Ala Asn Ala Gly Asp Lys Cys Lys
Cys Ser Cys Thr Ala Ile Pro Gly Cys Asn Glu Asn Gly His His Cys Lys Glu Gly Gln Cys Thr Lys Ala
His Cys Cys Ser Glu Cys His Ser Gln Cys Tyr Arg Asn Ala Gly Thr Tyr Ala Val Cys Ser Cys Lys Pro Pro Cys
Pro Gly Tyr Arg Asn Ala Ser Leu Val His Asn Ala Pro Val Cys Gly Cys Gly Thr Ile Thr Cys Asn Glu
Asp Glu Gly Cys His Pro Cys Tyr Arg Lys Gly Leu Gly Asp Val Val Thr Lys Ser Asp Cys His Ser Pro Gly
Pro Ser Glu

SEQ ID NO: 73
Met Arg Lys Val Ile Asn Ser Gly Ser Ser Ile Lys Tyr Gln Leu Ile Glu Met Glu Glu Lys His Gly Lys Val Leu
Cys Lys Ile Gly Leu Arg Ile Glu Gly Ile Leu Gly Leu Lys Tyr Arg Leu Val His Arg Leu Asn Thr Lys Leu Asn Thr Arg Lys Leu Leu Ala Val Ile Glu
Arg Glu Leu Pro Asp His Ile Leu Glu Ala Val His Gly Val Glu Arg Phe Lys Pro Ala Asn Leu Val Ile
Asp Ser Pro Leu Lys Glu Leu Ile Ala Leu Pro Val Pro Asn Val Phe Ala Phe His Gln Thr Ile Met Gly Ile
Lys Ala Ala Met Lys Leu Pro Gly Tyr Ala Ile Leu Tyr Lys Tyr Arg Arg Gly Phe His Gly
Pro Gln Leu Lys Ala Tyr Ser Arg Val Ala Ser Val Ala Val Leu Tyr Gly Val Leu Lys Leu Ile Thr Cys
Thr Ser His Ser Arg Tyr Val Leu Lys Glu Thr Ser Met Thr Ser Met Gly Phe Pro Leu
Glu Gly Leu Asn Met Gly Met Thr Ala Ser Gly Lys Leu Ser Gly Val Leu Pro Ile Leu Pro Phe Gly Leu Asp
Ser Pro Gln Glu Met Glu Gly Lys Ala Lys Met Val Pro Ala Leu Trp Cys Val Leu Tyr Lys Gly Ile Phe Ser Asp
Met Lys Asp Tyr Glu Gly Ala Ile Val Lys Ala Asp Val Ala Ile Met Phe Leu Val Tyr Arg Ile
Ala Lys Tyr Ile Arg Thr Ile Tyr Arg Glu Ala Glu Met Ala Gly Leu Phe Leu Lys Leu Asp Lys Leu Asn Glu
Ser Pro Ile Thr Arg Glu Val Cys Ser Tyr Leu Cys Val Asp Ala Ile Ala Val Phe Leu Lys Leu Lys Glu Asn Glu

-continued

SEQUENCE LISTING

Glu Thr Ile Arg Gly Lys Glu Gly Ile Ile Ser Thr Pro Asp Ser Arg Val Lys Val Leu Val Pro Thr Asn Glu
Glu Leu Met Ile Ala Arg Asp Val Gly Ile Glu Val Lys Ile Gly Lys Ile Ala Val Arg Val Pro Cys Asp Leu Ser Ile
Lys Ser Lys Leu Lys Gln Gly Thr Lys Ala Thr Ala Gly Asn Ala Ala Val Arg Thr Thr Gly Thr Leu Ser Gly
Val Val Lys Cys Ala Val Val Arg Thr Pro Ser Val Glu Lys Lys Ala Ala Val Ala Thr Gly Ala Val Ala Val
Ser Ala Ser Ala Ala Asn Gly Phe Phe Leu Cys Asn Leu Lys Gly Lys Leu Ala Thr Thr Gly Gln Ile Ile Ala Asp Ala Asn
Thr Lys Val Lys Thr Lys Thr Ala Gly Lys Ser Gly Thr Gly Val Gly Thr Ile Gln Ile Ala Asp Ala Asn
Gly Gly Val Ser Gly Lys Ser Leu Lys Leu Asp Leu Thr Lys Phe Gly Leu Lys Phe Val Lys Thr Glu Lys
Lys Gln Gly Thr Ala Thr Ser Ser Gly His Lys Ala Ser Gly Val Gly His Ser Val Phe Lys Val Leu Asn Glu
Ala Glu Thr Leu Leu Glu Leu Ser Gly Leu

SEQ ID NO: 73

Val Pro Pro Cys Asp Leu Ser Leu Ile Lys Leu Lys Gln Val Gly Ala Thr Ala Gly Asn Ala Ala Val Thr
Thr Thr Gly Thr Leu Ser Gly Val Val Lys Cys Val Val Arg Thr Pro Thr Ser Val Glu Lys Lys Ala Ala
Val Gly Asn Thr Gly Leu Ser Ala Ala Asn Gly Phe Phe Leu Lys Gly Asn Gly Leu Lys Val Ala Ser Ala
Thr Glu Val Lys Thr Lys Thr Asp Ala Ala Asn Gly Lys Val Ser Lys Thr Gly Ala Lys Leu Ala Ser Pro Lys Ala Asp Ala Asn
Thr Thr Ile Gln Ile Ala Asp Ala Asn Gly Lys Leu Lys Ser Gly Asn Gly Leu Lys Val Ala Ser Ala
Lys Phe Val Lys Val Leu Glu Leu Ala Thr Lys Ser Ser Gly His Lys Ala Ser Gly Val Gly His Ser
Ser Val Phe Lys Val Leu Asn Glu Leu Thr Lys Phe Gly Leu Met Arg Arg Val Leu Gly Ile Ala Asn Ser
Gly Ser Ser Ile Lys Tyr Gln Leu Ile Arg His Arg Val Gly Val Asp Gly Lys Ser His Gly Leu Pro Asp His Gly Ile
Cys Ile Glu Gly Leu Val His Ala Asn Thr Leu Asn Val Val Asp Glu Leu Lys Leu Glu Val Lys Val Ala Leu Leu
Val Gly His Arg Ala Val Val His Gly Tyr Gly Leu Phe Lys Asn Pro Ala Phe Asn Leu Gly Ile Val Lys Leu Ala
Glu Glu Val Ser Pro Leu Pro Ala Asn Val Ala Val Phe Asp Thr His Pro Gln Ser Ala Ile Leu Ala Met Lys Leu Leu
Pro Tyr Val Pro Tyr Glu Leu Tyr Lys Tyr Ile Arg Arg Tyr Arg His Ser Arg Gly Lys Ala Tyr Leu Tyr Ala Ile
Ala Ala Glu Ile Leu Leu Lys Lys Leu Ile Ile Thr Cys His Ile Arg Gly Ala Ala Ser Val Ala Ala
Val Lys Tyr Gly Cys Val Ala Val Val Thr Ser Met Gly Ser Gln Gly Asp Leu Gly Met Gly Leu Val Val Leu Gly Leu Arg Ser
Val Lys Asp Pro Phe Ser Asp Ala Ile Leu Lys Thr Gly Ala Gln Leu Tyr Leu Lys Leu Met
Lys Gly Tyr Lys Ile Leu Leu Lys Val Tyr Lys Leu Leu Ala Lys Ile Tyr Leu Lys Ala Asp Ala Leu
Val Asp Ala Gly Ile Leu Leu Ala Leu Lys Leu Lys Tyr Lys Leu Lys Leu Lys Asp Tyr Ala Leu
Lys Gly Phe Leu Leu Leu Leu Met Asn Leu Lys Tyr Asp Met Gly Lys Gly Ala Ile Leu Lys Leu Leu Met
Asn Leu Glu Lys Asp Pro Leu Lys Leu Phe Leu Gly Tyr Ala Lys Leu Lys Ser Leu Glu Arg Leu Pro Ala
Val Lys Glu Pro Asp Arg Ala Val Lys Lys Gly Leu Leu Lys Val Leu Phe Arg Leu Ala Leu Ala Ala Leu Glu Pro
Ile Lys Ser Thr Pro Asp Ser Arg Val Lys Val Leu Val Pro Thr Asn Glu Met Lys Leu Leu Val Arg Lys Lys
Glu Val Pro Tyr Lys Ile Gly Leu Val

SEQ ID NO: 74

Met Lys Tyr Thr Leu Ala Leu Leu Phe Leu Thr Leu Ile Ile Ala Ile Thr Phe Val Ala Ala Ile Lys His His Asp His
Gly Leu Tyr Ser Cys Ser Lys His Pro Cys Tyr Ser His Thr Arg Cys Glu Cys Asn His His Arg Asp
Cys Asn Arg Ser His Lys Arg Cys Tyr Pro His Lys Val Ser Gly Val Asn Cys Asn Leu Thr
Pro Cys Asn Gln Lys Leu Cys Pro Cys Trp Arg Gly Leu Gly Lys Lys Arg Arg Cys Phe His Gly Asn
Ala Cys Asn Cys Asp Arg Leu Val Cys Asn Ala Lys Lys His Pro Cys Trp His Cys Asp Phe Cys

SEQ ID NO: 75

Ser Lys Leu Pro Cys Asn Asp Glu Ile Pro Cys Tyr Arg Lys Gly Leu Gly Gly Val Ser Cys Asp Cys Lys

SEQ ID NO: 76

Ser Lys Leu Pro Ser Asn Asp Glu His Pro Ser Tyr Arg Lys Gly Leu Gly Gly Val Ser Val Ser Asp Ser Lys

SEQ ID NO: 77

Lys Thr Ile Thr Cys Asn Glu Asp His Pro Cys Tyr His Ser Tyr Glu Asp Gly Val Thr Lys Ser Asp Cys
Asp Cys Glu

SEQUENCE LISTING

SEQ ID NO: 78
Met Arg Ile Leu Gly Ala Pro Gly Ala Gly Lys Gly Thr Gln Ala Gln Phe Ile Met Glu Lys Tyr Gly Ile
Pro Gln Ile Ser Thr Gly Asp Met Leu Arg Ala Ala Val Lys Ser Gly Ser Glu Leu Gly Lys Gln Ala Lys Asp Ile
Met Asp Ala Gly Lys Leu Val Thr Asp Glu Leu Val Ile Ala Leu Val Lys Glu Arg Ile Ala Gln Glu Asp Cys Arg
Asn Gly Phe Leu Leu Asp Gly Phe Pro Arg Thr Ile Pro Gln Ala Asp Ala Met Lys Glu Ala Gly Ile Asn Val
Asp Tyr Val Leu Glu Phe Asp Val Pro Asp Glu Leu Ile Val Glu Arg Ile Val Gly Arg Arg Val His Ala Pro Ser
Gly Arg Val Tyr His Val Lys Phe Asn Pro Pro Lys Val Glu Gly Lys Asp Asp Val Thr Gly Glu Glu Leu Thr
Thr Arg Lys Asp Asp Gln Glu Glu Thr Val Arg Lys Arg Leu Val Glu Tyr His Gln Met Thr Ala Pro Leu Ile Gly
Tyr Tyr Ser Lys Glu Ala Glu Ala Gly Asn Thr Lys Tyr Ala Lys Val Asp Gly Thr Lys Pro Val Ala Glu Val Arg
Ala Asp Leu Glu Lys Ile Leu Gly

SEQ ID NO: 79
Met Lys Lys Thr Lys Ile Val Cys Thr Ile Gly Pro Lys Thr Glu Ser Glu Glu Met Leu Ala Lys Met Leu Asp
Ala Gly Met Asn Val Met Arg Leu Asn Phe Ser His Gly Asp Tyr Ala Glu His Gly Gln Arg Ile Gln Asn Leu
Arg Asn Val Met Ser Lys Thr Gly Lys Thr Ala Ala Ile Leu Leu Asp Thr Lys Gly Pro Glu Ile Arg Thr Met Lys
Leu Glu Gly Gly Asn Asp Val Ser Leu Lys Ala Gly Gln Thr Phe Thr Phe Thr Thr Asp Lys Ser Val Ile Gly Asn
Asn Glu Met Val Ala Val Thr Tyr Glu Gly Phe Thr Thr Asp Leu Ser Val Gly Asn Thr Val Leu Val Asp Asp
Gly Leu Ile Gly Met Glu Val Thr Ala Ile Glu Gly Asn Lys Val Ile Cys Lys Val Leu Asn Asn Gly Asp Leu
Gly Glu Asn Lys Gly Val Asn Leu Pro Gly Val Ser Ile Ala Leu Pro Ala Leu Ala Glu Lys Asp Lys Gln Asp Leu Ile
Leu Ile Phe Gly Val Arg Asp Phe Gly Val Arg Ala Asn Phe Gly Ile Glu Ile Leu Lys Ala Ser Gly Val Leu Gly Ala Ser Asp Leu
Arg Gly Leu Asn Phe Ser His Gly Asp His Ala Ser His Leu Val Ser Arg Gln Arg Ile Leu Asn Val Arg Asp Gly Arg Ile Leu Pro
Val Asp Leu Pro Val His Ile Ser Val Asp Ser Val Thr Glu Ile Gln Arg Leu Glu Ile Lys Gln Gly Val Asn Leu Pro Asn Val Thr Gly Asp Leu Pro Val Leu Ser Lys Ile Glu Lys Asp Pro Thr Gln Ala Ile Ser Ala Asp Ala Ile Leu Asp Gly Ser Asp Cys Ile Met Leu Ser Gly Glu Thr Ala Lys Gly Asn Phe Pro Val Glu Ala Val Gln Met Gln His Ala Ile Ile Cys Glu Ala Glu Ala Ala Leu Asp His Leu Pro Leu Leu Glu Lys Glu Met Leu Glu Gly Gly Leu Thr Asp Ile Ile Thr Gln Ala Val Gly Thr Ile Arg Glu Arg Met Lys Glu Met Val Lys Ala Gly Arg Pro Val Ile Val Val Thr Arg Thr Gln Arg Thr Ala Arg Ala Leu Ala Arg Ala Arg Pro Ala Ile Pro Ile Phe Ala Ala Val Thr Pro Val Leu Glu Thr Ala Arg Gln Leu Asn Leu Tyr Arg Gly Val Glu Ala Val Gln Val Arg Phe Thr Pro Ala Glu Gly Tyr Ala Lys Leu Ala Glu Leu Ile Glu Arg Leu Gly Val Phe Gly Pro Asp Pro Ala Leu Gly Val Ala Val Ser Pro Gly Ser Leu Val Ile Glu Met Ala Thr Val Gly Pro Gln Val His Asp Met Pro Gln Arg Ala Ile Asp Thr Ala Glu Ala Thr Gly Arg Thr Ala Lys Arg Val Leu Gly Ser Pro Ala Ser Ala Ser Ile Tyr Asp Val Asp His Leu Val Thr Lys Ile Leu Asp Val Gln Gln Leu Pro Leu Leu Leu Arg Pro Pro Asn Arg Arg Ile Ala Arg Asn Pro Pro Leu Val Gly Thr Gly Val Lys Glu Pro Gln His Gly Asn Ala Gln Leu Asp Ser Pro Tyr Ala Ser Ser Arg Lys Gly Val Glu Val Gln Met Gly Thr Val Gln Ala Lys Asn Pro Arg Ile Ala Asp Thr Val Leu Leu Gln Lys Glu Leu Leu Val Glu Ile Ala His Val Phe Glu His Pro Ile Val Asp Leu Arg Pro Lys Glu Gly Thr Lys Met Asn Ala Ser Phe Ala Ala Val Val Ala Ala Val Leu Glu Arg Ser Gly Val Ser Ala Glu Val Leu Asp Arg Met Ala Thr Gly Asn

SEQ ID NO: 80
Met Ser Ser Lys Leu Val Leu Val Leu Asn Cys Gly Ser Ser Ser Leu Lys Phe Ala Ile Ile Asp Ala Val Asn
Gly Glu Glu Tyr Leu Ser Gly Leu Ala Glu Cys Phe His Leu Pro Glu Ala Arg Ile Lys Trp Lys Met Asp Gly
Asn Lys Gln Glu Ala Ala Leu Gly Ala Gly Ala Ala His Ser Glu Ala Leu Asn Phe Ile Val Asn Thr Ile Leu Ala
Gln Leu Pro Gly Leu Ser Ala Gln Leu Thr Ala Ile Gly His Arg Ile Val His Gly Gly Glu Lys Phe Thr Ser Ser
Val Val Ile Asp Glu Ser Val Ile Gln Gly Ile Lys Asp Ala Ala Ser Phe Ala Pro Leu His Asn Pro Ala His Leu
Ile Gly Ile Glu Val Ala Leu Lys Ser Leu Pro Gly Val Pro His Val Ala Val Phe Asp Thr Ala Phe His Gln Thr Met Pro Glu Ala Ala Tyr Leu Tyr Ala Leu Pro Tyr Asn Leu Tyr Lys Glu Leu Gly Ile Arg Arg Tyr Gly Ala His Gly Thr Ser His Phe Tyr Val Thr Gln Glu Ala Ala Lys Met Leu Asn Lys Pro Val Glu Glu Leu Asn Ile Ile Thr Cys His Leu Gly Asn Gly Gly Ser Val Ser Ala Ile Arg Asn Gly Lys Cys Val Asp Thr Ser Met Gly Leu Thr Pro Leu Glu Gly Leu Val Met Gly Thr Arg Ser Gly Asp Ile Asp Pro Ala Ile Ile Phe His Leu His Asp Thr Leu Gly Met Ser Val Asp Ala Ile Asn Lys Leu Leu Asn Lys Glu Ser Gly Leu Leu Gly Leu Thr Glu Val Thr Ser Asp Cys Arg Tyr Val Glu Asp Asn Tyr Ala Thr Lys Glu Asp Ala Lys Arg Ala Met Asp Val Tyr Cys His Arg Leu Ala Lys Tyr Ile Gly Ala Tyr Thr Ala Leu Met Asp Gly Arg Leu Asp Ala Val Val Phe Thr Gly Gly Ile Gly Glu Asn Ala Ala Met Val Arg Glu Leu Ser Leu Gly Lys Leu Gly Val Leu Gly Phe Glu Val Asp His Glu Arg Asn Leu Ala Ala Arg Phe Gly Lys Ser Gly Phe Ile Asn Lys Glu Gly Thr Arg Pro Ala Val Val Ile
Pro Thr Asn Glu Glu Leu Val Ile Ala Gln Asp Ala Ser Arg Leu Thr Ala

-continued

SEQUENCE LISTING

SEQ ID NO: 81
Met Lys Asn Arg Lys Val Val Val Thr Gly Pro Gly Val Gly Ser Thr Thr Ser Ser Gln Leu Ala Met Asp
Asn Leu Val Gly Lys Val Asn Tyr Lys Met Val Ser Phe Gly Ser Val Met Glu Val Ala Lys Glu Glu
Arg Lys Ile Ala Met Ala Lys Glu Met Arg Lys Met Asp Pro Glu Thr Gln Lys Arg Ile Gln Lys Met Ala Gly
Leu Pro Gly Leu Pro Ser Trp Val Leu Asn Glu Leu Asn Pro Asp Leu Ile Ile Thr Thr His Ser Thr Val Ser Thr Pro Lys Gly Tyr
Glu Ile Leu Met Arg Arg Met Ser Asp Gly Thr Arg Val Arg Asp Asp Ala Ser Thr Ile Glu Thr Gly Asp
Phe Met Asn Arg Cys Ala Ala Met Ser Tyr Gly Val Leu Thr Gly Ala Thr Val Lys Ile Val Gln Asn Arg Asn
Gly Leu Leu Asp Gln Ala Val Glu Gln Leu Thr Asn Ala Val Leu Arg

SEQ ID NO: 82
Met Lys Asn Lys Leu Val Val Thr Gly Pro Gly Val Gly Gly Thr Ile Thr Gln Lys Ala Met Glu Lys
Leu Ser Glu Gly Ile Ile Asn Tyr Lys Met Val Asn Phe Gly Val Met Phe Glu Val Ala Gln Glu Glu Asn
Leu Val Glu Ala Asp Arg Gln Met Lys Leu Asp Pro Asp Thr Gln Lys Arg Ile Gln Lys Leu Ala Gly Arg
Lys Ile Ala Glu Met Val Lys Ser Pro Val Val Asp Pro Asp Leu Ile Ile Ser Thr Pro Lys Thr Gly Tyr Leu
Pro Gly Leu Pro Val Trp Val Leu Asn Glu Leu Asn Pro Asp Leu Ile Ile Thr Thr Val Glu Gly Glu Ile
Leu Ile Arg Arg Leu Asn Asp Gly Thr Arg Val Arg Asp Asp Ala Ser Leu Gln Ala Thr Ile Glu Thr Gly Asp His Gln Ile Met
Asn Arg Ala Ala Met Thr Tyr Gly Val Leu Thr Gly Ala Thr Val Lys Ile Ile Gln Asn Lys Asn Asn Leu Leu
Asp Tyr Ala Val Glu Leu Ile Ser Val Leu Arg

SEQ ID NO: 83
Met Asn Ile Val Leu Met Gly Leu Pro Gly Ala Gly Lys Gly Thr Gln Ala Asp Arg Ile Val Glu Lys Tyr Gly Thr
Pro His Ile Ser Thr Gly Asp Met Phe Arg Ala Ala Ile Lys Gln Gly Thr Glu Leu Gly Leu Val Ala Lys Ser Phe
Met Asp Gln Gly Ala Leu Val Pro Asp Glu Val Thr Ile Gly Ile Val Arg Glu Arg Leu Ser Lys Ser Asp Cys Asp
Asn Gly Phe Leu Leu Asp Gly Phe Pro Arg Thr Val Pro Gln Ala Glu Ala Leu Asp Ala Leu Arg Gly Arg Met Ile
Gly Lys Phe Leu Glu His Val Leu Asn Ile Glu Leu Asn Phe Leu Glu Phe Val Pro Gln Val Glu Leu Val Cys Lys Ser Asp Gly
Cys Lys Val Cys Gly Thr Ser Tyr His Leu Leu Phe Asn Pro Pro Gln Val Glu Gly Val Cys Asp Lys Asp Gly Gly
Gly Glu Leu Tyr Gln Arg Ala Asp Asp Asn Pro Glu Thr Val Thr Asn Arg Leu Glu Val Asn Met Asn Gln Thr
Ala Pro Leu Leu Ala Phe Tyr Asp Ser Lys Gly Leu Val Glu Val Ala Asn Ile Asp Gly Ile Gln Lys Asp Val
Phe Lys Asp Leu Asp Val Ile Leu Asp Gly Leu Gln

SEQ ID NO: 84
Met Asn Leu Val Leu Met Gly Leu Pro Gly Ala Gly Lys Gly Thr Gln Gly Glu Arg Ile Val Glu Asp Tyr Gly Ile
Pro His Ile Ser Thr Gly Asp Met Phe Arg Ala Ala Met Lys Glu Gly Thr Pro Leu Gly Leu Ala Lys Ser Tyr
Ile Asp Lys Gly Glu Leu Val Pro Asp Glu Val Thr Ile Gly Ile Val Lys Glu Arg Leu Gly Lys Asp Asp Cys Glu
Arg Gly Phe Leu Leu Asp Gly Phe Pro Arg Thr Val Ala Gln Ala Glu Ala Leu Glu Glu Ile Leu Glu Glu Tyr
Gly Lys Pro Ile Asp Tyr Val Ile Glu Phe Asp Val Pro Asp Ser Val Ile Val Glu Arg Met Ser Gly Arg Arg Ile
Cys Ser Val Cys Gly Thr Thr Tyr His Leu Val Phe Asn Pro Pro Lys Thr Pro Gly Ile Cys Asp Lys Asp Gly
Gly Glu Leu Tyr Gln Arg Ala Asp Asp Asn Glu Glu Thr Val Ser Lys Arg Leu Glu Val Asn Met Lys Gln
Thr Gln Pro Leu Leu Asp Phe Tyr Ser Gly Lys Gly Tyr Leu Ala Asn Val Asn Gly Gln Gln Asp Ile Gln Asp
Val Tyr Ala Asp Val Lys Asp Leu Leu Gly Gly Leu Lys Lys

The invention is now described in specific embodiments in the following examples and with reference to the accompanying drawings in which:

FIG. 1 shows activity of adenylate kinase (AK) enzymes after treatment at 70° C. (A), 80° C. (B) and 90° C. (C);

FIG. 2 shows the stability of a range of AK enzymes recombinantly expressed in E. coli. Genes encoding AK enzymes were cloned and expressed as described in Example 3. All genes were expressed from the vector pET28a except for S. acidocaldarius clone I which was expressed from pET3a as described previously. Expression levels were similar for each done but a proportion of the Pyrococcus furiosus (P. fu) enzyme was in the insoluble fraction and this is likely to have reduced the amount of this enzyme being assayed. The stability of the recombinant enzymes was measured following incubation at 80° C. for 30 minute in a crude E. coli lysate at 10-fold serial dilutions from 1 mg/ml total cellular protein (such that column 12 is equivalent to 1 fg/ml total protein). Enzymes from Thermotoga maritima and Archaeoglobus fulgidus showed significantly greater stability than the other enzymes tested, although the remaining enzymes (Sulfolobus solfataricus (S. so P2), Aeropyrum pernix and P. fu) showed similar activity to the S. acidocaldarius enzyme used as the basis of previous assays (data labelled as S. ac I);

FIGS. 3A & 3B show the relative lever of non-reporter adenylate kinase activity (FIG. 3A) and ATP (FIG. 3B) in a variety of samples relevant to clinical diagnosis. Samples from healthy donors were assessed for the levels of ATP generated by non-reporter adenylate kinase (after addition of ADP as substrate; FIG. 3A) or present naturally in the sample (FIG. 3B). This information can be used to assist in deciding which background reduction steps need to be included in assays for particular samples, although this information does not preclude their use in any assay type, particularly where infections can influence the background levels of either ATP or reporter kinase. Samples are whole blood and sera from sheep, mouse brain homogenate (MBH; representative of tissue biopsy samples), cows' milk, and two saliva samples (1 and 2) collected using either a citric acid ("ca") method or swab device ("r"). The relative light units generated from the raw assay are converted into ATP units based on a standard curve;

FIGS. 4A & 4B show the differential inhibition of reporter kinase and non-reporter (endogenous) tissue kinase using Ap5a (Diadenosine pentaphosphate pentasodium salt) (FIG. 4A) and the effect of Ap5a on luciferase (FIG. 4B). The reporter adenylate kinases from S. acidocaldarius or T. maritima were purified as described previously. Rabbit myokinase (muscle adenylate kinase) was obtained from Sigma. 100 ng of each enzyme was incubated with the inhibitor at the concentrations shown in reaction buffer (15 mM MgAc, 10 mM tris, 1 mM EDTA pH 7.75) for 5 minutes. ADP was added to a final concentration of 70 μM and the reaction incubated before addition of luciferin and luciferase. The generated following detection with luciferase/luciferin were converted to equivalent ATP units using a standard curve and the results are shown in FIG. 4A. An $IC_{50}$ (the concentration of inhibitor which reduces the activity of the enzyme by 50%) was calculated and gives values of 10.4 μM (Sac), 4.3 μM (Tma) and 0.06 μM (Rabbit myokinase). The presence of Ap5A does not have a detrimental effect on the activity of the luciferase (see FIG. 4B);

Figure 4A:
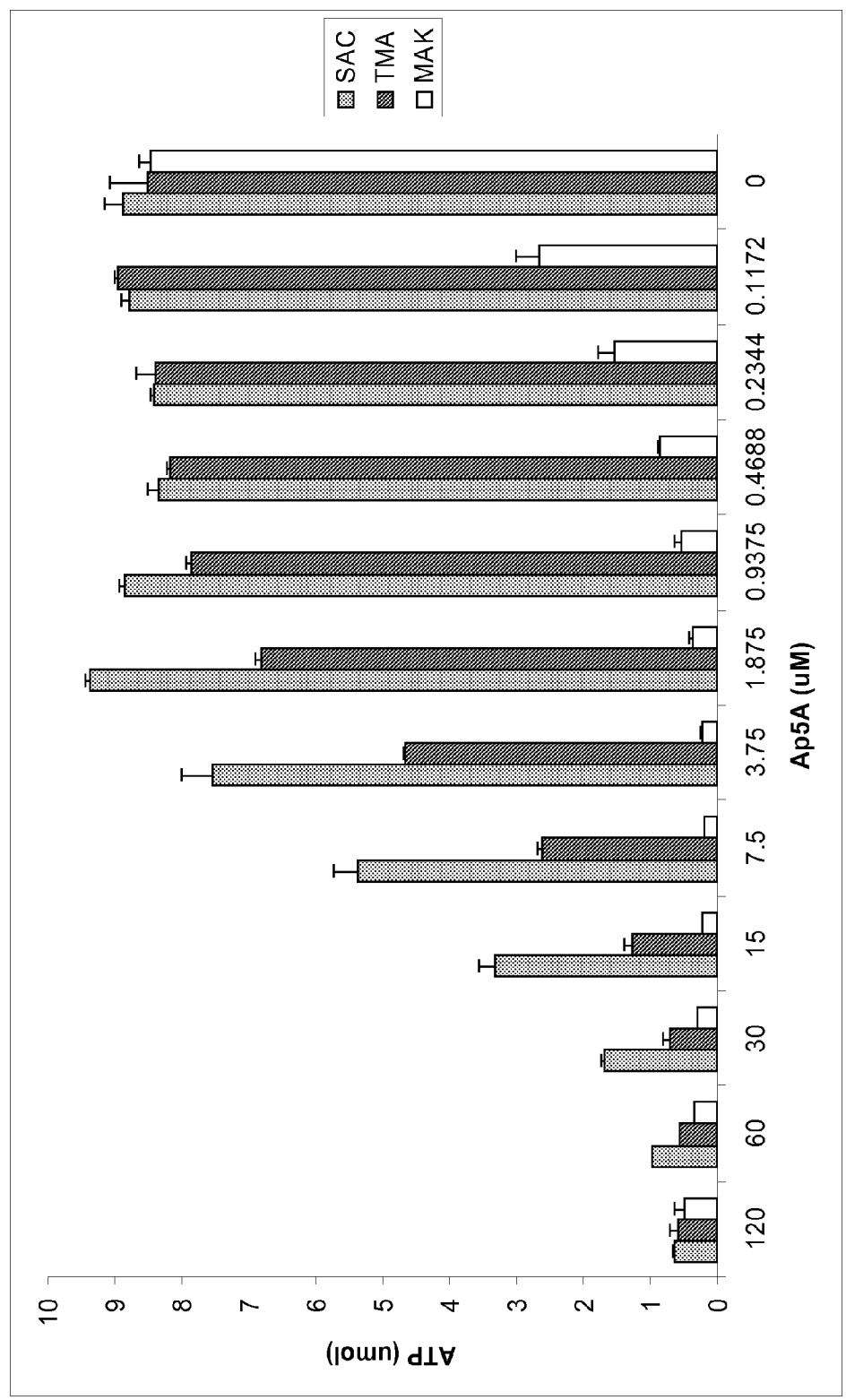
Figure 4B:
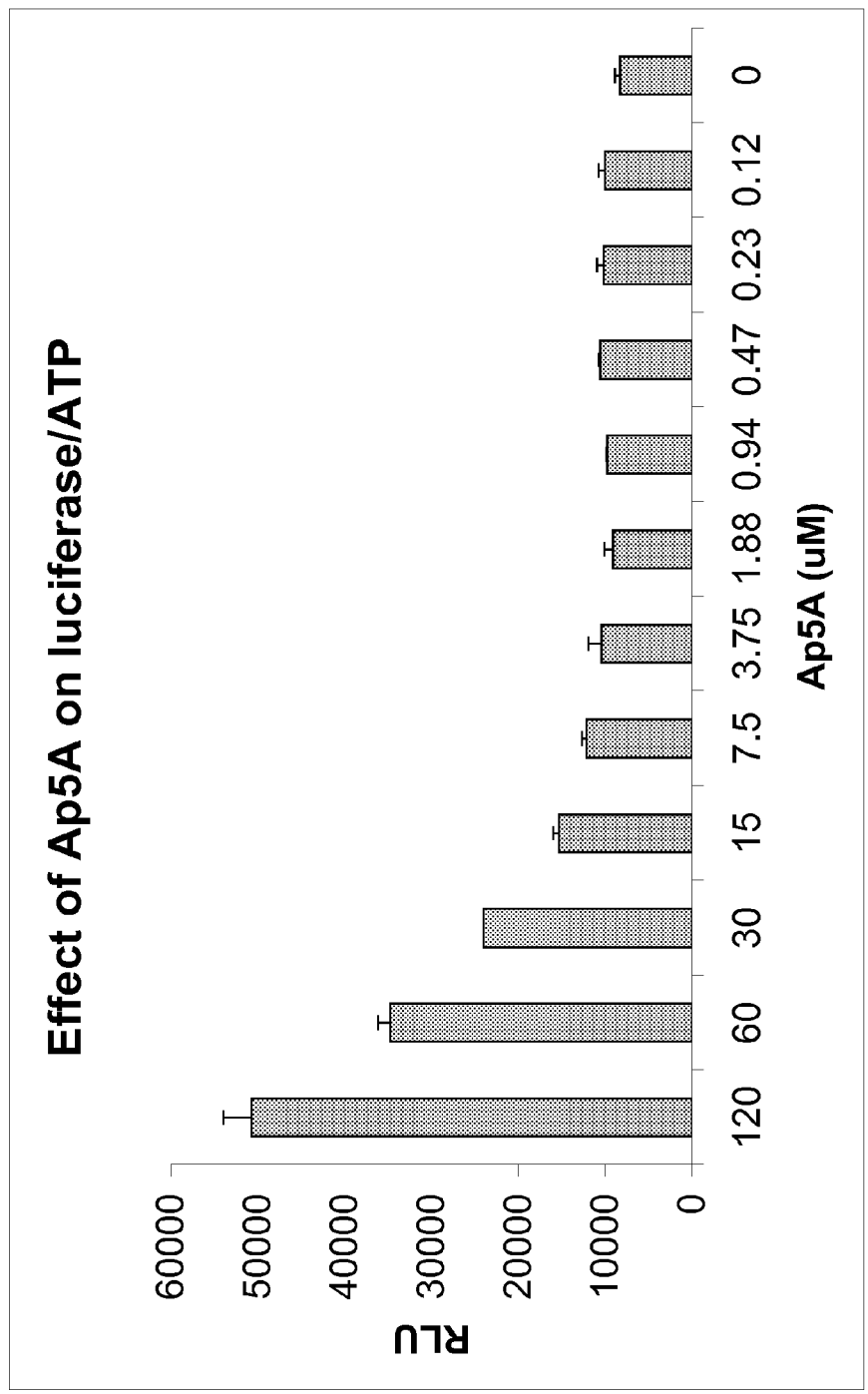

FIGS. 7A and 7B show the effects of further inhibitors on the background activity derived from mammalian tissues or samples and/or background from other sources (e.g. yeast contamination). Experiments were carried out essentially as described for FIG. 4. No adverse effect on the activity of luciferase was observed for any of the inhibitors examined (results not shown). Yeast adenylate kinase was obtained from Sigma. FIG. 7A; comparison of inhibition of adenylate kinases by Ap6A, MAK=rabbit muscle AK (myokinase); YAK=yeast AK; SAC=S. acidocaldarius AK; TMA=T. maritima AK. FIG. 7B; comparison of Ap5A and Ap6A for inhibition of contaminating background adenylate kinase from either mammalian cells (MAK) or yeast (YAK). AP4A (not shown) and Ap6A gives similar profiles to Ap5A for differentiating between an example of a monomeric (bacterial) reporter adenylate kinases (from Thermotoga maritima) and an example of a trimeric (archaeal) adenylate kinase from Sulfolobus acidocaldarius when either is compared to a representative example of non-reporter mammalian tissue adenylate kinase (FIG. 7A). Ap4A (not shown) and Ap6A do not allow for an assay to distinguish between the bacterial and Archael enzymes and an enzyme of fungal origin (represented here by the AK from Saccharomyces cerevisiae) (FIG. 7B). In this case Ap5A can still be used to distinguish the reporter adenylate kinases from the yeast enzyme.

EXAMPLE 1

Purification of Native Adenylate Kinase Enzymes

Biomass was produced from twenty-four diverse microorganisms (Table 3).

Eight members of the Archaea were represented along with sixteen diverse aerobic and anaerobic bacteria, AKs from each of these organisms were purified by affinity chromatography using selective absorption and desorption from Cibacron Blue 3A (Blue Sepharose). All enzymes were further characterised and purified by gel filtration (Superdex G200). This enabled identification of the major AK fraction and estimation of molecular mass.

TABLE 3

List of organisms cultured to produce biomass for isolation of AKs.

| | Organism | Domain | Growth | $T_{opt}$ | $pH_{opt}$ |
|---|---|---|---|---|---|
| 1 | Aeropyrum pernix | Archaeon | Aerobe | 95° C. | 7.0 |
| 2 | Alicyclobacillus acidocaldarius | Bacterium | Aerobe | 65° C. | 3.5 |
| 3 | Aquifex pyrophilus | Bacterium | Microaerophileebe-rophile | 85° C. | 6.5 |
| 4 | Bacillus caldotenax BT1 | Bacterium | Aerobe | 65° C. | 7.0 |
| 5 | Bacillus species PS3 | Bacterium | Aerobe | 65° C. | 7.0 |
| 6 | Bacillus stearothermophilus 11057 | Bacterium | Aerobe | 65° C. | 7.0 |
| 7 | Bacillus stearothermophilus 12001 | Bacterium | Aerobe | 65° C. | 7.0 |
| 8 | Bacillus thermocatenulatus | Bacterium | Aerobe | 65° C. | 7.0 |
| 9 | Clostridium stercocorarium | Bacterium | Anaerobe | 55° C. | 7.0 |
| 10 | Meiothermus ruber | Bacterium | Aerobe | 60° C. | 6.5 |
| 11 | Pyrococcus furiosus | Archaeon | Anaerobe | 95° C. | 7.5 |
| 12 | Pyrococcus horikoshii | Archaeon | Anaerobe | 95° C. | 7.0 |
| 13 | Pyrococcus woesei | Archaeon | Anaerobe | 95° C. | 7.0 |
| 14 | Rhodothermus marinus | Bacterium | Aerobe | 70° C. | 6.5 |
| 15 | Sulfolobus acidocaldarius 98-3 | Archaeon | Aerobe | 75° C. | 2.5 |
| 16 | Sulfolobus shibatae B21 | Archaeon | Aerobe | 75° C. | 2.5 |
| 17 | Sulfolobus solfataricus P2 | Archaeon | Aerobe | 75° C. | 2.5 |
| 18 | Thermoanaerobacter ethanollcus | Bacterium | Anaerobe | 65° C. | 6.0 |
| 19 | Thermoanaerobacter-thermosulfurogenes | Bacterium | Anaerobe | 65° C. | 6.5 |

TABLE 3-continued

List of organisms cultured to produce biomass for isolation of AKs.

|    | Organism                  | Domain    | Growth    | $T_{opt}$ | $pH_{opt}$ |
|----|---------------------------|-----------|-----------|-----------|------------|
| 20 | Thermobrachium celere     | Bacterium | Anaerobe  | 60° C.    | 7.0        |
| 21 | Thermococcus litorialls   | Archaeon  | Anaerobe  | 85° C.    | 6.5        |
| 22 | Thermus aquaticus YT1     | Bacterium | Aerobe    | 70° C.    | 8.0        |
| 23 | Thermus caldophilus GK24  | Bacterium | Aerobe    | 70° C.    | 8.0        |
| 24 | Thermus thermophilus HB8  | Bacterium | Aerobe    | 70° C.    | 8.0        |

EXAMPLE 2

Analysis of Stability of Native Adenylate Kinases

Figure 1B:
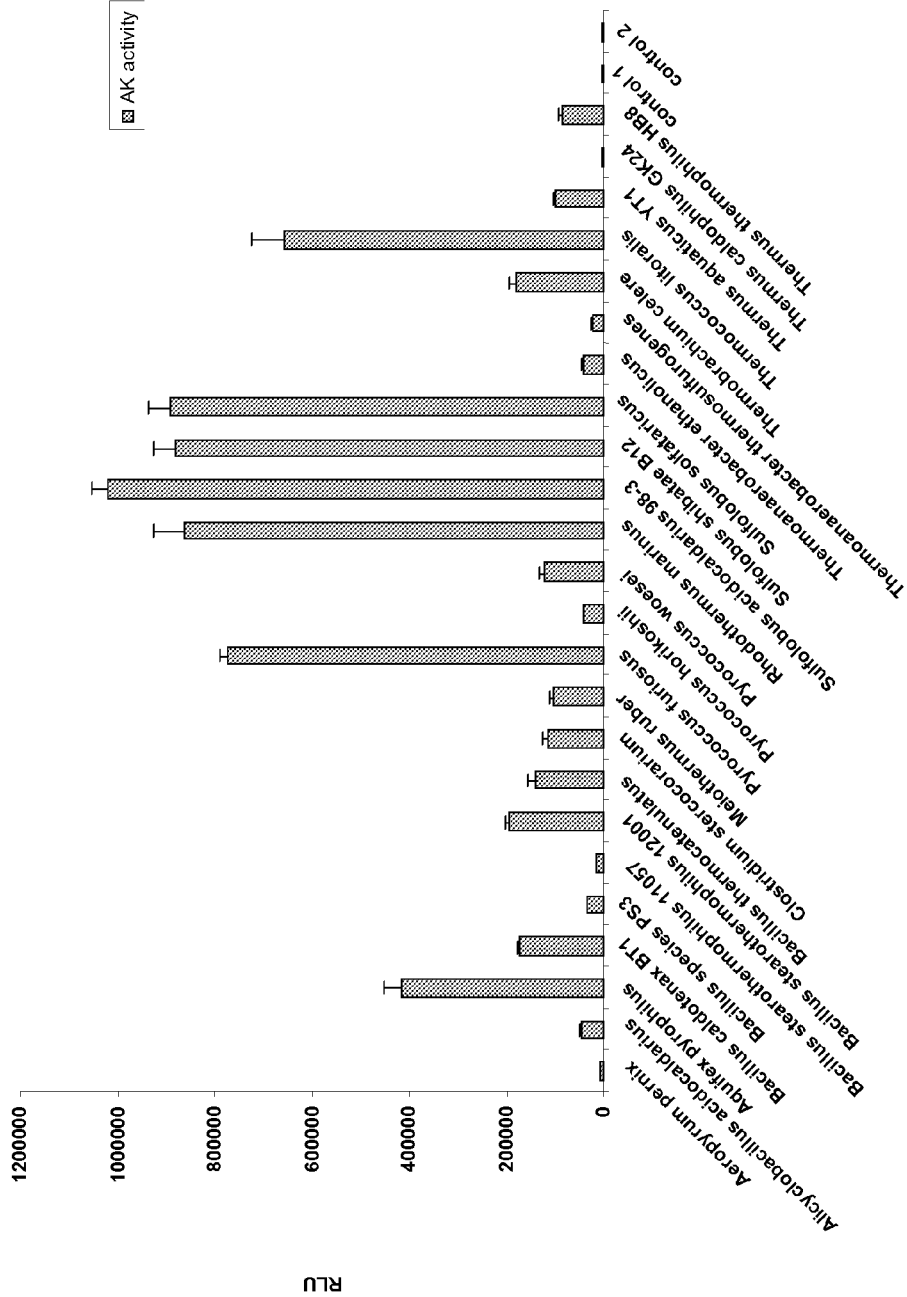
Figure 1C:
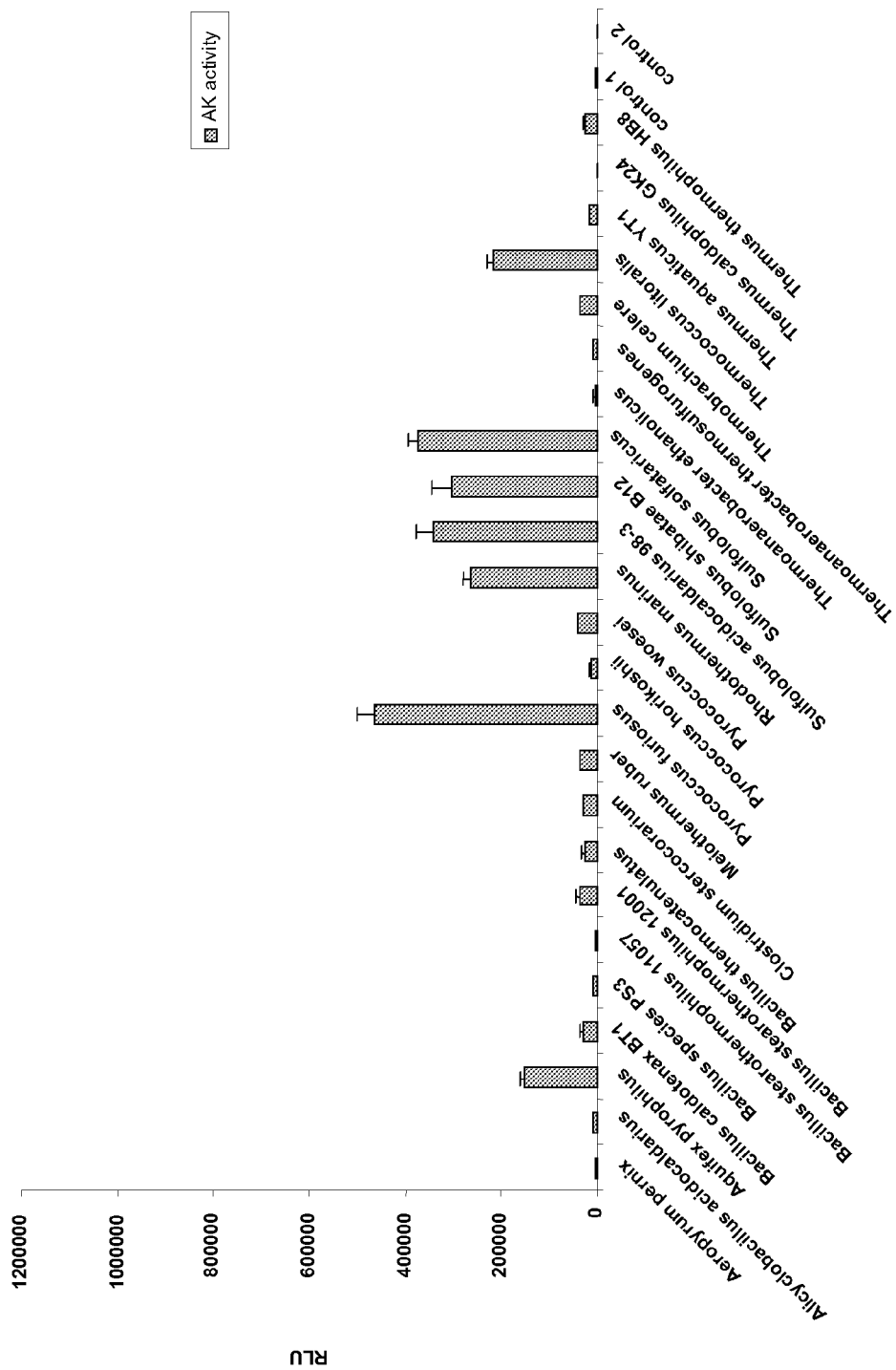

The stability at 70, 80 and 90° C. of adenylate kinases isolated from biomass from organisms was assessed, and the results shown in FIG. 1.

The adenylate kinases were isolated from the biomass by affinity chromatography using selective absorption and desorption from Cibacron Blue 3A (Blue Sepharose). The samples eluted from the columns were diluted 1:10 000 and then 10 µl of each added to a microtitre well. 2.5 µl of apyrase was added to each well to destroy the ATP present from the elution buffer, and incubated at 37° C. for 30 minutes. The apyrase was inactivated by heat treatment at 65° C. for 20 minutes.

ADP substrate was added and incubated at either 70 (panel A), 80 (panel B) or 90° C. (panel C) for 30 minutes and cooled to 25° C. before the addition of 10 µl of D-luciferin-luciferase reagent. The ATP produced was measured as RLU on a plate luminometer.

EXAMPLE 3

Expression and Purification of Recombinant Adenylate Kinases

Clones expressing representative AKs were secured and recombinant AKs from the archaeon *Sulfolobus acidocaldarius* and the bacterium, *Bacillus stearothermophilus* produced. The plasmids were transformed into *E. coli* and the cell extracts shown to contain protein bands on electrophoresis corresponding to the expected molecular masses of the AKs. AK activity was measured after incubation at the appropriate temperature (80° C. for the *Sulfolobus acidocaldarius* AK and 60° C. for the *Bacillus stearothermophilus* AK).

Purification methods for both AKs were established and included an initial heat treatment of incubation for 20 min at 80° C., to inactivate and aggregate proteins derived from *E. coli*, followed by affinity chromatography and gel filtration. The affinity chromatography involved adsorption of the enzyme to Blue Sepharose, followed by specific elution with a low concentration of AK co-factors (AMP+ATP and magnesium ions). The ATP and AMP (Sigma) in the elution buffer were degraded by incubation with mesophile apyrase, which is readily inactivated by subsequent heat treatment. Gel filtration chromatography was scaled up to utilise a preparation grade Superdex column to enable large quantities of both enzymes to be prepared.

Primers were designed for PCP, amplification of the AK genes from the organisms identified during the screening of candidate native enzymes.

The microorganisms were grown using individually defined growth conditions and genomic DNA isolated and used as templates for PCR amplification of the adenylate kinase genes from each organism. PCP amplified adenylate kinase genes from the organisms, *Thermotoga maritima*, *Aeropyrum pernix*, *Sulfolobus acidocaldarius* and *Sulfolobus solfataricus* were sub-cloned into the vector, pET28a and transformed into a codon enhanced *E. coli* strain expressing rare tRNAs (Zdanovsky et al, 2000). This *E. coli* strain is suitable for enhancing expression levels of AT-rich genes.

The success of the transformation was assessed by a mini-expression study, and the results analysed by SDS-PAGE of the culture supernatants before and after induction with IPTG. SDS-PAGE was also used to analyse the supernatants after inclusion of a heat treatment step, which consisted of heating the sample to 80° C. for 20 minutes prior to running on the SDS-PAGE gel to remove heat labile proteins present in the sample.

EXAMPLE 4

Analysis of the Stability of Recombinant Adenylate Kinases

The stability of recombinant tAK enzymes was assessed in crude *E. coli* cell lysates.

Cells were grown essentially as described in Example 3 and lysed by sonication. The AK activity of the crude extract was determined both before and after heat treatment at 80° C. for 30 minutes followed by 10-fold serial dilution.

Figure 2:
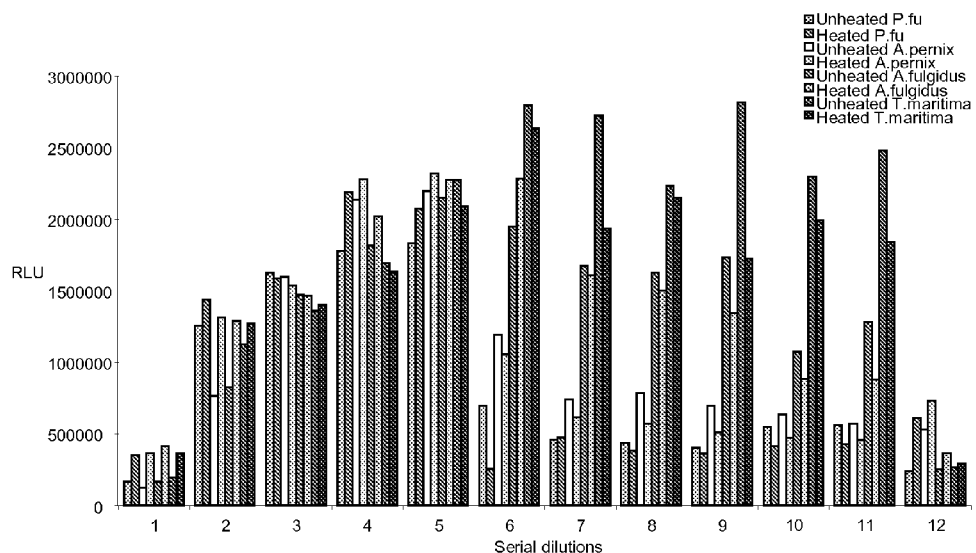
Figure 2:
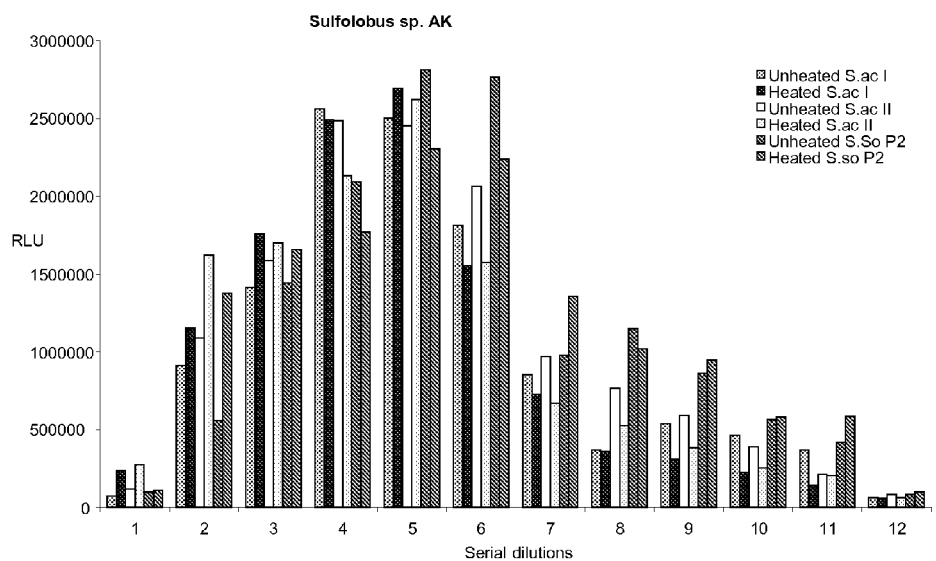
Figure 3A:
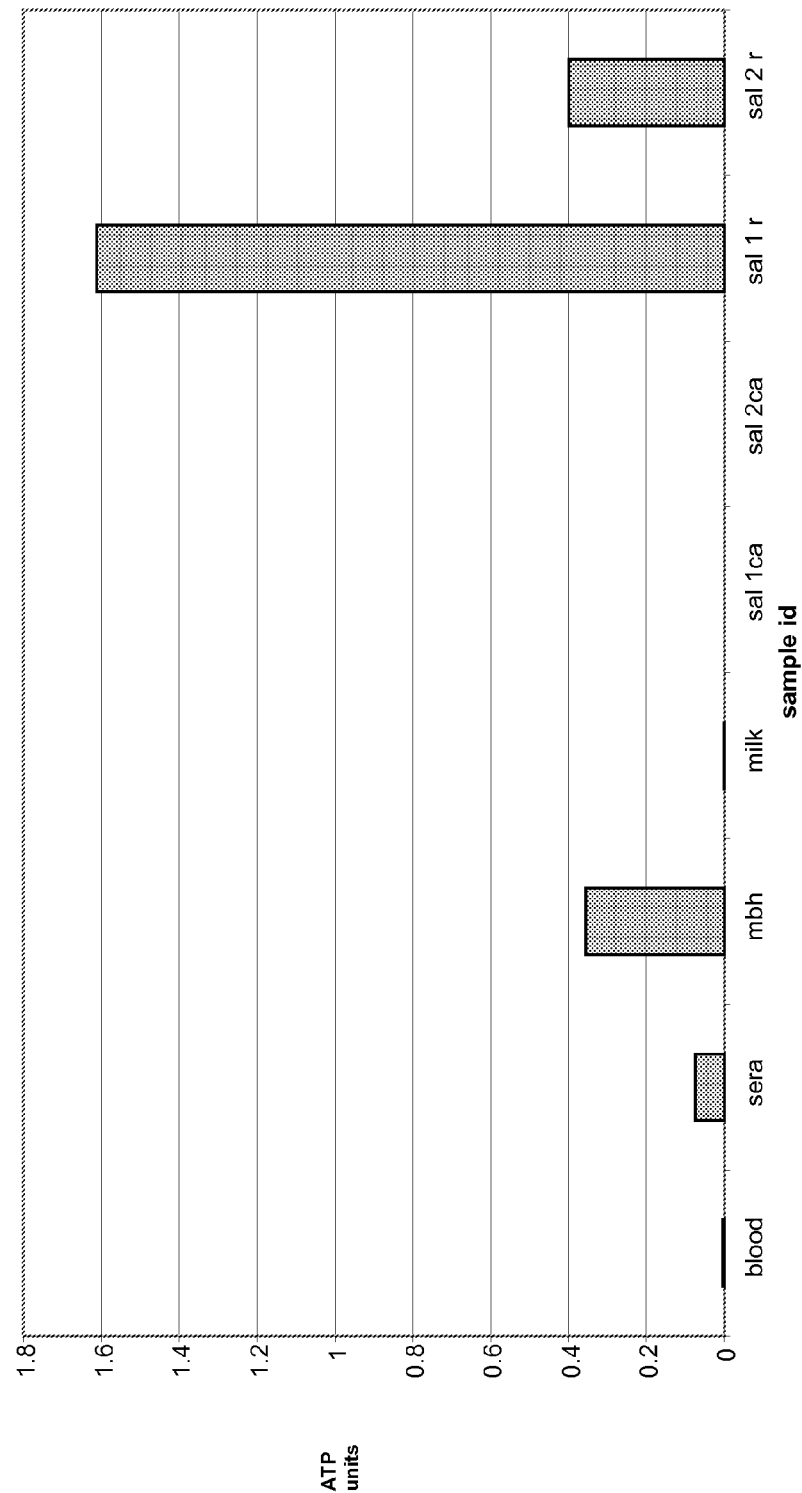
Figure 3B:
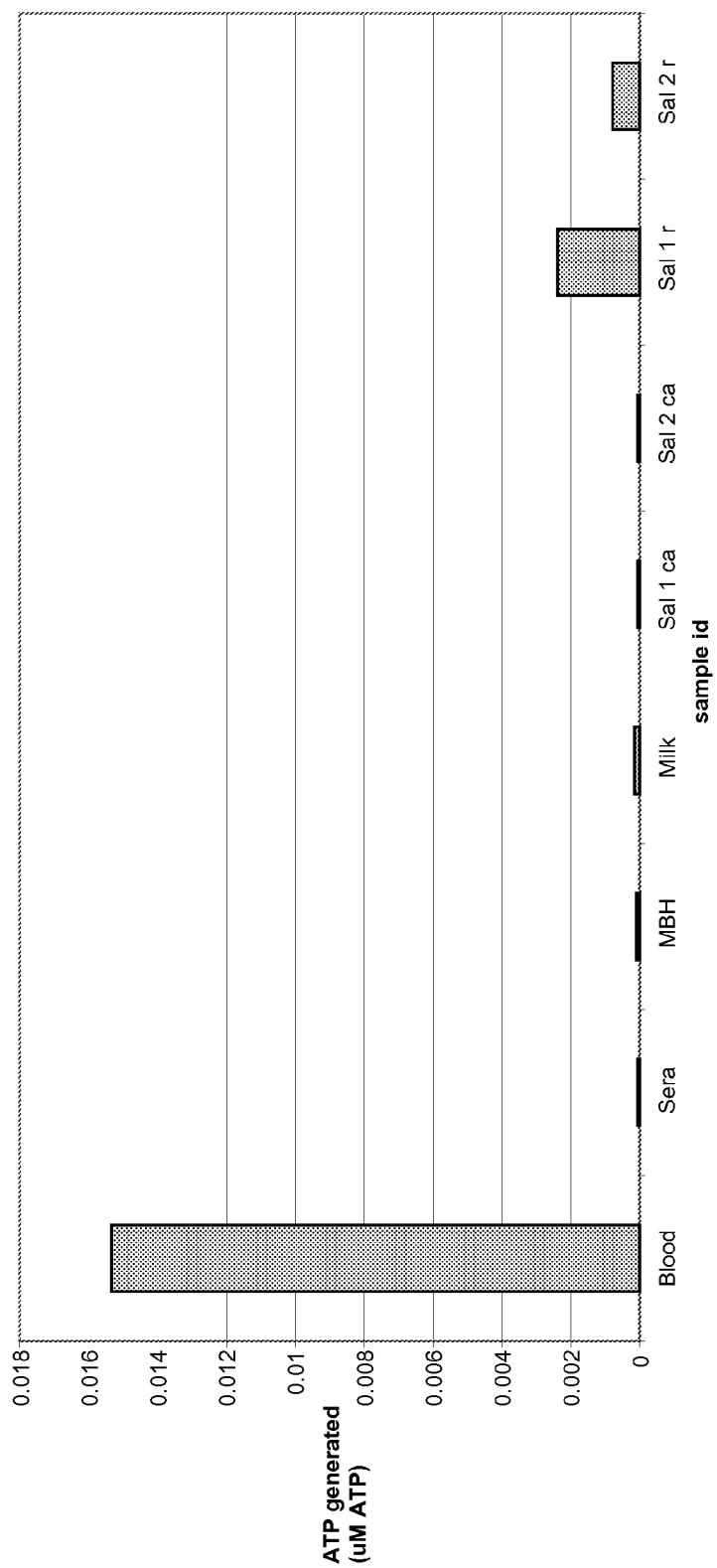

The results (see FIG. 2) demonstrate that a wide variety of recombinant enzymes are suitable for the use in the method of the invention. Particularly preferred AKs are those from *T. maritima*, *A. fulgidus* and *S. solfataricus*. Such enzymes are likely to provide a greater dynamic range for the bioluminescent assay, if required, to provide still further sensitivity.

EXAMPLE 5

Genetic Modification of Adenylate Kinases to Improve Stability

Site-directed mutants were constructed in the AK gene from *P. furiosus*, *P. horikoshii* and *S. acidocaldarius* as shown in Examples 6-8 and SEQ IDs 17-19 respectively, using standard methods known to those familiar with the art.

In addition to specific changes identified in each gene, the regions underlined in the *S. acidocaldarius* sequence form the core packing region of the archaeal adenylate kinase trimer structure. Hence amino acid substitutions that disturb the packing of this region are likely to have a major effect in decreasing the thermal and physical stability of the enzyme. Conversely amino acid substitutions that improve the core packing, in particular hydrophobic residues with lame side chains, may stabilise the enzyme to heat or other processes. Therefore in addition to the specific mutations already described a number of "selective" approaches were used with localised gene shuffling of related gene sequences in these regions (essentially as described in Stemmer (1994) Nature 370:389-391 and Crameri et al (1996) Nature Biotech, 14:315-319) and random PCR-based mutagenesis using degenerate oligonucleotides or modified nucleotide mixes (e.g. Vartanian et al (1996) Nucleic Acid Res. 24:2627-2633). A number of these modifications show altered stability when assessed by recombinant expression in *E. coli* and rapid assay of adenylate kinase activity in lysed cells at high temperature.

EXAMPLE 6

Adenylate Kinases from *Pyrococcus furiosus* Genetically Engineered to Provide Improved Stability (SEQ ID NO. 17)

MPFVVIITGI PGVGKSTITR LALQRTKAKF RLINF-GDLMF EEAVKAGLVK HRDEMRKLPL (K TO E) IQRELQMKA AKKI (T TO A) EMAKE HPILVDTHAT IKTPHGY (M TO L) LG LPYEVVKTLN PNFIVIIEAT PSEILGRRLR DLKRDRDVET EEQIQRHQDL NRAAA-IAYAM HSNALIKIIE NHEDKGLEEA VNELVKILDL AVNEYA

Mutations at one or more or all of the sites indicated modify the stability of the enzyme. In addition to the three defined changes highlighted, modification of the alanine at position 157 to another small hydrophobic residue (such as I, L) or larger hydrophobic residue (such as F) increases the stability of the recombinant protein. Hence, there are 35 variants possible through combination of modifications at these sites. Modification of amino acid 157 to a polar residue such as the T (as observed at the equivalent position in AdkA of *P. horikoshii*), S Y, D, E, K, R results in a decrease in stability.

EXAMPLE 7

Adenylate Kinases from *Pyrococcus horikoshii* Genetically Engineered to Provide Improved Stability (SEQ ID NO. 18)

The modification of either or both of the residues shown in bold and underlined increases the stability of the enzyme (3 variants are possible).

MPFVVIITGI PGVGKSTITK LALQRTRAKF KLINF-GDLMF EEALKLGLVK HRDEMRKLPL EVORELQMNA AKKIAEMAKN YPILLDTHAT IKTPH-GYLLG LPYEVIKILN PNFIVIIEAT PSEILGRRLR DLKRDRDVET EEQIQRHQDL NRAAAIAYAM HSNA-LIKIIE NHEDKGLEEA VNELVKILDL AVKEYA

EXAMPLE 8

Adenylate Kinase from *Sulfolobus acidocaldarius* Genetically Engineered to Provide Improved Stability (SEQ ID NO. 19)

The modification of the underlined residues shown can increase the stability of the enzyme.

MKIGIVTGIP GVGKSTVLAK VKEILDNQGI NNKI-INYGDE MLATALKLGY AKDRDEMRKL SVEKQKKLQI DAAKGIAEEA RAGGEGYLFI DTHA VIRTPSGY(ATOM)PGLPSYV ITEINPSVIF LLEADPKIIL SRQKRDTTRN RNDYSDESVI LET INFARYAATASAVLAGSTVKVIVNVEG DPSIAANEII RSMK

EXAMPLE 9

Expression of Acetate and Pyruvate Kinases

Following the methods of Example 3, we expressed acetate and pyruvate kinases:
- SEQ ID 20—Acetate kinase from *Thermotoga maritima*
- SEQ ID 21—Pyruvate kinase from *Pyrococcus horikoshii*
- SEQ ID 22—Pyruvate kinase from *Sulfolobus solfataricus*
- SEQ ID 23—Pyruvate kinase from *Thermotoga maritima*
- SEQ ID 24—Pyruvate kinase from *Pyrococcus furiosus*
- SEQ ID 25—Acetate kinase from *Methanosarcina thermophila*
- SEQ ID 78—Adenylate kinase from *E. coli*
- SEQ ID 79—Pyruvate kinase from *E. coli*
- SEQ ID 80—Acetate kinase from *E. coli*
- SEQ ID 81—Adenylate kinase from *Methanococcus voltae* (MVO)
- SEQ ID 82—Adenylate kinase from *Methanococcus thermolithotrophicus* (MTH).
- SEQ ID 83—Adenylate kinase from *Bacillus globisporus*
- SEQ ID 84—Adenylate kinase from *Bacillus subtilis*

EXAMPLE 10

Detection of Hepatitis C in an Oral Fluid Sample

Antibodies are raised against Hepatitis C surface antigens derived from either structural proteins (e.g. E1 and E2) or non-structural proteins (e.g. NS2, NS3, NS4A, NS4B, NS5A, NS5B) using standard methods. In brief, the proteins are expressed as either recombinant proteins in *E. coli*, or synthesized as short immunogenic peptides. Short peptides are conjugated to a suitable carrier, such as HLA, and injected intramuscularly into rabbits or guinea pigs at concentrations of approximately 100 µg/ml. Freund's complete adjuvant is used for the first stage of immunization, with incomplete adjuvant used subsequently.

Polyclonal serum is collected after three monthly challenges over a time-course of 3 months. IgG is purified from the blood and conjugated to Tma tAK using standard coupling chemistry. In brief, the antibody is derivatised using SPDP (Pierce Chemical company) at a molar ratio of 3 SPDP to 1 Tma tAK. The free sulfhydryl in the Tma is released by limited treatment with DTT and the protein reacts with the derivatised antibody. The antibody-tAK conjugate is then separated using gel filtration chromatography.

An or crevicular fluid sample is collected using a suitable swab device. The device is heated for 1 minute at 90° C. in a dry oven and then mixed with 1 ml of solution containing the anti-HCV polyclonal antibody-tAK conjugate. The swab is then rinsed in cold water to remove any unbound conjugate and inserted into a reagent tube containing a reagent mix comprising Mg-ADP, luciferin and luciferase. The swab is incubated for 2 minutes and then the entire reagent tube is inserted into a hand-held hygiene monitor and the read-out measured immediately.

EXAMPLE 11

Detection of Immune Status in a Sample of Serum or Whole Blood e.g. Following Immunisation with Measles Vaccine or at an Early Stage Following Exposure to Infectious Measles Virus A fragment of the measles glycoprotein, other measles virus surface components or heat inactivated measles virus, is used to coat a solid support, such as a dipstick. A sample of whole blood, diluted 1:2 with PBS including up to 2M urea to inactivate any non-reporter kinase is applied to the dipstick and antibodies against the measles components are allowed to bind (binding step 1; 5 minutes at 30° C.). Apyrase is added to the blood sample to inactivate any ATP during this phase. After brief rinsing with phosphate buffered saline (PBS; pH7.4), the dipstick is immersed in a solution containing anti-human IgG conjugated to tAK and incubated (binding step 2; 5 minutes at 30° C.). Again the dipstick is rinsed briefly and then placed within a reagent tube. Luciferin/luciferase and ADP were added simultaneously and the reaction measured using a hand held luminometer after 5 minutes.

EXAMPLE 12

Sample Preparation for Detection of Norovirus in Stool Samples

Norovirus is routinely measured in diarrheal samples (i.e. stool sample) for the purposes of clinical diagnosis.

To reduce the levels of contaminating kinase activity the stool sample is diluted between 1:2 and 1:4 with a buffer designed to inactivate the contaminating kinase. This buffer includes one or more of the following components:

2M urea; 2M guanidine; 1% SDS; 1% deoxycholate; 1% Triton X100

The addition of the above components also makes the norovirus antigen more readily detectable by the antibody conjugates described in the next example, increasing the assay signal as well as reducing assay noise. Optionally, apyrase may also be added to the sample destroy any ATP that may be present.

The same types of additive can also be used as sample processing components for the detection of norovirus in vomitus, a sample which would be useful to test for norovirus but which has not, to date, been suitable for analysis.

EXAMPLE 13

Lateral Flow Essay for the Detection of Norovirus and/or C-Difficile Toxin in a Stool Sample A reporter kinase conjugate is prepared by conjugating the adenylate kinase from *P. abyssi* to norovirus VP1 protein or fragments thereof (e.g. the P-domain (located between amino acids 362 and 703), the P2 domain (amino acids 414-589), or sub-fragments of the P1 domain (aa 362-413 or 590-703). The positions within the norovirus correspond to the numbering as described in Chen R, Neill J D, Estes M K, Prasad B V. X-ray structure of a native calicivirus: structural insights into antigenic diversity and host specificity. Proc Natl Acad Sci USA. (2006) 103 p 8048-53.

Figure 5:
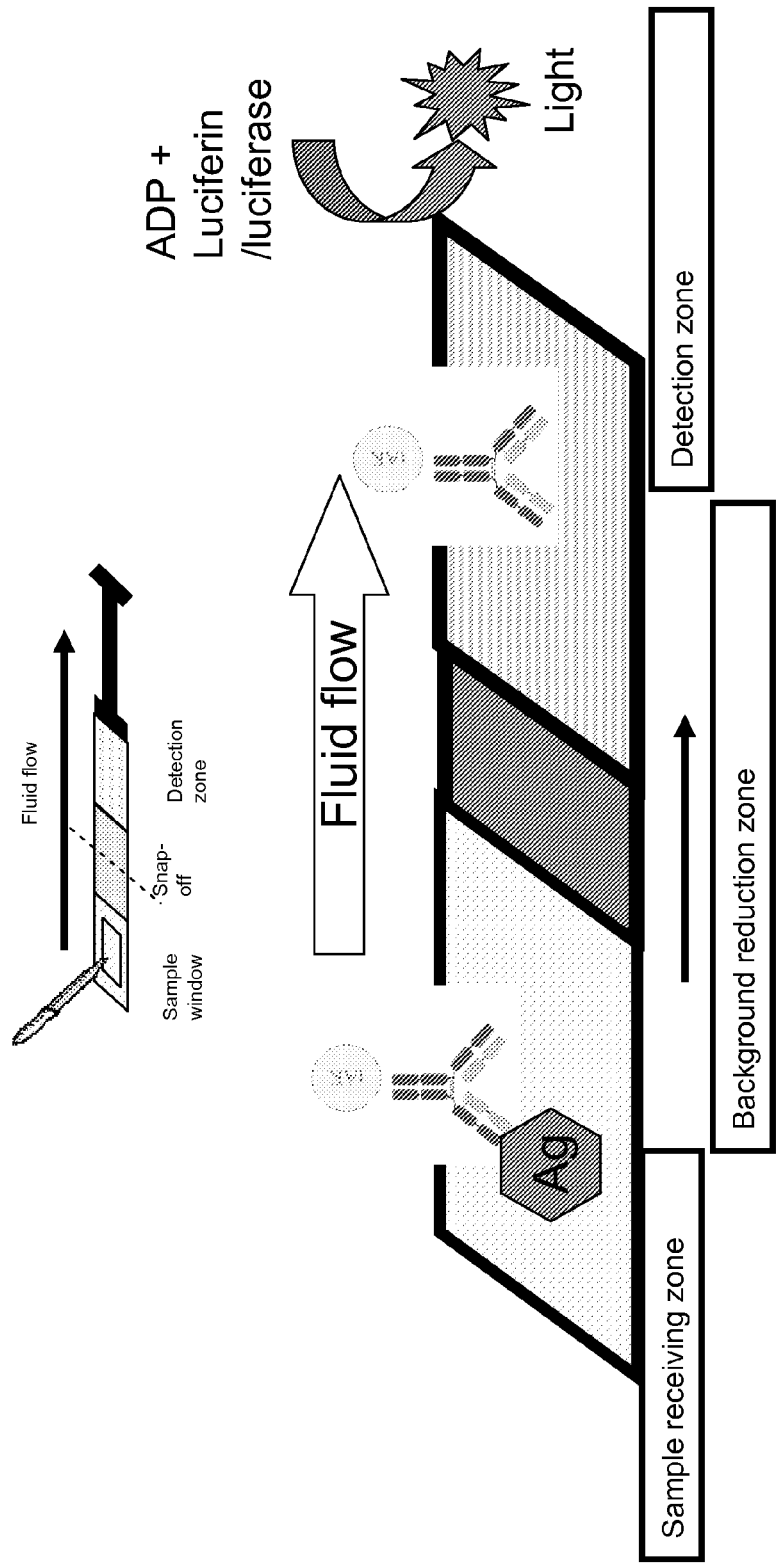
FIG. 5 shows the configuration of a lateral flow device for detection of an analyte in a sample.

A lateral flow device is prepared essentially as shown in FIG. 5. The sample-receiving zone is coated with an anti-norovirus antibody or antibodies (to provide detection of the antigenically diverse range of clinical isolates). The reporter kinase conjugate (described above) is then bound to the sample-receiving zone via the antibodies.

The clinical stool sample is processed as outlined in Example 12 above and applied to the sample-receiving zone of the device. In the presence of norovirus, the reporter kinase conjugate is displaced and migrates to the detection zone, via the background-reduction zone. The background-reduction zone comprises an anion exchange membrane which retains any ATP contained within the original sample. By using a buffer at neutral pH (such as PBS) the ATP is retained on the anion exchange membrane whilst the reporter kinase conjugate passes through as it remain below the isoelectric point and is therefore cationic. Non-reporter kinase has previously been removed in the sample preparation phase (see Example 12).

The lateral flow device is then snapped in two and the detection zone is then placed into a reagent tube containing ADP, luciferin and luciferase. The presence of norovirus in the original sample is determined by measurement of light output with an assay time of 2-5 minutes.

Similarly a lateral flow device may be provided to detect the presence of *C. difficile* toxin A or toxin B in a sample. Antibodies to these targets are well described in the literature and can be conjugated to reporter adenylate kinase(s) as described above. The stool sample is processed as in example 12 and the lateral flow assay carried out as described.

Optionally a device may be provided to detect the presence of either *C. difficile* toxin(s) or norovirus in a sample, enabling differential diagnosis of clinical samples to be carried out. The sample is processed as described in example 12 and mixed with diagnostic reagents for both norovirus and *C. difficile* toxin(s) in the same reaction. The sample may be run on two separate lateral flow devices set up to capture only one of the two targets or preferentially on a single device with two capture windows. These two devices or two windows are then assayed separately to determine the presence of one or more of the target species.

EXAMPLE 14

Detection of *Legionella* in a Water Sample

Figure 6:
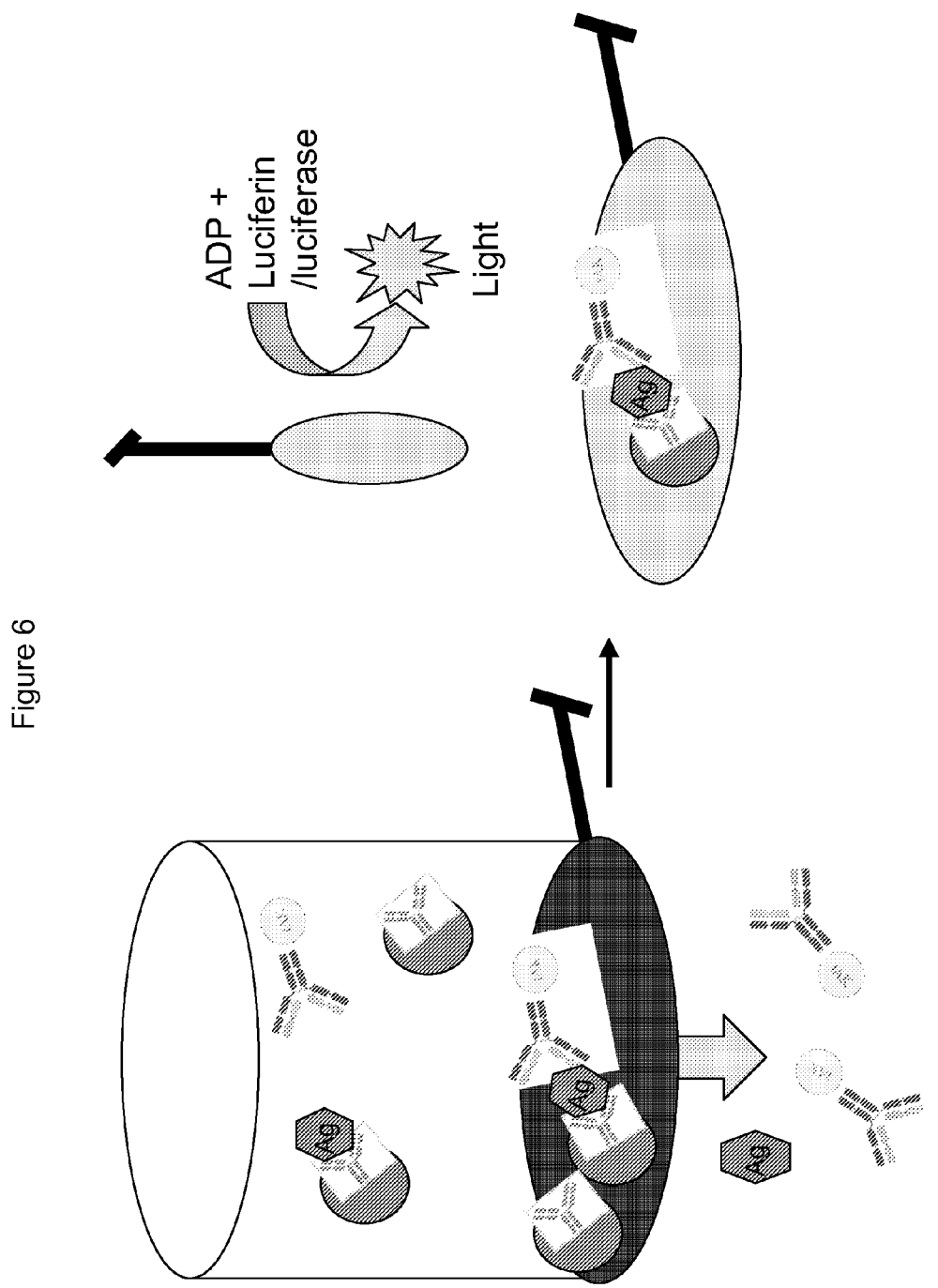
FIG. 6 shows the configuration of a filtration device for the detection of an analyte in a sample.

The assay is carried out using a device as set out in FIG. 6.

A water sample from a cooling tower is sampled at the point of routine maintenance. Typically 50 ml of water is added to a syringe which already contains latex beads coated with anti-*legionella* antibody (antibody A; or fragment thereof) and the reporter kinase from *A. fulgidus* chemically conjugated to a second anti-*legionella* antibody (antibody B). Optionally antibodies A and B may be the same antibody provided there are multiple binding sites on the surface of *legionella*. Preferably they are different antibodies recognising different epitopes of the *legionella*. If *legionella* is present in the water sample, it becomes bound to the latex bead via antibody A. The reporter kinase is bound to the latex bead via the interaction of antibody B with the already-bound *legionella*.

The syringe is shaken continuously for 5 minutes either by hand or optionally within a suitable automated shaker. The syringe is applied to a filtration device which contains a filter designed to allow the free passage of the water, non-reporter kinase, ATP, uncomplexed reporter kinase conjugate, and any uncomplexed microorganisms, but which will retain anything bound to the latex bead. Thus, any reporter kinase bound to the latex bead will be retained on the filter.

The filter is removed from the filter housing and transferred into a reagent tube. The presence of *legionella* is assessed by the addition of ADP, luciferin and luciferase and the measurement of light output using a portable luminometer.

EXAMPLE 15

Detection of *Chlamydia* in a Swab Sample

A swab device is used to collect a vaginal sample from the test individual. The swab is placed in a reagent tube that contains 1M urea to assist in disrupting the tissue and 2 µM Ap5A final concentration which blocks the activity of any non-reporter kinase. The presence of Ap5A does not have a detrimental effect on the activity of the luciferase (see FIG. 4B), hence even if it is present in the final reaction mixture it does not adversely affect the limits of detection.

A reporter kinase conjugate is prepared by conjugating the adenylate kinase from *S. solfataricus* to a *Chlamydia* antigen. A suitable *Chlamydia* antigen is the major outer membrane protein (MoMP) which is present in high copies on the surface of *Chlamydia*. A sores of polymorphic membrane proteins have also been described and may represent suitable target antigens for specific and sensitive detection. Antibodies can be generated to this protein, or peptides derived from it according to conventional protocols.

A lateral flow device is prepared as set out in FIG. 5. The sample-receiving zone of the device is coated with an antibody to a *Chlamydia* antigen. The reporter kinase conjugate is then applied onto the sample-receiving zone of the device, and becomes attached thereto via the interaction between the antigen of the conjugate and the coated antibody.

A small volume of the sample is then spotted onto the sample-receiving zone of the device. Any *chlamydia* antigen present in the sample displaces the reporter kinase conjugate from the sample-receiving zone and allows flow of the reporter kinase conjugate to the detection zone where it can be measured. The device is then placed in a reagent tube, and with ADP and luciferin/luciferase reagents. The light output signal is measured within 5 minutes.

As an alternative antigen, antibodies raised to the bacterial lipopolysaccharide from *Chlamydia* may be employed and conjugated to the reporter kinase. This multivalent target may provide greater sensitivity and specificity than other targets. Optionally more than one of the target antigens may be combined to amplify the signal detected.

EXAMPLE 16

Detection of *Listeria* in a Food Sample

A food sample suspected of containing *Listeria* is immobilized onto a microtitre plate by non-specifically binding sample components to the plate, treating the plate to prevent further non-specific binding thereto and washing.

A reporter kinase conjugate is prepared by conjugating an antibody specific to *Listeria* to the pyruvate kinase from *S. solfataricus*.

The reporter kinase conjugate is applied to the plate and allowed to bind, prior to further washing/recovery. The plate is now heated to about 90 C for about 1 minute in a cell extraction buffer (in a thermal cycler) to denature any non-reporter AK present and release any ATP that may be trapped within the micro-organism. The plate is then coded to 37° C. and a thermolabile ATPase such as apyrase added. The plate is incubated for about 5 minutes to remove the background ATP, then the temperatures is raised to about 90° C. to denature the thermolabile ATPase.

Next, ADP and a mixture of luciferin and luciferase mixture are added simultaneously to the plate. The kinase acts on the ADP to generate ATP, which subsequently reacts with the luciferin/luciferase to produce light. The light output is measured using a hand-held luminometer and is directly proportional to the concentration of the microorganism present.

EXAMPLE 17

Detection of *Salmonella* in a Food Sample

A solid phase is prepared by coating magnetic beads with a first anti-salmonella polyclonal antibody raised in Guinea pig.

A reporter kinase conjugate is prepared by conjugating the adenylate kinase from *T. maritima* to a second anti-salmonella polyclonal antibody raised in Guinea pig.

The food sample to be tested is dispersed in a buffer containing 1M urea plus 2 µM Ap5A and mixed for 5 minutes, in the presence of the magnetic beads and the reporter kinase conjugate. This mixing can be carried out at either room temperature or an elevated temperature. If *Salmonella* is present in the food sample, it will bind to the first anti-salmonella antibody on the magnetic bead. In turn, the reporter kinase conjugate will bind to the magnetic bead via the interaction between the second anti-salmonella antibody and the already-bound *salmonella*.

The magnetic beads are then collected by attraction to a strong magnet and washed with a neutral buffer. The magnet with beads attached is transferred to a reagent tube and ADP, luciferin and luciferase are added simultaneously. The light output signal is read in a luminometer, preferably hand-held, within 5 minutes.

EXAMPLE 18

Validation of Processes for Sterilising Bulk Liquids

Preparation of Indicator 1
A first indicator is prepared by covalently attaching 0.1 mg of pyruvate kinase from *Sulfolobus solfataricus* to a polystyrene strip.
Preparation of Indicator 2
A second indicator is prepared by attaching 0.1 mg of the adenylate kinase from *A. fulgidus* to the inner face of a semi-permeable membrane such as a dialysis tube. The *A. fulgidus* kinase contains a naturally occurring reactive cysteine residue (i.e. not disulfide-bonded within the native enzyme), which can be reacted with BMPH (Pierce). This generates a group capable of reacting with oxidised carbohydrates, as generated, for example, by the treatment of Visking tubing with a suitable oxidising agent. The enzyme is reacted with the oxidised membrane surface to generate a covalently linked indicator.
Validation
The indicator is then attached within the bulk liquid and the sterilisation process (such as autoclaving, the passage of oxidative gases or other chemical sterilisation) is carried out.

The indicator is removed from the bulk liquid on completion of the process, and the residual activity of the kinase is measured. To achieve the measurement the indicators are first incubated in the presence of apyrase, at a concentration of 10 µg/ml for 2 minutes. The apyrase can be inactivated by addition of Ap5A at a concentration of 5 µM. The two indicators can then be read independently by addition of a combined reagent containing ADP, luciferin and luciferase. The measurement is made within 5 minutes using a hand held luminometer, such as a hygiene monitor.

In this example any non-reporter kinase that might be present is destroyed by the treatment conditions and as such specific kinase-reduction steps are not required. The residual activity is then compared to a defined threshold value.

EXAMPLE 19

Validation of the Performance of Cloth Washing Cycles Using Biological Detergents Preparation of Indicator 1
A first indicator is prepared by cross-linking adenylate kinase from *S. solfataricus* onto a flexible polystyrene wand using a method based on disulfide bond formation. In this method, the adenylate kinase is derivatised with a heterobifunctional agent such as Sulfosuccinimidyl 6-(3'[2-pyridyldithio]-propionamido)hexanoate (SPDP; Pierce chemical company, UK) at a ratio of between 1-3 SPDP:protein. The derivatised kinase is then reduced by reaction with a reducing agent such as dithiothreitol (DTT), or 2-mercaptoethanesulfonic acid (MESNA), the reducing agent removed by dialysis, and the kinase reacted with a maleimide-derivatised polystyrene surface. Typically, 0.1 mg of kinase is, present on the indicator.

Preparation of Indicator 2

A second indicator is prepared by the non-specific adherence of an adenylate kinase from *S. acidocaldarius* onto a high-protein binding polystyrene strip. The kinase is prepared at a concentration of 0.5-2 mg/ml in a bicarbonate buffer (pH 9.6), optionally containing the stabilising agent sorbitol at between 0.1 and 2% w/v. The kinase in binding buffer is then incubated with the high protein-binding polystyrene strip for a period of 1-2 hours at 22° C. (or 4° C. overnight). The residual kinase is removed by washing in a phosphate buffered saline. Typically, 0.1 mg of kinase is present on the indicator.

Validation of Wash Cycles

The washer is loaded with the items to be washed, and the indicator is fixed within a suitable holder on the inside of a washer (to facilitate its recover). The wash cycle is then performed. At completion of the cycle, the indicator is removed and the residual activity of the kinase is assessed. In this example the washing process removes and/or inactivates both any non-reporter kinase and any residual ATP, hence neither interfere with the assay. The presence of the reporter kinase is determined by the addition of ADP, followed within 1 minute by the addition of luciferin and luciferase.

If the measurement of residual kinase activity is equal to or below a predetermined threshold level, then the load is cleared for further processing.

EXAMPLE 20

Preparation of a Fibrin-Based Indicator Device

Preparation of tAK Fusions for Cross-Linking to Fibrin

A transglutaminase substrate sequence (MNQEQVS-PLGG—SEQ ID No: 33) is added on to the N-terminus, the C-terminus, or both N- and C-termini, of the adenylate kinase from *S. acidocaldarius* encoded by a codon optimised gene done. This construct is transferred as an NdeI—SalI fragment into an in-house expression vector (pMTL 1015; as described in WO 2005/123764). The expression construct is confirmed by DNA sequencing and transferred into expressions hosts BL21 or RV308 for subsequent expression.

Similarly, the resynthesised tAK gene from *Thermatoga maritima* (SEQ ID 29) is fused to the transglutaminase sequence in the three orientations identified above. The cloning and preparation of the expression system is also as described above.

The fusion constructs can also be expressed in other expression vector-host combinations with the addition of affinity tags for subsequent purification. Particularly useful in this context are expression vectors which add 6-histidine tags on either the N- or C-terminus of the fusion proteins, modifications which aid purification and detection but do not interfere with the intrinsic properties of the fusion proteins. Vectors for this type of modification include pET series vectors (Novagen/Merck) and pQE series vectors (Qiagen).

To generate material for the indicator devices the expression strains are grown initially in 8-liter fermenters essentially under static culture conditions. In brief, the strains are prepared as seed stocks and subsequently diluted into the 8-liters of growth media (modified terrific broth containing additional glucose). The cultures are grown under standard fermentation conditions until the cultures reached an optical density (OD at 600 nm) demonstrating that they are entering stationary conditions (typically at around an OD=5). The fermenters are then held under minimally aerated conditions for up to 12 hours prior to harvesting of material by continual centrifugation.

Purification of tAK Fusions

The harvested material is then purified according to the following protocol.

Buffer A: 20 mM Tris-HCl; 900 mM NaCl, pH 7.5
Wash Buffer: 20 mM Tris-HCl; 200 mM NaCl, pH 7.5
Buffer B: 20 mM Tris-HCl; 200 mM NaCl, pH 7.5
   10 mM ATP; 10 mM AMP; 10 mM $MgCl_2$
MgAc buffer: 15 mM MgAc (1M Fluka BioChemika), pH 6.8

1. Weigh frozen cell paste (10 g) and resuspend in 3× (30 ml) volume of Buffer A, pH 7.5.
2. Sonicate on ice (~12,000 khz) using 25 cycles of 30 seconds on/30 seconds off. Take 1 ml sample.
3. Sonicated cell solution is centrifuged at 6,000 rpm for 30 mins at 4 degrees C. Supernatant carefully poured off and 1 ml sample taken.
4. Supernatant is heat treated at 80 degrees C. in a water bath for 20 mins. 1 ml sample taken. (This step is an optional step depending on thermal stability of the fusion proteins).
5. Heat treated solution centrifuged at 6000 rpm for 30 mins. at 4 degrees C. Pour off supernatant and take 1 ml sample.
6. Filter the sample with 0.2 µm low binding filter before loading onto column.
7. Equilibrate Blue Sepharose Fast Row column with 5 Column Volumes (CVs) of Buffer A.
8. Load the Wash column with wash buffer at 0.2 ml/min overnight.
9. Elute protein with 100% buffer B at a flow rate of 1 ml/min collect product in 2.5 ml fractions.
10. Once all proteins have eluted wash column with 100% buffer B at 5 ml/min for 5 CV's.
11. Re-equilibrate column with 5 CV's of buffer A.
12. Rinse column with 5 CVs 20% Ethanol for storage at 4° C.

Optionally, additional protein purification methods are applied to yield a higher purity product. Ion exchange chromatography on either SP-Sepharose Fast Row or Q-Sepharose Fast Flow resins is particularly effective.

The samples are then analysed using a standard assay format to identify fractions containing peak adenylate kinase activity. This is confirmed by SDS-PAGE analysis using standard techniques. In brief, the assay method is carried out using the following protocol:

1. Dilute the purified tAK fusion 1:1000 and 1:10,000 in Mg Ac Buffer. Add 100 µl per well.
2. Treat with Apyrase (50 µl/well at 2.5 units per ml stock concentration; Sigma Grade VI Apyrase from potato) and incubate for 30 mins at 30° C., with shaking, to remove ATP.
3. Incubate plate at 70° C. for 10 mins to denature Apyrase.
4. Add 50 µl/well of ADP (275 µM ADP in MgAc buffer) and seal. Incubate at 70° C. for 20 mins.
5. Remove plate and allow to cool to room temperature for 20 mins, warm Luciferase/Luciferin (L/L) reagent to room temperature for 20 mins.
6. Add 200 µl ATP standard to 1 or 2 empty wells per plate.
7. Set up injectors on luminometer and prime them with L/L reagent (ATP reagent, Biotherma). Inject 30 µl L/L reagent/well.
8. Read light generated immediately using luminometer.

The fractions with peak kinase activity are then dialysed extensively against phosphate buffered saline (PBS pH 7.4) and stored until required. Optionally a fusion can be prepared between tAK and the full length fibrinogen molecule to provide further means to incorporate the enzymatic activity within the fibrin film.

Deposition of tAK Fusions onto a Solid Support

The tAK-fibrin fusion is diluted to around 200 µg/ml in either PBS or bicarbonate buffer (pH 9.6) and applied to a solid support of 316 L grade stainless steel, plastic, glass or textiles. The protein is allowed to adhere to the surface for up to 2 hours at room temperature or overnight at 4° C.

Optionally, additional carrier molecules are added at this stage, e.g. sucrose at concentrations up to 1% w/v, albumin at up 1 mg/ml, pig mucin at up to 0.5% w/v. The addition of such carriers may be particularly important for certain types of indicator but the presence of the carrier should not interfere with subsequent interaction and cross-linking to the fibrin film applied in the next stage.

Overlay of Fibrin Containing Soil and Cross-Linking to Fibrin-tAK Fusion

A solution containing fibrinogen is added to effect the cross-linking of the indicator to the fibrin-containing test soil (biological matrix).

A solution containing up to 3 mg/ml fibrinogen (containing Factor XIII), 2.5 mM $CaCl_2$, and thrombin (up to 5 NIH units per ml) is mixed freshly and added to the coated surface of the solid support. The reaction is allowed to proceed at room temperature for up to 30 minutes, depending on the level of cross-linking required. Optionally, albumin (up to 80 mg/ml) and haemoglobin (up to 80 mg/ml) are added at this stage to provide a tougher and more realistic challenge for cleaning of a blood-like soil. After cross-linking, residual liquid is removed and the indicator device left to dry.

Optionally, the tAK-fibrin peptide fusion is added to the fibrin-containing test soil solution (biological matrix) prior its addition to the solid support surface. Cross-linking of the fibrin peptide to the matrix can be increased by adding more Factor XIII and/or extending the duration of the reaction. Cross-linking can also be enhanced by the use of the tAK fusion protein with fibrin peptides added to both ends of the molecule. Optionally a fibrinogen-tAK fusion could be added directly to this solution to provide further cross linkage of the indicator.

Covalent Chemical Cross-Linking of tAK to Fibrin or Fibrinogen.

tAK may be chemically joined to fibrin, fibrin peptides or fibrinogen by a wide range of methods familiar to those working in the field. For example purified protein preparations for fibrinogen or fibrin are obtained from commercial sources (e.g. Sigma). The tAK from *S. acidocaldarius* is prepared as described above. The tAK is derivatised using the amide reactive reagent SPDP (SPDP (N-Succinimidyl 3-(2-pyridyldithio)-propionate; Pierce chemical company) according to the manufacturer's instructions. The fibrin or fibrinogen is also derivatised using the same protocol. The derivatised tAK is reduced by reaction with mercaptoethanol to yield a reactive sulfhydryl group. This is then mixed with the SPDP-derivatised fibrin causing the formation of covalent bonds between the two molecules. The concentrations of the reaction partners should be determined empirically following the guidelines within the manufacturer's instructions for SPDP. The chemically linked tAK fibrin or fibrinogen can be used interchangeably or in addition to the fusion protein.

Uses of Fibrin-tAK Indicators

Use in a Washer Disinfector

An indicator is prepared as described above. Preferably the solid support is a rectangular stainless steel strip 55 mm×5 mm×0.75 mm, which may be coated on one or both surfaces. One or preferably several indicator strips are positioned within the chamber of the washer disinfector. Optimally these may be positioned in sites which may be the most difficult to clean, providing the highest degree of certainty that the wash process has been effective. Alternatively they may be positioned to monitor the function of multiple spray arms (i.e. where these may be independent of each other). The indicator strips are clipped to the shelves or other substructure of the washer-disinfector chamber to ensure that they do not move during the wash treatment. The orientation of the surrogate devices can be modified to provide further information about the efficacy of the wash process, for example by positioning them so that the coated surface are at right angles to the direction of water spray.

The instrument load is added and the standard run cycle performed. At the end of the run the devices are removed from the chamber and the presence of residual tAK-fusion assessed, as outlined below, prior to the removal of the instruments and any subsequent processing. Optionally devices can be removed during the wash process either by interrupting the process at carefully defined points or by using a machine that provides a method of withdrawing the indicator during the run.

Use in Endoscope Test Procedure

The indicator device for monitoring an endoscope reprocessing system is essentially similar to that outlined above. A similar size indicator surface, representative of either the stainless steel components within an endoscope, the PTFE tubing or other relevant materials is placed within a tubular chamber. This is attached, via suitable screw, push or bayonet fittings to either the front end of the endoscope or, more preferably the end which makes contact with patient tissues. This is placed within the endoscope reprocessing unit and the ends of the endoscope tubing and indicator device are coupled to the ports in the unit. The process is run as standard and the indicator device removed at the end of the run for analysis, prior to onward processing or the return of the endoscope to use.

Means of Assessing Cleaning Performance

The indicator device is removed at the end of the test process. The indicator strip is then placed into a reagent tube with ADP, luciferin and luciferase, added simultaneously, with signal being read-out on a hand-held luminometer with 2 minutes.

EXAMPLE 21

Preparation of tAK-Sup35 Fusion

Clones containing the N-terminal domain of Sup35 from *Saccharomyces cerevisiae* fused to either the N- or C-terminus, or both termini, of adenylate kinases from either *S. acidocaldarius* or *T. maritima* are generated by standard DNA manipulation techniques. All clones are transferred as NdeI—SalI fragments into the pMTL1015 expression vector and their sequences verified. The expression constructs are used to transform BL21 or RV308 expression strains and the material grown in large scale fermentation conditions, but with minimal aeration.

Expression and purification of a tAK-Sup35 fusion is essentially the same as for the fibrin-peptide fusions described in Example 20, except that the use of the thermal denaturation step (Step 4) is not part of the purification protocol. In brief, cell paste from the fermenter is resuspended in buffer A, and lysed by sonication. The cell debris is removed (no heat treatment is typically used for these type of fusions) and the supernatant used for column purification as outlined in Example 20.

Under certain growth conditions the fusion proteins may be insoluble, being apparent as inclusion bodies within the cells. In this case the cell pellets are prepared and lysed in the same way, but the resulting insoluble fraction, containing the inclusion bodies, is collected by centrifugation. This material is washed in a buffer (e.g. PBS) containing Triton X100 (up to concentrations of 5%). After each wash the pellet containing the fusion proteins is separated by centrifugation. After 5 washes the inclusion bodies are resolubilised in PBS containing 8M urea and agitated gently for up to 30 minutes. Any residual insoluble material is removed by centrifugation. The urea-solubilised material is dialysed against up to 5×10 volumes of PBS to remove the urea and allow the fusion proteins to refold. Optionally the urea may be removed more rapidly by spraying the urea-solubilised preparation through a fine gauge needle into 100 volumes of rapidly stirred PBS or buffer A as used for purification. The material is allowed to stand at room temperature with stirring for up to 30 minutes prior to subsequent processing.

Subsequent purification of the fusions is carried out essentially as described in Example 20. The supernatant from either lysed cells or solubilised and refolded inclusion bodies is loaded onto a pre-equilibrated Blue Sepharose Fast Flow column. After extensive washing in buffer A and subsequently in wash buffer, the protein is eluted using buffer B. Peak fractions are determined by SDS-PAGE analysis and enzyme assay. Fractions are then pooled and dialysed into PBS.

Conversion of tAK-Sup35 to an Amyloid Form

The Sup35-tAK fusions when assembled into fibrils are more representative of amyloid proteins such as prions which are key molecules against which to assess the efficacy of decontamination processes.

The amyloid form of the Sup35-tAK fusions is generated by either refolding of the purified soluble protein or by modifying the conditions used for dialysis of the urea-resolubilised inclusion body preparations, in the first case, a conformational change is induced by exposure of the fusion proteins to conditions around pH4 (e.g by dialysis into a suitably buffered solution at pH 7.4 optionally containing up to 1M NaCl). In the latter case, the resolubilised fusion proteins in 8M urea/PBS are dialysed for 6-12 hours at room temperature against 2M urea, 300 mM NaCl, in PBS (pH 7.4). Alternatively, the fibrilisation can be induced by dialysis against 20 mM Tris pH8.0 10 mM EDTA under similar incubation conditions. Optionally, the fusion proteins may be incorporated into fibrils containing normal Sup35. This is achieved by mixing the fusions with unfused Sup35 expressed in the same way, at ratios between 1:1 to 1:10 fusion:Sup35.

Deposition of tAK-Sup35 Fusions onto Solid Support.

Deposition of the fibrils onto a solid support is effected by simple protein adsorption in a suitable buffer (e.g. PBS pH 7.4 Bicarbonate buffer pH 9.6) in the presence of high levels of NaCl. The use of charged or precoated surfaces (e.g. plastics coated with Poly-L-lysine) is useful in providing surfaces which can more effectively bind the fusion proteins. Optionally, the fibrils may be deposited in a suitable carrier, such as sucrose (to 1%), pig mucin (up to 0.5%), or albumin (up to 1 mg/ml).

Overlay of Test Soil

A test soil (biological matrix) is then overlaid onto the amyloid preparation adhered onto the surface as described above.

Suitable biological matrices in which the amyloid indicator is embedded include e.g. 0.5% mucin, with or without albumin, a commercial test soil (such as that manufactured by Browne's) or any one of the test soils identified in guidance documents issues by national and international standards committees (e.g. Edinburgh soil as detailed in HTM 01/01 (UK).

Assembly of Amyloid Fibrils within the Test Soil

Given the ability of amyloids to self-assemble in complex matrices it is possible for the amyloid-tAK fusion to be mixed with soil components prior to fibril formation and subsequent deposit onto surfaces. This provides further options for indicators in which the amyloid fibrils may be mixed and interchelated with other soil components providing a different type of matrix that may be harder to remove from surfaces.

Use of tAK-Sup35 Indicator for Assessing Prion Removal from Surfaces in a Washing Process An indicator as described above is prepared as fibrils and dried down onto a steel surface in the presence of 0.5% mucin. The indicator is placed within the chamber of a washer disinfector at pre-determined locations. The instrument load is added. The process is started as per the manufacturer's instructions and any process records completed. At the end of the process, and before any instruments are taken from the machine, the indicator devices are removed and assessed as described in Example 20.

Use of tAK-Sup35 Indicator for Assessing Prion Inactivation in a Protease-Based Process Indicators as described above are prepared as fibrils with a high ratio of free Sup35:Sup35-tAK (n excess of 5:1) and deposited onto solid support strips in the presence of Edinburgh sod. The indicator devices are inserted into a pre-soak bath containing freshly made Prionzyme™ (Genencor International) prion inactivation treatment (at 60° C., pH 12). The indicator strips are cupped to the side of the bath such that the ends of the indicators are within the bulk of the liquid. Instruments are added as required and processed for 30 minutes. The indicator devices are removed from the bath at the end of the process, prior to removal of the instruments and assessed as described in Example 20.

Use of tAK-Sup35 Indicator for an Oxidative Process Aimed at Destroying Prions.

An indicator as described above is prepared as fibrils using only Sup35-tAK, and deposited onto a stainless steel surface (optionally in the presence of 0.1% w/v sucrose). The indicator is attached to the inside of the lid of a Genesis™ container in which the instruments are prepared for processing and the lid closed. The container is inserted into the load chamber of a suitable processor for oxidative challenge (e.g. the 125 L ozone steriliser; $TSO_3$ or a vapour phase hydrogen peroxide technology such as that described in published papers by Fichet et al 2004; Lancet) and the process run according to manufacturers' instructions. At the end of the process, the Genesis container is taken out of the chamber and the indicator devices are removed and processed as described in Example 20.

EXAMPLE 22

Detection of a Reporter Kinase in a Sample Due to an Infection; Use for Rapid Assay of Infection in Patient Sample A patient presented at the clinic with suspected infection from the obligate intracellular pathogen *Burkholderia pseudomallei*. A blood sample was removed and dispersed in a buffer containing 1M urea plus 5 μM Ap4A. The sample was assayed by addition of ADP and luciferin/luciferase reagent, incubated for 2 minutes and the light output measured in a hand-held luminometer. The signal generated is directly proportional to the amount of *B. pseudomallei* within the blood sample.

Detection of a Reporter Kinase in a Sample Due to an Infection; Use for Rapid Assay of Infection in Cell Models The study of intracellular bacterial pathogens is complicated by the need to grow them in mammalian cell culture systems. Measurement of viable cells the requires subsequent culture or re-infection into mammalian host cells, both of which are very time consuming methods. A rapid assay, such as provided by the invention, is invaluable in providing information that can be used in real-time to determine the results of an experiment.

A suitable isolate of *B. pseudomallei* was incubated with a permissive cell culture model capable of supporting growth of the bacteria within the cell. The culture was grown for an appropriate length of time to establish the infection.

Cells were isolated by centrifugation and lysed by resuspension in a buffer containing 1% Triton X-100, 5 μM Ap4A. A detection reagent containing ADP, luciferin and luciferase was added and incubated for 5 minutes. The light output was read in a 96-well plate luminometer. The amount of signal generated is proportional to the number of viable *B. pseudomallei* cells within the cell culture. Optionally this rapid assay method can be extended to measure the effects of vaccines or drugs that reduce the number of viable cells within the cell culture.

For example, antibodies raised in a patient immunised with a prototype *B. pseudomallei* vaccine are mixed with the organisms prior to addition to the permissive cell culture. After an incubation period sufficient to allow uptake of non-neutralised microorganisms, the cells are washed and incubated for a period of time sufficient to establish the infection. Cells are then washed and lysed as described above, again in the presence of inhibitor. The signal measured by simultaneous addition of ADP, luciferin and luciferase is proportional to the number of non-neutralised microorganisms giving a measure of the effectiveness of the vaccine and/or the immune response generated in a vaccinated individual. Such methods are suitable for high-throughput screening.

In a further example, infected cell cultures are set up as described above. After the infection is established, antibiotics are used to treat the infected culture, with the express aim of killing the bacteria within the host cells. After the antibiotics have been applied, the cultures are incubated for sufficient time for the antibiotic to have its effect. The cells are lysed in the presence of inhibitor as described above and the number of viable cells quantified by measurement of the reporter kinase, by addition of ADP, luciferin and luciferase.

The invention claimed is:

1. An assay for detecting the activity of an exogenous kinase, comprising:
   (i) adding said exogenous kinase to an assay mixture, wherein said exogenous kinase is contacted simultaneously with ADP and a bioluminescent reagent, wherein prior to contacting the exogenous kinase with ADP, the assay mixture is substantially free from kinase other than exogenous kinase; and
   (ii) detecting light output from the assay mixture.

2. The assay according to claim 1, wherein prior to contacting the exogenous kinase with the ADP, the assay mixture is substantially free from ADP.

3. The assay according to claim 2, wherein prior to contacting the exogenous kinase with the ADP, kinase other than exogenous kinase is substantially removed or inactivated.

4. The assay according to claim 3, wherein prior to contacting the exogenous kinase with the ADP, ATP is substantially removed.

5. The assay according to claim 1, wherein the exogenous kinase is an adenylate kinase.

6. The assay according to claim 1, wherein the exogenous kinase is a thermostable kinase.

7. The assay according to claim 1, wherein the assay is completed in less than 15 minutes, less than 10 minutes, less than 5 minutes, less than 2 minutes, less than 1 minute, or less than 30 seconds.

8. The assay according to claim 1, wherein the assay determines the presence of an analyte in a sample, wherein the assay comprises:
   (i) exposing the sample to an exogenous kinase coupled to a binding agent specific for the analyte, so that a complex is formed between the exogenous kinase and said analyte when present in the sample;
   (ii) separating complexed exogenous kinase from uncomplexed kinase;
   (iii) adding the complexed exogenous kinase to an assay mixture, wherein the complexed exogenous kinase is contacted simultaneously with ADP and a bioluminescent reagent, wherein prior to contacting the complexed exogenous kinase with ADP, the assay mixture is substantially free from kinase other than complexed exogenous kinase; and
   (iv) detecting light output from the assay mixture, thereby determining the presence of the analyte in the sample.

9. The assay according to claim 1, wherein the assay detects the presence of an analyte in a sample, wherein the assay comprises:
   (i) providing a solid support on which is attached a first binding agent specific for the analyte;
   (ii) exposing the solid support to the sample so that said analyte when present in the sample becomes attached to the solid support via said first binding agent;
   (iii) exposing the solid support to an exogenous kinase coupled to a second binding agent specific for the analyte, so that the exogenous kinase becomes attached to the solid support via the interaction between the second binding agent and the already-bound analyte;
   (iv) applying the mixture obtained in step (iii) to a filter membrane, wherein the solid support is retained on the filter membrane;
   (v) adding the retained exogenous kinase to an assay mixture, wherein the retained exogenous kinase is contacted simultaneously with ADP and a bioluminescent reagent, wherein prior to contacting the retained exogenous kinase with ADP, the assay mixture is substantially free from kinase other than complexed exogenous kinase; and
   (vi) detecting light output from the assay mixture, thereby detecting the presence of the analyte in the sample.

10. The assay according to claim 9, wherein the solid support is selected from the group consisting of a latex bead and a magnetic bead.

11. The assay according to claim 8, wherein the assay is completed in less than 15 minutes, less than 10 minutes, less than 5 minutes, or less than 2 minutes.

12. The assay according to claim 8, wherein prior to measuring the activity of the exogenous kinase, the sample is treated to substantially remove ATP and/or to substantially remove or inhibit kinase other than exogenous kinase.

13. The assay according to claim 8, further comprising the step of recording the light output data obtained in step (iv) on a suitable data carrier.

14. The assay according to claim 9, wherein prior to contacting the exogenous kinase with the ADP, the assay mixture is substantially free from ADP.

15. The assay according to claim 14, wherein prior to contacting the exogenous kinase with the ADP, kinase other than exogenous kinase is substantially removed or inactivated.

16. The assay according to claim 15, wherein prior to contacting the exogenous kinase with the ADP, ATP is substantially removed.

17. The assay according to claim 9, wherein the exogenous kinase is an adenylate kinase.

18. The assay according to claim 9, wherein the exogenous kinase is a thermostable kinase.

19. The assay according to claim 9, wherein the assay is completed in less than 15 minutes, less than 10 minutes, less than 5 minutes, less than 2 minutes, less than 1 minute, or less than 30 seconds.

20. The assay according to claim 8, wherein the exogenous kinase is an adenylate kinase.

* * * * *

UNITED STATES PATENT AND TRADEMARK OFFICE
CERTIFICATE OF CORRECTION

PATENT NO.        : 8,512,970 B2
APPLICATION NO. : 13/143722
DATED             : August 20, 2013
INVENTOR(S)       : Sutton et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 108 days.

Signed and Sealed this

Fifteenth Day of September, 2015

Michelle K. Lee
*Director of the United States Patent and Trademark Office*

SEQUENCE LISTING

```
<160> NUMBER OF SEQ ID NOS: 84

<210> SEQ ID NO 1
<211> LENGTH: 195
<212> TYPE: PRT
<213> ORGANISM: Sulfolobus solfataricus

<400> SEQUENCE: 1

Met Lys Ile Gly Ile Val Thr Gly Ile Pro Gly Val Gly Lys Thr Thr
1               5                   10                  15

Val Leu Ser Phe Ala Asp Lys Ile Leu Thr Glu Lys Gly Ile Ser His
            20                  25                  30

Lys Ile Val Asn Tyr Gly Asp Tyr Met Leu Asn Thr Ala Leu Lys Glu
        35                  40                  45

Gly Tyr Val Lys Ser Arg Asp Glu Ile Arg Lys Leu Gln Ile Glu Lys
    50                  55                  60

Gln Arg Glu Leu Gln Ala Leu Ala Ala Arg Arg Ile Val Glu Asp Leu
65                  70                  75                  80

Ser Leu Leu Gly Asp Glu Gly Ile Gly Leu Ile Asp Thr His Ala Val
                85                  90                  95

Ile Arg Thr Pro Ala Gly Tyr Leu Pro Gly Leu Pro Arg His Val Ile
            100                 105                 110

Glu Val Leu Ser Pro Lys Val Ile Phe Leu Leu Glu Ala Asp Pro Lys
        115                 120                 125

Ile Ile Leu Glu Arg Gln Lys Arg Asp Ser Ser Arg Ala Arg Thr Asp
    130                 135                 140

Tyr Ser Asp Thr Ala Val Ile Asn Glu Val Ile Gln Phe Ala Arg Tyr
145                 150                 155                 160

Ser Ala Met Ala Ser Ala Val Leu Val Gly Ala Ser Val Lys Val Val
                165                 170                 175

Val Asn Gln Glu Gly Asp Pro Ser Ile Ala Ala Ser Glu Ile Ile Asn
            180                 185                 190
```

```
Ser Leu Met
        195

<210> SEQ ID NO 2
<211> LENGTH: 194
<212> TYPE: PRT
<213> ORGANISM: Sulfolobus acidocaldarius

<400> SEQUENCE: 2

Met Lys Ile Gly Ile Val Thr Gly Ile Pro Gly Val Gly Lys Ser Thr
1               5                   10                  15

Val Leu Ala Lys Val Lys Glu Ile Leu Asp Asn Gln Gly Ile Asn Asn
            20                  25                  30

Lys Ile Ile Asn Tyr Gly Asp Phe Met Leu Ala Thr Ala Leu Lys Leu
        35                  40                  45

Gly Tyr Ala Lys Asp Arg Asp Glu Met Arg Lys Leu Ser Val Glu Lys
    50                  55                  60

Gln Lys Lys Leu Gln Ile Asp Ala Ala Lys Gly Ile Ala Glu Glu Ala
65                  70                  75                  80

Arg Ala Gly Gly Glu Gly Tyr Leu Phe Ile Asp Thr His Ala Val Ile
                85                  90                  95

Arg Thr Pro Ser Gly Tyr Leu Pro Gly Leu Pro Ser Tyr Val Ile Thr
            100                 105                 110

Glu Ile Asn Pro Ser Val Ile Phe Leu Leu Glu Ala Asp Pro Lys Ile
        115                 120                 125

Ile Leu Ser Arg Gln Lys Arg Asp Thr Thr Arg Asn Arg Asn Asp Tyr
    130                 135                 140

Ser Asp Glu Ser Val Ile Leu Glu Thr Ile Asn Phe Ala Arg Tyr Ala
145                 150                 155                 160

Ala Thr Ala Ser Ala Val Leu Ala Gly Ser Thr Val Lys Val Ile Val
                165                 170                 175

Asn Val Glu Gly Asp Pro Ser Ile Ala Ala Asn Glu Ile Ile Arg Ser
            180                 185                 190

Met Lys

<210> SEQ ID NO 3
<211> LENGTH: 197
<212> TYPE: PRT
<213> ORGANISM: Sulfolobus tokodaii

<400> SEQUENCE: 3

Met Ser Lys Met Lys Ile Gly Ile Val Thr Gly Ile Pro Gly Val Gly
1               5                   10                  15

Lys Thr Thr Val Leu Ser Lys Val Lys Glu Ile Leu Glu Glu Lys Lys
            20                  25                  30

Ile Asn Asn Lys Ile Val Asn Tyr Gly Asp Tyr Met Leu Met Thr Ala
        35                  40                  45

Met Lys Leu Gly Tyr Val Asn Asn Arg Asp Glu Met Arg Lys Leu Pro
    50                  55                  60

Val Glu Lys Gln Lys Gln Leu Gln Ile Glu Ala Ala Arg Gly Ile Ala
65                  70                  75                  80

Asn Glu Ala Lys Glu Gly Gly Asp Gly Leu Leu Phe Ile Asp Thr His
                85                  90                  95

Ala Val Ile Arg Thr Pro Ser Gly Tyr Leu Pro Gly Leu Pro Lys Tyr
            100                 105                 110

Val Ile Glu Glu Ile Asn Pro Arg Val Ile Phe Leu Leu Glu Ala Asp
        115                 120                 125
```

```
Pro Lys Val Ile Leu Asp Arg Gln Lys Arg Asp Thr Ser Arg Ser Arg
            130                 135                 140

Ser Asp Tyr Ser Asp Glu Arg Ile Ile Ser Glu Thr Ile Asn Phe Ala
145                 150                 155                 160

Arg Tyr Ala Ala Met Ala Ser Ala Val Leu Val Gly Ala Thr Val Lys
                165                 170                 175

Ile Val Ile Asn Val Glu Gly Asp Pro Ala Val Ala Ala Asn Glu Ile
            180                 185                 190

Ile Asn Ser Met Leu
            195

<210> SEQ ID NO 4
<211> LENGTH: 196
<212> TYPE: PRT
<213> ORGANISM: Pyrococcus furiosus

<400> SEQUENCE: 4

Met Pro Phe Val Val Ile Ile Thr Gly Ile Pro Gly Val Gly Lys Ser
1               5                   10                  15

Thr Ile Thr Arg Leu Ala Leu Gln Arg Thr Lys Ala Lys Phe Arg Leu
            20                  25                  30

Ile Asn Phe Gly Asp Leu Met Phe Glu Glu Ala Val Lys Ala Gly Leu
        35                  40                  45

Val Lys His Arg Asp Glu Met Arg Lys Leu Pro Leu Lys Ile Gln Arg
    50                  55                  60

Glu Leu Gln Met Lys Ala Ala Lys Lys Ile Thr Glu Met Ala Lys Glu
65                  70                  75                  80

His Pro Ile Leu Val Asp Thr His Ala Thr Ile Lys Thr Pro His Gly
                85                  90                  95

Tyr Met Leu Gly Leu Pro Tyr Glu Val Val Lys Thr Leu Asn Pro Asn
            100                 105                 110

Phe Ile Val Ile Ile Glu Ala Thr Pro Ser Glu Ile Leu Gly Arg Arg
        115                 120                 125

Leu Arg Asp Leu Lys Arg Asp Arg Asp Val Glu Thr Glu Glu Gln Ile
130                 135                 140

Gln Arg His Gln Asp Leu Asn Arg Ala Ala Ile Ala Tyr Ala Met
145                 150                 155                 160

His Ser Asn Ala Leu Ile Lys Ile Ile Glu Asn His Glu Asp Lys Gly
                165                 170                 175

Leu Glu Glu Ala Val Asn Glu Leu Val Lys Ile Leu Asp Leu Ala Val
            180                 185                 190

Asn Glu Tyr Ala
            195

<210> SEQ ID NO 5
<211> LENGTH: 196
<212> TYPE: PRT
<213> ORGANISM: Pyrococcus horikoshii

<400> SEQUENCE: 5

Met Pro Phe Val Val Ile Ile Thr Gly Ile Pro Gly Val Gly Lys Ser
1               5                   10                  15

Thr Ile Thr Lys Leu Ala Leu Gln Arg Thr Arg Ala Lys Phe Lys Leu
            20                  25                  30

Ile Asn Phe Gly Asp Leu Met Phe Glu Glu Ala Leu Lys Leu Lys Leu
        35                  40                  45
```

-continued

Val Lys His Arg Asp Glu Met Arg Lys Leu Pro Leu Glu Val Gln Arg
 50                  55                  60

Glu Leu Gln Met Asn Ala Ala Lys Lys Ile Ala Glu Met Ala Lys Asn
 65                  70                  75                  80

Tyr Pro Ile Leu Leu Asp Thr His Ala Thr Ile Lys Thr Pro His Gly
                 85                  90                  95

Tyr Leu Leu Gly Leu Pro Tyr Glu Val Ile Lys Ile Leu Asn Pro Asn
                100                 105                 110

Phe Ile Val Ile Ile Glu Ala Thr Pro Ser Glu Ile Leu Gly Arg Arg
                115                 120                 125

Leu Arg Asp Leu Lys Arg Asp Arg Asp Val Glu Thr Glu Glu Gln Ile
130                 135                 140

Gln Arg His Gln Asp Leu Asn Arg Ala Ala Ile Thr Tyr Ala Met
145                 150                 155                 160

His Ser Asn Ala Leu Ile Lys Ile Ile Glu Asn His Glu Asp Lys Gly
                165                 170                 175

Leu Glu Glu Ala Val Asn Glu Leu Val Lys Ile Leu Asp Leu Ala Val
                180                 185                 190

Lys Glu Tyr Ala
        195

<210> SEQ ID NO 6
<211> LENGTH: 196
<212> TYPE: PRT
<213> ORGANISM: Pyrococcus abyssi

<400> SEQUENCE: 6

Met Ser Phe Val Val Ile Ile Thr Gly Ile Pro Gly Val Gly Lys Ser
1               5                   10                  15

Thr Ile Thr Arg Leu Ala Leu Gln Arg Thr Lys Ala Lys Phe Lys Leu
                20                  25                  30

Ile Asn Phe Gly Asp Leu Met Phe Glu Glu Ala Val Lys Ala Gly Leu
                35                  40                  45

Val Asn His Arg Asp Glu Met Arg Lys Leu Pro Leu Glu Ile Gln Arg
 50                  55                  60

Asp Leu Gln Met Lys Val Ala Lys Lys Ile Ser Glu Met Ala Arg Gln
 65                  70                  75                  80

Gln Pro Ile Leu Leu Asp Thr His Ala Thr Ile Lys Thr Pro His Gly
                 85                  90                  95

Tyr Leu Leu Gly Leu Pro Tyr Glu Val Ile Lys Thr Leu Asn Pro Asn
                100                 105                 110

Phe Ile Val Ile Ile Glu Ala Thr Pro Ser Glu Ile Leu Gly Arg Arg
                115                 120                 125

Leu Arg Asp Leu Lys Arg Asp Arg Asp Val Glu Thr Glu Glu Gln Ile
130                 135                 140

Gln Arg His Gln Asp Leu Asn Arg Ala Ala Ile Ala Tyr Ala Met
145                 150                 155                 160

His Ser Asn Ala Leu Ile Lys Ile Ile Glu Asn His Glu Asp Lys Gly
                165                 170                 175

Leu Glu Glu Ala Val Asn Glu Leu Val Glu Ile Leu Asp Leu Ala Val
                180                 185                 190

Lys Glu Tyr Ala
        195

<210> SEQ ID NO 7
<211> LENGTH: 192

```
<212> TYPE: PRT
<213> ORGANISM: Methanococcus thermolithotrophicus

<400> SEQUENCE: 7

Met Lys Asn Lys Leu Val Val Thr Gly Val Pro Gly Val Gly Gly
1               5                   10                  15

Thr Thr Ile Thr Gln Lys Ala Met Glu Lys Leu Ser Glu Glu Gly Ile
            20                  25                  30

Asn Tyr Lys Met Val Asn Phe Gly Thr Val Met Phe Glu Val Ala Gln
            35                  40                  45

Glu Glu Asn Leu Val Glu Asp Arg Asp Gln Met Arg Lys Leu Asp Pro
50                  55                  60

Asp Thr Gln Lys Arg Ile Gln Lys Leu Ala Gly Arg Lys Ile Ala Glu
65                  70                  75                  80

Met Val Lys Glu Ser Pro Val Val Asp Thr His Ser Thr Ile Lys
                85                  90                  95

Thr Pro Lys Gly Tyr Leu Pro Gly Leu Pro Val Trp Val Leu Asn Glu
                100                 105                 110

Leu Asn Pro Asp Ile Ile Val Val Glu Thr Ser Gly Asp Glu Ile
        115                 120                 125

Leu Ile Arg Arg Leu Asn Asp Glu Thr Arg Asn Arg Asp Leu Glu Thr
130                 135                 140

Thr Ala Gly Ile Glu Glu His Gln Ile Met Asn Arg Ala Ala Ala Met
145                 150                 155                 160

Thr Tyr Gly Val Leu Thr Gly Ala Thr Val Lys Ile Ile Gln Asn Lys
                165                 170                 175

Asn Asn Leu Leu Asp Tyr Ala Val Glu Glu Leu Ile Ser Val Leu Arg
            180                 185                 190

<210> SEQ ID NO 8
<211> LENGTH: 192
<212> TYPE: PRT
<213> ORGANISM: Methanococcus voltae

<400> SEQUENCE: 8

Met Lys Asn Lys Val Val Val Thr Gly Val Pro Gly Val Gly Ser
1               5                   10                  15

Thr Thr Ser Ser Gln Leu Ala Met Asp Asn Leu Arg Lys Glu Gly Val
            20                  25                  30

Asn Tyr Lys Met Val Ser Phe Gly Ser Val Met Phe Glu Val Ala Lys
            35                  40                  45

Glu Glu Asn Leu Val Ser Asp Arg Asp Gln Met Arg Lys Met Asp Pro
50                  55                  60

Glu Thr Gln Lys Arg Ile Gln Lys Met Ala Gly Arg Lys Ile Ala Glu
65                  70                  75                  80

Met Ala Lys Glu Ser Pro Val Ala Val Asp Thr His Ser Thr Val Ser
                85                  90                  95

Thr Pro Lys Gly Tyr Leu Pro Gly Leu Pro Ser Trp Val Leu Asn Glu
                100                 105                 110

Leu Asn Pro Asp Leu Ile Ile Val Val Glu Thr Thr Gly Asp Glu Ile
        115                 120                 125

Leu Met Arg Arg Met Ser Asp Glu Thr Arg Val Arg Asp Leu Asp Thr
            130                 135                 140

Ala Ser Thr Ile Glu Gln His Gln Phe Met Asn Arg Cys Ala Ala Met
145                 150                 155                 160

Ser Tyr Gly Val Leu Thr Gly Ala Thr Val Lys Ile Val Gln Asn Arg
```

165                 170                 175
Asn Gly Leu Leu Asp Gln Ala Val Glu Glu Leu Thr Asn Val Leu Arg
                180                 185                 190

<210> SEQ ID NO 9
<211> LENGTH: 195
<212> TYPE: PRT
<213> ORGANISM: Methanococcus jannaschii

<400> SEQUENCE: 9

Met Met Met Met Lys Asn Lys Val Val Ile Val Gly Val Pro Gly
1               5                   10                  15

Val Gly Ser Thr Thr Val Thr Asn Lys Ala Ile Glu Glu Leu Lys Lys
                20                  25                  30

Glu Gly Ile Glu Tyr Lys Ile Val Asn Phe Gly Thr Val Met Phe Glu
            35                  40                  45

Ile Ala Lys Glu Glu Gly Leu Val Glu His Arg Asp Gln Leu Arg Lys
50                  55                  60

Leu Pro Pro Glu Glu Gln Lys Arg Ile Gln Lys Leu Ala Gly Lys Lys
65                  70                  75                  80

Ile Ala Glu Met Ala Lys Glu Phe Asn Ile Val Val Asp Thr His Ser
                85                  90                  95

Thr Ile Lys Thr Pro Lys Gly Tyr Leu Pro Gly Leu Pro Ala Trp Val
            100                 105                 110

Leu Glu Glu Leu Asn Pro Asp Ile Ile Val Leu Val Glu Ala Glu Asn
        115                 120                 125

Asp Glu Ile Leu Met Arg Arg Leu Lys Asp Glu Thr Arg Gln Arg Asp
    130                 135                 140

Phe Glu Ser Thr Glu Asp Ile Gly Glu His Ile Phe Met Asn Arg Cys
145                 150                 155                 160

Ala Ala Met Thr Tyr Ala Val Leu Thr Gly Ala Thr Val Lys Ile Ile
                165                 170                 175

Lys Asn Arg Asp Phe Leu Leu Asp Lys Ala Val Gln Glu Leu Ile Glu
            180                 185                 190

Val Leu Lys
        195

<210> SEQ ID NO 10
<211> LENGTH: 191
<212> TYPE: PRT
<213> ORGANISM: Methanopyrus kandleri

<400> SEQUENCE: 10

Met Gly Tyr Val Ile Val Ala Thr Gly Val Pro Gly Val Gly Ala Thr
1               5                   10                  15

Thr Val Thr Thr Glu Ala Val Lys Glu Leu Glu Gly Tyr Glu His Val
                20                  25                  30

Asn Tyr Gly Asp Val Met Leu Glu Ile Ala Lys Glu Glu Gly Leu Val
            35                  40                  45

Glu His Arg Asp Glu Ile Arg Lys Leu Pro Ala Glu Lys Gln Arg Glu
        50                  55                  60

Ile Gln Arg Leu Ala Ala Arg Arg Ile Ala Lys Met Ala Glu Glu Lys
65                  70                  75                  80

Glu Gly Ile Ile Val Asp Thr His Cys Thr Ile Lys Thr Pro Ala Gly
                85                  90                  95

Tyr Leu Pro Gly Leu Pro Ile Trp Val Leu Glu Glu Leu Gln Pro Asp
            100                 105                 110

Val Ile Val Leu Ile Glu Ala Asp Pro Asp Glu Ile Met Met Arg Arg
            115                 120                 125

Val Lys Asp Ser Glu Glu Arg Gln Arg Asp Tyr Asp Arg Ala His Glu
    130                 135                 140

Ile Glu Glu His Gln Lys Met Asn Arg Met Ala Ala Met Ala Tyr Ala
145                 150                 155                 160

Ala Leu Thr Gly Ala Thr Val Lys Ile Ile Glu Asn His Asp Asp Arg
            165                 170                 175

Leu Glu Glu Ala Val Arg Glu Phe Val Glu Thr Val Arg Ser Leu
            180                 185                 190

<210> SEQ ID NO 11
<211> LENGTH: 192
<212> TYPE: PRT
<213> ORGANISM: Methanotorris igneus

<400> SEQUENCE: 11

Met Lys Asn Lys Val Val Val Thr Gly Val Pro Gly Val Gly Gly
1               5                   10                  15

Thr Thr Leu Thr Gln Lys Thr Ile Glu Lys Leu Lys Glu Glu Gly Ile
            20                  25                  30

Glu Tyr Lys Met Val Asn Phe Gly Thr Val Met Phe Glu Val Ala Lys
            35                  40                  45

Glu Glu Gly Leu Val Glu Asp Arg Asp Gln Met Arg Lys Leu Asp Pro
    50                  55                  60

Asp Thr Gln Lys Arg Ile Gln Lys Leu Ala Gly Arg Lys Ile Ala Glu
65                  70                  75                  80

Met Ala Lys Glu Ser Asn Val Ile Val Asp Thr His Ser Thr Val Lys
            85                  90                  95

Thr Pro Lys Gly Tyr Leu Ala Gly Leu Pro Ile Trp Val Leu Glu Glu
            100                 105                 110

Leu Asn Pro Asp Ile Ile Val Ile Val Glu Thr Ser Ser Asp Glu Ile
            115                 120                 125

Leu Met Arg Arg Leu Gly Asp Ala Thr Arg Asn Arg Asp Ile Glu Leu
            130                 135                 140

Thr Ser Asp Ile Asp Glu His Gln Phe Met Asn Arg Cys Ala Ala Met
145                 150                 155                 160

Ala Tyr Gly Val Leu Thr Gly Ala Thr Val Lys Ile Ile Lys Asn Arg
            165                 170                 175

Asp Gly Leu Leu Asp Lys Ala Val Glu Glu Leu Ile Ser Val Leu Lys
            180                 185                 190

<210> SEQ ID NO 12
<211> LENGTH: 197
<212> TYPE: PRT
<213> ORGANISM: Pyrobaculum aerophilum

<400> SEQUENCE: 12

Met Lys Ile Val Ile Val Ala Leu Pro Gly Ser Gly Lys Thr Thr Ile
1               5                   10                  15

Leu Asn Phe Val Lys Gln Lys Leu Pro Asp Val Lys Ile Val Asn Tyr
            20                  25                  30

Gly Asp Val Met Leu Glu Ile Ala Lys Lys Arg Phe Gly Ile Gln His
            35                  40                  45

Arg Asp Glu Met Arg Lys Lys Ile Pro Val Asp Glu Tyr Arg Lys Val
    50                  55                  60

```
Gln Glu Glu Ala Ala Glu Tyr Ile Ala Ser Leu Thr Gly Asp Val Ile
 65                  70                  75                  80

Ile Asp Thr His Ala Ser Ile Lys Ile Gly Gly Tyr Tyr Pro Gly
                 85                  90                  95

Leu Pro Asp Arg Ile Ile Ser Lys Leu Lys Pro Asp Val Ile Leu Leu
                100                 105                 110

Leu Glu Tyr Asp Pro Lys Val Ile Leu Glu Arg Arg Lys Lys Asp Pro
            115                 120                 125

Asp Arg Phe Arg Asp Leu Glu Ser Glu Glu Ile Glu Met His Gln
130                 135                 140

Gln Ala Asn Arg Tyr Tyr Ala Phe Ala Ala Asn Ala Gly Glu Ser
145                 150                 155                 160

Thr Val His Val Leu Asn Phe Arg Gly Lys Pro Glu Ser Arg Pro Phe
                165                 170                 175

Glu His Ala Glu Val Ala Ala Glu Tyr Ile Val Asn Leu Ile Leu Arg
            180                 185                 190

Thr Arg Gln Lys Ser
            195

<210> SEQ ID NO 13
<211> LENGTH: 220
<212> TYPE: PRT
<213> ORGANISM: Thermotoga maritima

<400> SEQUENCE: 13

Met Met Ala Tyr Leu Val Phe Leu Gly Pro Pro Gly Ala Gly Lys Gly
  1               5                  10                  15

Thr Tyr Ala Lys Arg Ile Gln Glu Lys Thr Gly Ile Pro His Ile Ser
             20                  25                  30

Thr Gly Asp Ile Phe Arg Asp Ile Val Lys Lys Glu Asn Asp Glu Leu
         35                  40                  45

Gly Lys Lys Ile Lys Glu Ile Met Glu Lys Gly Glu Leu Val Pro Asp
 50                  55                  60

Glu Leu Val Asn Glu Val Val Lys Arg Arg Leu Ser Glu Lys Asp Cys
 65                  70                  75                  80

Glu Lys Gly Phe Ile Leu Asp Gly Tyr Pro Arg Thr Val Ala Gln Ala
                 85                  90                  95

Glu Phe Leu Asp Ser Phe Leu Glu Ser Gln Asn Lys Gln Leu Thr Ala
            100                 105                 110

Ala Val Leu Phe Asp Val Pro Glu Asp Val Val Gln Arg Leu Thr
            115                 120                 125

Ser Arg Arg Ile Cys Pro Lys Cys Gly Arg Ile Tyr Asn Met Ile Ser
130                 135                 140

Leu Pro Pro Lys Glu Asp Glu Leu Cys Asp Asp Cys Lys Val Lys Leu
145                 150                 155                 160

Val Gln Arg Asp Asp Lys Glu Glu Thr Val Arg His Arg Tyr Lys
                165                 170                 175

Val Tyr Leu Glu Lys Thr Gln Pro Val Ile Asp Tyr Tyr Gly Lys Lys
            180                 185                 190

Gly Ile Leu Lys Arg Val Asp Gly Thr Ile Gly Ile Asp Asn Val Val
            195                 200                 205

Ala Glu Val Leu Lys Ile Ile Gly Trp Ser Asp Lys
210                 215                 220

<210> SEQ ID NO 14
<211> LENGTH: 204
```

```
<212> TYPE: PRT
<213> ORGANISM: Aeropyrum pernix

<400> SEQUENCE: 14

Met Lys Val Arg His Pro Phe Lys Val Val Val Thr Gly Val Pro
1               5                   10                  15

Gly Val Gly Lys Thr Thr Val Ile Lys Glu Leu Gln Gly Leu Ala Glu
                20                  25                  30

Lys Glu Gly Val Lys Leu His Ile Val Asn Phe Gly Ser Phe Met Leu
                35                  40                  45

Asp Thr Ala Val Lys Leu Gly Leu Val Glu Asp Arg Asp Lys Ile Arg
50                  55                  60

Thr Leu Pro Leu Arg Arg Gln Leu Glu Leu Gln Arg Glu Ala Ala Lys
65                  70                  75                  80

Arg Ile Val Ala Glu Ala Ser Lys Ala Leu Gly Gly Asp Gly Val Leu
                85                  90                  95

Ile Ile Asp Thr His Ala Leu Val Lys Thr Val Ala Gly Tyr Trp Pro
                100                 105                 110

Gly Leu Pro Lys His Val Leu Asp Glu Leu Lys Pro Asp Met Ile Ala
                115                 120                 125

Val Val Glu Ala Ser Pro Glu Glu Val Ala Ala Arg Gln Ala Arg Asp
130                 135                 140

Thr Thr Arg Tyr Arg Val Asp Ile Gly Gly Val Glu Gly Val Lys Arg
145                 150                 155                 160

Leu Met Glu Asn Ala Arg Ala Ala Ser Ile Ala Ser Ala Ile Gln Tyr
                165                 170                 175

Ala Ser Thr Val Ala Ile Val Glu Asn Arg Glu Gly Glu Ala Ala Lys
                180                 185                 190

Ala Ala Glu Glu Leu Leu Arg Leu Ile Lys Asn Leu
                195                 200

<210> SEQ ID NO 15
<211> LENGTH: 216
<212> TYPE: PRT
<213> ORGANISM: Archaeoglobus fulgidus

<400> SEQUENCE: 15

Met Asn Leu Ile Phe Leu Gly Pro Pro Gly Ala Gly Lys Gly Thr Gln
1               5                   10                  15

Ala Lys Arg Val Ser Glu Lys Tyr Gly Ile Pro Gln Ile Ser Thr Gly
                20                  25                  30

Asp Met Leu Arg Glu Ala Val Ala Lys Gly Thr Glu Leu Gly Lys Lys
                35                  40                  45

Ala Lys Glu Tyr Met Asp Lys Gly Glu Leu Val Pro Asp Glu Val Val
50                  55                  60

Ile Gly Ile Val Lys Glu Arg Leu Gln Gln Pro Asp Cys Glu Lys Gly
65                  70                  75                  80

Phe Ile Leu Asp Gly Phe Pro Arg Thr Leu Ala Gln Ala Glu Ala Leu
                85                  90                  95

Asp Glu Met Leu Lys Glu Leu Asn Lys Lys Ile Asp Ala Val Ile Asn
                100                 105                 110

Val Val Val Pro Glu Glu Val Val Lys Arg Ile Thr Tyr Arg Arg
                115                 120                 125

Thr Cys Arg Asn Cys Gly Ala Val Tyr His Leu Ile Tyr Ala Pro Pro
130                 135                 140

Lys Glu Asp Asn Lys Cys Asp Lys Cys Gly Gly Glu Leu Tyr Gln Arg
```

```
                    145                 150                 155                 160

Asp Asp Lys Glu Glu Thr Val Arg Glu Arg Tyr Arg Val Tyr Lys Gln
                165                 170                 175

Asn Thr Glu Pro Leu Ile Asp Tyr Tyr Arg Lys Lys Gly Ile Leu Tyr
            180                 185                 190

Asp Val Asp Gly Thr Lys Asp Ile Glu Gly Val Trp Lys Glu Ile Glu
        195                 200                 205

Ala Ile Leu Glu Lys Ile Lys Ser
    210                 215

<210> SEQ ID NO 16
<211> LENGTH: 220
<212> TYPE: PRT
<213> ORGANISM: Pyrococcus abyssi

<400> SEQUENCE: 16

Met Asn Ile Leu Ile Phe Gly Pro Pro Gly Ser Gly Lys Ser Thr Gln
1               5                   10                  15

Ala Arg Arg Ile Thr Glu Arg Tyr Gly Leu Thr Tyr Ile Ala Ser Gly
            20                  25                  30

Asp Ile Ile Arg Ala Glu Ile Lys Ala Arg Thr Pro Leu Gly Ile Glu
        35                  40                  45

Met Glu Arg Tyr Leu Ser Arg Gly Asp Leu Ile Pro Asp Thr Ile Val
    50                  55                  60

Asn Thr Leu Ile Ile Ser Lys Leu Arg Val Arg Glu Asn Phe Ile
65                  70                  75                  80

Met Asp Gly Tyr Pro Arg Thr Pro Glu Gln Val Ile Thr Leu Glu Asn
                85                  90                  95

Tyr Leu Tyr Asp His Gly Ile Lys Leu Asp Val Ala Ile Asp Ile Tyr
            100                 105                 110

Ile Thr Lys Glu Glu Ser Val Arg Arg Ile Ser Gly Arg Arg Ile Cys
        115                 120                 125

Ser Lys Cys Gly Ala Val Tyr His Val Glu Phe Asn Pro Pro Lys Val
    130                 135                 140

Pro Gly Lys Cys Asp Ile Cys Gly Gly Glu Leu Ile Gln Arg Pro Asp
145                 150                 155                 160

Asp Arg Pro Glu Ile Val Glu Lys Arg Tyr Asp Ile Tyr Ser Lys Asn
                165                 170                 175

Met Glu Pro Ile Ile Lys Phe Tyr Gln Lys Gln Gly Ile Tyr Val Arg
            180                 185                 190

Ile Asp Gly His Gly Ser Ile Asp Glu Val Trp Glu Arg Ile Arg Pro
        195                 200                 205

Leu Leu Asp Tyr Ile Tyr Asn Gln Glu Asn Arg Arg
    210                 215                 220

<210> SEQ ID NO 17
<211> LENGTH: 196
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (61)..(61)
<223> OTHER INFORMATION: The amino acid "X" may be K or E.
<220> FEATURE:
<221> NAME/KEY: MISC_FEATURE
<222> LOCATION: (75)..(75)
<223> OTHER INFORMATION: The amino acid "X" may be T or A.
<220> FEATURE:
```

```
<221> NAME/KEY: MISC_FEATURE
<222> LOCATION: (98)..(98)
<223> OTHER INFORMATION: The amino acid "X" may be M or L.
<220> FEATURE:
<221> NAME/KEY: MISC_FEATURE
<222> LOCATION: (157)..(157)
<223> OTHER INFORMATION: The amino acid "X" may be A, or a small
      hydrophobic residue (e.g. I or L) or a large hydrophobic residue
      (e.g. F), that increases the thermal stability of the enzyme.

<400> SEQUENCE: 17

Met Pro Phe Val Val Ile Ile Thr Gly Ile Pro Gly Val Gly Lys Ser
1               5                   10                  15

Thr Ile Thr Arg Leu Ala Leu Gln Arg Thr Lys Ala Lys Phe Arg Leu
            20                  25                  30

Ile Asn Phe Gly Asp Leu Met Phe Glu Glu Ala Val Lys Ala Gly Leu
        35                  40                  45

Val Lys His Arg Asp Glu Met Arg Lys Leu Pro Leu Xaa Ile Gln Arg
    50                  55                  60

Glu Leu Gln Met Lys Ala Ala Lys Lys Ile Xaa Glu Met Ala Lys Glu
65                  70                  75                  80

His Pro Ile Leu Val Asp Thr His Ala Thr Ile Lys Thr Pro His Gly
                85                  90                  95

Tyr Xaa Leu Gly Leu Pro Tyr Glu Val Val Lys Thr Leu Asn Pro Asn
            100                 105                 110

Phe Ile Val Ile Ile Glu Ala Thr Pro Ser Glu Ile Leu Gly Arg Arg
        115                 120                 125

Leu Arg Asp Leu Lys Arg Asp Arg Asp Val Glu Thr Glu Glu Gln Ile
    130                 135                 140

Gln Arg His Gln Asp Leu Asn Arg Ala Ala Ile Xaa Tyr Ala Met
145                 150                 155                 160

His Ser Asn Ala Leu Ile Lys Ile Ile Glu Asn His Glu Asp Lys Gly
                165                 170                 175

Leu Glu Glu Ala Val Asn Glu Leu Val Lys Ile Leu Asp Leu Ala Val
            180                 185                 190

Asn Glu Tyr Ala
            195

<210> SEQ ID NO 18
<211> LENGTH: 196
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (47)..(47)
<223> OTHER INFORMATION: The amino acid "X" may be G, or may be any
      other residue that increases the thermal stability of the enzyme.
<220> FEATURE:
<221> NAME/KEY: MISC_FEATURE
<222> LOCATION: (157)..(157)
<223> OTHER INFORMATION: The amino acid "X" may be A, or a small
      hydrophobic residue (e.g. I or L) or a large hydrophobic residue
      (e.g. F), that increases the thermal stability of the enzyme.

<400> SEQUENCE: 18

Met Pro Phe Val Val Ile Ile Thr Gly Ile Pro Gly Val Gly Lys Ser
1               5                   10                  15

Thr Ile Thr Lys Leu Ala Leu Gln Arg Thr Arg Ala Lys Phe Lys Leu
            20                  25                  30

Ile Asn Phe Gly Asp Leu Met Phe Glu Glu Ala Leu Lys Leu Xaa Leu
        35                  40                  45
```

```
Val Lys His Arg Asp Glu Met Arg Lys Leu Pro Leu Glu Val Gln Arg
     50                  55                  60
Glu Leu Gln Met Asn Ala Ala Lys Lys Ile Ala Glu Met Ala Lys Asn
 65                  70                  75                  80
Tyr Pro Ile Leu Leu Asp Thr His Ala Thr Ile Lys Thr Pro His Gly
                 85                  90                  95
Tyr Leu Leu Gly Leu Pro Tyr Glu Val Ile Lys Ile Leu Asn Pro Asn
            100                 105                 110
Phe Ile Val Ile Ile Glu Ala Thr Pro Ser Glu Ile Leu Gly Arg Arg
            115                 120                 125
Leu Arg Asp Leu Lys Arg Asp Arg Asp Val Glu Thr Glu Glu Gln Ile
130                 135                 140
Gln Arg His Gln Asp Leu Asn Arg Ala Ala Ala Ile Xaa Tyr Ala Met
145                 150                 155                 160
His Ser Asn Ala Leu Ile Lys Ile Ile Glu Asn His Glu Asp Lys Gly
                165                 170                 175
Leu Glu Glu Ala Val Asn Glu Leu Val Lys Ile Leu Asp Leu Ala Val
            180                 185                 190
Lys Glu Tyr Ala
            195

<210> SEQ ID NO 19
<211> LENGTH: 194
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (103)..(103)
<223> OTHER INFORMATION: The amino acid "X" may be A or M.

<400> SEQUENCE: 19

Met Lys Ile Gly Ile Val Thr Gly Ile Pro Gly Val Gly Lys Ser Thr
 1               5                  10                  15
Val Leu Ala Lys Val Lys Glu Ile Leu Asp Asn Gln Gly Ile Asn Asn
             20                  25                  30
Lys Ile Ile Asn Tyr Gly Asp Phe Met Leu Ala Thr Ala Leu Lys Leu
         35                  40                  45
Gly Tyr Ala Lys Asp Arg Asp Glu Met Arg Lys Leu Ser Val Glu Lys
     50                  55                  60
Gln Lys Lys Leu Gln Ile Asp Ala Ala Lys Gly Ile Ala Glu Glu Ala
 65                  70                  75                  80
Arg Ala Gly Gly Glu Gly Tyr Leu Phe Ile Asp Thr His Ala Val Ile
                 85                  90                  95
Arg Thr Pro Ser Gly Tyr Xaa Pro Gly Leu Pro Ser Tyr Val Ile Thr
            100                 105                 110
Glu Ile Asn Pro Ser Val Ile Phe Leu Leu Glu Ala Asp Pro Lys Ile
            115                 120                 125
Ile Leu Ser Arg Gln Lys Arg Asp Thr Thr Arg Asn Arg Asn Asp Tyr
130                 135                 140
Ser Asp Glu Ser Val Ile Leu Glu Thr Ile Asn Phe Ala Arg Tyr Ala
145                 150                 155                 160
Ala Thr Ala Ser Ala Val Leu Ala Gly Ser Thr Val Lys Val Ile Val
                165                 170                 175
Asn Val Glu Gly Asp Pro Ser Ile Ala Ala Asn Glu Ile Ile Arg Ser
            180                 185                 190
```

Met Lys

<210> SEQ ID NO 20
<211> LENGTH: 403
<212> TYPE: PRT
<213> ORGANISM: Thermotoga maritima

<400> SEQUENCE: 20

Met Arg Val Leu Val Ile Asn Ser Gly Ser Ser Ile Lys Tyr Gln
1               5                   10                  15

Leu Ile Glu Met Glu Gly Glu Lys Val Leu Cys Lys Gly Ile Ala Glu
            20                  25                  30

Arg Ile Gly Ile Glu Gly Ser Arg Leu Val His Arg Val Gly Asp Glu
            35                  40                  45

Lys His Val Ile Glu Arg Glu Leu Pro Asp His Glu Glu Ala Leu Lys
        50                  55                  60

Leu Ile Leu Asn Thr Leu Val Asp Glu Lys Leu Gly Val Ile Lys Asp
65                  70                  75                  80

Leu Lys Glu Ile Asp Ala Val Gly His Arg Val Val His Gly Gly Glu
                85                  90                  95

Arg Phe Lys Glu Ser Val Leu Val Asp Glu Val Leu Lys Ala Ile
            100                 105                 110

Glu Glu Val Ser Pro Leu Ala Pro Leu His Asn Pro Ala Asn Leu Met
            115                 120                 125

Gly Ile Lys Ala Ala Met Lys Leu Leu Pro Gly Val Pro Asn Val Ala
        130                 135                 140

Val Phe Asp Thr Ala Phe His Gln Thr Ile Pro Gln Lys Ala Tyr Leu
145                 150                 155                 160

Tyr Ala Ile Pro Tyr Glu Tyr Tyr Glu Lys Tyr Lys Ile Arg Arg Tyr
                165                 170                 175

Gly Phe His Gly Thr Ser His Arg Tyr Val Ser Lys Arg Ala Ala Glu
            180                 185                 190

Ile Leu Gly Lys Lys Leu Glu Glu Leu Lys Ile Ile Thr Cys His Ile
        195                 200                 205

Gly Asn Gly Ala Ser Val Ala Ala Val Lys Tyr Gly Lys Cys Val Asp
    210                 215                 220

Thr Ser Met Gly Phe Thr Pro Leu Glu Gly Leu Val Met Gly Thr Arg
225                 230                 235                 240

Ser Gly Asp Leu Asp Pro Ala Ile Pro Phe Phe Ile Met Glu Lys Glu
                245                 250                 255

Gly Ile Ser Pro Gln Glu Met Tyr Asp Ile Leu Asn Lys Lys Ser Gly
            260                 265                 270

Val Tyr Gly Leu Ser Lys Gly Phe Ser Ser Asp Met Arg Asp Ile Glu
        275                 280                 285

Glu Ala Ala Leu Lys Gly Asp Glu Trp Cys Lys Leu Val Leu Glu Ile
    290                 295                 300

Tyr Asp Tyr Arg Ile Ala Lys Tyr Ile Gly Ala Tyr Ala Ala Met
305                 310                 315                 320

Asn Gly Val Asp Ala Ile Val Phe Thr Ala Gly Val Gly Glu Asn Ser
                325                 330                 335

Pro Ile Thr Arg Glu Asp Val Cys Ser Tyr Leu Glu Phe Leu Gly Val
            340                 345                 350

Lys Leu Asp Lys Gln Lys Asn Glu Glu Thr Ile Arg Gly Lys Glu Gly
        355                 360                 365

```
Ile Ile Ser Thr Pro Asp Ser Arg Val Lys Val Leu Val Pro Thr
        370                 375                 380

Asn Glu Glu Leu Met Ile Ala Arg Asp Thr Lys Glu Ile Val Glu Lys
385                 390                 395                 400

Ile Gly Arg

<210> SEQ ID NO 21
<211> LENGTH: 478
<212> TYPE: PRT
<213> ORGANISM: Pyrococcus horikoshii

<400> SEQUENCE: 21

Met Arg Arg Met Lys Leu Pro Ser His Lys Thr Lys Ile Val Ala Thr
1               5                   10                  15

Ile Gly Pro Ala Thr Asn Ser Lys Lys Met Ile Lys Lys Leu Ile Glu
            20                  25                  30

Ala Gly Met Asn Val Ala Arg Ile Asn Phe Ser His Gly Thr Phe Glu
        35                  40                  45

Glu His Ala Lys Ile Ile Glu Met Val Arg Glu Gln Ser Gln Lys Leu
    50                  55                  60

Asp Arg Arg Val Ala Ile Leu Ala Asp Leu Pro Gly Leu Lys Ile Arg
65                  70                  75                  80

Val Gly Glu Ile Lys Gly Gly Tyr Val Glu Leu Glu Arg Gly Glu Lys
                85                  90                  95

Val Thr Leu Thr Thr Lys Asp Ile Glu Gly Asp Glu Thr Thr Ile Pro
            100                 105                 110

Val Glu Tyr Lys Asp Phe Pro Lys Leu Val Ser Lys Gly Asp Val Ile
        115                 120                 125

Tyr Leu Ser Asp Gly Tyr Ile Val Leu Arg Val Glu Asp Val Lys Glu
    130                 135                 140

Asn Glu Val Glu Ala Val Val Ile Ser Gly Gly Lys Leu Phe Ser Arg
145                 150                 155                 160

Lys Gly Ile Asn Ile Pro Lys Ala Tyr Leu Pro Val Glu Ala Ile Thr
                165                 170                 175

Pro Arg Asp Ile Glu Ile Met Lys Phe Ala Ile Glu His Gly Val Asp
            180                 185                 190

Ala Ile Gly Leu Ser Phe Val Gly Asn Val Tyr Asp Val Leu Lys Ala
        195                 200                 205

Lys Ser Phe Leu Glu Arg Asn Gly Ala Gly Asp Thr Phe Val Ile Ala
    210                 215                 220

Lys Ile Glu Arg Pro Asp Ala Val Arg Asn Phe Asn Glu Ile Leu Asn
225                 230                 235                 240

Ala Ala Asp Gly Ile Met Ile Ala Arg Gly Asp Leu Gly Val Glu Met
                245                 250                 255

Pro Ile Glu Gln Leu Pro Ile Leu Gln Lys Arg Leu Ile Arg Lys Ala
            260                 265                 270

Asn Met Glu Gly Lys Pro Val Ile Thr Ala Thr Gln Met Leu Val Ser
        275                 280                 285

Met Thr Met Glu Lys Val Pro Thr Arg Ala Glu Val Thr Asp Val Ala
    290                 295                 300

Asn Ala Ile Leu Asp Gly Thr Asp Ala Val Met Leu Ser Glu Glu Thr
305                 310                 315                 320

Ala Val Gly Lys Phe Pro Ile Glu Ala Val Glu Met Met Ala Arg Ile
                325                 330                 335

Ala Lys Val Thr Glu Glu Tyr Arg Glu Ser Phe Gly Ile Thr Arg Met
```

```
                    340                 345                 350
Arg Glu Phe Leu Glu Gly Thr Lys Arg Gly Thr Ile Lys Glu Ala Ile
        355                 360                 365

Thr Arg Ser Ile Ile Asp Ala Ile Cys Thr Ile Gly Ile Lys Phe Ile
        370                 375                 380

Leu Thr Pro Thr Lys Thr Gly Arg Thr Ala Arg Leu Ile Ser Arg Phe
385                 390                 395                 400

Lys Pro Lys Gln Trp Ile Leu Ala Phe Ser Thr Arg Glu Lys Val Cys
                405                 410                 415

Asn Asn Leu Met Phe Ser Tyr Gly Val Tyr Pro Phe Cys Met Glu Glu
            420                 425                 430

Gly Phe Asn Glu Asn Asp Ile Val Arg Leu Ile Lys Gly Leu Gly Leu
        435                 440                 445

Val Gly Ser Asp Asp Ile Val Leu Met Thr Glu Gly Lys Pro Ile Glu
    450                 455                 460

Lys Thr Val Gly Thr Asn Ser Ile Lys Ile Phe Gln Ile Ala
465                 470                 475

<210> SEQ ID NO 22
<211> LENGTH: 452
<212> TYPE: PRT
<213> ORGANISM: Sulfolobus solfataricus

<400> SEQUENCE: 22

Met Arg Lys Thr Lys Ile Val Ala Thr Leu Gly Pro Ser Ser Glu Glu
1               5                   10                  15

Lys Val Lys Glu Leu Ala Glu Tyr Val Asp Val Phe Arg Ile Asn Phe
            20                  25                  30

Ala His Gly Asp Glu Thr Ser His Arg Lys Tyr Phe Asp Leu Ile Arg
        35                  40                  45

Thr Tyr Ala Pro Glu Ser Ser Ile Ile Val Asp Leu Pro Gly Pro Lys
    50                  55                  60

Leu Arg Leu Gly Glu Leu Lys Glu Pro Ile Glu Val Lys Lys Gly Asp
65                  70                  75                  80

Lys Ile Val Phe Ser Gln Lys Asp Gly Ile Pro Val Asp Asp Glu Leu
                85                  90                  95

Phe Tyr Ser Ala Val Lys Glu Asn Ser Asp Ile Leu Ile Ala Asp Gly
            100                 105                 110

Thr Ile Arg Val Arg Val Lys Ser Lys Ala Lys Asp Arg Val Glu Gly
        115                 120                 125

Thr Val Ile Glu Gly Gly Ile Leu Leu Ser Arg Lys Gly Ile Asn Ile
    130                 135                 140

Pro Asn Val Asn Leu Lys Ser Gly Ile Thr Asp Asn Asp Leu Lys Leu
145                 150                 155                 160

Leu Lys Arg Ala Leu Asp Leu Gly Ala Asp Tyr Ile Gly Leu Ser Phe
                165                 170                 175

Val Ile Ser Glu Asn Asp Val Lys Lys Val Lys Glu Phe Val Gly Asp
            180                 185                 190

Glu Ala Trp Val Ile Ala Lys Ile Glu Lys Ser Glu Ala Leu Lys Asn
        195                 200                 205

Leu Thr Asn Ile Val Asn Glu Ser Asp Gly Ile Met Val Ala Arg Gly
    210                 215                 220

Asp Leu Gly Val Glu Thr Gly Leu Glu Asn Leu Pro Leu Ile Gln Arg
225                 230                 235                 240

Arg Ile Val Arg Thr Ser Arg Val Phe Gly Lys Pro Val Ile Leu Ala
```

```
                       245                 250                 255
Thr Gln Val Leu Thr Ser Met Ile Asn Ser Pro Ile Pro Thr Arg Ala
            260                 265                 270

Glu Ile Ile Asp Ile Ser Asn Ser Ile Met Gln Gly Val Asp Ser Ile
        275                 280                 285

Met Leu Ser Asp Glu Thr Ala Ile Gly Asn Tyr Pro Val Glu Ser Val
        290                 295                 300

Arg Thr Leu His Asn Ile Ile Ser Asn Val Glu Lys Ser Val Lys His
305                 310                 315                 320

Arg Pro Ile Gly Pro Leu Asn Ser Glu Ser Asp Ala Ile Ala Leu Ala
                325                 330                 335

Ala Val Asn Ala Ser Lys Val Ser Lys Ala Asp Val Ile Val Val Tyr
            340                 345                 350

Ser Arg Ser Gly Asn Ser Ile Leu Arg Val Ser Arg Leu Arg Pro Glu
        355                 360                 365

Arg Asn Ile Ile Gly Val Ser Pro Asp Pro Arg Leu Ala Lys Lys Phe
        370                 375                 380

Lys Leu Cys Tyr Gly Val Ile Pro Ile Ser Ile Asn Lys Lys Met Gln
385                 390                 395                 400

Ser Ile Asp Glu Ile Ile Asp Val Ser Ala Lys Leu Met Gln Glu Lys
                405                 410                 415

Ile Lys Asp Leu Lys Phe Lys Lys Ile Val Ile Val Gly Gly Asp Pro
            420                 425                 430

Lys Gln Glu Ala Gly Lys Thr Asn Phe Val Ile Val Lys Thr Leu Glu
        435                 440                 445

Gln Gln Lys Lys
    450

<210> SEQ ID NO 23
<211> LENGTH: 466
<212> TYPE: PRT
<213> ORGANISM: Thermotoga maritima

<400> SEQUENCE: 23

Met Arg Ser Thr Lys Ile Val Cys Thr Val Gly Pro Arg Thr Asp Ser
1               5                   10                  15

Tyr Glu Met Ile Glu Lys Met Ile Asp Leu Gly Val Asn Val Phe Arg
            20                  25                  30

Ile Asn Thr Ser His Gly Asp Trp Asn Glu Gln Glu Gln Lys Ile Leu
        35                  40                  45

Lys Ile Lys Asp Leu Arg Glu Lys Lys Lys Pro Val Ala Ile Leu
50                  55                  60

Ile Asp Leu Ala Gly Pro Lys Ile Arg Thr Gly Tyr Leu Glu Lys Glu
65                  70                  75                  80

Phe Val Glu Leu Lys Glu Gly Gln Ile Phe Thr Leu Thr Thr Lys Glu
            85                  90                  95

Ile Leu Gly Asn Glu His Ile Val Ser Val Asn Leu Ser Ser Leu Pro
        100                 105                 110

Lys Asp Val Lys Lys Gly Asp Thr Ile Leu Leu Ser Asp Gly Glu Ile
    115                 120                 125

Val Leu Glu Val Ile Glu Thr Thr Asp Thr Glu Val Lys Thr Val Val
        130                 135                 140

Lys Val Gly Gly Lys Ile Thr His Arg Gly Val Asn Val Pro Thr
145                 150                 155                 160

Ala Asp Leu Ser Val Glu Ser Ile Thr Asp Arg Asp Arg Glu Phe Ile
```

```
                       165                 170                 175
Lys Leu Gly Thr Leu His Asp Val Glu Phe Phe Ala Leu Ser Phe Val
            180                 185                 190

Arg Lys Pro Glu Asp Val Leu Lys Ala Lys Glu Ile Arg Lys His
            195                 200                 205

Gly Lys Glu Ile Pro Val Ile Ser Lys Ile Glu Thr Lys Lys Ala Leu
            210                 215                 220

Glu Arg Leu Glu Glu Ile Ile Lys Val Ser Asp Gly Ile Met Val Ala
225                 230                 235                 240

Arg Gly Asp Leu Gly Val Glu Ile Pro Ile Glu Glu Val Pro Ile Val
            245                 250                 255

Gln Lys Glu Ile Ile Lys Leu Ser Lys Tyr Tyr Ser Lys Pro Val Ile
            260                 265                 270

Val Ala Thr Gln Ile Leu Glu Ser Met Ile Glu Asn Pro Phe Pro Thr
            275                 280                 285

Arg Ala Glu Val Thr Asp Ile Ala Asn Ala Ile Phe Asp Gly Ala Asp
            290                 295                 300

Ala Leu Leu Leu Thr Ala Glu Thr Ala Val Gly Lys His Pro Leu Glu
305                 310                 315                 320

Ala Ile Lys Val Leu Ser Lys Val Ala Lys Glu Ala Glu Lys Lys Leu
            325                 330                 335

Glu Phe Phe Arg Thr Ile Glu Tyr Asp Thr Ser Asp Ile Ser Glu Ala
            340                 345                 350

Ile Ser His Ala Cys Trp Gln Leu Ser Glu Ser Leu Asn Ala Lys Leu
            355                 360                 365

Ile Ile Thr Pro Thr Ile Ser Gly Ser Thr Ala Val Arg Val Ser Lys
            370                 375                 380

Tyr Asn Val Ser Gln Pro Ile Val Ala Leu Thr Pro Glu Glu Lys Thr
385                 390                 395                 400

Tyr Tyr Arg Leu Ser Leu Val Arg Lys Val Ile Pro Val Leu Ala Glu
            405                 410                 415

Lys Cys Ser Gln Glu Leu Glu Phe Ile Glu Lys Gly Leu Lys Lys Val
            420                 425                 430

Glu Glu Met Gly Leu Ala Glu Lys Gly Asp Leu Val Val Leu Thr Ser
            435                 440                 445

Gly Val Pro Gly Lys Val Gly Thr Thr Asn Thr Ile Arg Val Leu Lys
            450                 455                 460

Val Asp
465

<210> SEQ ID NO 24
<211> LENGTH: 477
<212> TYPE: PRT
<213> ORGANISM: Pyrococcus furiosus

<400> SEQUENCE: 24

Met Arg Arg Val Lys Leu Pro Ser His Lys Thr Lys Ile Val Ala Thr
1               5                   10                  15

Ile Gly Pro Ala Thr Asn Ser Arg Lys Met Ile Lys Gln Leu Ile Lys
            20                  25                  30

Ala Gly Met Asn Val Ala Arg Ile Asn Phe Ser His Gly Ser Phe Glu
            35                  40                  45

Glu His Ala Arg Val Ile Glu Ile Ile Arg Glu Glu Ala Gln Lys Leu
            50                  55                  60

Asp Arg Arg Val Ala Ile Leu Ala Asp Leu Pro Gly Leu Lys Ile Arg
```

```
            65                  70                  75                  80
Val Gly Glu Ile Lys Gly Gly Tyr Val Glu Leu Lys Arg Gly Glu Lys
                    85                  90                  95
Val Ile Leu Thr Thr Lys Asp Val Glu Gly Asp Glu Thr Thr Ile Pro
                    100                 105                 110
Val Asp Tyr Lys Gly Phe Pro Asn Leu Val Ser Lys Gly Asp Ile Ile
                    115                 120                 125
Tyr Leu Asn Asp Gly Tyr Ile Val Leu Lys Val Glu Asn Val Arg Glu
                    130                 135                 140
Asn Glu Val Glu Ala Val Val Leu Ser Gly Gly Lys Leu Phe Ser Arg
145                 150                 155                 160
Lys Gly Val Asn Ile Pro Lys Ala Tyr Leu Pro Val Glu Ala Ile Thr
                    165                 170                 175
Pro Lys Asp Phe Glu Ile Met Lys Phe Ala Ile Glu His Gly Val Asp
                    180                 185                 190
Ala Ile Gly Leu Ser Phe Val Gly Ser Val Tyr Asp Val Leu Lys Ala
                    195                 200                 205
Lys Ser Phe Leu Glu Lys Asn Asn Ala Glu Asp Val Phe Val Ile Ala
                    210                 215                 220
Lys Ile Glu Arg Pro Asp Ala Val Arg Asn Phe Asp Glu Ile Leu Asn
225                 230                 235                 240
Ala Ala Asp Gly Ile Met Ile Ala Arg Gly Asp Leu Gly Val Glu Met
                    245                 250                 255
Pro Ile Glu Gln Leu Pro Ile Leu Gln Lys Lys Leu Ile Arg Lys Ala
                    260                 265                 270
Asn Met Glu Gly Lys Pro Val Ile Thr Ala Thr Gln Met Leu Val Ser
                    275                 280                 285
Met Thr Thr Glu Lys Val Pro Thr Arg Ala Glu Val Thr Asp Val Ala
                    290                 295                 300
Asn Ala Ile Leu Asp Gly Thr Asp Ala Val Met Leu Ser Glu Glu Thr
305                 310                 315                 320
Ala Ile Gly Lys Phe Pro Ile Glu Thr Val Glu Met Met Gly Lys Ile
                    325                 330                 335
Ala Lys Val Thr Glu Glu Tyr Arg Glu Ser Phe Gly Leu Ser Arg Ile
                    340                 345                 350
Arg Glu Phe Met Glu Ile Lys Lys Gly Thr Ile Lys Glu Ala Ile Thr
                    355                 360                 365
Arg Ser Ile Ile Asp Ala Ile Cys Thr Ile Asp Ile Lys Phe Ile Leu
                    370                 375                 380
Thr Pro Thr Arg Thr Gly Arg Thr Ala Arg Leu Ile Ser Arg Phe Lys
385                 390                 395                 400
Pro Lys Gln Trp Ile Leu Ala Phe Ser Thr Asn Glu Arg Val Cys Asn
                    405                 410                 415
Asn Leu Met Phe Ser Tyr Gly Val Tyr Pro Phe Cys Leu Glu Glu Gly
                    420                 425                 430
Phe Asp Glu Asn Asp Ile Val Arg Leu Ile Lys Gly Leu Gly Leu Val
                    435                 440                 445
Glu Ser Asp Asp Met Val Leu Met Thr Glu Gly Lys Pro Ile Glu Lys
                    450                 455                 460
Thr Val Gly Thr Asn Ser Ile Lys Ile Phe Gln Ile Ala
465                 470                 475

<210> SEQ ID NO 25
<211> LENGTH: 408
```

```
<212> TYPE: PRT
<213> ORGANISM: Methanosarcina thermophila

<400> SEQUENCE: 25

Met Lys Val Leu Val Ile Asn Ala Gly Ser Ser Leu Lys Tyr Gln
1               5                   10                  15

Leu Ile Asp Met Thr Asn Glu Ser Ala Leu Ala Val Gly Leu Cys Glu
            20                  25                  30

Arg Ile Gly Ile Asp Asn Ser Ile Thr Gln Lys Lys Phe Asp Gly
            35                  40                  45

Lys Lys Leu Glu Lys Leu Thr Asp Leu Pro Thr His Lys Asp Ala Leu
50                  55                  60

Glu Val Val Lys Ala Leu Thr Asp Asp Glu Phe Gly Val Ile Lys
65                  70                  75                  80

Asp Met Gly Glu Ile Asn Ala Val Gly His Arg Val Val His Gly Gly
                85                  90                  95

Glu Lys Phe Thr Thr Ser Ala Leu Tyr Asp Glu Gly Val Glu Lys Ala
                100                 105                 110

Ile Lys Asp Cys Phe Glu Leu Ala Pro Leu His Asn Pro Asn Met
        115                 120                 125

Met Gly Ile Ser Ala Cys Ala Glu Ile Met Pro Gly Thr Pro Met Val
130                 135                 140

Ile Val Phe Asp Thr Ala Phe His Gln Thr Met Pro Pro Tyr Ala Tyr
145                 150                 155                 160

Met Tyr Ala Leu Pro Tyr Asp Leu Tyr Glu Lys His Gly Val Arg Lys
                165                 170                 175

Tyr Gly Phe His Gly Thr Ser His Lys Tyr Val Ala Glu Arg Ala Ala
                180                 185                 190

Leu Met Leu Gly Lys Pro Ala Glu Glu Thr Lys Ile Ile Thr Cys His
        195                 200                 205

Leu Gly Asn Gly Ser Ser Ile Thr Ala Val Glu Gly Gly Lys Ser Val
210                 215                 220

Glu Thr Ser Met Gly Phe Thr Pro Leu Glu Gly Leu Ala Met Gly Thr
225                 230                 235                 240

Arg Cys Gly Ser Ile Asp Pro Ala Ile Val Pro Phe Leu Met Glu Lys
                245                 250                 255

Glu Gly Leu Thr Thr Arg Glu Ile Asp Thr Leu Met Asn Lys Lys Ser
                260                 265                 270

Gly Val Leu Gly Val Ser Gly Leu Ser Asn Asp Phe Arg Asp Leu Asp
        275                 280                 285

Glu Ala Ala Ser Lys Gly Asn Arg Lys Ala Glu Leu Ala Leu Glu Ile
290                 295                 300

Phe Ala Tyr Lys Val Lys Lys Phe Ile Gly Glu Tyr Ser Ala Val Leu
305                 310                 315                 320

Asn Gly Ala Asp Ala Val Val Phe Thr Ala Gly Ile Gly Glu Asn Ser
                325                 330                 335

Ala Ser Ile Arg Lys Arg Ile Leu Thr Gly Leu Asp Gly Ile Gly Ile
                340                 345                 350

Lys Ile Asp Asp Glu Lys Asn Lys Ile Arg Gly Gln Glu Ile Asp Ile
        355                 360                 365

Ser Thr Pro Asp Ala Lys Val Arg Val Phe Val Ile Pro Thr Asn Glu
370                 375                 380

Glu Leu Ala Ile Ala Arg Glu Thr Lys Glu Ile Val Glu Thr Glu Val
385                 390                 395                 400
```

<210> SEQ ID NO 26
<211> LENGTH: 585
<212> TYPE: DNA
<213> ORGANISM: Sulfolobus acidocaldarius

<400> SEQUENCE: 26

```
atgaagattg gtattgtaac tggaattcct ggtgtaggga aaagtactgt cttggctaaa      60
gttaaagaga tattggataa tcaaggtata aataacaaga tcataaatta tggagatttt     120
atgttagcaa cagcattaaa attaggctat gctaaagata gagacgaaat gagaaaatta     180
tctgtagaaa agcagaagaa attgcagatt gatgcggcta aggtatagc tgaagaggca      240
agagcaggtg gagaaggata tctgttcata gatacgcatg ctgtgatacg tacaccctct     300
ggatatttac ctggtttacc gtcatatgta attacagaaa taaatccgtc tgttatcttt     360
ttactgaaag ctgatcctaa gataatatta tcaaggcaaa agagagatac aacaaggaat     420
agaaatgatt atagtgacga atcagttata ttagaaacca taaacttcgc tagatatgca     480
gctactgctt ctgcagtatt agccggttct actgttaagg taattgtaaa cgtggaagga     540
gatcctagta tagcagctaa tgagataata aggtctatga agtaa                    585
```

<210> SEQ ID NO 27
<211> LENGTH: 585
<212> TYPE: DNA
<213> ORGANISM: Artificial Sequence
<220> FEATURE:
<223> OTHER INFORMATION: Synthetic

<400> SEQUENCE: 27

```
atgaaaatcg gtatcgttac cggtatcccg ggtgttggta atctaccgt tctggctaaa       60
gttaaagaaa tcctggacaa ccagggtatc aacaacaaaa tcatcaacta cggtgacttc     120
atgctggcta ccgctctgaa actgggttac gctaaagacc gtgacgaaat gcgtaaactg     180
tctgttgaaa acagaaaaa actgcagatc gacgctgcta aggtatcgc tgaagaagct       240
cgtgctggtg gtgaaggtta cctgttcatc gacacccacg ctgttatccg taccccgtct     300
ggttacctgc cgggtctgcc gtcttacgtt atcaccgaaa tcaacccgtc tgttatcttc     360
ctgctggaag ctgacccgaa aatcatcctg tctcgtcaga acgtgacac cacccgtaac     420
cgtaacgact actctgacga atctgttatc ctggaaacca tcaacttcgc tcgttacgct     480
gctaccgctt ctgctgttct ggctggttct accgttaaag ttatcgttaa cgttgaaggt     540
gacccgtcta tcgctgctaa cgaaatcatc cgttctatga atag                     585
```

<210> SEQ ID NO 28
<211> LENGTH: 663
<212> TYPE: DNA
<213> ORGANISM: Thermotoga maritima

<400> SEQUENCE: 28

```
atgatggcgt accttgtctt tctaggacct ccaggtgcag gaaaaggaac ctacgcaaag     60
agattgcagg aaataacggg gattcctcat atatccaccg gtgacatttt cagggacatt    120
gtaaaaaaag agaacgacga gcttgggaaa agataaaag atcatgga aggggagaa        180
ctcgttccgg acgaactcgt gaacgaggtt gtgaaagaa gactctcaga aaagattgt      240
gaaagaggat tcatactgga cggctatcca agaaccgttg ctcaggcgga attcctcgac    300
ggcttttgaa aaactcaaaa caaagagctc acggctgctg tactctttga agttcctgag    360
```

-continued

```
gaagtggtcg ttcagaggct cacggccaga aggatctgcc cgaaatgtgg aagaatttac    420
aatttgattt cgctccctcc aaaagaagac gaactgtgcg atgattgtaa agtgaagctc    480
gttcagagag aagacgacaa agaagaaaca gtgagacaca gatacaaggt ttatctcgaa    540
aagacacagc cagtgattga ttactacgat aaaaagggca ttctcaaacg agtggatggt    600
accataggaa tagacaacgt gatcgctgaa gtgttaaaga aatagggtg gagtgataaa    660 tga                                                                  663
```

<210> SEQ ID NO 29
<211> LENGTH: 660
<212> TYPE: DNA
<213> ORGANISM: Artificial Sequence
<220> FEATURE:
<223> OTHER INFORMATION: Synthetic

<400> SEQUENCE: 29

```
atgatggcct atctggtttt tcttggtcca ccgggggcag gcaaaggtac atatgcgaaa     60
cgtttacagg aaatcaccgg catcccgcac attagcacgg cgacattttt cgtgatatt    120 gtcaaaaagg aaaatgacga attaggtaag aaaattaaag aaattatgga gcgcggcgag    180
ttggtgccgg acgaactggt gaatgaagtt gtcaaacgtc ggctgtctga aaaggattgc    240
gaacgtggct ttattttgga cggttacccg cgtacagtag ctcaggcaga gtttctcgac    300
ggcttcctga agactcagaa taaggagtta acggctgcgg tcctgttcga ggtgcctgaa    360
gaggtggtcg ttcagcgtct gaccgcgcgg cgtatctgcc cgaagtgtgg tcgtatttac    420
aacctgattt cacttcctcc aaaagaagat gaactgtgtg atgactgcaa agtaaaactg    480
gtgcaacgcg aagatgataa agaggaaact gtgcgccatc gctacaaagt atatctggaa    540
aaaacccaac cggttatcga ttattatgat aaaaaggca ttttgaaacg cgttgatggg    600
accatcggca tcgataacgt gattgccgaa gttctcaaaa tcattgggtg gagtgataaa    660
```

<210> SEQ ID NO 30
<211> LENGTH: 651
<212> TYPE: DNA
<213> ORGANISM: Artificial Sequence
<220> FEATURE:
<223> OTHER INFORMATION: Synthetic

<400> SEQUENCE: 30

```
atgaacctga ttttcctggg tccgcctggg gcaggcaaag gcacccaggc gaaacgtgtg     60
tctgaaaagt acggtatccc gcagattagt accggcgata tgctgcgtga agcggttgct    120
aagggtacgg aactggggaa aaaggcgaaa gaatatatgg acaaagggga acttgttccg    180
gatgaagtag ttattggaat cgtgaaagaa cgcctccagc aaccggattg tgagaagggc    240
tttattctgg acggttttcc gcgtacgtta gcacaagccg aagctctgga cgaaatgtta    300
aaagaattga ataagaaaat tgacgccgta atcaacgtgg tcgtaccgga gaggaagtt    360 gtcaagcgta ttacctatcg tcgcacttgc cgcaattgcg gcgccgtgta ccatctcatt    420
tatgcacctc aaaagagga taataaatgt gataaatgcg gcggtgagct ttatcagcgt    480
gatgacgata agaagagac agtccgcgag cgttaccgtg tgtataaaca gaacacagag    540
ccattgatcg attattaccg taaaagggga atcctgtatg atgtggatgg tactaaagac    600
atcgaaggag tttggaaaga aattgaggcg attctggaaa aaattaaaag c             651
```

<210> SEQ ID NO 31
<211> LENGTH: 194

```
<212> TYPE: PRT
<213> ORGANISM: Sulfolobus acidocaldarius

<400> SEQUENCE: 31

Met Lys Ile Gly Ile Val Thr Gly Ile Pro Gly Val Gly Lys Ser Thr
1               5                   10                  15

Val Leu Ala Lys Val Lys Glu Ile Leu Asp Asn Gln Gly Ile Asn Asn
            20                  25                  30

Lys Ile Ile Asn Tyr Gly Asp Phe Met Leu Ala Thr Ala Leu Lys Leu
        35                  40                  45

Gly Tyr Ala Lys Asp Arg Asp Glu Met Arg Lys Leu Ser Val Glu Lys
50                  55                  60

Gln Lys Lys Leu Gln Ile Asp Ala Ala Lys Gly Ile Ala Glu Glu Ala
65                  70                  75                  80

Arg Ala Gly Gly Glu Gly Tyr Leu Phe Ile Asp Thr His Ala Val Ile
                85                  90                  95

Arg Thr Pro Ser Gly Tyr Leu Pro Gly Leu Pro Ser Tyr Val Ile Thr
            100                 105                 110

Glu Ile Asn Pro Ser Val Ile Phe Leu Leu Glu Ala Asp Pro Lys Ile
        115                 120                 125

Ile Leu Ser Arg Gln Lys Arg Asp Thr Thr Arg Asn Arg Asn Asp Tyr
130                 135                 140

Ser Asp Glu Ser Val Ile Leu Gly Thr Ile Asn Phe Ala Arg Tyr Ala
145                 150                 155                 160

Ala Thr Ala Ser Ala Val Leu Ala Gly Ser Thr Val Lys Val Ile Val
                165                 170                 175

Asn Val Glu Gly Asp Pro Ser Ile Ala Ala Asn Glu Ile Ile Arg Ser
            180                 185                 190

Met Lys

<210> SEQ ID NO 32
<211> LENGTH: 220
<212> TYPE: PRT
<213> ORGANISM: Thermotoga maritima

<400> SEQUENCE: 32

Met Met Ala Tyr Leu Val Phe Leu Gly Pro Pro Gly Ala Gly Lys Gly
1               5                   10                  15

Thr Tyr Ala Lys Arg Leu Gln Glu Ile Thr Gly Ile Pro His Ile Ser
            20                  25                  30

Thr Gly Asp Ile Phe Arg Asp Ile Val Lys Lys Glu Asn Asp Glu Leu
        35                  40                  45

Gly Lys Lys Ile Lys Glu Ile Met Glu Arg Gly Glu Leu Val Pro Asp
50                  55                  60

Glu Leu Val Asn Glu Val Val Lys Arg Arg Leu Ser Glu Lys Asp Cys
65                  70                  75                  80

Glu Arg Gly Phe Ile Leu Asp Gly Tyr Pro Arg Thr Val Ala Gln Ala
                85                  90                  95

Glu Phe Leu Asp Gly Phe Leu Lys Thr Gln Asn Lys Glu Leu Thr Ala
            100                 105                 110

Ala Val Leu Phe Glu Val Pro Glu Val Val Val Gln Arg Leu Thr
        115                 120                 125

Ala Arg Arg Ile Cys Pro Lys Cys Gly Arg Ile Tyr Asn Leu Ile Ser
130                 135                 140

Leu Pro Pro Lys Glu Asp Glu Leu Cys Asp Asp Cys Lys Val Lys Leu
145                 150                 155                 160
```

Val Gln Arg Glu Asp Asp Lys Glu Thr Val Arg His Arg Tyr Lys
                165                 170                 175

Val Tyr Leu Glu Lys Thr Gln Pro Val Ile Asp Tyr Asp Lys Lys
            180                 185                 190

Gly Ile Leu Lys Arg Val Asp Gly Thr Ile Gly Ile Asp Asn Val Ile
        195                 200                 205

Ala Glu Val Leu Lys Ile Ile Gly Trp Ser Asp Lys
    210                 215                 220

<210> SEQ ID NO 33
<211> LENGTH: 11
<212> TYPE: PRT
<213> ORGANISM: Artificial Sequence
<220> FEATURE:
<223> OTHER INFORMATION: transglutaminase substrate

<400> SEQUENCE: 33

Met Asn Gln Glu Gln Val Ser Pro Leu Gly Gly
1               5                   10

<210> SEQ ID NO 34
<211> LENGTH: 204
<212> TYPE: PRT
<213> ORGANISM: Artificial Sequence
<220> FEATURE:
<223> OTHER INFORMATION: Protein sequence of thermostable adenylate
      kinase from Sulfolobus acidcaldarius fused at the N-terminus with
      a transglutaminase (Factor XIII) substrate sequence

<400> SEQUENCE: 34

Met Asn Gln Glu Gln Val Ser Pro Leu Gly Gly Lys Ile Gly Ile Val
1               5                   10                  15

Thr Gly Ile Pro Gly Val Gly Lys Ser Thr Val Leu Ala Lys Val Lys
            20                  25                  30

Glu Ile Leu Asp Asn Gln Gly Ile Asn Asn Lys Ile Ile Asn Tyr Gly
        35                  40                  45

Asp Phe Met Leu Ala Thr Ala Leu Lys Leu Gly Tyr Ala Lys Asp Arg
    50                  55                  60

Asp Glu Met Arg Lys Leu Ser Val Glu Lys Gln Lys Lys Leu Gln Ile
65                  70                  75                  80

Asp Ala Ala Lys Gly Ile Ala Glu Glu Ala Arg Ala Gly Gly Glu Gly
                85                  90                  95

Tyr Leu Phe Ile Asp Thr His Ala Val Ile Arg Thr Pro Ser Gly Tyr
            100                 105                 110

Leu Pro Gly Leu Pro Ser Tyr Val Ile Thr Glu Ile Asn Pro Ser Val
        115                 120                 125

Ile Phe Leu Leu Glu Ala Asp Pro Lys Ile Ile Leu Ser Arg Gln Lys
    130                 135                 140

Arg Asp Thr Thr Arg Asn Arg Asn Asp Tyr Ser Asp Glu Ser Val Ile
145                 150                 155                 160

Leu Glu Thr Ile Asn Phe Ala Arg Tyr Ala Ala Thr Ala Ser Ala Val
                165                 170                 175

Leu Ala Gly Ser Thr Val Lys Val Ile Val Asn Val Glu Gly Asp Pro
            180                 185                 190

Ser Ile Ala Ala Asn Glu Ile Ile Arg Ser Met Lys
        195                 200

<210> SEQ ID NO 35
<211> LENGTH: 204

```
<212> TYPE: PRT
<213> ORGANISM: Artificial Sequence
<220> FEATURE:
<223> OTHER INFORMATION: Protein sequence of thermostable adenylate
      kinase from Sulfolobus acidcaldarius fused at the C-terminus with
      a transglutaminase (factor VIII) substrate sequence

<400> SEQUENCE: 35

Met Lys Ile Gly Ile Val Thr Gly Ile Pro Gly Val Gly Lys Ser Thr
1               5                   10                  15

Val Leu Ala Lys Val Lys Glu Ile Leu Asp Asn Gln Gly Ile Asn Asn
            20                  25                  30

Lys Ile Ile Asn Tyr Gly Asp Phe Met Leu Ala Thr Ala Leu Lys Leu
        35                  40                  45

Gly Tyr Ala Lys Asp Arg Asp Glu Met Arg Lys Leu Ser Val Glu Lys
    50                  55                  60

Gln Lys Lys Leu Gln Ile Asp Ala Ala Lys Gly Ile Ala Glu Glu Ala
65                  70                  75                  80

Arg Ala Gly Gly Glu Gly Tyr Leu Phe Ile Asp Thr His Ala Val Ile
                85                  90                  95

Arg Thr Pro Ser Gly Tyr Leu Pro Gly Leu Pro Ser Tyr Val Ile Thr
            100                 105                 110

Glu Ile Asn Pro Ser Val Ile Phe Leu Leu Glu Ala Asp Pro Lys Ile
        115                 120                 125

Ile Leu Ser Arg Gln Lys Arg Asp Thr Thr Arg Asn Arg Asn Asp Tyr
130                 135                 140

Ser Asp Glu Ser Val Ile Leu Glu Thr Ile Asn Phe Ala Arg Tyr Ala
145                 150                 155                 160

Ala Thr Ala Ser Ala Val Leu Ala Gly Ser Thr Val Lys Val Ile Val
            165                 170                 175

Asn Val Glu Gly Asp Pro Ser Ile Ala Ala Asn Glu Ile Ile Arg Ser
        180                 185                 190

Met Lys Gly Gly Asn Gln Glu Gln Val Ser Pro Leu
    195                 200

<210> SEQ ID NO 36
<211> LENGTH: 214
<212> TYPE: PRT
<213> ORGANISM: Artificial Sequence
<220> FEATURE:
<223> OTHER INFORMATION: Protein sequence of thermostable adenylate
      kinase from Sulfolobus acidcaldarius fused at the N-terminus and
      C-terminus with a transglutaminase (Factor XIII) substrate
      sequence

<400> SEQUENCE: 36

Met Asn Gln Glu Gln Val Ser Pro Leu Gly Gly Lys Ile Gly Ile Val
1               5                   10                  15

Thr Gly Ile Pro Gly Val Gly Lys Ser Thr Val Leu Ala Lys Val Lys
            20                  25                  30

Glu Ile Leu Asp Asn Gln Gly Ile Asn Asn Lys Ile Ile Asn Tyr Gly
        35                  40                  45

Asp Phe Met Leu Ala Thr Ala Leu Lys Leu Gly Tyr Ala Lys Asp Arg
    50                  55                  60

Asp Glu Met Arg Lys Leu Ser Val Glu Lys Gln Lys Lys Leu Gln Ile
65                  70                  75                  80

Asp Ala Ala Lys Gly Ile Ala Glu Glu Ala Arg Ala Gly Gly Glu Gly
                85                  90                  95

Tyr Leu Phe Ile Asp Thr His Ala Val Ile Arg Thr Pro Ser Gly Tyr
```

```
            100                 105                 110
Leu Pro Gly Leu Pro Ser Tyr Val Ile Thr Glu Ile Asn Pro Ser Val
            115                 120                 125

Ile Phe Leu Leu Glu Ala Asp Pro Lys Ile Ile Leu Ser Arg Gln Lys
    130                 135                 140

Arg Asp Thr Thr Arg Asn Arg Asn Asp Tyr Ser Asp Glu Ser Val Ile
145                 150                 155                 160

Leu Glu Thr Ile Asn Phe Ala Arg Tyr Ala Ala Thr Ala Ser Ala Val
                165                 170                 175

Leu Ala Gly Ser Thr Val Lys Val Ile Val Asn Val Glu Gly Asp Pro
            180                 185                 190

Ser Ile Ala Ala Asn Glu Ile Ile Arg Ser Met Lys Gly Gly Asn Gln
        195                 200                 205

Glu Gln Val Ser Pro Leu
    210

<210> SEQ ID NO 37
<211> LENGTH: 704
<212> TYPE: DNA
<213> ORGANISM: Artificial Sequence
<220> FEATURE:
<223> OTHER INFORMATION: DNA sequence of transglutaminase (Factor XIII)
      substrate sequence fused to the 5' end of adenylate kinase from
      Thermotoga maritima.

<400> SEQUENCE: 37
atgaatcaag aacaagtcag cccgctgggc ggcatcatcg cctatctggt ttttcttggt      60
ccaccggggg caggcaaagg tacctatgcg aaacgtttac aggaaatcac cggcatcccg     120
cacattagca cgggcgacat ttttcgtgat attgtcaaaa aggaaaatga cgaattaggt     180
aagaaaatta agaaattat ggagcgcggc gagttggtgc cggacgaact ggtgaatgaa      240
gttgtcaaac gtcggctgtc tgaaaaggat tgcgaacgtg cttttatttt ggacggttac     300
ccgcgtacag tagctcaggc agagtttctc gacggcttcc tgaagactca gaataaggag     360
ttaacggctg cggtcctgtt cgaggtgcct gaagaggtgg tcgttcagcg tctgaccgcg     420
cggcgtatct gcccgaagtg tggtcgtatt tacaacctga tttcacttcc tccaaaagaa     480
gatgaactgt gtgatgactg caaagtaaaa ctggtgcaac gcgaagatga taaagaggaa     540
actgtgcgcc atcgctacaa agtatatctg gaaaaaccc aaccggttat cgattattat      600
gataaaaaag cattttgaa acgcgttgat gggaccatcg gcatcgataa cgtgattgcc      660
gaagttctca aaatcattgg gtggagtgat aaataggtcg acgc                     704

<210> SEQ ID NO 38
<211> LENGTH: 231
<212> TYPE: PRT
<213> ORGANISM: Artificial Sequence
<220> FEATURE:
<223> OTHER INFORMATION: Protein sequence of adenylate kinase from
      Thermotoga maritime fused at the N-terminal with a
      transglutaminase (Factor XIII) substrate sequence.

<400> SEQUENCE: 38

Met Asn Gln Glu Gln Val Ser Pro Leu Gly Gly Ile Ile Ala Tyr Leu
1               5                   10                  15

Val Phe Leu Gly Pro Pro Gly Ala Gly Lys Gly Thr Tyr Ala Lys Arg
            20                  25                  30

Leu Gln Glu Ile Thr Gly Ile Pro His Ile Ser Thr Gly Asp Ile Phe
        35                  40                  45
```

```
Arg Asp Ile Val Lys Lys Glu Asn Asp Glu Leu Gly Lys Lys Ile Lys
 50                  55                  60
Glu Ile Met Glu Arg Gly Glu Leu Val Pro Asp Glu Leu Val Asn Glu
 65                  70                  75                  80
Val Val Lys Arg Arg Leu Ser Glu Lys Asp Cys Glu Arg Gly Phe Ile
                 85                  90                  95
Leu Asp Gly Tyr Pro Arg Thr Val Ala Gln Ala Glu Phe Leu Asp Gly
                100                 105                 110
Phe Leu Lys Thr Gln Asn Lys Glu Leu Thr Ala Ala Val Leu Phe Glu
            115                 120                 125
Val Pro Glu Glu Val Val Gln Arg Leu Thr Ala Arg Arg Ile Cys
130                 135                 140
Pro Lys Cys Gly Arg Ile Tyr Asn Leu Ile Ser Leu Pro Pro Lys Glu
145                 150                 155                 160
Asp Glu Leu Cys Asp Asp Cys Lys Val Lys Leu Val Gln Arg Glu Asp
                165                 170                 175
Asp Lys Glu Glu Thr Val Arg His Arg Tyr Lys Val Tyr Leu Glu Lys
                180                 185                 190
Thr Gln Pro Val Ile Asp Tyr Tyr Asp Lys Lys Gly Ile Leu Lys Arg
            195                 200                 205
Val Asp Gly Thr Ile Gly Ile Asp Asn Val Ile Ala Glu Val Leu Lys
210                 215                 220
Ile Ile Gly Trp Ser Asp Lys
225                 230
```

<210> SEQ ID NO 39
<211> LENGTH: 696
<212> TYPE: DNA
<213> ORGANISM: Artificial Sequence
<220> FEATURE:
<223> OTHER INFORMATION: DNA sequence of transglutaminase (Factor XIII) substrate sequence fused to the 3' end of adenylate kinase from Thermotoga maritima.

<400> SEQUENCE: 39

```
atgatggcct atctggtttt tcttggtcca ccgggggcag gcaaaggtac ctatgcgaaa      60
cgtttacagg aaatcaccgg catcccgcac attagcacgg cgacattttt cgtgatatt     120
gtcaaaaagg aaaatgacga attaggtaag aaaattaaag aaattatgga gcgcggcgag    180
ttggtgccgg acgaactggt gaatgaagtt gtcaaacgtc ggctgtctga aaaggattgc    240
gaacgtggct ttattttgga cggttacccg cgtacagtag ctcaggcaga gtttctcgac    300
ggcttcctga agactcagaa taaggagtta acggctgcgg tcctgttcga ggtgcctgaa    360
gaggtggtcg ttcagcgtct gaccgcgcgg cgtatctgcc cgaagtgtgg tcgtatttac    420
aacctgattt cacttcctcc aaaagaagat gaactgtgtg atgactgcaa agtaaaactg    480
gtgcaacgcg aagatgataa agaggaaact gtgcgccatc gctacaaagt atatctggaa    540
aaaacccaac cggttatcga ttattatgat aaaaaaggca ttttgaaacg cgttgatggg    600
accatcggca tcgataacgt gattgccgaa gttctcaaaa tcattgggtg gagtgataaa    660
ctgggcggca atcaagaaca agtcagcccg ctgtaa                              696
```

<210> SEQ ID NO 40
<211> LENGTH: 231
<212> TYPE: PRT
<213> ORGANISM: Artificial Sequence
<220> FEATURE:
<223> OTHER INFORMATION: Protein sequence of adenylate kinase from Thermotoga maritime fused at the C-terminal with a transglutaminase (Factor XIII) substrate sequence.

<400> SEQUENCE: 40

Met Met Ala Tyr Leu Val Phe Leu Gly Pro Pro Gly Ala Gly Lys Gly
1               5                   10                  15

Thr Tyr Ala Lys Arg Leu Gln Glu Ile Thr Gly Ile Pro His Ile Ser
            20                  25                  30

Thr Gly Asp Ile Phe Arg Asp Ile Val Lys Lys Glu Asn Asp Glu Leu
        35                  40                  45

Gly Lys Lys Ile Lys Glu Ile Met Glu Arg Gly Glu Leu Val Pro Asp
    50                  55                  60

Glu Leu Val Asn Glu Val Val Lys Arg Arg Leu Ser Glu Lys Asp Cys
65                  70                  75                  80

Glu Arg Gly Phe Ile Leu Asp Gly Tyr Pro Arg Thr Val Ala Gln Ala
                85                  90                  95

Glu Phe Leu Asp Gly Phe Leu Lys Thr Gln Asn Lys Glu Leu Thr Ala
            100                 105                 110

Ala Val Leu Phe Glu Val Pro Glu Glu Val Val Gln Arg Leu Thr
        115                 120                 125

Ala Arg Arg Ile Cys Pro Lys Cys Gly Arg Ile Tyr Asn Leu Ile Ser
    130                 135                 140

Leu Pro Pro Lys Glu Asp Glu Leu Cys Asp Asp Cys Lys Val Lys Leu
145                 150                 155                 160

Val Gln Arg Glu Asp Asp Lys Glu Glu Thr Val Arg His Arg Tyr Lys
                165                 170                 175

Val Tyr Leu Glu Lys Thr Gln Pro Val Ile Asp Tyr Tyr Asp Lys Lys
            180                 185                 190

Gly Ile Leu Lys Arg Val Asp Gly Thr Ile Gly Ile Asp Asn Val Ile
        195                 200                 205

Ala Glu Val Leu Lys Ile Ile Gly Trp Ser Asp Lys Leu Gly Gly Asn
    210                 215                 220

Gln Glu Gln Val Ser Pro Leu
225                 230

<210> SEQ ID NO 41
<211> LENGTH: 729
<212> TYPE: DNA
<213> ORGANISM: Artificial Sequence
<220> FEATURE:
<223> OTHER INFORMATION: DNA sequence of transglutaminase (Factor XIII)
      substrate sequence fused to both the 5' and 3' ends of adenylate
      kinase from Thermotoga maritima.

<400> SEQUENCE: 41
atgaatcaag aacaagtcag cccgctgggc ggcatcatcg cctatctggt ttttcttggt      60
ccaccggggg caggcaaagg tacctatgcg aaacgtttac aggaaatcac cggcatcccg     120
cacattagca cgggcgacat ttttcgtgat attgtcaaaa aggaaaatga cgaattaggt     180
aagaaaatta agaaattat ggagcgcggc gagttggtgc cggacgaact ggtgaatgaa      240
gttgtcaaac gtcggctgtc tgaaaaggat tgcgaacgtg gctttatttt ggacggttac     300
ccgcgtacag tagctcaggc agagtttctc gacggcttcc tgaagactca gaataaggag     360
ttaacggctg cggtcctgtt cgaggtgcct gaagaggtgg tcgttcagcg tctgaccgcg     420
cggcgtatct gcccgaagtg tggtcgtatt tacaacctga tttcacttcc tccaaaagaa     480
gatgaactgt gtgatgactg caaagtaaaa ctggtgcaac gcgaagatga taagaggaa      540 actgtgcgcc atcgctacaa agtatatctg gaaaaaaccc aaccggttat cgattattat     600

-continued

```
gataaaaaag gcattttgaa acgcgttgat gggaccatcg gcatcgataa cgtgattgcc    660
gaagttctca aatcattgg gtggagtgat aaactgggcg gcaatcaaga acaagtcagc    720
ccgctgtaa                                                            729
```

<210> SEQ ID NO 42
<211> LENGTH: 242
<212> TYPE: PRT
<213> ORGANISM: Artificial Sequence
<220> FEATURE:
<223> OTHER INFORMATION: Protein sequence of adenylate kinase from
      Thermotoga maritime fused at the N- and C-terminal with a
      transglutaminase (Factor XIII) substrate sequence.

<400> SEQUENCE: 42

```
Met Asn Gln Glu Gln Val Ser Pro Leu Gly Gly Ile Ile Ala Tyr Leu
1               5                   10                  15

Val Phe Leu Gly Pro Pro Gly Ala Gly Lys Gly Thr Tyr Ala Lys Arg
            20                  25                  30

Leu Gln Glu Ile Thr Gly Ile Pro His Ile Ser Thr Gly Asp Ile Phe
        35                  40                  45

Arg Asp Ile Val Lys Lys Glu Asn Asp Glu Leu Lys Lys Ile Lys
    50                  55                  60

Glu Ile Met Glu Arg Gly Glu Leu Val Pro Asp Glu Leu Val Asn Glu
65                  70                  75                  80

Val Val Lys Arg Arg Leu Ser Glu Lys Asp Cys Glu Arg Gly Phe Ile
                85                  90                  95

Leu Asp Gly Tyr Pro Arg Thr Val Ala Gln Ala Glu Phe Leu Asp Gly
            100                 105                 110

Phe Leu Lys Thr Gln Asn Lys Glu Leu Thr Ala Ala Val Leu Phe Glu
        115                 120                 125

Val Pro Glu Glu Val Val Gln Arg Leu Thr Ala Arg Arg Ile Cys
    130                 135                 140

Pro Lys Cys Gly Arg Ile Tyr Asn Leu Ile Ser Leu Pro Pro Lys Glu
145                 150                 155                 160

Asp Glu Leu Cys Asp Asp Cys Lys Val Lys Leu Val Gln Arg Glu Asp
                165                 170                 175

Asp Lys Glu Glu Thr Val Arg His Arg Tyr Lys Val Tyr Leu Glu Lys
            180                 185                 190

Thr Gln Pro Val Ile Asp Tyr Tyr Asp Lys Lys Gly Ile Leu Lys Arg
        195                 200                 205

Val Asp Gly Thr Ile Gly Ile Asp Asn Val Ile Ala Glu Val Leu Lys
    210                 215                 220

Ile Ile Gly Trp Ser Asp Lys Leu Gly Gly Asn Gln Glu Gln Val Ser
225                 230                 235                 240

Pro Leu
```

<210> SEQ ID NO 43
<211> LENGTH: 1288
<212> TYPE: DNA
<213> ORGANISM: Artificial Sequence
<220> FEATURE:
<223> OTHER INFORMATION: DNA sequence of complete Sup35 gene construct
      from Saccharomyces cerevisiae

<400> SEQUENCE: 43

```
gattcaaacc aaggcaacaa tcagcaaaac taccagcaat acagccagaa cggtaaccaa    60
caacaaggta acaacagata ccaaggttat caagcttaca atgctcaagc ccaacctggg    120
```

-continued

```
ggtgggtact accaaaatta ccaaggttat tctgggtacc aacaaggtgg ctatcaacag    180
tacaatcccg acgccggtta ccagcaacag tataatcctc aaggaggcta tcaacagtac    240
aatcctcaag gcggttatca gcaccaattc aatccacaag gtggccgtgg aaattacaaa    300
aacttcaact acaataacaa tttgcaagga tatcaagctg gtttccaacc acagtctcaa    360
ggtatgtctt tgaacgactt tcaaaagcaa caaaagcagg ccgctcccaa accaaagaag    420
actttgaagc ttgtctccag ttcctgtatc aagttggcca atgctaccaa gaaggttgac    480
acaaaacctg ccgaatctga taagaaagag gaagagaagt ctgctgaaac caaagaacca    540
actaaagagc aacaaaaggt cgaagaacca gttaaaaagg aggagaaacc agtccagact    600
gaagaaaaga cggaggaaaa atcggaactt ccaaaggtag aagaccttaa aatctctgaa    660
tcaacacata ataccaacaa tgccaatgtt accagtgctg atgccttgat caaggaacag    720
gaagaagaag tggatgacga agttgttaac gatatgtttg gtggtaaaga tcacgtttct    780
ttaattttca tgggtcatgt tgatgccggt aaatctacta tgggtggtaa tctactatac    840
ttgactggct ctgtggataa gagaactatt gagaaatatg aaagagaagc caaggatgca    900
ggcagacaag gttggtactt gtcatgggtc atggatacca caaagaaga aagaaatgat    960 ggtaagacta tcgaagttgg taaggcctac ttgaaactg aaaaaaggcg ttataccata   1020
ttggatgctc ctggtcataa aatgtacgtt tccgagatga tcgtggtgc ttctcaagct   1080 gatgttggtg ttttggtcat ttccgccaga aagggtgagt acgaaaccgg ttttgagaga   1140
ggtggtcaaa ctcgtgaaca cgccctattg ccaagaccc aaggtgttaa taagatggtt   1200
gtcgtcgtaa ataagatgga tgacccaacc gttaactggt ctaaggaacg ttacgaccaa   1260
tgtgtgagta atgtcagcaa tttcttga                                     1288
```

<210> SEQ ID NO 44
<211> LENGTH: 429
<212> TYPE: PRT
<213> ORGANISM: Artificial Sequence
<220> FEATURE:
<223> OTHER INFORMATION: Protein sequence of complete Sup35 from Saccharomyces cerevisiae

<400> SEQUENCE: 44

```
Asp Ser Asn Gln Gly Asn Asn Gln Gln Asn Tyr Gln Gln Tyr Ser Gln
 1               5                  10                  15

Asn Gly Asn Gln Gln Gln Gly Asn Asn Arg Tyr Gln Gly Tyr Gln Ala
            20                  25                  30

Tyr Asn Ala Gln Ala Gln Pro Gly Gly Gly Tyr Tyr Gln Asn Tyr Gln
        35                  40                  45

Gly Tyr Ser Gly Tyr Gln Gln Gly Gly Tyr Gln Gln Tyr Asn Pro Asp
    50                  55                  60

Ala Gly Tyr Gln Gln Gln Tyr Asn Pro Gln Gly Gly Tyr Gln Gln Tyr
65                  70                  75                  80

Asn Pro Gln Gly Gly Tyr Gln His Gln Phe Asn Pro Gln Gly Gly Arg
                85                  90                  95

Gly Asn Tyr Lys Asn Phe Asn Tyr Asn Asn Asn Leu Gln Gly Tyr Gln
            100                 105                 110

Ala Gly Phe Gln Pro Gln Ser Gln Gly Met Ser Leu Asn Asp Phe Gln
        115                 120                 125

Lys Gln Gln Lys Gln Ala Ala Pro Lys Pro Lys Lys Thr Leu Lys Leu
    130                 135                 140

Val Ser Ser Ser Cys Ile Lys Leu Ala Asn Ala Thr Lys Lys Val Asp
```

145         150             155             160
Thr Lys Pro Ala Glu Ser Asp Lys Lys Glu Glu Lys Ser Ala Glu
                165             170             175
Thr Lys Glu Pro Thr Lys Glu Pro Thr Lys Val Glu Glu Pro Val Lys
            180             185             190
Lys Glu Glu Lys Pro Val Gln Thr Glu Glu Lys Thr Glu Glu Lys Ser
        195             200             205
Glu Leu Pro Lys Val Glu Asp Leu Lys Ile Ser Glu Ser Thr His Asn
    210             215             220
Thr Asn Asn Ala Asn Val Thr Ser Ala Asp Ala Leu Ile Lys Glu Gln
225             230             235             240
Glu Glu Glu Val Asp Asp Glu Val Val Asn Asp Met Phe Gly Gly Lys
                245             250             255
Asp His Val Ser Leu Ile Phe Met Gly His Val Asp Ala Gly Lys Ser
                260             265             270
Thr Met Gly Gly Asn Leu Leu Tyr Leu Thr Gly Ser Val Asp Lys Arg
            275             280             285
Thr Ile Glu Lys Tyr Glu Arg Glu Ala Lys Asp Ala Gly Arg Gln Gly
        290             295             300
Trp Tyr Leu Ser Trp Val Met Asp Thr Asn Lys Glu Glu Arg Asn Asp
305             310             315             320
Gly Lys Thr Ile Glu Val Gly Lys Ala Tyr Phe Glu Thr Glu Lys Arg
                325             330             335
Arg Tyr Thr Ile Leu Asp Ala Pro Gly His Lys Met Tyr Val Ser Glu
                340             345             350
Met Ile Gly Gly Ala Ser Gln Ala Asp Val Gly Val Leu Val Ile Ser
            355             360             365
Ala Arg Lys Gly Glu Tyr Glu Thr Gly Phe Glu Arg Gly Gly Gln Thr
        370             375             380
Arg Glu His Ala Leu Leu Ala Lys Thr Gln Gly Val Asn Lys Met Val
385             390             395             400
Val Val Val Asn Lys Met Asp Asp Pro Thr Val Asn Trp Ser Lys Glu
                405             410             415
Arg Tyr Asp Gln Cys Val Ser Asn Val Ser Asn Phe Leu
                420             425

<210> SEQ ID NO 45
<211> LENGTH: 348
<212> TYPE: DNA
<213> ORGANISM: Artificial Sequence
<220> FEATURE:
<223> OTHER INFORMATION: DNA sequence of sup35N (N-terminal domain)
      codon-biased for optimal expression in E. coli

<400> SEQUENCE: 45
atggactcta accagggtaa caaccagcag aactaccagc agtactctca gaacggtaac      60
cagcagcagg gtaacaaccg ttaccagggt taccaggctt acaacgctca ggctcagccg     120
ggtggtggtt actaccagaa ctaccagggt tactccggat atcaacaggg tggttaccaa     180
caatataatc agacgctggg ttaccagcag cagtacaacc cgcagggtgg ttaccagcag     240
tacaacccgc aaggcggata tcaacaccag ttcaatccgc agggtggtcg tggtaactac     300
aaaaacttca actacaacaa caacctgcag ggttaccagg ctggttaa                  348

<210> SEQ ID NO 46
<211> LENGTH: 115
<212> TYPE: PRT

<213> ORGANISM: Artificial Sequence
<220> FEATURE:
<223> OTHER INFORMATION: Protein sequence of sup35N (N-terminal domain)

<400> SEQUENCE: 46

Met Asp Ser Asn Gln Gly Asn Asn Gln Gln Asn Tyr Gln Gln Tyr Ser
1               5                   10                  15

Gln Asn Gly Asn Gln Gln Gln Gly Asn Asn Arg Tyr Gln Gly Tyr Gln
                20                  25                  30

Ala Tyr Asn Ala Gln Ala Gln Pro Gly Gly Gly Tyr Tyr Gln Asn Tyr
            35                  40                  45

Gln Gly Tyr Ser Gly Tyr Gln Gln Gly Gly Tyr Gln Gln Tyr Asn Pro
        50                  55                  60

Asp Ala Gly Tyr Gln Gln Gln Tyr Asn Pro Gln Gly Gly Tyr Gln Gln
65                  70                  75                  80

Tyr Asn Pro Gln Gly Gly Tyr Gln His Gln Phe Asn Pro Gln Gly Gly
                85                  90                  95

Arg Gly Asn Tyr Lys Asn Phe Asn Tyr Asn Asn Asn Leu Gln Gly Tyr
                100                 105                 110

Gln Ala Gly
        115

<210> SEQ ID NO 47
<211> LENGTH: 941
<212> TYPE: DNA
<213> ORGANISM: Artificial Sequence
<220> FEATURE:
<223> OTHER INFORMATION: DNA sequence of E-coli codon biased Adenylate
      kinase from Sulfolobus acidcaldarius fused at the N-terminus with
      Sup35 N-terminal domain from Saccharomyces cerevisiae

<400> SEQUENCE: 47
atggactcta accagggtaa caaccagcag aactaccagc agtactctca gaacggtaac      60
cagcagcagg gtaacaaccg ttaccagggt taccaggctt acaacgctca ggctcagccg     120
ggtggtggtt actaccagaa ctaccagggt tactccggtt atcagcaagg tggctaccaa     180
caatataatc cagacgctgg ctatcaacag caatataatc ctcagggtgg ttaccagcag     240
tacaacccgc aaggcggtta tcaacaccag ttcaatccgc agggtggtcg tggtaactac     300
aaaaacttca actacaacaa caacctgcag ggttaccagg ctggaattat gaagatcggc     360
attgtgaccg gcattccggg cgttggcaaa agcaccgttc tggcaaaggt gaaggagatc     420
ctggacaacc agggcattaa taacaaaatt attaattatg gtgattttat gctggcgacc     480
gcgctgaagc tgggctacgc aaaagatcgt gacgaaatgc gcaaactgag cgtggaaaaa     540
cagaagaagc tgcagattga tgcggcgaag ggcattgcgg aagaggcacg cgcgggcggc     600
gaaggctacc tgtttatcga tacccatgcg gtgatccgca ccccgagcgg ttatctgccg     660
ggcctgccgt cttacgtgat tacggaaatc aacccgagcg ttattttttct gctggaggca     720
gatccgaaga ttattctgag ccgccagaag cgcgatacca cccgcaaccg caacgattat     780
agcgacgaaa gcgttatcct ggagaccatc aactttgcgc gctatgcggc aaccgcgagc     840
gcggttctgg caggctctac cgttaaagtg atcgtgaacg tggagggtga tccaagcatc     900
gcggcgaacg aaatcattcg cagcatgaaa taagtcgacg c                         941

<210> SEQ ID NO 48
<211> LENGTH: 310
<212> TYPE: PRT
<213> ORGANISM: Artificial Sequence
<220> FEATURE:

<223> OTHER INFORMATION: Protein sequence of Adenylate kinase from
     Sulfolobus acidcaldarius fused at the N-terminus with Sup35
     N-terminal domain from Saccharomyces cerevisiae

<400> SEQUENCE: 48

Met Asp Ser Asn Gln Gly Asn Asn Gln Gln Asn Tyr Gln Gln Tyr Ser
1               5                   10                  15

Gln Asn Gly Asn Gln Gln Gly Asn Asn Arg Tyr Gln Gly Tyr Gln
            20                  25                  30

Ala Tyr Asn Ala Gln Ala Gln Pro Gly Gly Tyr Tyr Gln Asn Tyr
        35                  40                  45

Gln Gly Tyr Ser Gly Tyr Gln Gly Gly Tyr Gln Gln Tyr Asn Pro
    50                  55                  60

Asp Ala Gly Tyr Gln Gln Gln Tyr Asn Pro Gln Gly Gly Tyr Gln Gln
65                  70                  75                  80

Tyr Asn Pro Gln Gly Gly Tyr Gln His Gln Phe Asn Pro Gln Gly Gly
                85                  90                  95

Arg Gly Asn Tyr Lys Asn Phe Asn Tyr Asn Asn Asn Leu Gln Gly Tyr
            100                 105                 110

Gln Ala Gly Ile Met Lys Ile Gly Ile Val Thr Gly Ile Pro Gly Val
        115                 120                 125

Gly Lys Ser Thr Val Leu Ala Lys Val Lys Glu Ile Leu Asp Asn Gln
    130                 135                 140

Gly Ile Asn Asn Lys Ile Ile Asn Tyr Gly Asp Phe Met Leu Ala Thr
145                 150                 155                 160

Ala Leu Lys Leu Gly Tyr Ala Lys Asp Arg Asp Glu Met Arg Lys Leu
                165                 170                 175

Ser Val Glu Lys Gln Lys Lys Leu Gln Ile Asp Ala Ala Lys Gly Ile
            180                 185                 190

Ala Glu Glu Ala Arg Ala Gly Gly Glu Gly Tyr Leu Phe Ile Asp Thr
        195                 200                 205

His Ala Val Ile Arg Thr Pro Ser Gly Tyr Leu Pro Gly Leu Pro Ser
    210                 215                 220

Tyr Val Ile Thr Glu Ile Asn Pro Ser Val Ile Phe Leu Leu Glu Ala
225                 230                 235                 240

Asp Pro Lys Ile Ile Leu Ser Arg Gln Lys Arg Asp Thr Thr Arg Asn
                245                 250                 255

Arg Asn Asp Tyr Ser Asp Glu Ser Val Ile Leu Glu Thr Ile Asn Phe
            260                 265                 270

Ala Arg Tyr Ala Ala Thr Ala Ser Ala Val Leu Ala Gly Ser Thr Val
        275                 280                 285

Lys Val Ile Val Asn Val Glu Gly Asp Pro Ser Ile Ala Ala Asn Glu
    290                 295                 300

Ile Ile Arg Ser Met Lys
305                 310

<210> SEQ ID NO 49
<211> LENGTH: 947
<212> TYPE: DNA
<213> ORGANISM: Artificial Sequence
<220> FEATURE:
<223> OTHER INFORMATION: DNA sequence of E. coli codon biased Adenylate
     kinase from Sulfolobus acidcaldarius fused at the C-terminus with
     Sup35 N-terminal domain from Saccharomyces cerevisiae

<400> SEQUENCE: 49
atgaagatcg gcattgtgac cggcattccg ggcgttggca aaagcaccgt tctggcaaag      60

```
gtgaaggaga tcctggacaa ccagggcatt aataacaaaa ttattaatta tggtgatttt    120
atgctggcga ccgcgctgaa gctgggctac gcaaaagatc gtgacgaaat gcgcaaactg    180
agcgtggaaa acagaagaa gctgcagatt gatgcggcga agggcattgc ggaagaggca    240
cgcgcgggcg gcgaaggcta cctgtttatc gatacccatg cggtgatccg cacccccgagc   300 ggttatctgc cgggcctgcc gtcttacgtg attacggaaa tcaacccgag cgttattttt    360
ctgctggagg cagatccgaa gattattctg agccgccaga agcgcgatac cacccgcaac    420
cgcaacgatt atagcgacga aagcgttatc ctggagacca tcaactttgc gcgctatgcg    480
gcaaccgcga gcgcggttct ggcaggctct accgttaaag tgatcgtgaa cgtggagggt    540
gatccaagca tcgcggcgaa cgaaatcatt cgcagcatga acagtcgag tatggactct    600 aaccagggta caaccagca gaactaccag cagtactctc agaacggtaa ccagcagcag    660
ggtaacaacc gttaccaggg ttaccaggct acaacgctc aggctcagcc gggtggtggt    720
tactaccaga actaccaggg ttactccggt tatcagcaag gtggctacca acaatataat    780
ccagacgctg gctatcaaca gcaatataat cctcagggtg ttaccagca gtacaacccg    840 caaggcggtt atcaacacca gttcaatccg cagggtggtc gtggtaacta caaaaacttc    900
aactacaaca caacctgca gggttaccag gctggttaag tcgacgc                   947
```

<210> SEQ ID NO 50
<211> LENGTH: 312
<212> TYPE: PRT
<213> ORGANISM: Artificial Sequence
<220> FEATURE:
<223> OTHER INFORMATION: Protein sequence of Adenylate kinase from
      Sulfolobus acidcaldarius fused at the C-terminus with Sup35
      N-terminal domain from Saccharomyces cerevisiae

<400> SEQUENCE: 50

```
Met Lys Ile Gly Ile Val Thr Gly Ile Pro Gly Val Gly Lys Ser Thr
1               5                   10                  15

Val Leu Ala Lys Val Lys Glu Ile Leu Asp Asn Gln Gly Ile Asn Asn
            20                  25                  30

Lys Ile Ile Asn Tyr Gly Asp Phe Met Leu Ala Thr Ala Leu Lys Leu
        35                  40                  45

Gly Tyr Ala Lys Asp Arg Asp Glu Met Arg Lys Leu Ser Val Glu Lys
    50                  55                  60

Gln Lys Lys Leu Gln Ile Asp Ala Ala Lys Gly Ile Ala Glu Glu Ala
65                  70                  75                  80

Arg Ala Gly Gly Glu Gly Tyr Leu Phe Ile Asp Thr His Ala Val Ile
                85                  90                  95

Arg Thr Pro Ser Gly Tyr Leu Pro Gly Leu Pro Ser Tyr Val Ile Thr
            100                 105                 110

Glu Ile Asn Pro Ser Val Ile Phe Leu Leu Glu Ala Asp Pro Lys Ile
        115                 120                 125

Ile Leu Ser Arg Gln Lys Arg Asp Thr Thr Arg Asn Arg Asn Asp Tyr
    130                 135                 140

Ser Asp Glu Ser Val Ile Leu Glu Thr Ile Asn Phe Ala Arg Tyr Ala
145                 150                 155                 160

Ala Thr Ala Ser Ala Val Leu Ala Gly Ser Thr Val Lys Val Ile Val
                165                 170                 175

Asn Val Glu Gly Asp Pro Ser Ile Ala Ala Asn Glu Ile Ile Arg Ser
            180                 185                 190

Met Lys Gln Ser Ser Met Asp Ser Asn Gln Gly Asn Asn Gln Gln Asn
        195                 200                 205
```

Tyr Gln Gln Tyr Ser Gln Asn Gly Asn Gln Gln Gly Asn Asn Arg
            210                 215                 220

Tyr Gln Gly Tyr Gln Ala Tyr Asn Ala Gln Ala Gln Pro Gly Gly Gly
225                 230                 235                 240

Tyr Tyr Gln Asn Tyr Gln Gly Tyr Ser Gly Tyr Gln Gln Gly Tyr
            245                 250                 255

Gln Gln Tyr Asn Pro Asp Ala Gly Tyr Gln Gln Tyr Asn Pro Gln
        260                 265                 270

Gly Gly Tyr Gln Gln Tyr Asn Pro Gln Gly Gly Tyr Gln His Gln Phe
            275                 280                 285

Asn Pro Gln Gly Gly Arg Gly Asn Tyr Lys Asn Phe Asn Tyr Asn Asn
        290                 295                 300

Asn Leu Gln Gly Tyr Gln Ala Gly
305                 310

<210> SEQ ID NO 51
<211> LENGTH: 1011
<212> TYPE: DNA
<213> ORGANISM: Artificial Sequence
<220> FEATURE:
<223> OTHER INFORMATION: DNA sequence of Sup35N fused at the 5' end of
      adenylate kinase from Thermotoga maritima.

<400> SEQUENCE: 51
atggactcta accagggtaa caaccagcag aactaccagc agtactctca gaacggtaac      60
cagcagcagg gtaacaaccg ttaccagggt taccaggctt acaacgctca ggctcagccg     120
ggtggtggtt actaccagaa ctaccagggt tactccggtt atcagcaagg tggctaccaa     180
caatataatc cagacgctgg ctatcaacag caatataatc ctcagggtgg ttaccagcag     240
tacaacccgc aaggcggtta tcaacaccag ttcaatccgc agggtggtcg tggtaactac     300
aaaaacttca actacaacaa caacctgcag ggttaccagg ctggaattat gatggcctat     360
ctggtttttc ttggtccacc gggggcaggc aaaggtacct atgcgaaacg tttacaggaa     420
atcaccggca tcccgcacat tagcacgggc gacatttttc gtgatattgt caaaaaggaa     480
aatgacgaat taggtaagaa aattaaagaa attatggagc gcggcgagtt ggtgccggac     540
gaactggtga tgaagttgt caaacgtcgg ctgtctgaaa aggattgcga acgtggcttt     600
attttggacg gttacccgcg tacagtagct caggcagagt ttctcgacgg cttcctgaag     660
actcagaata aggagttaac ggctgcggtc ctgttcgagg tgcctgaaga ggtggtcgtt     720
cagcgtctga ccgcgcggcg tatctgcccg aagtgtggtc gtatttacaa cctgatttca     780
cttcctccaa aagaagatga actgtgtgat gactgcaaag taaaactggt gcaacgcgaa     840
gatgataaag aggaaactgt gcgccatcgc tacaaagtat atctggaaaa acccaaccg     900 gttatcgatt attatgataa aaaaggcatt tgaaacgcg ttgatgggac catcggcatc     960
gataacgtga ttgccgaagt tctcaaaatc attgggtgga gtgataaata g            1011

<210> SEQ ID NO 52
<211> LENGTH: 336
<212> TYPE: PRT
<213> ORGANISM: Artificial Sequence
<220> FEATURE:
<223> OTHER INFORMATION: Protein sequence of adenylate kinase from
      Thermotoga maritima fused at the N-terminal with Sup35N.

<400> SEQUENCE: 52

Met Asp Ser Asn Gln Gly Asn Asn Gln Gln Asn Tyr Gln Gln Tyr Ser
1               5                   10                  15

-continued

```
Gln Asn Gly Asn Gln Gln Gly Asn Asn Arg Tyr Gln Gly Tyr Gln
             20                  25                  30
Ala Tyr Asn Ala Gln Ala Gln Pro Gly Gly Gly Tyr Tyr Gln Asn Tyr
         35                  40                  45
Gln Gly Tyr Ser Gly Tyr Gln Gln Gly Gly Tyr Gln Gln Tyr Asn Pro
     50                  55                  60
Asp Ala Gly Tyr Gln Gln Gln Tyr Asn Pro Gln Gly Gly Tyr Gln Gln
65                  70                  75                  80
Tyr Asn Pro Gln Gly Gly Tyr Gln His Gln Phe Asn Pro Gln Gly Gly
                 85                  90                  95
Arg Gly Asn Tyr Lys Asn Phe Asn Tyr Asn Asn Asn Leu Gln Gly Tyr
             100                 105                 110
Gln Ala Gly Ile Met Met Ala Tyr Leu Val Phe Leu Gly Pro Pro Gly
         115                 120                 125
Ala Gly Lys Gly Thr Tyr Ala Lys Arg Leu Gln Glu Ile Thr Gly Ile
     130                 135                 140
Pro His Ile Ser Thr Gly Asp Ile Phe Arg Asp Ile Val Lys Lys Glu
145                 150                 155                 160
Asn Asp Glu Leu Gly Lys Lys Ile Lys Glu Ile Met Glu Arg Gly Glu
                 165                 170                 175
Leu Val Pro Asp Glu Leu Val Asn Glu Val Val Lys Arg Arg Leu Ser
             180                 185                 190
Glu Lys Asp Cys Glu Arg Gly Phe Ile Leu Asp Gly Tyr Pro Arg Thr
         195                 200                 205
Val Ala Gln Ala Glu Phe Leu Asp Gly Phe Leu Lys Thr Gln Asn Lys
     210                 215                 220
Glu Leu Thr Ala Ala Val Leu Phe Glu Val Pro Glu Glu Val Val Val
225                 230                 235                 240
Gln Arg Leu Thr Ala Arg Arg Ile Cys Pro Lys Cys Gly Arg Ile Tyr
                 245                 250                 255
Asn Leu Ile Ser Leu Pro Pro Lys Glu Asp Glu Leu Cys Asp Asp Cys
             260                 265                 270
Lys Val Lys Leu Val Gln Arg Glu Asp Asp Lys Glu Glu Thr Val Arg
         275                 280                 285
His Arg Tyr Lys Val Tyr Leu Glu Lys Thr Gln Pro Val Ile Asp Tyr
     290                 295                 300
Tyr Asp Lys Lys Gly Ile Leu Lys Arg Val Asp Gly Thr Ile Gly Ile
305                 310                 315                 320
Asp Asn Val Ile Ala Glu Val Leu Lys Ile Ile Gly Trp Ser Asp Lys
                 325                 330                 335
```

<210> SEQ ID NO 53
<211> LENGTH: 1025
<212> TYPE: PRT
<213> ORGANISM: Artificial Sequence
<220> FEATURE:
<223> OTHER INFORMATION: DNA sequence of Sup35N fused at the 3' end of adenylate kinase from Thermotoga maritima.

<400> SEQUENCE: 53

```
Ala Thr Gly Ala Thr Gly Gly Cys Cys Thr Ala Thr Cys Thr Gly Gly
1               5                   10                  15
Thr Thr Thr Thr Thr Cys Thr Thr Gly Gly Thr Cys Cys Ala Cys Cys
                 20                  25                  30
Gly Gly Gly Gly Gly Cys Ala Gly Gly Cys Ala Ala Ala Gly Gly Thr
             35                  40                  45
```

-continued

```
Ala Cys Cys Thr Ala Thr Gly Cys Gly Ala Ala Ala Cys Gly Thr Thr
    50                  55                  60

Thr Ala Cys Ala Gly Gly Ala Ala Ala Thr Cys Ala Cys Cys Gly Gly
65                  70                  75                  80

Cys Ala Thr Cys Cys Cys Gly Cys Ala Cys Ala Thr Thr Ala Gly Cys
                85                  90                  95

Ala Cys Gly Gly Gly Cys Gly Ala Cys Ala Thr Thr Thr Thr Thr Cys
            100                 105                 110

Gly Thr Gly Ala Thr Ala Thr Thr Gly Thr Cys Ala Ala Ala Ala Ala
        115                 120                 125

Gly Gly Ala Ala Ala Ala Thr Gly Ala Cys Gly Ala Ala Thr Thr Ala
    130                 135                 140

Gly Gly Thr Ala Ala Gly Ala Ala Ala Ala Thr Thr Ala Ala Ala Gly
145                 150                 155                 160
Ala Ala Ala Thr Thr Ala Thr Gly Gly Ala Gly Cys Gly Cys Gly Gly
                165                 170                 175
Cys Gly Ala Gly Thr Thr Gly Gly Thr Gly Cys Cys Gly Gly Ala Cys
            180                 185                 190

Gly Ala Ala Cys Thr Gly Gly Thr Gly Ala Ala Thr Gly Ala Ala Gly
        195                 200                 205

Thr Thr Gly Thr Cys Ala Ala Ala Cys Gly Thr Cys Gly Gly Cys Thr
    210                 215                 220

Gly Thr Cys Thr Gly Ala Ala Ala Ala Gly Gly Ala Thr Thr Gly Cys
225                 230                 235                 240
Gly Ala Ala Cys Gly Thr Gly Gly Cys Thr Thr Thr Ala Thr Thr Thr
                245                 250                 255

Thr Gly Gly Ala Cys Gly Gly Thr Thr Ala Cys Cys Cys Gly Cys Gly
            260                 265                 270

Thr Ala Cys Ala Gly Thr Ala Gly Cys Thr Cys Ala Gly Gly Cys Ala
        275                 280                 285

Gly Ala Gly Thr Thr Thr Cys Thr Cys Gly Ala Cys Gly Gly Cys Thr
    290                 295                 300

Thr Cys Cys Thr Gly Ala Ala Gly Ala Cys Thr Cys Ala Gly Ala Ala
305                 310                 315                 320

Thr Ala Ala Gly Gly Ala Gly Thr Thr Ala Ala Cys Gly Gly Cys Thr
                325                 330                 335
Gly Cys Gly Gly Thr Cys Cys Thr Gly Thr Thr Cys Gly Ala Gly Gly
            340                 345                 350
Thr Gly Cys Cys Thr Gly Ala Ala Gly Ala Gly Gly Thr Gly Gly Thr
        355                 360                 365

Cys Gly Thr Thr Cys Ala Gly Cys Gly Thr Cys Thr Gly Ala Cys Cys
    370                 375                 380
Gly Cys Gly Cys Gly Gly Cys Gly Thr Ala Thr Cys Thr Gly Cys Cys
385                 390                 395                 400

Cys Gly Ala Ala Gly Thr Gly Thr Gly Gly Thr Cys Gly Thr Ala Thr
                405                 410                 415

Thr Thr Ala Cys Ala Ala Cys Cys Thr Gly Ala Thr Thr Thr Cys Ala
            420                 425                 430

Cys Thr Thr Cys Cys Thr Cys Cys Ala Ala Ala Ala Gly Ala Ala Gly
        435                 440                 445

Ala Thr Gly Ala Ala Cys Thr Gly Thr Gly Thr Gly Ala Thr Gly Ala
    450                 455                 460

Cys Thr Gly Cys Ala Ala Ala Gly Thr Ala Ala Ala Ala Cys Thr Gly
```

```
                465                 470                 475                 480
Gly Thr Gly Cys Ala Ala Cys Gly Cys Gly Ala Ala Gly Ala Thr Gly
                    485                 490                 495
Ala Thr Ala Ala Ala Gly Ala Gly Gly Ala Ala Ala Cys Thr Gly Thr
                500                 505                 510
Gly Cys Gly Cys Cys Ala Thr Cys Gly Cys Thr Ala Cys Ala Ala Ala
            515                 520                 525
Gly Thr Ala Thr Ala Thr Cys Thr Gly Gly Ala Ala Ala Ala Ala Ala
        530                 535                 540
Cys Cys Cys Ala Ala Cys Cys Gly Gly Thr Thr Ala Thr Cys Gly Ala
545                 550                 555                 560
Thr Thr Ala Thr Thr Ala Thr Gly Ala Thr Ala Ala Ala Ala Ala Ala
                565                 570                 575
Gly Gly Cys Ala Thr Thr Thr Gly Ala Ala Cys Gly Cys Gly
            580                 585                 590
Thr Thr Gly Ala Thr Gly Gly Ala Cys Cys Ala Thr Cys Gly Gly
        595                 600                 605
Cys Ala Thr Cys Gly Ala Thr Ala Ala Cys Gly Thr Gly Ala Thr Thr
    610                 615                 620
Gly Cys Cys Gly Ala Ala Gly Thr Thr Cys Thr Cys Ala Ala Ala Ala
625                 630                 635                 640
Thr Cys Ala Thr Thr Gly Gly Gly Thr Gly Ala Gly Thr Gly Ala
                645                 650                 655
Thr Ala Ala Ala Cys Thr Gly Thr Cys Gly Ala Gly Thr Ala Thr Gly
                660                 665                 670
Gly Ala Cys Thr Cys Thr Ala Ala Cys Cys Ala Gly Gly Thr Ala
            675                 680                 685
Ala Cys Ala Ala Cys Cys Ala Gly Cys Ala Gly Ala Ala Cys Thr Ala
        690                 695                 700
Cys Cys Ala Gly Cys Ala Gly Thr Ala Cys Thr Cys Thr Cys Ala Gly
705                 710                 715                 720
Ala Ala Cys Gly Gly Thr Ala Ala Cys Cys Ala Gly Cys Ala Gly Cys
                725                 730                 735
Ala Gly Gly Gly Thr Ala Ala Cys Ala Ala Cys Cys Gly Thr Thr Ala
                740                 745                 750
Cys Cys Ala Gly Gly Gly Thr Thr Ala Cys Ala Gly Gly Cys Thr
            755                 760                 765
Thr Ala Cys Ala Ala Cys Gly Cys Thr Cys Ala Gly Gly Cys Thr Cys
        770                 775                 780
Ala Gly Cys Cys Gly Gly Gly Thr Gly Gly Thr Gly Gly Thr Ala
785                 790                 795                 800
Cys Thr Ala Cys Cys Ala Gly Ala Ala Cys Thr Ala Cys Cys Ala Gly
                805                 810                 815
Gly Gly Thr Thr Ala Cys Thr Cys Cys Gly Gly Thr Thr Ala Thr Cys
                820                 825                 830
Ala Gly Cys Ala Ala Gly Gly Thr Gly Gly Cys Thr Ala Cys Cys Ala
            835                 840                 845
Ala Cys Ala Ala Thr Ala Thr Ala Ala Thr Cys Cys Ala Gly Ala Cys
        850                 855                 860
Gly Cys Thr Gly Gly Cys Thr Ala Thr Cys Ala Ala Cys Ala Gly Cys
865                 870                 875                 880
Ala Ala Thr Ala Thr Ala Ala Thr Cys Cys Thr Cys Ala Gly Gly Gly
                885                 890                 895
```

```
                                     -continued

Thr Gly Gly Thr Thr Ala Cys Cys Ala Gly Cys Ala Gly Thr Ala Cys
                900                 905                 910

Ala Ala Cys Cys Cys Gly Cys Ala Gly Gly Cys Gly Thr Thr
        915                 920                 925

Ala Thr Cys Ala Ala Cys Ala Cys Cys Ala Gly Thr Thr Cys Ala Ala
        930                 935                 940

Thr Cys Cys Gly Cys Ala Gly Gly Thr Gly Gly Thr Cys Gly Thr
945                 950                 955                 960

Gly Gly Thr Ala Ala Cys Thr Ala Cys Ala Ala Ala Cys Thr
                965                 970                 975

Thr Cys Ala Ala Cys Thr Ala Cys Ala Ala Cys Ala Ala Cys Ala Ala
        980                 985                 990

Cys Cys Thr Gly Cys Ala Gly Gly  Gly Thr Thr Ala Cys  Cys Ala Gly
        995                 1000                 1005

Gly Cys  Thr Gly Gly Thr Thr  Ala Ala Gly Thr Cys  Gly Ala Cys
    1010                 1015                 1020

Gly Cys
    1025

<210> SEQ ID NO 54
<211> LENGTH: 338
<212> TYPE: PRT
<213> ORGANISM: Artificial Sequence
<220> FEATURE:
<223> OTHER INFORMATION: Protein sequence of adenylate kinase from
      Thermotoga maritima fused at the C-terminal fusion with Sup35N

<400> SEQUENCE: 54

Met Met Ala Tyr Leu Val Phe Leu Gly Pro Pro Gly Ala Gly Lys Gly
1               5                   10                  15

Thr Tyr Ala Lys Arg Leu Gln Glu Ile Thr Gly Ile Pro His Ile Ser
            20                  25                  30

Thr Gly Asp Ile Phe Arg Asp Ile Val Lys Lys Glu Asn Asp Glu Leu
        35                  40                  45

Gly Lys Lys Ile Lys Glu Ile Met Glu Arg Gly Glu Leu Val Pro Asp
    50                  55                  60

Glu Leu Val Asn Glu Val Val Lys Arg Arg Leu Ser Glu Lys Asp Cys
65                  70                  75                  80

Glu Arg Gly Phe Ile Leu Asp Gly Tyr Pro Arg Thr Val Ala Gln Ala
                85                  90                  95

Glu Phe Leu Asp Gly Phe Leu Lys Thr Gln Asn Lys Glu Leu Thr Ala
            100                 105                 110

Ala Val Leu Phe Glu Val Pro Glu Glu Val Val Gln Arg Leu Thr
        115                 120                 125

Ala Arg Arg Ile Cys Pro Lys Cys Gly Arg Ile Tyr Asn Leu Ile Ser
    130                 135                 140

Leu Pro Pro Lys Glu Asp Glu Leu Cys Asp Asp Cys Lys Val Lys Leu
145                 150                 155                 160

Val Gln Arg Glu Asp Asp Lys Glu Glu Thr Val Arg His Arg Tyr Lys
                165                 170                 175

Val Tyr Leu Glu Lys Thr Gln Pro Val Ile Asp Tyr Tyr Asp Lys Lys
            180                 185                 190

Gly Ile Leu Lys Arg Val Asp Gly Thr Ile Gly Ile Asp Asn Val Ile
        195                 200                 205

Ala Glu Val Leu Lys Ile Ile Gly Trp Ser Asp Lys Leu Ser Ser Met
    210                 215                 220
```

```
Asp Ser Asn Gln Gly Asn Asn Gln Gln Asn Tyr Gln Gln Tyr Ser Gln
225                 230                 235                 240

Asn Gly Asn Gln Gln Gln Gly Asn Asn Arg Tyr Gln Gly Tyr Gln Ala
                245                 250                 255

Tyr Asn Ala Gln Ala Gln Pro Gly Gly Gly Tyr Tyr Gln Asn Tyr Gln
            260                 265                 270

Gly Tyr Ser Gly Tyr Gln Gln Gly Gly Tyr Gln Gln Tyr Asn Pro Asp
        275                 280                 285

Ala Gly Tyr Gln Gln Gln Tyr Asn Pro Gln Gly Gly Tyr Gln Gln Tyr
    290                 295                 300

Asn Pro Gln Gly Gly Tyr Gln His Gln Phe Asn Pro Gln Gly Gly Arg
305                 310                 315                 320

Gly Asn Tyr Lys Asn Phe Asn Tyr Asn Asn Asn Leu Gln Gly Tyr Gln
                325                 330                 335

Ala Gly
```

<210> SEQ ID NO 55
<211> LENGTH: 21
<212> TYPE: DNA
<213> ORGANISM: Artificial Sequence
<220> FEATURE:
<223> OTHER INFORMATION: DNA sequence encoding a short Sup35 peptide capable of aggregating to form amyloid fibrils; for use as a fusion peptide with tAK genes.

<400> SEQUENCE: 55

```
ggtaacaacc agcagaacta c                                              21
```

<210> SEQ ID NO 56
<211> LENGTH: 7
<212> TYPE: PRT
<213> ORGANISM: Artificial Sequence
<220> FEATURE:
<223> OTHER INFORMATION: Sup35 derived amyloid peptide

<400> SEQUENCE: 56

```
Gly Asn Asn Gln Gln Asn Tyr
1               5
```

<210> SEQ ID NO 57
<211> LENGTH: 1593
<212> TYPE: DNA
<213> ORGANISM: Artificial Sequence
<220> FEATURE:
<223> OTHER INFORMATION: DNA sequence encoding a Norovirus capsid protein (58kDa)

<400> SEQUENCE: 57

```
atgatgatgg cgtctaagga cgctacatca agcgtggatg gcgctagtgg cgctggtcag     60
ttggtaccgg aggttaatgc ttctgaccct cttgcaatgg atcctgtagc aggttcttcg    120
acagcagtcg cgactgctgg acaagttaat cctattgatc cctggataat taataatttt    180
gtgcaagccc cccaaggtga atttactatt tccccaaata atacccccgg tgatgttttg    240
tttgatttga gtttgggtcc ccatcttaat cctttcttgc tccatctatc acaaatgtat    300
aatggttggg ttggtaacat gagagtcagg attatgctag ctggtaatgc ctttactgcg    360
gggaagataa tagtttcctg catacccccct ggttttggtt cacataatct tactatagca    420
caagcaactc tctttccaca tgtgattgct gatgttagga ctctagaccc cattgaggtg    480
cctttggaag atgttaggaa tgttctcttt cataataatg atagaaatca acaaaccatg    540
cgccttgtgt gcatgctgta cacccccctc cgcactggtg gtggtactgg tgattctttt    600
```

-continued

```
gtagttgcag ggcgagttat gacttgcccc agtcctgatt ttaatttctt gttttagtc      660 cctcctacgg tggagcagaa accaggccc ttcacactcc caaatctgcc attgagttct      720
ctgtctaact cacgtgcccc tctcccaatc agtagtatgg gcatttcccc agacaatgtc     780
cagagtgtgc agttccaaaa tggtcggtgt actctggatg gccgcctggt tggcaccacc     840
ccagtttcat tgtcacatgt tgccaagata gagggacct ccaatggcac tgtaatcaac      900
cttactgaat tggatggcac acccttttcac ccttttgagg gccctgcccc cattgggttt    960
ccagacctcg gtggttgtga ttggcatatc aatatgacac agtttggcca ttctagccag    1020
acccagtatg atgtagacac cacccctgac acttttgtcc cccatcttgg ttcaattcag    1080
gcaaatggca ttggcagtgg taattatgtt ggtgttctta gctggatttc cccccccatca   1140 cacccgtctg gctcccaagt tgacctttgg aagatcccca attatgggtc aagtattacg    1200
gaggcaacac atctagcccc ttctgtatac cccctggtt tcggagaggt attggtcttt     1260
ttcatgtcaa aaatgccagg tcctggtgct tataatttgc cctgtctatt accacaagag    1320
tacatttcac atcttgctag tgaacaagcc cctactgtag gtgaggctgc cctgctccac    1380
tatgttgacc ctgataccgg tcggaatctt ggggaattca agcatacccc tgatggtttc    1440
ctcacttgtg tccccaatgg ggctagctcg ggtccacaac agctgccgat caatgggtc     1500 tttgtctttg tttcatgggt gtccagattt atcaattaa agcctgtggg aactgccagc     1560
tcggcaagag gtaggcttgg tctgcgccga taa                                  1593
```

<210> SEQ ID NO 58
<211> LENGTH: 530
<212> TYPE: PRT
<213> ORGANISM: Artificial Sequence
<220> FEATURE:
<223> OTHER INFORMATION: Protein sequence of Norovirus capsid protein (58kDa)

<400> SEQUENCE: 58

```
Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
                20                  25                  30

Met Asp Pro Val Ala Gly Ser Ser Thr Ala Val Ala Thr Ala Gly Gln
            35                  40                  45

Val Asn Pro Ile Asp Pro Trp Ile Ile Asn Asn Phe Val Gln Ala Pro
        50                  55                  60

Gln Gly Glu Phe Thr Ile Ser Pro Asn Asn Thr Pro Gly Asp Val Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
                100                 105                 110

Leu Ala Gly Asn Ala Phe Thr Ala Gly Lys Ile Ile Val Ser Cys Ile
            115                 120                 125

Pro Pro Gly Phe Gly Ser His Asn Leu Thr Ile Ala Gln Ala Thr Leu
        130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
```

```
                      180                 185                 190
Gly Gly Gly Thr Gly Asp Ser Phe Val Val Ala Gly Arg Val Met Thr
            195                 200                 205
Cys Pro Ser Pro Asp Phe Asn Phe Leu Phe Leu Val Pro Pro Thr Val
        210                 215                 220
Glu Gln Lys Thr Arg Pro Phe Thr Leu Pro Asn Leu Pro Leu Ser Ser
225                 230                 235                 240
Leu Ser Asn Ser Arg Ala Pro Leu Pro Ile Ser Ser Met Gly Ile Ser
                245                 250                 255
Pro Asp Asn Val Gln Ser Val Gln Phe Gln Asn Gly Arg Cys Thr Leu
            260                 265                 270
Asp Gly Arg Leu Val Gly Thr Thr Pro Val Ser Leu Ser His Val Ala
        275                 280                 285
Lys Ile Arg Gly Thr Ser Asn Gly Thr Val Ile Asn Leu Thr Glu Leu
        290                 295                 300
Asp Gly Thr Pro Phe His Pro Phe Glu Gly Pro Ala Pro Ile Gly Phe
305                 310                 315                 320
Pro Asp Leu Gly Gly Cys Asp Trp His Ile Asn Met Thr Gln Phe Gly
                325                 330                 335
His Ser Ser Gln Thr Gln Tyr Asp Val Asp Thr Thr Pro Asp Thr Phe
            340                 345                 350
Val Pro His Leu Gly Ser Ile Gln Ala Asn Gly Ile Gly Ser Gly Asn
        355                 360                 365
Tyr Val Gly Val Leu Ser Trp Ile Ser Pro Pro Ser His Pro Ser Gly
        370                 375                 380
Ser Gln Val Asp Leu Trp Lys Ile Pro Asn Tyr Gly Ser Ser Ile Thr
385                 390                 395                 400
Glu Ala Thr His Leu Ala Pro Ser Val Tyr Pro Pro Gly Phe Gly Glu
                405                 410                 415
Val Leu Val Phe Phe Met Ser Lys Met Pro Gly Pro Gly Ala Tyr Asn
            420                 425                 430
Leu Pro Cys Leu Leu Pro Gln Glu Tyr Ile Ser His Leu Ala Ser Glu
        435                 440                 445
Gln Ala Pro Thr Val Gly Glu Ala Ala Leu Leu His Tyr Val Asp Pro
        450                 455                 460
Asp Thr Gly Arg Asn Leu Gly Glu Phe Lys Ala Tyr Pro Asp Gly Phe
465                 470                 475                 480
Leu Thr Cys Val Pro Asn Gly Ala Ser Ser Gly Pro Gln Gln Leu Pro
                485                 490                 495
Ile Asn Gly Val Phe Val Phe Val Ser Trp Val Ser Arg Phe Tyr Gln
            500                 505                 510
Leu Lys Pro Val Gly Thr Ala Ser Ser Ala Arg Gly Arg Leu Gly Leu
        515                 520                 525
Arg Arg
    530

<210> SEQ ID NO 59
<211> LENGTH: 1593
<212> TYPE: DNA
<213> ORGANISM: Artificial Sequence
<220> FEATURE:
<223> OTHER INFORMATION: DNA sequence for a synthetic gene encoding a
      Norovirus capsid protein (58kDa) optimised for expression in
      E.coli

<400> SEQUENCE: 59
```

```
atgatgatgg cttctaaaga cgctacctct tctgttgacg gtgcttctgg tgctggtcag    60
ctggttccgg aagttaacgc ttctgacccg ctggctatgg acccggttgc tggttcttct   120
accgctgttg ctaccgctgg tcaggttaac ccgatcgacc cgtggatcat caacaacttc   180
gttcaggctc cgcagggtga attcaccatc tctccgaaca cacccggg tgacgttctg    240
ttcgacctgt ctctgggtcc gcacctgaac ccgttcctgc tgcacctgtc tcagatgtac   300
aacggttggg ttggtaacat gcgtgttcgt atcatgctgg ctggtaacgc tttcaccgct   360
ggtaaaatca tcgtttcttg catcccgccg ggtttcggtt ctcacaacct gaccatcgct   420
caggctaccc tgttcccgca cgttatcgct gacgttcgta ccctggaccc gatcgaagtt   480
ccgctggaag acgttcgtaa cgttctgttc cacaacaacg accgtaacca gcagaccatg   540
cgtctggttt gcatgctgta cacccgctg cgtaccggtg tggtaccgg tgactctttc   600
gttgttgctg gtcgtgttat gacctgcccg tctccggact tcaacttcct gttcctggtt   660
ccgccgaccg ttgaacagaa aacccgtccg ttcaccctgc cgaacctgcc gctgtcttct   720
ctgtctaact ctcgtgctcc gctgccgatc tcttctatgg gtatctctcc ggacaacgtt   780
cagtctgttc agttccagaa cggtcgttgc accctggacg tcgtctggt tggtaccacc   840
ccggttctc tgtctcacgt tgctaaaatc cgtggtacct caacggtac cgttatcaac   900
ctgaccgaac tggacggtac cccgttccac ccgttcgaag gtccggctcc gatcggtttc   960
ccggacctgg gtgttgcga ctggcacatc aacatgaccc agttcggtca ctcttctcag  1020
acccagtacg acgttgacac cacccggac accttcgttc cgcacctggg ttctatccag  1080
gctaacggta tcggttctgg taactacgtt ggtgttctgt cttggatctc tccgccgtct  1140
cacccgtctg gttctcaggt tgacctgtgg aaaatcccga actacggttc ttctatcacc  1200
gaagctaccc cctggctcc gtctgtttac cgccgggtt tcggtgaagt tctggttttc  1260
ttcatgtcta aaatgccggg tccgggtgct acaacctgc cgtgcctgct gccgcaggaa  1320
tacatctctc acctggcttc tgaacaggct ccgaccgttg tgaagctgc tctgctgcac  1380
tacgttgacc cggacaccgg tcgtaacctg ggtgaattca agcttaccc ggacggtttc  1440
ctgacctgcg ttccgaacgg tgcttcttct ggtccgcagc agctgccgat caacggtgtt  1500
ttcgttttcg tttcttgggt ttctcgtttc taccagctga aaccggttgg taccgcttct  1560
tctgctcgtg gtcgtctggg tctgcgtcgt tag                                1593

<210> SEQ ID NO 60
<211> LENGTH: 2250
<212> TYPE: DNA
<213> ORGANISM: Artificial Sequence
<220> FEATURE:
<223> OTHER INFORMATION: DNA sequence for a synthetic gene encoding a
      Norovirus capsid protein (58kDa) optimised for expression in
      E.coli fused at the 5' end of a gene encoding the tAK from
      Thermotoga maritima.

<400> SEQUENCE: 60
atgatgatgg cttctaaaga cgctacctct tctgttgacg gtgcttctgg tgctggtcag    60
ctggttccgg aagttaacgc ttctgacccg ctggctatgg acccggttgc tggttcttct   120
accgctgttg ctaccgctgg tcaggttaac ccgatcgacc cgtggatcat caacaacttc   180
gttcaggctc cgcagggtga attcaccatc tctccgaaca cacccggg tgacgttctg    240
ttcgacctgt ctctgggtcc gcacctgaac ccgttcctgc tgcacctgtc tcagatgtac   300
aacggttggg ttggtaacat gcgtgttcgt atcatgctgg ctggtaacgc tttcaccgct   360
ggtaaaatca tcgtttcttg catcccgccg ggtttcggtt ctcacaacct gaccatcgct   420
```

```
caggctaccc tgttcccgca cgttatcgct gacgttcgta ccctggaccc gatcgaagtt    480
ccgctggaag acgttcgtaa cgttctgttc cacaacaacg accgtaacca gcagaccatg    540
cgtctggttt gcatgctgta caccccgctg cgtaccggtg gtggtaccgg tgactctttc    600
gttgttgctg gtcgtgttat gacctgcccg tctccggact tcaacttcct gttcctggtt    660
ccgccgaccg ttgaacagaa acccgtccg ttcaccctgc cgaacctgcc gctgtcttct    720
ctgtctaact ctcgtgctcc gctgccgatc tcttctatgg gtatctctcc ggacaacgtt    780
cagtctgttc agttccagaa cggtcgttgc accctggacg tcgtctggt ggtaccacc    840 ccggtttctc tgtctcacgt tgctaaaatc cgtggtacct caacggtac cgttatcaac    900 ctgaccgaac tggacggtac cccgttccac ccgttcgaag tccggctcc gatcggtttc    960 ccggacctgg gtggttgcga ctggcacatc aacatgaccc agttcggtca ctcttctcag   1020
acccagtacg acgttgacac caccccggac accttcgttc cgcacctggg ttctatccag   1080
gctaacggta tcggttctgg taactacgtt ggtgttctgt cttggatctc tccgccgtct   1140
cacccgtctg ttctcaggt tgacctgtgg aaaatcccga actacggttc ttctatcacc   1200
gaagctaccc acctggctcc gtctgtttac ccgccgggtt tcggtgaagt tctggttttc   1260
ttcatgtcta aaatgccggg tccgggtgct acaacctgc cgtgcctgct gccgcaggaa   1320
tacatctctc acctggcttc tgaacaggct ccgaccgttg tgaagctgc tctgctgcac   1380 tacgttgacc cggacaccgg tcgtaacctg ggtgaattca aagcttaccc ggacggtttc   1440
ctgacctgcg ttccgaacgg tgcttcttct ggtccgcagc agctgccgat caacggtgtt   1500
ttcgttttcg tttcttgggt ttctcgtttc taccagctga accggttgg taccgcttct   1560 tctgctcgtg gtcgtctggg tctgcgtcgt atgatggcct atctggtttt tcttggtcca   1620
ccgggggcag gcaaaggtac ctatgcgaaa cgtttacagg aaatcaccgg catcccgcac   1680
attagcacgg gcgacatttt tcgtgatatt gtcaaaaagg aaaatgacga attaggtaag   1740
aaaattaaag aaattatgga gcgcggcgag ttggtgccgg acgaactggt gaatgaagtt   1800
gtcaaacgtc ggctgtctga aaaggattgc gaacgtggct ttattttgga cggttacccg   1860
cgtacagtag ctcaggcaga gtttctcgac ggcttcctga agactcagaa taaggagtta   1920
acggctgcgg tcctgttcga ggtgcctgaa gaggtggtcg ttcagcgtct gaccgcgcgg   1980
cgtatctgcc cgaagtgtgg tcgtatttac aacctgattt cacttcctcc aaaagaagat   2040
gaactgtgtg atgactgcaa agtaaaactg gtgcaacgcg aagatgataa agaggaaact   2100
gtgcgccatc gctacaaagt atatctggaa aaacccaac cggttatcga ttattatgat   2160
aaaaaaggca ttttgaaacg cgttgatggg accatcggca tcgataacgt gattgccgaa   2220
gttctcaaaa tcattgggtg gagtgataaa                                    2250
```

<210> SEQ ID NO 61
<211> LENGTH: 750
<212> TYPE: PRT
<213> ORGANISM: Artificial Sequence
<220> FEATURE:
<223> OTHER INFORMATION: Protein sequence of a Norovirus capsid protein
    (58kDa) fused at the N-terminus of the adenylate kinase from
    Thermotoga maritima

<400> SEQUENCE: 61

```
Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30
```

```
Met Asp Pro Val Ala Gly Ser Ser Thr Ala Val Ala Thr Ala Gly Gln
         35                  40                  45

Val Asn Pro Ile Asp Pro Trp Ile Ile Asn Asn Phe Val Gln Ala Pro
 50                  55                  60

Gln Gly Glu Phe Thr Ile Ser Pro Asn Asn Thr Pro Gly Asp Val Leu
 65                  70                  75                  80

Phe Asp Leu Ser Leu Gly Pro His Leu Asn Pro Phe Leu Leu His Leu
                 85                  90                  95

Ser Gln Met Tyr Asn Gly Trp Val Gly Asn Met Arg Val Arg Ile Met
                100                 105                 110

Leu Ala Gly Asn Ala Phe Thr Ala Gly Lys Ile Ile Val Ser Cys Ile
            115                 120                 125

Pro Pro Gly Phe Gly Ser His Asn Leu Thr Ile Ala Gln Ala Thr Leu
        130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Gln Lys Thr Arg Pro Phe Thr Leu Pro Asn Leu Pro Leu Ser Ser
225                 230                 235                 240

Leu Ser Asn Ser Arg Ala Pro Leu Pro Ile Ser Ser Met Gly Ile Ser
                245                 250                 255

Pro Asp Asn Val Gln Ser Val Gln Phe Gln Asn Gly Arg Cys Thr Leu
            260                 265                 270

Asp Gly Arg Leu Val Gly Thr Thr Pro Val Ser Leu Ser His Val Ala
        275                 280                 285

Lys Ile Arg Gly Thr Ser Asn Gly Thr Val Ile Asn Leu Thr Glu Leu
    290                 295                 300

Asp Gly Thr Pro Phe His Pro Phe Glu Gly Pro Ala Pro Ile Gly Phe
305                 310                 315                 320

Pro Asp Leu Gly Gly Cys Asp Trp His Ile Asn Met Thr Gln Phe Gly
                325                 330                 335

His Ser Ser Gln Thr Gln Tyr Asp Val Asp Thr Thr Pro Asp Thr Phe
            340                 345                 350

Val Pro His Leu Gly Ser Ile Gln Ala Asn Gly Ile Gly Ser Gly Asn
        355                 360                 365

Tyr Val Gly Val Leu Ser Trp Ile Ser Pro Ser His Pro Ser Gly
    370                 375                 380

Ser Gln Val Asp Leu Trp Lys Ile Pro Asn Tyr Gly Ser Ser Ile Thr
385                 390                 395                 400

Glu Ala Thr His Leu Ala Pro Ser Val Tyr Pro Pro Gly Phe Gly Glu
                405                 410                 415

Val Leu Val Phe Phe Met Ser Lys Met Pro Gly Pro Gly Ala Tyr Asn
            420                 425                 430

Leu Pro Cys Leu Leu Pro Gln Glu Tyr Ile Ser His Leu Ala Ser Glu
        435                 440                 445

Gln Ala Pro Thr Val Gly Glu Ala Ala Leu Leu His Tyr Val Asp Pro
```

-continued

```
            450                 455                 460
Asp Thr Gly Arg Asn Leu Gly Glu Phe Lys Ala Tyr Pro Asp Gly Phe
465                 470                 475                 480

Leu Thr Cys Val Pro Asn Gly Ala Ser Ser Gly Pro Gln Gln Leu Pro
                485                 490                 495

Ile Asn Gly Val Phe Val Phe Val Ser Trp Val Ser Arg Phe Tyr Gln
                500                 505                 510

Leu Lys Pro Val Gly Thr Ala Ser Ser Ala Arg Gly Arg Leu Gly Leu
                515                 520                 525

Arg Arg Met Met Ala Tyr Leu Val Phe Leu Gly Pro Pro Gly Ala Gly
                530                 535                 540

Lys Gly Thr Tyr Ala Lys Arg Leu Gln Glu Ile Thr Gly Ile Pro His
545                 550                 555                 560

Ile Ser Thr Gly Asp Ile Phe Arg Asp Ile Val Lys Glu Asn Asp
                565                 570                 575

Glu Leu Gly Lys Lys Ile Lys Glu Ile Met Glu Arg Gly Glu Leu Val
                580                 585                 590

Pro Asp Glu Leu Val Asn Glu Val Val Lys Arg Arg Leu Ser Glu Lys
                595                 600                 605

Asp Cys Glu Arg Gly Phe Ile Leu Asp Gly Tyr Pro Arg Thr Val Ala
610                 615                 620

Gln Ala Glu Phe Leu Asp Gly Phe Leu Lys Thr Gln Asn Lys Glu Leu
625                 630                 635                 640

Thr Ala Ala Val Leu Phe Glu Val Pro Glu Glu Val Val Gln Arg
                645                 650                 655

Leu Thr Ala Arg Arg Ile Cys Pro Lys Cys Gly Arg Ile Tyr Asn Leu
                660                 665                 670

Ile Ser Leu Pro Pro Lys Glu Asp Glu Leu Cys Asp Asp Cys Lys Val
                675                 680                 685

Lys Leu Val Gln Arg Glu Asp Asp Lys Glu Glu Thr Val Arg His Arg
                690                 695                 700

Tyr Lys Val Tyr Leu Glu Lys Thr Gln Pro Val Ile Asp Tyr Tyr Asp
705                 710                 715                 720

Lys Lys Gly Ile Leu Lys Arg Val Asp Gly Thr Ile Gly Ile Asp Asn
                725                 730                 735

Val Ile Ala Glu Val Leu Lys Ile Ile Gly Trp Ser Asp Lys
                740                 745                 750

<210> SEQ ID NO 62
<211> LENGTH: 130
<212> TYPE: PRT
<213> ORGANISM: Bacteriophage MS2

<400> SEQUENCE: 62

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
                20                  25                  30

Trp Ile Ser Ser Asn Ser Arg Ser Gln Ala Tyr Lys Val Thr Cys Ser
            35                  40                  45

Val Arg Gln Ser Ser Ala Gln Asn Arg Lys Tyr Thr Ile Lys Val Glu
        50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
```

```
            85                  90                  95
Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
    130

<210> SEQ ID NO 63
<211> LENGTH: 127
<212> TYPE: PRT
<213> ORGANISM: Bacteriophage PP7

<400> SEQUENCE: 63

Ser Lys Thr Ile Val Leu Ser Val Gly Glu Ala Thr Arg Thr Leu Thr
1               5                   10                  15

Glu Ile Gln Ser Thr Ala Asp Arg Gln Ile Phe Glu Glu Lys Val Gly
            20                  25                  30

Pro Leu Val Gly Arg Leu Arg Leu Thr Ala Ser Leu Arg Gln Asn Gly
        35                  40                  45

Ala Lys Thr Ala Tyr Arg Val Asn Leu Lys Leu Asp Gln Ala Asp Val
    50                  55                  60

Val Asp Cys Ser Thr Ser Val Cys Gly Glu Leu Pro Lys Val Arg Tyr
65                  70                  75                  80

Thr Gln Val Trp Ser His Asp Val Thr Ile Val Ala Asn Ser Thr Glu
                85                  90                  95

Ala Ser Arg Lys Ser Leu Tyr Asp Leu Thr Lys Ser Leu Val Val Gln
            100                 105                 110

Ala Thr Ser Glu Asp Leu Val Val Asn Leu Val Pro Leu Gly Arg
        115                 120                 125

<210> SEQ ID NO 64
<211> LENGTH: 245
<212> TYPE: PRT
<213> ORGANISM: Bacteriophage PP7

<400> SEQUENCE: 64

Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Val Val Asp Ser Gly Leu Pro Lys Val Arg Tyr Thr Gln Val Trp Ser
65                  70                  75                  80

His Asp Val Thr Ile Val Ala Asn Ser Thr Glu Ala Ser Arg Lys Ser
                85                  90                  95

Leu Tyr Asp Leu Thr Lys Ser Leu Val Ala Thr Ser Gln Val Glu Asp
            100                 105                 110

Leu Val Val Asn Leu Val Pro Leu Gly Arg Tyr Gly Ser Lys Thr Ile
        115                 120                 125

Val Leu Ser Val Gly Glu Ala Thr Arg Thr Leu Thr Glu Ile Gln Ser
    130                 135                 140

Thr Ala Asp Arg Gln Ile Phe Glu Glu Lys Val Gly Pro Leu Val Gly
145                 150                 155                 160
```

```
Arg Leu Arg Leu Thr Ala Ser Leu Arg Gln Asn Gly Ala Lys Thr Ala
                165                 170                 175

Tyr Arg Val Asn Leu Lys Leu Asp Gln Ala Asp Val Val Asp Ser Gly
            180                 185                 190

Leu Pro Lys Val Arg Tyr Thr Gln Val Trp Ser His Asp Val Thr Ile
        195                 200                 205

Val Ala Asn Ser Thr Glu Ala Ser Arg Lys Ser Leu Tyr Asp Leu Thr
    210                 215                 220

Lys Ser Leu Val Ala Thr Ser Gln Val Glu Asp Leu Val Val Asn Leu
225                 230                 235                 240

Val Pro Leu Gly Arg
                245

<210> SEQ ID NO 65
<211> LENGTH: 151
<212> TYPE: PRT
<213> ORGANISM: Escherichia coli

<400> SEQUENCE: 65

Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Gly Asn His
            20                  25                  30

Gly Gly Gly Gly Asn Asn Ser Gly Pro Asn Ser Glu Leu Asn Ile Tyr
        35                  40                  45

Gln Tyr Gly Gly Gly Asn Ser Ala Leu Ala Leu Gln Thr Asp Ala Arg
    50                  55                  60

Asn Ser Asp Leu Thr Ile Thr Gln His Gly Gly Gly Asn Gly Ala Asp
65                  70                  75                  80

Val Gly Gln Gly Ser Asp Asp Ser Ser Ile Asp Leu Thr Gln Arg Gly
                85                  90                  95

Phe Gly Asn Ser Ala Thr Leu Asp Gln Trp Asn Gly Lys Asn Ser Glu
            100                 105                 110

Met Thr Val Lys Gln Phe Gly Gly Gly Asn Gly Ala Ala Val Asp Gln
        115                 120                 125

Thr Ala Ser Asn Ser Ser Val Asn Val Thr Gln Val Gly Phe Gly Asn
    130                 135                 140

Asn Ala Thr Ala His Gln Tyr
145                 150

<210> SEQ ID NO 66
<211> LENGTH: 151
<212> TYPE: PRT
<213> ORGANISM: Artificial Sequence
<220> FEATURE:
<223> OTHER INFORMATION: Protein sequence of AgfA protein from
      Salmonella

<400> SEQUENCE: 66

Met Lys Leu Leu Lys Val Ala Ala Phe Ala Ala Ile Val Val Ser Gly
1               5                   10                  15

Ser Ala Leu Ala Gly Val Val Pro Gln Trp Gly Gly Gly Gly Asn His
            20                  25                  30

Asn Gly Gly Gly Asn Ser Ser Gly Pro Asp Ser Thr Leu Ser Ile Tyr
        35                  40                  45

Gln Tyr Gly Ser Ala Asn Ala Ala Leu Ala Leu Gln Ser Asp Ala Arg
    50                  55                  60
```

```
Lys Ser Glu Thr Thr Ile Thr Gln Ser Gly Tyr Gly Asn Gly Ala Asp
 65                  70                  75                  80

Val Gly Gln Gly Ala Asp Asn Ser Thr Ile Glu Leu Thr Gln Asn Gly
                 85                  90                  95

Phe Arg Asn Asn Ala Thr Ile Asp Gln Trp Asn Ala Lys Asn Ser Asp
            100                 105                 110

Ile Thr Val Gly Gln Tyr Gly Gly Asn Asn Ala Ala Leu Val Asn Gln
        115                 120                 125

Thr Ala Ser Asp Ser Ser Val Met Val Arg Gln Val Gly Phe Gly Asn
    130                 135                 140

Asn Ala Thr Ala Asn Gln Tyr
145                 150
```

<210> SEQ ID NO 67
<211> LENGTH: 353
<212> TYPE: PRT
<213> ORGANISM: Artificial Sequence
<220> FEATURE:
<223> OTHER INFORMATION: Protein sequence of adenylate kinase from
      Thermotoga maritima fused to the N terminus of E.coli CsgA

<400> SEQUENCE: 67

```
Met Met Ala Tyr Leu Val Phe Leu Gly Pro Pro Gly Ala Gly Lys Gly
 1               5                  10                  15

Thr Tyr Ala Lys Arg Ile Gln Glu Lys Thr Gly Ile Pro His Ile Ser
                20                  25                  30

Thr Gly Asp Ile Phe Arg Asp Ile Val Lys Lys Glu Asn Asp Glu Leu
            35                  40                  45

Gly Lys Lys Ile Lys Glu Ile Met Glu Lys Gly Glu Leu Val Pro Asp
        50                  55                  60

Glu Leu Val Asn Glu Val Val Lys Arg Arg Leu Ser Glu Lys Asp Cys
 65                  70                  75                  80

Glu Lys Gly Phe Ile Leu Asp Gly Tyr Pro Arg Thr Val Ala Gln Ala
                 85                  90                  95

Glu Phe Leu Asp Ser Phe Leu Glu Ser Gln Asn Lys Gln Leu Thr Ala
            100                 105                 110

Ala Val Leu Phe Asp Val Pro Glu Asp Val Val Gln Arg Leu Thr
        115                 120                 125

Ser Arg Arg Ile Cys Pro Lys Cys Gly Arg Ile Tyr Asn Met Ile Ser
130                 135                 140

Leu Pro Pro Lys Glu Asp Glu Leu Cys Asp Asp Cys Lys Val Lys Leu
145                 150                 155                 160

Val Gln Arg Asp Asp Lys Glu Glu Thr Val Arg His Arg Tyr Lys
                165                 170                 175

Val Tyr Leu Glu Lys Thr Gln Pro Val Ile Asp Tyr Tyr Gly Lys Lys
            180                 185                 190

Gly Ile Leu Lys Arg Val Asp Gly Thr Ile Gly Ile Asp Asn Val Val
        195                 200                 205

Ala Glu Val Leu Lys Ile Ile Gly Trp Ser Asp Lys Gly Ser Gly Val
    210                 215                 220

Val Pro Gln Tyr Gly Gly Gly Asn His Gly Gly Gly Gly Asn Asn
225                 230                 235                 240

Ser Gly Pro Asn Ser Glu Leu Asn Ile Tyr Gln Tyr Gly Gly Gly Asn
                245                 250                 255

Ser Ala Leu Ala Leu Gln Thr Asp Ala Arg Asn Ser Asp Leu Thr Ile
            260                 265                 270
```

```
Thr Gln His Gly Gly Asn Gly Ala Asp Val Gly Gln Gly Ser Asp
        275                 280                 285

Asp Ser Ser Ile Asp Leu Thr Gln Arg Gly Phe Gly Asn Ser Ala Thr
290                 295                 300

Leu Asp Gln Trp Asn Gly Lys Asn Ser Glu Met Thr Val Lys Gln Phe
305                 310                 315                 320

Gly Gly Gly Asn Gly Ala Ala Val Asp Gln Thr Ala Ser Asn Ser Ser
                325                 330                 335

Val Asn Val Thr Gln Val Gly Phe Gly Asn Asn Ala Thr Ala His Gln
                340                 345                 350

Tyr

<210> SEQ ID NO 68
<211> LENGTH: 83
<212> TYPE: PRT
<213> ORGANISM: Artificial Sequence
<220> FEATURE:
<223> OTHER INFORMATION: Protein sequence of hydrophobin 3 protein from
      Fusarium species

<400> SEQUENCE: 68

Met Gln Phe Ser Thr Leu Thr Thr Val Phe Ala Leu Val Ala Ala Ala
1               5                   10                  15

Val Ala Ala Pro His Gly Ser Ser Gly Gly Asn Asn Pro Val Cys Ser
                20                  25                  30

Ala Gln Asn Asn Gln Val Cys Cys Asn Gly Leu Leu Ser Cys Ala Val
            35                  40                  45

Gln Val Leu Gly Ser Asn Cys Asn Gly Asn Ala Tyr Cys Cys Asn Thr
        50                  55                  60

Glu Ala Pro Thr Gly Thr Leu Ile Asn Val Ala Leu Leu Asn Cys Val
65                  70                  75                  80

Lys Leu Leu

<210> SEQ ID NO 69
<211> LENGTH: 98
<212> TYPE: PRT
<213> ORGANISM: Artificial Sequence
<220> FEATURE:
<223> OTHER INFORMATION: Protein sequence of hydrophobin 5 protein from
      Fusarium species

<400> SEQUENCE: 69

Met Lys Phe Ser Leu Ala Ala Val Ala Leu Leu Gly Ala Val Val Ser
1               5                   10                  15

Ala Leu Pro Ala Asn Glu Lys Arg Gln Ala Tyr Ile Pro Cys Ser Gly
                20                  25                  30

Leu Tyr Gly Thr Ser Gln Cys Cys Ala Thr Asp Val Leu Gly Val Ala
            35                  40                  45

Asp Leu Asp Cys Gly Asn Pro Pro Ser Ser Pro Thr Asp Ala Asp Asn
        50                  55                  60

Phe Ser Ala Val Cys Ala Glu Ile Gly Gln Arg Ala Arg Cys Cys Val
65                  70                  75                  80

Leu Pro Ile Leu Asp Gln Gly Ile Leu Cys Asn Thr Pro Thr Gly Val
                85                  90                  95

Gln Asp

<210> SEQ ID NO 70
<211> LENGTH: 173
<212> TYPE: PRT
```

<213> ORGANISM: Balanus albicostatus

<400> SEQUENCE: 70

```
Val Pro Pro Pro Cys Asp Leu Ser Ile Lys Ser Lys Leu Lys Gln Val
1               5                   10                  15
Gly Ala Thr Ala Gly Asn Ala Ala Val Thr Thr Thr Gly Thr Thr Ser
            20                  25                  30
Gly Ser Gly Val Val Lys Cys Val Val Arg Thr Pro Thr Ser Val Glu
        35                  40                  45
Lys Lys Ala Ala Val Gly Asn Thr Gly Leu Ser Ala Val Ser Ala Ser
    50                  55                  60
Ala Ala Asn Gly Phe Phe Lys Asn Leu Gly Lys Ala Thr Thr Glu Val
65                  70                  75                  80
Lys Thr Thr Lys Asp Gly Thr Lys Val Lys Thr Lys Ala Gly Lys
                85                  90                  95
Gly Lys Thr Gly Gly Thr Ala Thr Thr Ile Gln Ile Ala Asp Ala Asn
            100                 105                 110
Gly Gly Val Ser Glu Lys Ser Leu Lys Leu Asp Leu Thr Asp Gly
        115                 120                 125
Leu Lys Phe Val Lys Val Thr Glu Lys Lys Gln Gly Thr Ala Thr Ser
    130                 135                 140
Ser Ser Gly His Lys Ala Ser Gly Val Gly His Ser Val Phe Lys Val
145                 150                 155                 160
Leu Asn Glu Ala Glu Thr Glu Leu Glu Leu Lys Gly Leu
                165                 170
```

<210> SEQ ID NO 71
<211> LENGTH: 202
<212> TYPE: PRT
<213> ORGANISM: Megabalanus rosa

<400> SEQUENCE: 71

```
Met Lys Trp Phe Leu Phe Leu Leu Thr Thr Ala Val Leu Ala Ala Val
1               5                   10                  15
Val Ser Ala His Glu Glu Asp Gly Val Cys Asn Ser Asn Ala Pro Cys
            20                  25                  30
Tyr His Cys Asp Ala Asn Gly Glu Asn Cys Ser Cys Asn Cys Glu Leu
        35                  40                  45
Phe Asp Cys Glu Ala Lys Lys Pro Asp Gly Ser Tyr Ala His Pro Cys
    50                  55                  60
Arg Arg Cys Asp Ala Asn Asn Ile Cys Lys Cys Ser Cys Thr Ala Ile
65                  70                  75                  80
Pro Cys Asn Glu Asp His Pro Cys His His Cys His Glu Glu Asp Asp
                85                  90                  95
Gly Asp Thr His Cys His Cys Ser Cys Glu His Ser His Asp His His
            100                 105                 110
Asp Asp Asp Thr His Gly Glu Cys Thr Lys Lys Ala Pro Cys Trp Arg
        115                 120                 125
Cys Glu Tyr Asn Ala Asp Leu Lys His Asp Val Cys Gly Cys Glu Cys
    130                 135                 140
Ser Lys Leu Pro Cys Asn Asp Glu His Pro Cys Tyr Arg Lys Glu Gly
145                 150                 155                 160
Gly Val Val Ser Cys Asp Cys Lys Thr Ile Thr Cys Asn Glu Asp His
                165                 170                 175
Pro Cys Tyr His Ser Tyr Glu Glu Asp Gly Val Thr Lys Ser Asp Cys
            180                 185                 190
```

Asp Cys Glu His Ser Pro Gly Pro Ser Glu
        195                 200

<210> SEQ ID NO 72
<211> LENGTH: 576
<212> TYPE: PRT
<213> ORGANISM: Artificial Sequence
<220> FEATURE:
<223> OTHER INFORMATION: Protein sequence of fusion of the barnacle
      protein from Balanus albicostatus with the adenylate kinase from
      Thermotgoa maritima; N-terminal fusion

<400> SEQUENCE: 72

Met Arg Val Leu Val Ile Asn Ser Gly Ser Ser Ile Lys Tyr Gln
1               5                   10                  15

Leu Ile Glu Met Glu Gly Glu Lys Val Leu Cys Lys Gly Ile Ala Glu
            20                  25                  30

Arg Ile Gly Ile Glu Gly Ser Arg Leu Val His Arg Val Gly Asp Glu
            35                  40                  45

Lys His Val Ile Glu Arg Glu Leu Pro Asp His Glu Glu Ala Leu Lys
        50                  55                  60

Leu Ile Leu Asn Thr Leu Val Asp Glu Lys Leu Gly Val Ile Lys Asp
65                  70                  75                  80

Leu Lys Glu Ile Asp Ala Val Gly His Arg Val Val His Gly Gly Glu
                85                  90                  95

Arg Phe Lys Glu Ser Val Leu Val Asp Glu Glu Val Leu Lys Ala Ile
            100                 105                 110

Glu Glu Val Ser Pro Leu Ala Pro Leu His Asn Pro Ala Asn Leu Met
            115                 120                 125

Gly Ile Lys Ala Ala Met Lys Leu Leu Pro Gly Val Pro Asn Val Ala
        130                 135                 140

Val Phe Asp Thr Ala Phe His Gln Thr Ile Pro Gln Lys Ala Tyr Leu
145                 150                 155                 160

Tyr Ala Ile Pro Tyr Glu Tyr Tyr Glu Lys Tyr Lys Ile Arg Arg Tyr
                165                 170                 175

Gly Phe His Gly Thr Ser His Arg Tyr Val Ser Lys Arg Ala Ala Glu
            180                 185                 190

Ile Leu Gly Lys Lys Leu Glu Glu Leu Lys Ile Ile Thr Cys His Ile
        195                 200                 205

Gly Asn Gly Ala Ser Val Ala Ala Val Lys Tyr Gly Lys Cys Val Asp
    210                 215                 220

Thr Ser Met Gly Phe Thr Pro Leu Glu Gly Leu Val Met Gly Thr Arg
225                 230                 235                 240

Ser Gly Asp Leu Asp Pro Ala Ile Pro Phe Phe Ile Met Glu Lys Glu
                245                 250                 255

Gly Ile Ser Pro Gln Glu Met Tyr Asp Ile Leu Asn Lys Lys Ser Gly
            260                 265                 270

Val Tyr Gly Leu Ser Lys Gly Phe Ser Ser Asp Met Arg Asp Ile Glu
        275                 280                 285

Glu Ala Ala Leu Lys Gly Asp Glu Trp Cys Lys Leu Val Leu Glu Ile
    290                 295                 300

Tyr Asp Tyr Arg Ile Ala Lys Tyr Ile Gly Ala Tyr Ala Ala Ala Met
305                 310                 315                 320

Asn Gly Val Asp Ala Ile Val Phe Thr Ala Gly Val Gly Glu Asn Ser
                325                 330                 335

Pro Ile Thr Arg Glu Asp Val Cys Ser Tyr Leu Glu Phe Leu Gly Val

```
                      340                 345                 350
Lys Leu Asp Lys Gln Lys Asn Glu Glu Thr Ile Arg Gly Lys Glu Gly
            355                 360                 365

Ile Ile Ser Thr Pro Asp Ser Arg Val Lys Val Leu Val Val Pro Thr
        370                 375                 380

Asn Glu Glu Leu Met Ile Ala Arg Asp Thr Lys Glu Ile Val Glu Lys
385                 390                 395                 400

Ile Gly Arg Val Pro Pro Cys Asp Leu Ser Ile Lys Ser Lys Leu
                405                 410                 415

Lys Gln Val Gly Ala Thr Ala Gly Asn Ala Ala Val Thr Thr Thr Gly
            420                 425                 430

Thr Thr Ser Gly Ser Gly Val Val Lys Cys Val Val Arg Thr Pro Thr
        435                 440                 445

Ser Val Glu Lys Lys Ala Ala Val Gly Asn Thr Gly Leu Ser Ala Val
    450                 455                 460

Ser Ala Ser Ala Ala Asn Gly Phe Phe Lys Asn Leu Gly Lys Ala Thr
465                 470                 475                 480

Thr Glu Val Lys Thr Thr Lys Asp Gly Thr Lys Val Lys Thr Lys Thr
                485                 490                 495

Ala Gly Lys Gly Lys Thr Gly Gly Thr Ala Thr Thr Ile Gln Ile Ala
            500                 505                 510

Asp Ala Asn Gly Gly Val Ser Glu Lys Ser Leu Lys Leu Asp Leu Leu
        515                 520                 525

Thr Asp Gly Leu Lys Phe Val Lys Val Thr Glu Lys Lys Gln Gly Thr
    530                 535                 540

Ala Thr Ser Ser Ser Gly His Lys Ala Ser Gly Val Gly His Ser Val
545                 550                 555                 560

Phe Lys Val Leu Asn Glu Ala Glu Thr Glu Leu Glu Leu Lys Gly Leu
                565                 570                 575

<210> SEQ ID NO 73
<211> LENGTH: 575
<212> TYPE: PRT
<213> ORGANISM: Artificial Sequence
<220> FEATURE:
<223> OTHER INFORMATION: Protein sequence of fusion of barnacle protein
      from Balanus albicostatus with the adenylate kinase from
      Thermotoga maritima; C-terminal fusion

<400> SEQUENCE: 73

Val Pro Pro Pro Cys Asp Leu Ser Ile Lys Ser Lys Leu Lys Gln Val
1               5                   10                  15

Gly Ala Thr Ala Gly Asn Ala Ala Val Thr Thr Thr Gly Thr Thr Ser
            20                  25                  30

Gly Ser Gly Val Val Lys Cys Val Val Arg Thr Pro Thr Ser Val Glu
        35                  40                  45

Lys Lys Ala Ala Val Gly Asn Thr Gly Leu Ser Ala Val Ser Ala Ser
    50                  55                  60

Ala Ala Asn Gly Phe Phe Lys Asn Leu Gly Lys Ala Thr Thr Glu Val
65                  70                  75                  80

Lys Thr Thr Lys Asp Gly Thr Lys Val Lys Thr Lys Thr Ala Gly Lys
                85                  90                  95

Gly Lys Thr Gly Gly Thr Ala Thr Thr Ile Gln Ile Ala Asp Ala Asn
            100                 105                 110

Gly Gly Val Ser Glu Lys Ser Leu Lys Leu Asp Leu Leu Thr Asp Gly
        115                 120                 125
```

```
Leu Lys Phe Val Lys Val Thr Glu Lys Lys Gln Gly Thr Ala Thr Ser
    130                 135                 140

Ser Ser Gly His Lys Ala Ser Gly Val Gly His Ser Val Phe Lys Val
145                 150                 155                 160

Leu Glu Ala Glu Thr Glu Leu Glu Leu Lys Gly Leu Met Arg Val Leu
                165                 170                 175

Val Ile Asn Ser Gly Ser Ser Ile Lys Tyr Gln Leu Ile Glu Met
                180                 185                 190

Glu Gly Glu Lys Val Leu Cys Lys Gly Ile Ala Glu Arg Ile Gly Ile
                195                 200                 205

Glu Gly Ser Arg Leu Val His Arg Val Gly Asp Glu Lys His Val Ile
    210                 215                 220

Glu Arg Glu Leu Pro Asp His Glu Glu Ala Leu Lys Leu Ile Leu Asn
225                 230                 235                 240

Thr Leu Val Asp Glu Lys Leu Gly Val Ile Lys Asp Leu Lys Glu Ile
                245                 250                 255

Asp Ala Val Gly His Arg Val Val His Gly Gly Glu Arg Phe Lys Glu
                260                 265                 270

Ser Val Leu Val Asp Glu Glu Val Leu Lys Ala Ile Glu Glu Val Ser
                275                 280                 285

Pro Leu Ala Pro Leu His Asn Pro Ala Asn Leu Met Gly Ile Lys Ala
    290                 295                 300

Ala Met Lys Leu Leu Pro Gly Val Pro Asn Val Ala Val Phe Asp Thr
305                 310                 315                 320

Ala Phe His Gln Thr Ile Pro Gln Lys Ala Tyr Leu Tyr Ala Ile Pro
                325                 330                 335

Tyr Glu Tyr Tyr Glu Lys Tyr Lys Ile Arg Arg Tyr Gly Phe His Gly
                340                 345                 350

Thr Ser His Arg Tyr Val Ser Lys Arg Ala Ala Glu Ile Leu Gly Lys
                355                 360                 365

Lys Leu Glu Glu Leu Lys Ile Ile Thr Cys His Ile Gly Asn Gly Ala
    370                 375                 380

Ser Val Ala Ala Val Lys Tyr Gly Lys Cys Val Asp Thr Ser Met Gly
385                 390                 395                 400

Phe Thr Pro Leu Glu Gly Leu Val Met Gly Thr Arg Ser Gly Asp Leu
                405                 410                 415

Asp Pro Ala Ile Pro Phe Phe Ile Met Glu Lys Glu Gly Ile Ser Pro
                420                 425                 430

Gln Glu Met Tyr Asp Ile Leu Asn Lys Ser Gly Val Tyr Gly Leu
                435                 440                 445

Ser Lys Gly Phe Ser Ser Asp Met Arg Asp Ile Glu Glu Ala Ala Leu
    450                 455                 460

Lys Gly Asp Glu Trp Cys Lys Leu Val Leu Glu Ile Tyr Asp Tyr Arg
465                 470                 475                 480

Ile Ala Lys Tyr Ile Gly Ala Tyr Ala Ala Met Asn Gly Val Asp
                485                 490                 495

Ala Ile Val Phe Thr Ala Gly Val Gly Glu Asn Ser Pro Ile Thr Arg
                500                 505                 510

Glu Asp Val Cys Ser Tyr Leu Glu Phe Leu Gly Val Lys Leu Asp Lys
                515                 520                 525

Gln Lys Asn Glu Glu Thr Ile Arg Gly Lys Glu Gly Ile Ile Ser Thr
    530                 535                 540

Pro Asp Ser Arg Val Lys Val Leu Val Val Pro Thr Asn Glu Glu Leu
545                 550                 555                 560
```

```
Met Ile Ala Arg Asp Thr Lys Glu Ile Val Glu Lys Ile Gly Arg
            565                 570                 575

<210> SEQ ID NO 74
<211> LENGTH: 125
<212> TYPE: PRT
<213> ORGANISM: Balanus albicostatus

<400> SEQUENCE: 74

Met Lys Tyr Thr Leu Ala Leu Leu Phe Leu Thr Ala Ile Ile Ala Thr
1               5                   10                  15

Phe Val Ala Ala His Lys His His Asp His Gly Lys Ser Cys Ser Lys
            20                  25                  30

Ser His Pro Cys Tyr His Cys His Thr Asp Cys Glu Cys Asn His His
        35                  40                  45

His Asp Asp Cys Asn Arg Ser His Arg Cys Trp His Lys Val His Gly
    50                  55                  60

Val Val Ser Gly Asn Cys Asn Cys Asn Leu Leu Thr Pro Cys Asn Gln
65                  70                  75                  80

Lys His Pro Cys Trp Arg Arg His Gly Lys Lys His Gly Leu His Arg
                85                  90                  95

Lys Phe His Gly Asn Ala Cys Asn Cys Asp Arg Leu Val Cys Asn Ala
            100                 105                 110

Lys His Pro Cys Trp His Lys His Cys Asp Cys Phe Cys
        115                 120                 125

<210> SEQ ID NO 75
<211> LENGTH: 24
<212> TYPE: PRT
<213> ORGANISM: Artificial Sequence
<220> FEATURE:
<223> OTHER INFORMATION: Protein sequence of a peptide derived from a
      barnacle cement protein

<400> SEQUENCE: 75

Ser Lys Leu Pro Cys Asn Asp Glu His Pro Cys Tyr Arg Lys Glu Gly
1               5                   10                  15

Gly Val Val Ser Cys Asp Cys Lys
            20

<210> SEQ ID NO 76
<211> LENGTH: 24
<212> TYPE: PRT
<213> ORGANISM: Artificial Sequence
<220> FEATURE:
<223> OTHER INFORMATION: Protein sequence of a peptide derived from a
      barnacle cement protein

<400> SEQUENCE: 76

Ser Lys Leu Pro Ser Asn Asp Glu His Pro Ser Tyr Arg Lys Glu Gly
1               5                   10                  15

Gly Val Val Ser Ser Asp Ser Lys
            20

<210> SEQ ID NO 77
<211> LENGTH: 28
<212> TYPE: PRT
<213> ORGANISM: Artificial Sequence
<220> FEATURE:
<223> OTHER INFORMATION: Protein sequence of a peptide derived from a
      barnacle cement protein

<400> SEQUENCE: 77
```

```
Lys Thr Ile Thr Cys Asn Glu Asp His Pro Cys Tyr His Ser Tyr Glu
1               5                   10                  15

Glu Asp Gly Val Thr Lys Ser Asp Cys Asp Cys Glu
                20                  25
```

```
<210> SEQ ID NO 78
<211> LENGTH: 214
<212> TYPE: PRT
<213> ORGANISM: Escherichia coli

<400> SEQUENCE: 78

Met Arg Ile Ile Leu Leu Gly Ala Pro Gly Ala Gly Lys Gly Thr Gln
1               5                   10                  15

Ala Gln Phe Ile Met Glu Lys Tyr Gly Ile Pro Gln Ile Ser Thr Gly
                20                  25                  30

Asp Met Leu Arg Ala Ala Val Lys Ser Gly Ser Glu Leu Gly Lys Gln
            35                  40                  45

Ala Lys Asp Ile Met Asp Ala Gly Lys Leu Val Thr Asp Glu Leu Val
    50                  55                  60

Ile Ala Leu Val Lys Glu Arg Ile Ala Gln Glu Asp Cys Arg Asn Gly
65                  70                  75                  80

Phe Leu Leu Asp Gly Phe Pro Arg Thr Ile Pro Gln Ala Asp Ala Met
                85                  90                  95

Lys Glu Ala Gly Ile Asn Val Asp Tyr Val Leu Glu Phe Asp Val Pro
                100                 105                 110

Asp Glu Leu Ile Val Asp Arg Ile Val Gly Arg Arg Val His Ala Pro
            115                 120                 125

Ser Gly Arg Val Tyr His Val Lys Phe Asn Pro Pro Lys Val Glu Gly
    130                 135                 140

Lys Asp Asp Val Thr Gly Glu Glu Leu Thr Thr Arg Lys Asp Asp Gln
145                 150                 155                 160

Glu Glu Thr Val Arg Lys Arg Leu Val Glu Tyr His Gln Met Thr Ala
                165                 170                 175

Pro Leu Ile Gly Tyr Tyr Ser Lys Glu Ala Glu Ala Gly Asn Thr Lys
                180                 185                 190

Tyr Ala Lys Val Asp Gly Thr Lys Pro Val Ala Glu Val Arg Ala Asp
            195                 200                 205

Leu Glu Lys Ile Leu Gly
            210
```

```
<210> SEQ ID NO 79
<211> LENGTH: 470
<212> TYPE: PRT
<213> ORGANISM: Escherichia coli

<400> SEQUENCE: 79

Met Lys Lys Thr Lys Ile Val Cys Thr Ile Gly Pro Lys Thr Glu Ser
1               5                   10                  15

Glu Glu Met Leu Ala Lys Met Leu Asp Ala Gly Met Asn Val Met Arg
                20                  25                  30

Leu Asn Phe Ser His Gly Asp Tyr Ala Glu His Gly Gln Arg Ile Gln
            35                  40                  45

Asn Leu Arg Asn Val Met Ser Lys Thr Gly Lys Thr Ala Ala Ile Leu
    50                  55                  60

Leu Asp Thr Lys Gly Pro Glu Ile Arg Thr Met Lys Leu Glu Gly Gly
65                  70                  75                  80
```

Asn Asp Val Ser Leu Lys Ala Gly Gln Thr Phe Thr Phe Thr Thr Asp
                85                  90                  95

Lys Ser Val Ile Gly Asn Ser Glu Met Val Ala Val Thr Tyr Glu Gly
                100                 105                 110

Phe Thr Thr Asp Leu Ser Val Gly Asn Thr Val Leu Val Asp Asp Gly
                115                 120                 125

Leu Ile Gly Met Glu Val Thr Ala Ile Glu Gly Asn Lys Val Ile Cys
            130                 135                 140

Lys Val Leu Asn Asn Gly Asp Leu Gly Glu Asn Lys Gly Val Asn Leu
145                 150                 155                 160

Pro Gly Val Ser Ile Ala Leu Pro Ala Leu Ala Glu Lys Asp Lys Gln
                165                 170                 175

Asp Leu Ile Phe Gly Cys Glu Gln Gly Val Asp Phe Val Ala Ala Ser
                180                 185                 190

Phe Ile Arg Lys Arg Ser Asp Val Ile Glu Ile Arg Glu His Leu Lys
                195                 200                 205

Ala His Gly Gly Glu Asn Ile His Ile Ile Ser Lys Ile Glu Asn Gln
            210                 215                 220

Glu Gly Leu Asn Asn Phe Asp Glu Ile Leu Glu Ala Ser Asp Gly Ile
225                 230                 235                 240

Met Val Ala Arg Gly Asp Leu Gly Val Glu Ile Pro Val Glu Glu Val
                245                 250                 255

Ile Phe Ala Gln Lys Met Met Ile Glu Lys Cys Ile Arg Ala Arg Lys
                260                 265                 270

Val Val Ile Thr Ala Thr Gln Met Leu Asp Ser Met Ile Lys Asn Pro
            275                 280                 285

Arg Pro Thr Arg Ala Glu Ala Gly Asp Val Ala Asn Ala Ile Leu Asp
290                 295                 300

Gly Thr Asp Ala Val Met Leu Ser Gly Glu Ser Ala Lys Gly Lys Tyr
305                 310                 315                 320

Pro Leu Glu Ala Val Ser Ile Met Ala Thr Ile Cys Glu Arg Thr Asp
                325                 330                 335

Arg Val Met Asn Ser Arg Leu Glu Phe Asn Asn Asp Asn Arg Lys Leu
                340                 345                 350

Arg Ile Thr Glu Ala Val Cys Arg Gly Ala Val Glu Thr Ala Glu Lys
            355                 360                 365

Leu Asp Ala Pro Leu Ile Val Val Ala Thr Gln Gly Gly Lys Ser Ala
370                 375                 380

Arg Ala Val Arg Lys Tyr Phe Pro Asp Ala Thr Ile Leu Ala Leu Thr
385                 390                 395                 400

Thr Asn Glu Lys Thr Ala His Gln Leu Val Leu Ser Lys Gly Val Val
                405                 410                 415

Pro Gln Leu Val Lys Glu Ile Thr Ser Thr Asp Asp Phe Tyr Arg Leu
                420                 425                 430

Gly Lys Glu Leu Ala Leu Gln Ser Gly Leu Ala His Lys Gly Asp Val
            435                 440                 445

Val Val Met Val Ser Gly Ala Leu Val Pro Ser Gly Thr Thr Asn Thr
450                 455                 460

Ala Ser Val His Val Leu
465                 470

<210> SEQ ID NO 80
<211> LENGTH: 400
<212> TYPE: PRT
<213> ORGANISM: Escherichia coli

<400> SEQUENCE: 80

```
Met Ser Ser Lys Leu Val Leu Val Leu Asn Cys Gly Ser Ser Ser Leu
1               5                   10                  15

Lys Phe Ala Ile Ile Asp Ala Val Asn Gly Glu Glu Tyr Leu Ser Gly
            20                  25                  30

Leu Ala Glu Cys Phe His Leu Pro Glu Ala Arg Ile Lys Trp Lys Met
        35                  40                  45

Asp Gly Asn Lys Gln Glu Ala Leu Gly Ala Gly Ala Ala His Ser
    50                  55                  60

Glu Ala Leu Asn Phe Ile Val Asn Thr Ile Leu Ala Gln Lys Pro Glu
65                  70                  75                  80

Leu Ser Ala Gln Leu Thr Ala Ile Gly His Arg Ile Val His Gly Gly
                85                  90                  95

Glu Lys Tyr Thr Ser Ser Val Val Ile Asp Glu Ser Val Ile Gln Gly
            100                 105                 110

Ile Lys Asp Ala Ala Ser Phe Ala Pro Leu His Asn Pro Ala His Leu
        115                 120                 125

Ile Gly Ile Glu Glu Ala Leu Lys Ser Phe Pro Gln Leu Lys Asp Lys
    130                 135                 140

Asn Val Ala Val Phe Asp Thr Ala Phe His Gln Thr Met Pro Glu Glu
145                 150                 155                 160

Ser Tyr Leu Tyr Ala Leu Pro Tyr Asn Leu Tyr Lys Glu His Gly Ile
                165                 170                 175

Arg Arg Tyr Gly Ala His Gly Thr Ser His Phe Tyr Val Thr Gln Glu
            180                 185                 190

Ala Ala Lys Met Leu Asn Lys Pro Val Glu Glu Leu Asn Ile Ile Thr
        195                 200                 205

Cys His Leu Gly Asn Gly Gly Ser Val Ser Ala Ile Arg Asn Gly Lys
    210                 215                 220

Cys Val Asp Thr Ser Met Gly Leu Thr Pro Leu Glu Gly Leu Val Met
225                 230                 235                 240

Gly Thr Arg Ser Gly Asp Ile Asp Pro Ala Ile Ile Phe His Leu His
                245                 250                 255

Asp Thr Leu Gly Met Ser Val Asp Ala Ile Asn Lys Leu Leu Thr Lys
            260                 265                 270

Glu Ser Gly Leu Leu Gly Leu Thr Glu Val Thr Ser Asp Cys Arg Tyr
        275                 280                 285

Val Glu Asp Asn Tyr Ala Thr Lys Glu Asp Ala Lys Arg Ala Met Asp
    290                 295                 300

Val Tyr Cys His Arg Leu Ala Lys Tyr Ile Gly Ala Tyr Thr Ala Leu
305                 310                 315                 320

Met Asp Gly Arg Leu Asp Ala Val Val Phe Thr Gly Gly Ile Gly Glu
                325                 330                 335

Asn Ala Ala Met Val Arg Glu Leu Ser Leu Gly Lys Leu Gly Val Leu
            340                 345                 350

Gly Phe Glu Val Asp His Glu Arg Asn Leu Ala Ala Arg Phe Gly Lys
        355                 360                 365

Ser Gly Phe Ile Asn Lys Glu Gly Thr Arg Pro Ala Val Val Ile Pro
    370                 375                 380

Thr Asn Glu Glu Leu Val Ile Ala Gln Asp Ala Ser Arg Leu Thr Ala
385                 390                 395                 400
```

<210> SEQ ID NO 81

```
<211> LENGTH: 192
<212> TYPE: PRT
<213> ORGANISM: Methanococcus voltae

<400> SEQUENCE: 81
```

Met Lys Asn Lys Val Val Val Thr Gly Val Pro Gly Val Gly Ser
1               5                   10                  15

Thr Thr Ser Ser Gln Leu Ala Met Asp Asn Leu Arg Lys Glu Gly Val
            20                  25                  30

Asn Tyr Lys Met Val Ser Phe Gly Ser Val Met Phe Glu Val Ala Lys
        35                  40                  45

Glu Glu Asn Leu Val Ser Asp Arg Asp Gln Met Arg Lys Met Asp Pro
    50                  55                  60

Glu Thr Gln Lys Arg Ile Gln Lys Met Ala Gly Arg Lys Ile Ala Glu
65                  70                  75                  80

Met Ala Lys Glu Ser Pro Val Ala Val Asp Thr His Ser Thr Val Ser
                85                  90                  95

Thr Pro Lys Gly Tyr Leu Pro Gly Leu Pro Ser Trp Val Leu Asn Glu
            100                 105                 110

Leu Asn Pro Asp Leu Ile Ile Val Val Glu Thr Gly Asp Glu Ile
        115                 120                 125

Leu Met Arg Arg Met Ser Asp Glu Thr Arg Val Arg Asp Leu Asp Thr
    130                 135                 140

Ala Ser Thr Ile Glu Gln His Gln Phe Met Asn Arg Cys Ala Ala Met
145                 150                 155                 160

Ser Tyr Gly Val Leu Thr Gly Ala Thr Val Lys Ile Val Gln Asn Arg
                165                 170                 175

Asn Gly Leu Leu Asp Gln Ala Val Glu Glu Leu Thr Asn Val Leu Arg
            180                 185                 190

```
<210> SEQ ID NO 82
<211> LENGTH: 192
<212> TYPE: PRT
<213> ORGANISM: Methanococcus thermolithotrophicus

<400> SEQUENCE: 82
```

Met Lys Asn Lys Leu Val Val Thr Gly Val Pro Gly Val Gly Gly
1               5                   10                  15

Thr Thr Ile Thr Gln Lys Ala Met Glu Lys Leu Ser Glu Glu Gly Ile
            20                  25                  30

Asn Tyr Lys Met Val Asn Phe Gly Thr Val Met Phe Glu Val Ala Gln
        35                  40                  45

Glu Glu Asn Leu Val Glu Asp Arg Asp Gln Met Arg Lys Leu Asp Pro
    50                  55                  60

Asp Thr Gln Lys Arg Ile Gln Lys Leu Ala Gly Arg Lys Ile Ala Glu
65                  70                  75                  80

Met Val Lys Glu Ser Pro Val Val Asp Thr His Ser Thr Ile Lys
                85                  90                  95

Thr Pro Lys Gly Tyr Leu Pro Gly Leu Pro Val Trp Val Leu Asn Glu
            100                 105                 110

Leu Asn Pro Asp Ile Ile Ile Val Val Glu Thr Ser Gly Asp Glu Ile
        115                 120                 125

Leu Ile Arg Arg Leu Asn Asp Glu Thr Arg Asn Arg Asp Leu Glu Thr
    130                 135                 140

Thr Ala Gly Ile Glu Glu His Gln Ile Met Asn Arg Ala Ala Ala Met
145                 150                 155                 160

```
Thr Tyr Gly Val Leu Thr Gly Ala Thr Val Lys Ile Ile Gln Asn Lys
            165                 170                 175

Asn Asn Leu Leu Asp Tyr Ala Val Glu Glu Leu Ile Ser Val Leu Arg
            180                 185                 190
```

<210> SEQ ID NO 83
<211> LENGTH: 217
<212> TYPE: PRT
<213> ORGANISM: Bacillus globisporus

<400> SEQUENCE: 83

```
Met Asn Ile Val Leu Met Gly Leu Pro Gly Ala Gly Lys Gly Thr Gln
1               5                   10                  15

Ala Asp Arg Ile Val Glu Lys Tyr Gly Thr Pro His Ile Ser Thr Gly
            20                  25                  30

Asp Met Phe Arg Ala Ala Ile Gln Glu Gly Thr Glu Leu Gly Val Lys
        35                  40                  45

Ala Lys Ser Phe Met Asp Gln Gly Ala Leu Val Pro Asp Glu Val Thr
    50                  55                  60

Ile Gly Ile Val Arg Glu Arg Leu Ser Lys Ser Asp Cys Asp Asn Gly
65                  70                  75                  80

Phe Leu Leu Asp Gly Phe Pro Arg Thr Val Pro Gln Ala Glu Ala Leu
                85                  90                  95

Asp Gln Leu Leu Ala Asp Met Gly Arg Lys Ile Glu His Val Leu Asn
            100                 105                 110

Ile Gln Val Glu Lys Glu Glu Leu Ile Ala Arg Leu Thr Gly Arg Arg
        115                 120                 125

Ile Cys Lys Val Cys Gly Thr Ser Tyr His Leu Leu Phe Asn Pro Pro
    130                 135                 140

Gln Val Glu Gly Lys Cys Asp Lys Asp Gly Gly Glu Leu Tyr Gln Arg
145                 150                 155                 160

Ala Asp Asp Asn Pro Asp Thr Val Thr Asn Arg Leu Glu Val Asn Met
                165                 170                 175

Asn Gln Thr Ala Pro Leu Leu Ala Phe Tyr Asp Ser Lys Glu Val Leu
            180                 185                 190

Val Asn Ile Asn Gly Gln Lys Asp Ile Lys Asp Val Phe Lys Asp Leu
        195                 200                 205

Asp Val Ile Leu Gln Gly Asn Gly Gln
    210                 215
```

<210> SEQ ID NO 84
<211> LENGTH: 217
<212> TYPE: PRT
<213> ORGANISM: Bacillus subtilis

<400> SEQUENCE: 84

```
Met Asn Leu Val Leu Met Gly Leu Pro Gly Ala Gly Lys Gly Thr Gln
1               5                   10                  15

Gly Glu Arg Ile Val Glu Asp Tyr Gly Ile Pro His Ile Ser Thr Gly
            20                  25                  30

Asp Met Phe Arg Ala Ala Met Lys Glu Glu Thr Pro Leu Gly Leu Glu
        35                  40                  45

Ala Lys Ser Tyr Ile Asp Lys Gly Glu Leu Val Pro Asp Glu Val Thr
    50                  55                  60

Ile Gly Ile Val Lys Glu Arg Leu Gly Lys Asp Asp Cys Glu Arg Gly
65                  70                  75                  80

Phe Leu Leu Asp Gly Phe Pro Arg Thr Val Ala Gln Ala Glu Ala Leu
```

-continued

```
                        85                      90                      95
Glu Glu Ile Leu Glu Glu Tyr Gly Lys Pro Ile Asp Tyr Val Ile Asn
            100                 105                 110

Ile Glu Val Asp Lys Asp Val Leu Met Glu Arg Leu Thr Gly Arg Arg
        115                 120                 125

Ile Cys Ser Val Cys Gly Thr Thr Tyr His Leu Val Phe Asn Pro Pro
    130                 135                 140

Lys Thr Pro Gly Ile Cys Asp Lys Asp Gly Gly Glu Leu Tyr Gln Arg
145                 150                 155                 160

Ala Asp Asp Asn Glu Glu Thr Val Ser Lys Arg Leu Glu Val Asn Met
                165                 170                 175

Lys Gln Thr Gln Pro Leu Leu Asp Phe Tyr Ser Glu Lys Gly Tyr Leu
            180                 185                 190

Ala Asn Val Asn Gly Gln Gln Asp Ile Gln Asp Val Tyr Ala Asp Val
        195                 200                 205

Lys Asp Leu Leu Gly Gly Leu Lys Lys
210                 215
```